(12) United States Patent
Beard et al.

(10) Patent No.: US 8,193,203 B2
(45) Date of Patent: Jun. 5, 2012

(54) BICYCLIC COMPOUNDS HAVING ACTIVITY AT THE CXCR4 RECEPTOR

(75) Inventors: Richard L. Beard, Newport Beach, CA (US); Tien T. Duong, Rancho Santa Margarita, CA (US); Thong H. Vu, Garden Grove, CA (US); Vidyasagar Vuligonda, Irvine, CA (US); John E. Donello, Dana Point, CA (US); Michael E. Garst, Newport Beach, CA (US); Gerard A. Rodrigues, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 394 days.

(21) Appl. No.: 12/467,575

(22) Filed: May 18, 2009

(65) Prior Publication Data
US 2009/0312305 A1 Dec. 17, 2009

Related U.S. Application Data

(60) Provisional application No. 61/055,248, filed on May 22, 2008.

(51) Int. Cl.
*A01N 43/54* (2006.01)
*A61K 31/517* (2006.01)
*C07D 239/72* (2006.01)
(52) U.S. Cl. .................. 514/266.1; 544/283
(58) Field of Classification Search .............. 544/283; 514/266.1
See application file for complete search history.

(56) References Cited

FOREIGN PATENT DOCUMENTS
FR 2891829 4/2007
WO WO 2006-034235 3/2006
WO WO 2007/071055 6/2007

OTHER PUBLICATIONS

Stefan Kubicek et al.; "Reversal of H3K9me2 by a Small Molecule Inhibitor for the G9a Histone Methyltransferase". Molecular Cell Press; pp. 473-481; Feb. 2007.
Richard B. Silverman; "Organic Chemistry of Drug Design and Drug Action", 2d Ed., Elsevier Academic Press: Amsterdam, 2004, pp. 496-557.

*Primary Examiner* — Paul V. Ward
(74) *Attorney, Agent, or Firm* — Doina G. Ene; John E. Wurst; Kevin J. Forrestal

(57) ABSTRACT

A compound represented by the structural formula:

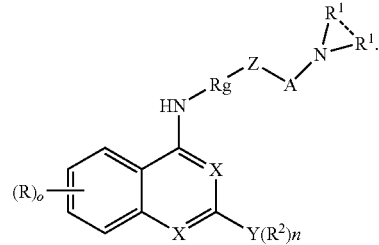

Therapeutic methods, compositions, and medicaments related thereto are also disclosed.

15 Claims, No Drawings

BICYCLIC COMPOUNDS HAVING ACTIVITY AT THE CXCR4 RECEPTOR

CROSS REFERENCE TO RELATED APPLICATIONS

This application is based on, and claims the benefit of, U.S. Provisional Application Ser. No. 61/055,248, filed May 22, 2008 which is incorporated herein by reference in its entirety.

DESCRIPTION OF THE INVENTION

Disclosed herein are compounds represented by the structural formula:

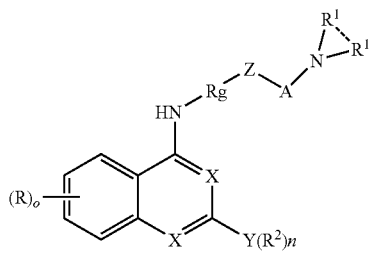

wherein a dashed line represents the presence or absence of a bond
o is 0, 1, 2, 3, 4, 5, or 6;
X is independently C, CH or N;
Y is independently N, NH, $CH_2$, CH, C, O, or S;
A is aryl or heteroaryl having 0, 1, 2, 3, or 4 substituents, wherein Z and the N atom are attached to adjacent carbon atoms, and wherein each substituent of A independently has a formula $C_{0-10}H_{0-27}N_{0-3}O_{0-3}S_{0-2}P_{0-1}F_{0-3}Cl_{0-1}Br_{0-1}I_{0-1}$;
Z is $CH_2$, CHOH, or C=O;
Rg is a 3- to 7-membered ring having a formula $C_{2-10}H_{2-21}N_{0-1}$, wherein if an N atom is present, it is directly attached to Z;
R is independently H, OH, SH, $C_{1-3}$ alkyl, O—($C_{1-3}$ alkyl), S—($C_{1-3}$ alkyl), or halo, wherein two R moieties may together form a ring;
$R^1$ is independently H, O, $C_{1-8}$ hydrocarbyl, $C_{1-8}$ hydroxyalkyl, $C_{1-8}$ alkylthiol, $C_{1-8}$ alkylalkoxy, $C_{1-8}$ alkylthioalkyl, or $C_{1-8}$ aminoalkyl; and
$Y(R^2)_n$ is a substituent having a formula $C_{1-20}H_{0-45}N_{0-5}O_{0-5}S_{0-5}F_{0-5}Cl_{0-5}Br_{0-5}I_{0-5}$, wherein $Y(R^2)_n$ may include one or more rings, each $R^2$ is independent, and n is 1, 2, or 3.

These compounds are useful for the treatment of diseases or conditions such as: wet and dry age-related macular degeneration (ARMD), diabetic retinopathy (proliferative), retinopathy of prematurity (ROP), diabetic macular edema, uveitis, retinal vein occlusion, cystoid macular edema, glaucoma, branch vein occlusion, Best's vitelliform macular degeneration, retinitis pigmentosa, proliferative vitreoretinopathy (PVR), and any other degenerative disease of either the photoreceptors or the RPE. The compound is incorporated into a dosage form or a medicament and administered to the mammal, such as a person, in need thereof. Different types of suitable dosage forms and medicaments are well known in the art, and can be readily adapted for delivery of the compounds disclosed herein.

For the purposes of this disclosure, "treat," "treating," or "treatment" refer to the diagnosis, cure, mitigation, treatment, or prevention of disease or other undesirable condition.

Unless otherwise indicated, reference to a compound should be construed broadly to include compounds, pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

In every structure where a dashed line is present, the dashed line represents the presence or absence of a bond. Therefore compounds such as those represented by one of the structural formulas below are possible.

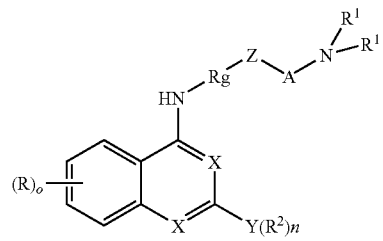

-continued

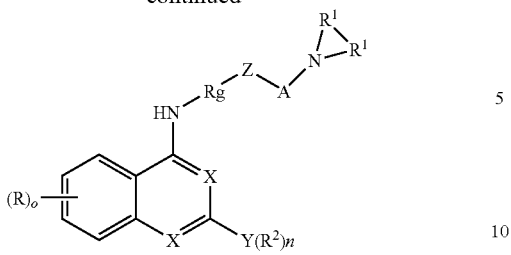

5

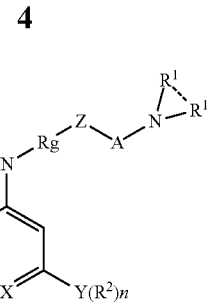

Since o is 0, 1, 2, 3, 4, 5, or 6, R groups could be on any carbon in the ring system. Thus, R could be attached to X if it is C. For example, compounds represented by one of the structural formulas below are contemplated, wherein each R group is independent.

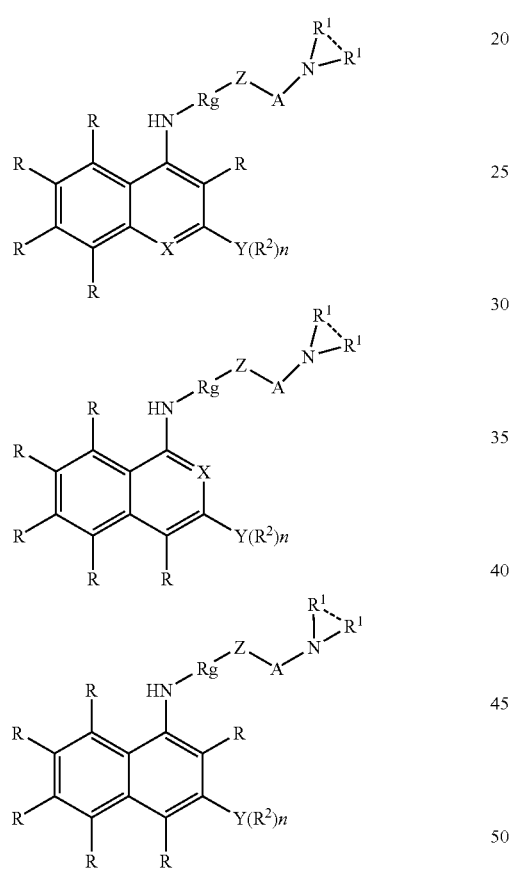

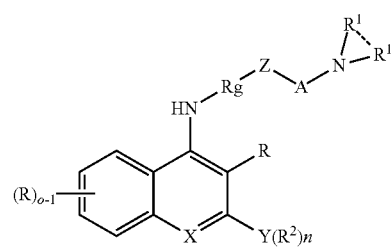

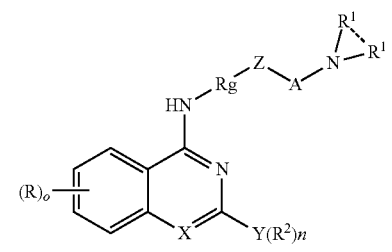

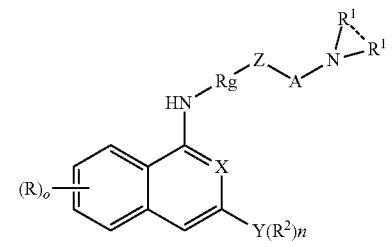

In one embodiment, o is from 0 to 4.
In another embodiment, o is from 0 to 2.
In another embodiment, o is 0.
In another embodiment, o is 1.
In another embodiment, o is 2.
In another embodiment, o is 3.
In another embodiment, o is 4.
In another embodiment, o is 5.
In another embodiment, o is 6.

X is independently C, CH or N. Thus, compounds represented by the structural formulas below are contemplated. In some of the structures, "(R)o₁" is included to indicate that since the structure already includes a "R" moiety as a substituent to C, there are o-1 substituents remaining on the ring system.

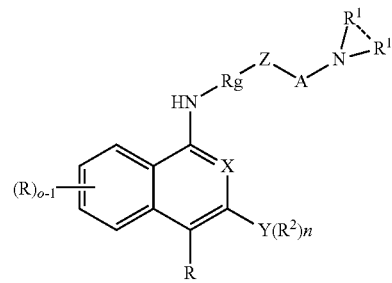

Y is N, NH, CH$_2$, CH, C, O, or S. Therefore, compounds represented by the structural formulas below are contemplated.

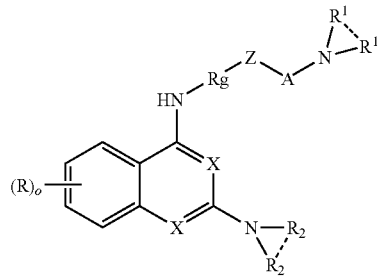

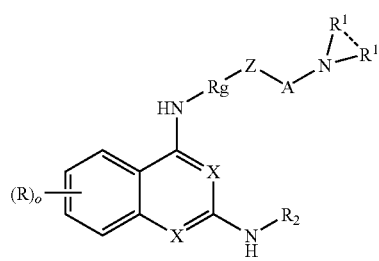

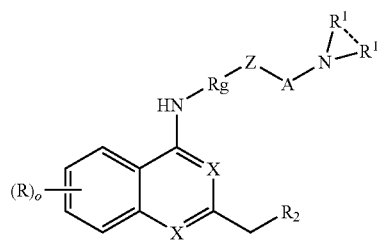

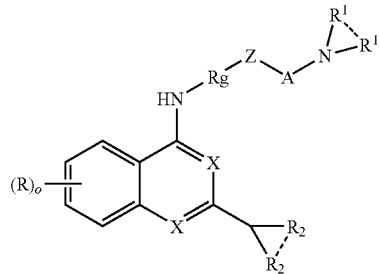

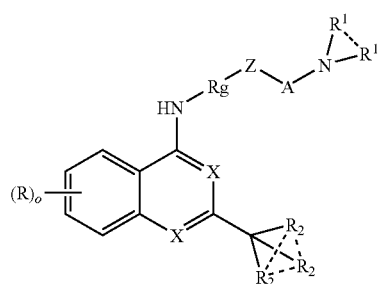

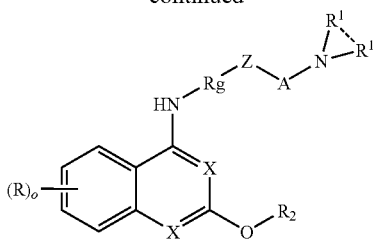

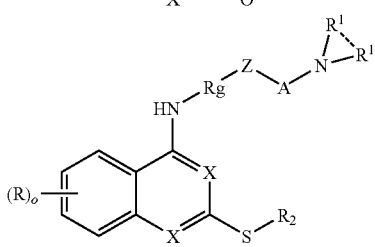

A is aryl or heteroaryl having 0, 1, 2, 3, or 4 substituents, wherein Z and the N atom are attached to adjacent carbon atoms, and wherein each substituent of A independently has a formula $CO_{1-10}H_{0-27}N_{0-3}O_{0-3}S_{0-2}P_{0-1}F_{0-3}Cl_{0-1}Br_{0-1}I_{0-1}$.

Aryl is an aromatic ring or ring system such as phenyl, biphenyl, or naphthyl.

Heteroaryl is an aromatic ring or ring system containing from 1 to 4 atoms independently selected from N, O, and S in one or more of the rings. Examples include thienyl, furyl, pyridinyl, benzothienyl, benzofuryl, quinolinyl, oxazolyl, thiazolyl, imidazolyl, etc.

In one embodiment A is phenyl having 0, 1, or 2 substituents.

In another embodiment A is pyridinyl having 0, 1, or 2 substituents.

In another embodiment A is thienyl having 0, 1, or 2 substituents.

In another embodiment A is furyl having 0, 1, or 2 substituents.

Z and N are attached to adjacent carbon atoms, such as in the examples below.

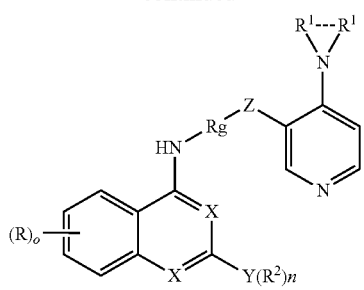

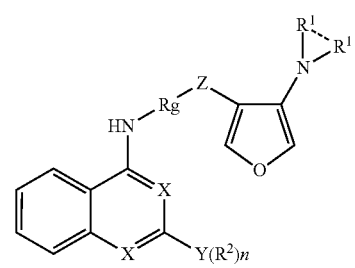

A substituent is a moiety attached to one or more ring carbons, and 2 or more substituents may themselves form an additional ring or rings incorporating the aryl or heteroaryl ring or ring system.

Furthermore, a substituent is a moiety where each carbon atom forms exactly 4 covalent bonds, where a double bond counts as 2 bonds and a triple bond counts as 3 bonds. Each hydrogen, fluorine, chlorine, bromine, or iodine in a substituent forms exactly 1 bond. Fluorine, chlorine, bromine, and iodine bond directly to a carbon atom. The remaining atoms in a substituent are part of one of the functional groups depicted below. A functional group is one of the moieties depicted below.

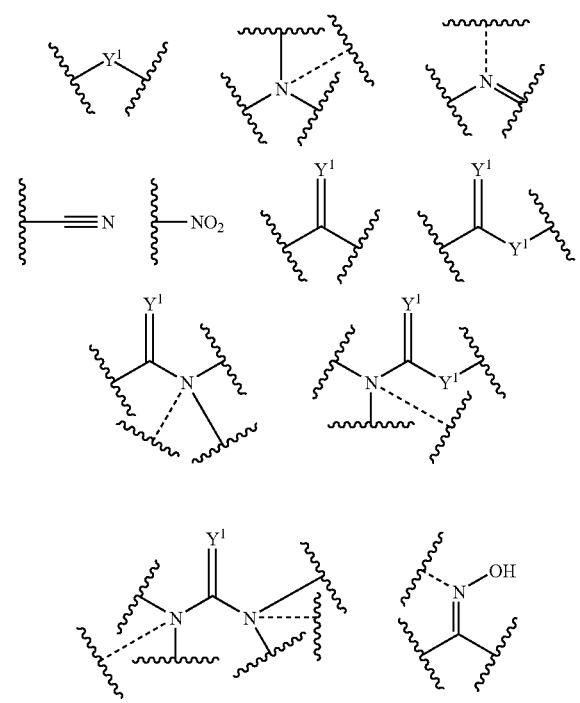

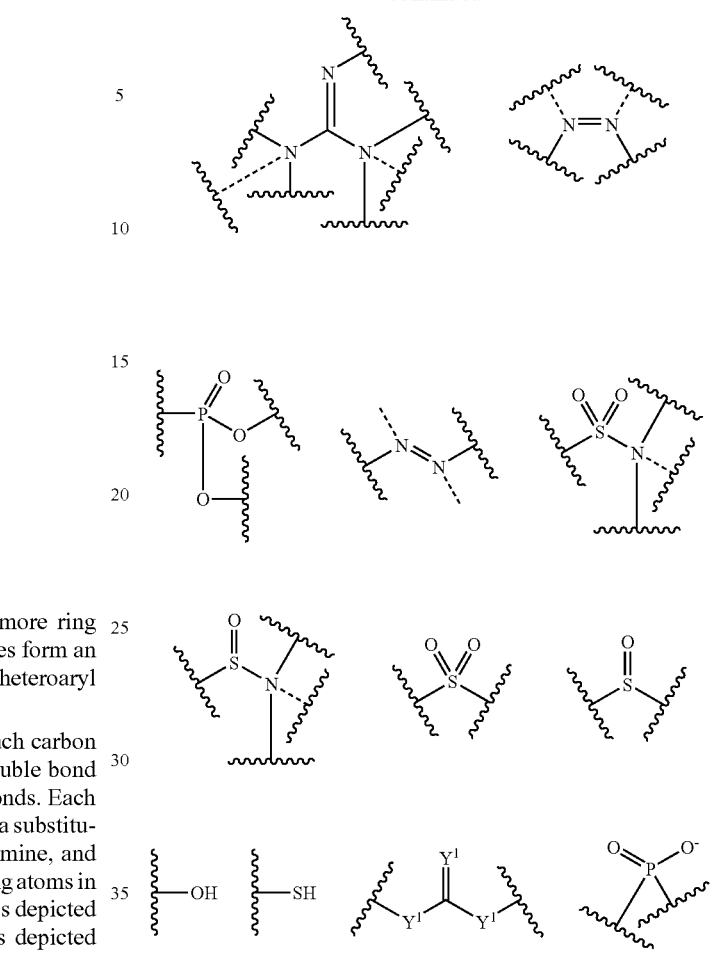

The wavy lines indicate attachment to another atom. Each $Y^1$ is independently S or O. A functional group bonds directly to a hydrogen or a carbon atom, provided that the following are not present.

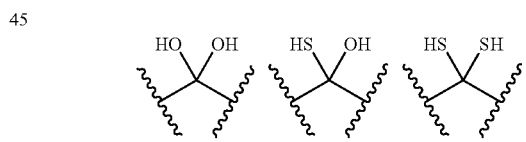

If a functional group is asymmetric, it may be oriented in any way possible. For example, the ester functional group is intended to indicate both of the structures below.

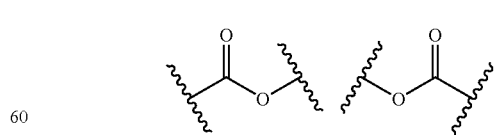

The dashed lines on the functional groups indicate that any nitrogen atom on a functional group may form an additional bond with another carbon atom, a hydrogen atom, or may form a double bond with one of the depicted bonds so that an ammonium or a quaternary ammonium type of functional group is formed. Thus, the dashed line functional groups actually represent a group of individual functional groups. For example, the functional group:

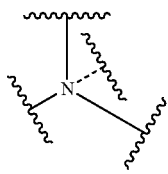

represents the following possible structures:

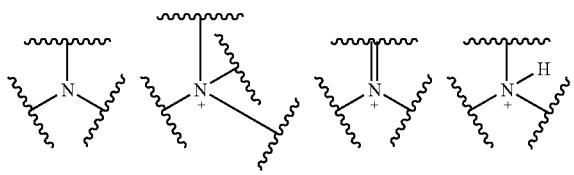

Similarly, the functional group:

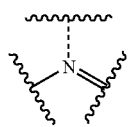

represents the following possible structures:

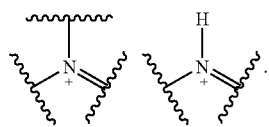

The formula $C_{0-10}H_{00-27}N_{03}O_{0-3}S_{0-2}P_{0-1}F_{0-3}Cl_{0-1}Br_{0-1}I_{0-1}$ means that the substituent has 0-10 carbon atoms, 0-27 hydrogen atoms, 0-3 nitrogen atoms, 0-3 oxygen atoms, 0-2 sulfur atoms, 0-1 phosphorous atoms, 0-3 fluorine atoms, 0-1 chlorine atoms, 0-1 bromine atoms, and 0-1 iodine atoms.

A substituent attaches to the ring or ring system in place of hydrogen. Thus, the number of hydrogen atoms on the unsubstituted aryl or heteroaryl ring or ring system determines the number of substituents may be present. If, after A attaches to Z and N, the number of hydrogen atoms on the ring or ring system is less than 4, A may have up to that number of substituents. If, after A attaches to Z and N, the number of hydrogen atoms on the ring or ring system is 4 or more, A may have up to 4 substituents.

In one embodiment, A has from 0 to 2 substituents.

In one embodiment, each substituent is independently selected from: alkyl, alkenyl, alkynyl, halo, haloalkyl, hydroxyl (—OH), alkoxyl (—OR³), alkylcarbonyl(—C(O)R³), formyl(—C(O)H), oxycarbonyl(—OC(O)R³), carboxyl (—CO₂H), alkyl carboxylate(—C(O)OR³), alkyl amide(—C(O)NR³₂), aminocarbonyl(—R³NC(O)R³), amino(—NR³₂), cyano(—CN), nitro(—NO₂), phosphate(—P(O)(OR³)₃), thio(—SR³), sulfoxyl(—S(O)R³), sulfonyl(—S(O)₂R³), —OR³OH, —OR³OR³, —OR³SH, —OR³SR³, —OR³NH₂, —OR³NHR³, or —OR³NR³₂, wherein R³ is independently alkyl or hydrogen.

Alkyl is a moiety consisting of carbon and hydrogen having no double or triple bonds.

In one embodiment $R^3$ is $C_{1-6}$ alkyl, meaning alkyl having 1, 2, 3, 4, 5, or 6 carbon atoms such as methyl, ethyl, n-propyl, isopropyl, cyclopropyl, etc.

Z is CH₂, CHOH, or C=O.

In one embodiment, Z is CH₂.

In another embodiment, Z is CHOH.

In another embodiment, Z is C=O.

Rg is a 3- to 7-membered ring having a formula $C_{2-10}H_{2-21}N_{0-1}$, wherein if an N atom is present, it is directly attached to Z. A 3- to 7-membered ring is a closed shell ring that may optionally have substituents, meaning that all the carbon atoms in the ring or in any substituents on the ring have exactly 4 covalent bonds, all the hydrogen atoms on the ring or the substituents have exactly 1 covalent bond, and the nitrogen atom has 3 covalent bonds.

Thus, if Rg is a 3-membered ring, the —NH—Rg—Z— portion of the molecule would have one of the structures below, wherein each $R^4$ is independently H or alkyl, subject to the constraint that Rg has a formula $C_{2-10}H_{2-21}N_{0-1}$.

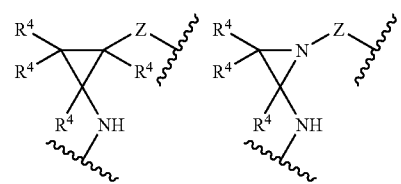

If Rg is a 4-membered ring, typical examples of the —NH—Rg—Z— portion of the molecule are depicted below, wherein each $R^4$ is independently H or alkyl, subject to the constraint that Rg has a formula $C_{2-10}H_{2-21}N_{0-1}$.

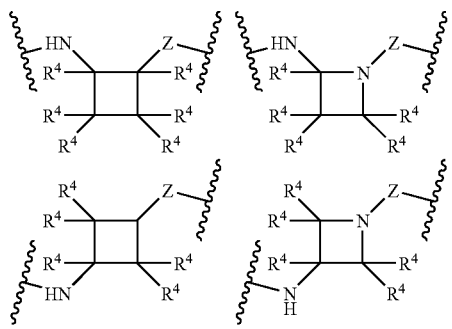

If Rg is a 5-membered ring, typical examples of the —NH—Rg—Z— portion of the molecule are depicted below, wherein each $R^4$ is independently H or alkyl, subject to the constraint that Rg has a formula $C_{2-10}H_{2-21}N_{0-1}$.

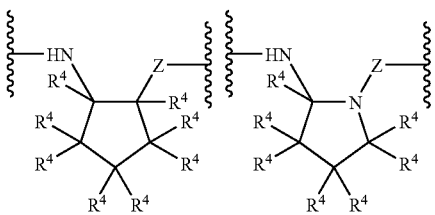

-continued

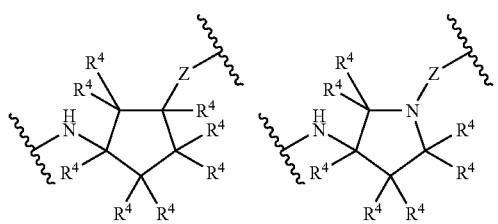

If Rg is a 6-membered ring, typical examples of the —NH—Rg—Z— portion of the molecule are depicted below, wherein each $R^4$ is independently H or alkyl, subject to the constraint that Rg has a formula $C_{2-10}H_{2-21}N_{0-1}$.

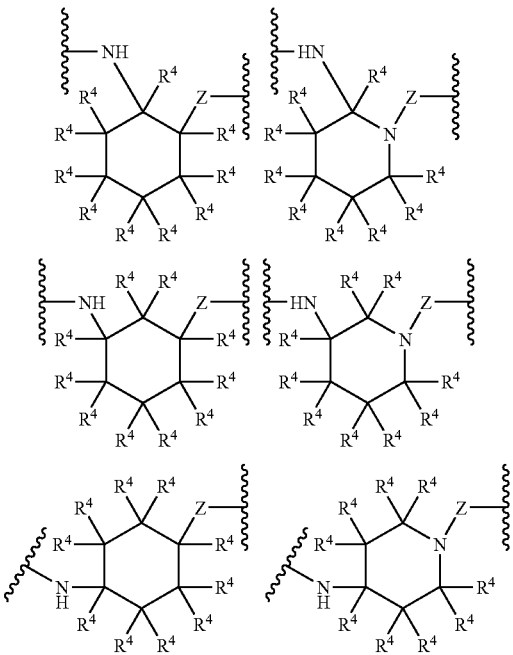

If Rg is a 7-membered ring, typical examples of the —NH—Rg—Z— portion of the molecule are depicted below, wherein each $R^4$ is independently H or alkyl, subject to the constraint that Rg has a formula $C_{2-10}H_{2-21}N_{0-1}$.

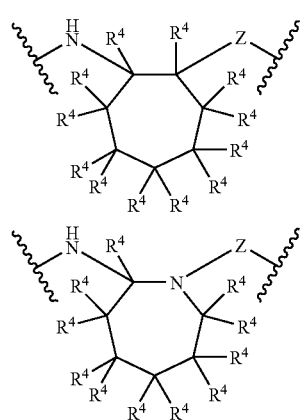

-continued

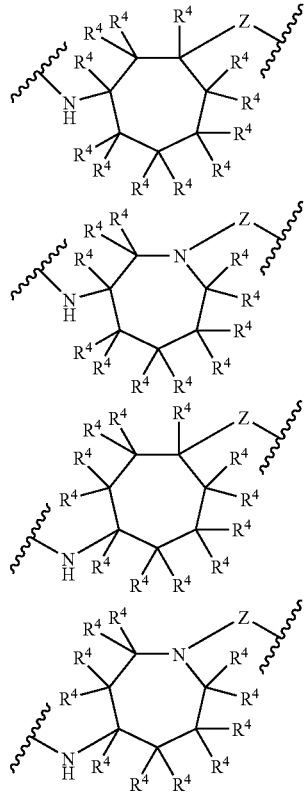

In one embodiment, Rg is a 4-membered ring, a 5-membered ring, a 6-membered ring, or a 7-membered ring.

In another embodiment, Rg is a 4-membered ring or a 6-membered ring. R is independently H, OH, SH, $C_{1-3}$ alkyl, O—($C_{1-3}$ alkyl), S—($C_{1-3}$ alkyl), or halo, wherein two R moieties may together form a ring.

$C_{1-3}$ alkyl is alkyl having 1, 2, or 3 carbon atoms, e.g. methyl, ethyl, propyl, isopropyl, cyclopropyl, etc.

O—($C_{1-3}$ alkyl) is O directly attached to $C_{1-3}$ alkyl, e.g. O—$CH_3$, O—$CH_2CH_3$, O—$CH_2CH_2CH_3$, O—$CH(CH_3)_2$, O-cyclopropyl, etc.

S—($C_{1-3}$ alkyl) is S directly attached to $C_{1-3}$ alkyl, e.g. S—$CH_3$, S—$CH_2CH_3$, S—$CH_2CH_2CH_3$, S—$CH(CH_3)_2$, S-cyclopropyl, etc.

$R^1$ is independently H, O, $C_{1-8}$ hydrocarbyl, $C_{1-8}$ hydroxyalkyl, $C_{1-8}$ alkylthiol, $C_{1-8}$ alkylalkoxy, $C_{1-8}$ alkylthioalkyl, or $C_{1-8}$ aminoalkyl.

Hydrocarbyl is a moiety consisting of only carbon and hydrogen, including alkyl, alkenyl, alkynyl, phenyl, etc. $C_{1-8}$ hydrocarbyl is hydrocarbyl having 1, 2, 3, 4, 5, 6, 7, or 8 carbon atoms.

Alkyl is hydrocarbyl having no double or triple bonds. $C_{1-8}$ alkyl is alkyl having 1, 2, 3, 4, 5, 6, 7, or 8 carbon atoms, e.g. methyl, ethyl, propyl isomers, butyl isomers, pentyl isomers, hexyl isomers, heptyl isomers, octyl isomers, cyclopropyl, cyclobutyl, cyclopentyl, cyclohexyl, cycloheptyl, cyclooctyl, etc.

Hydroxyalkyl is -alkyl-OH. $C_{1-8}$ hydroxyalkyl is hydroxyalkyl having 1, 2, 3, 4, 5, 6, 7, or 8 carbon atoms. Examples include hydroxymethyl(—$CH_2OH$), hydroxyethyl(—$CHOHCH_3$ or —$CH_2CH_2OH$), and isomers of: hydroxypropyl, hydroxybutyl, hydroxyhexyl, hydroxyheptyl, hydroxyoctyl, etc.

Alkylthiol is -alkyl-SH. $C_{1-8}$ alkylthiol is alkylthiol having 1, 2, 3, 4, 5, 6, 7, or 8 carbon atoms. Examples include methylthiol($-CH_2SH$), ethylthiol($-CHSHCH_3$ or $-CH_2CH_2SH$), and isomers of: propylthiol, butylthiol, hexylthiol, heptylthiol, octylthiol, etc.

Alkylalkoxy is alkyl-O-alkyl, wherein each alkyl is independent. $C_{1-8}$ alkylalkoxy is alkylalkoxy having 1, 2, 3, 4, 5, 6, 7, or 8 carbon atoms. Examples include $-CH_2OCH_3$, $-CH_2CH_2OCH_3$, $-(CH_2)_3OCH_3$, $-(CH_2)_4OCH_3$, $-CH_2CH_2OCH_2CH_3$, $-(CH_2)_3OCH_2CH_3$, $-(CH_2)_4OCH_2CH_3$, etc.

Alkylthioalkyl is alkyl-S-alkyl, wherein each alkyl is independent. $C_{1-8}$ alkylthioalkyl is alkylthioalkyl having 1, 2, 3, 4, 5, 6, 7, or 8 carbon atoms. Examples include $-CH_2SCH_3$, $-CH_2CH_2SCH_3$, $-(CH_2)_3SCH_3$, $-(CH_2)_4SCH_3$, $-CH_2CH_2SCH_2CH_3$, $-(CH_2)_3SCH_2CH_3$, $-(CH_2)_4SCH_2CH_3$, etc.

Aminoalkyl is alkyl-$NH_2$, alkyl-NH-alkyl, or alkyl-N(alkyl)$_2$, wherein each alkyl is independent. $C_{1-8}$ aminoalkyl is aminoalkyl having 1, 2, 3, 4, 5, 6, 7, or 8 carbon atoms. Examples include $-CH_2NH_2$, $-CH_2NHCH_3$, $-CH_2CH_2NHCH_3$, $-(CH_2)_3NHCH_3$, $-(CH_2)_4NHCH_3$, $-CH_2CH_2NHCH_2CH_3$, $-(CH_2)_3NHCH_2CH_3$, $-(CH_2)_4NHCH_2CH_3$, $-CH_2CH_2N(CH_3)_2$, $-(CH_2)_3N(CH_3)_2CH_2CH_3$, $-(CH_2)_4N(CH_3)_2$, etc.

$Y(R^2)_n$ is a substituent having a formula $C_{1-20}H_{0-45}N_{0-5}O_{0-5}S_{0-5}F_{0-5}Cl_{0-15}Br_{0-5}I_{0-5}$, wherein $Y(R^2)_n$ may include one or more rings, each $R^2$ is independent, and n is 1, 2, or 3.

The formula $C_{1-20}H_{0-45}N_{0-5}O_{0-5}S_{0-5}F_{0-5}Cl_{0-5}Br_{0-5}I_{0-5}$ means that there are from 1-20 carbon atoms, 0-45 hydrogen atoms, 0-5 nitrogen atoms, 0-5 sulfur atoms, 0-5 fluorine atoms, 0-5 chlorine atoms, 0-5 bromine atoms, and 0-5 iodine atoms.

"Substituent" is defined above.

$Y(R^2)_n$ may include one or more rings. This may be accomplished by any combination of Y, any or all $R^2$ moieties, and a substituent on an adjacent carbon, forming one or more rings. One or more of the $R^2$ moieties may also be H. For examples, compounds according to any of the structural formulas below are possible.

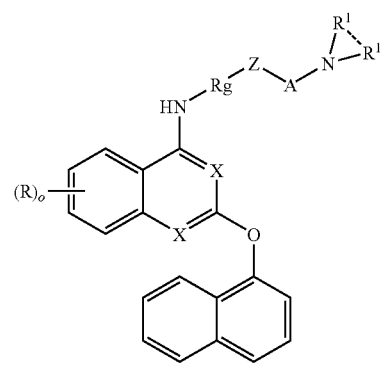

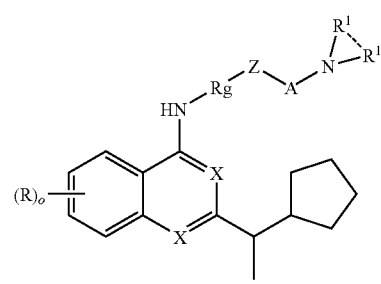

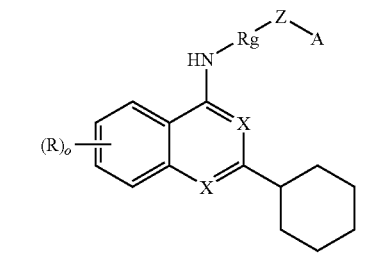

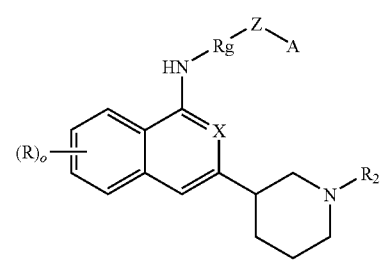

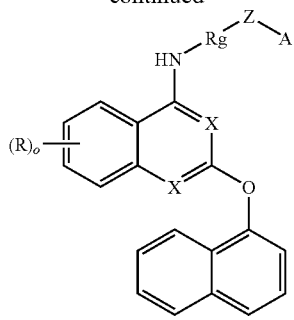

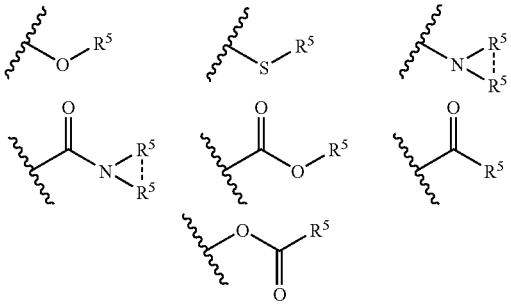

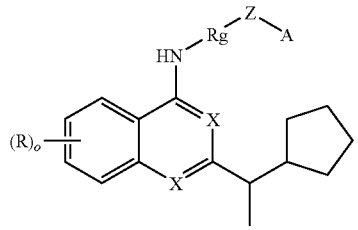

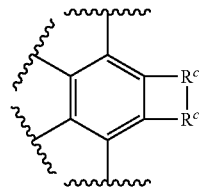

Two $R^c$ moieties may together form a ring so that a ring structure like that shown below is possible.

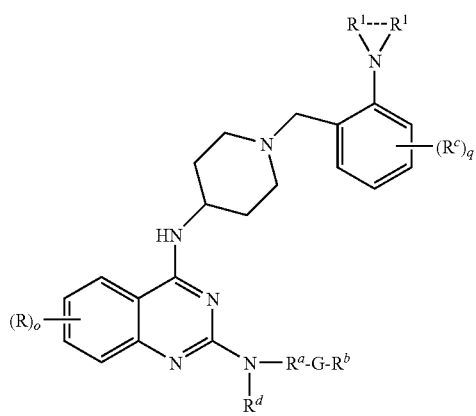

Another embodiment is a compound represented by the formula wherein each $R^c$ is independently F, Br, Cl, Br, —OH, —CN, $R^5$ or $Y^a$—$R^5$, wherein $Y^a$ is independently —O—, —S—, —N($R^5$)—, —CO$_2$—, —C(O)—, —OC(O)—, or —C(O)N($R^5$)—, wherein two $R^c$ moieties may together form a ring;

each $R^5$ is independently H, $C_{1-8}$ alkyl, $C_{1-8}$ hydroxyalkyl, $C_{1-8}$ alkylthiol, $C_{1-8}$ alkylalkoxy, $C_{1-8}$ alkylthioalkyl, or $C_{1-16}$ aminoalkyl;

o, q, r, and s are independently 0, 1, 2, 3, or 4;

$R^a$ is a bond, H, or $C_{1-8}$ alkyl;

$R^b$ and $R^d$ are independently H, or $C_{1-8}$ alkyl; and

G is a bond or $Y^a$.

In one embodiment, each $R^5$ is independently H, $C_{1-8}$ alkyl, $C_{1-8}$ hydroxyalkyl, $C_{1-8}$ alkylthiol, $C_{1-8}$ alkylalkoxy, $C_{1-8}$ alkylthioalkyl, or $C_{1-8}$ aminoalkyl;

$R^c$ may be $Y^a$—$R^5$, wherein $Y^a$ is independently —O—, —S—, —N($R^5$)—, —CO$_2$—, —C(O)—, —OC(O)—, or —C(O)N($R^5$)—. Thus, in addition to F, Br, Cl, Br, —OH, —CN, and $R^5$, $R^c$ may be one of the moieties depicted below.

$R^b$ is H, or $C_{1-8}$ alkyl.

In one embodiment Rc is —O(CH$_2$)$_{2-4}$N(alkyl)$_2$ with from 1 to 16 carbon atoms, meaning that there can be 2, 3 or 4 (CH$_2$) groups, i.e. —O(CH$_2$)$_2$N(alkyl)$_2$, —O(CH$_2$)$_3$N(alkyl)$_2$, or —O(CH$_2$)$_4$N(alkyl)$_2$.

In another embodiment Rc is —O(CH$_2$)$_{2-4}$N(alkyl)$_2$ with from 1 to 8 carbon atoms, meaning that there can be 2, 3 or 4 (CH$_2$) groups, i.e. —O(CH$_2$)$_2$N(alkyl)$_2$, —O(CH$_2$)$_3$N(alkyl)$_2$, or —O(CH$_2$)$_4$N(alkyl)$_2$.

G is a bond or $Y^a$[—, —S—, —N($R^5$)—, —CO$_2$—, —C(O)—, —OC(O)—, or —C(O)N($R^5$)—].

In one embodiment G is —N($R^5$)—

In another embodiment $R^a$ is —(CH$_2$)$_t$—, wherein t is from 1 to 8.

In another embodiment, t is from 2 to 4.

In another embodiment, each R is H or —OCH$_3$.

In another embodiment, each R is H or —OCH$_3$.

In another embodiment, G is —C(O)N($R^5$)—.

In another embodiment, $R^a$ and $R^d$ together form a ring with from 3 to 8 carbon atoms.

Another embodiment is a compound represented by the structural formula:

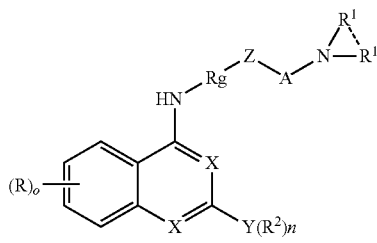

wherein a dashed line represents the presence or absence of a bond o is 0, 1, 2, 3, 4, 5, or 6;

X is independently C, CH or N;

Y is independently N, NH, $CH_2$, CH, C, O, or S;

A is aryl or heteroaryl having 0, 1, 2, 3, or 4 substituents, wherein Z and the N atom are attached to adjacent carbon atoms, and wherein each substituent of A independently has a formula $C_{0-10}H_{0-27}N_{0-3}O_{0-3}S_{0-2}P_{0-1}F_{0-3}Cl_{0-1}Br_{0-1}I_{0-1}$;

Z is $CH_2$, CHOH, or C=O;

Rg is a 3- to 7-membered ring having a formula $C_{2-10}H_{2-21}N_{0-1}$, wherein if an N atom is present, it is directly attached to Z;

R is independently H, OH, SH, $C_{1-3}$ alkyl, O—($C_{1-3}$ alkyl), S—($C_{1-3}$ alkyl), or halo, wherein two R moieties may together form a ring;

$R^1$ is independently H, $C_{1-8}$ alkyl, $C_{1-8}$ hydroxyalkyl, $C_{1-8}$ alkylthiol, $C_{1-8}$ alkylalkoxy, $C_{1-8}$ alkylthioalkyl, or $C_{1-8}$ aminoalkyl; and $Y(R^2)_n$ is a substituent having a formula $C_{1-20}H_{0-45}N_{0-5}O_{0-5}S_{0-5}F_{0-5}Cl_{0-5}Br_{0-5}I_{0-5}$, wherein $Y(R^2)_n$ may include one or more rings, each $R^2$ is independent, and n is 1, 2, or 3.

Another embodiment is a compound selected from:

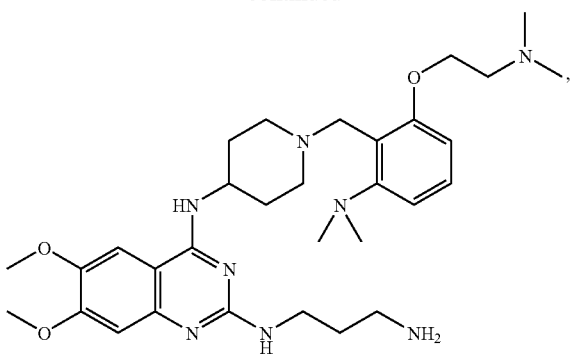

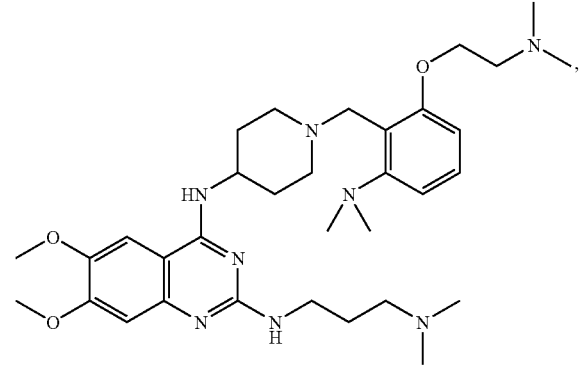

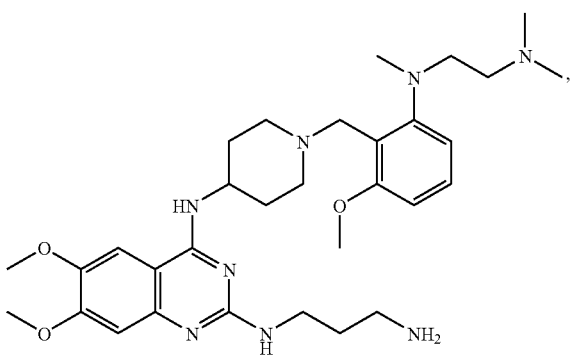

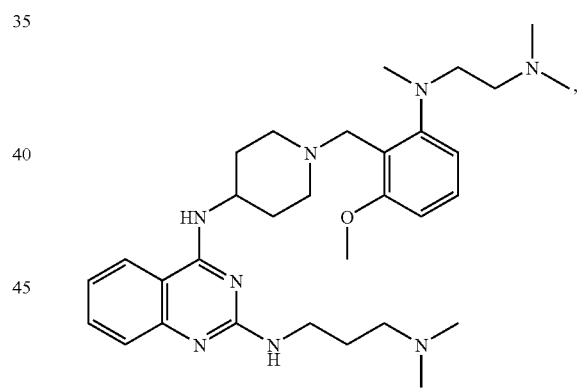

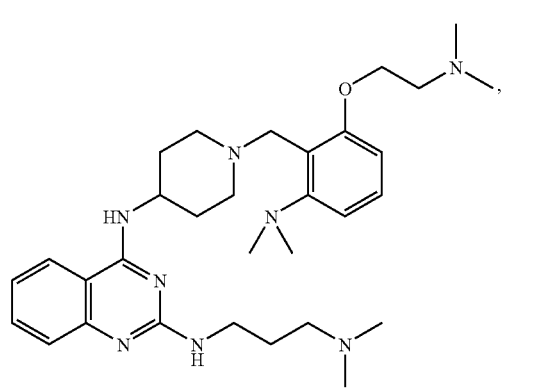

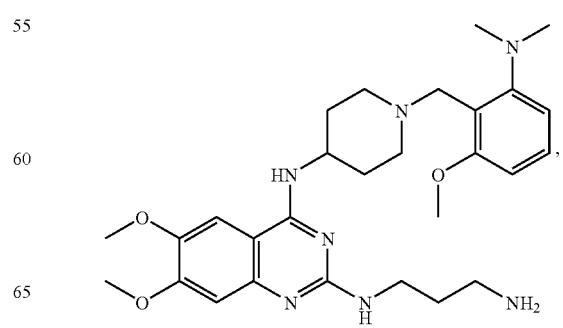

-continued
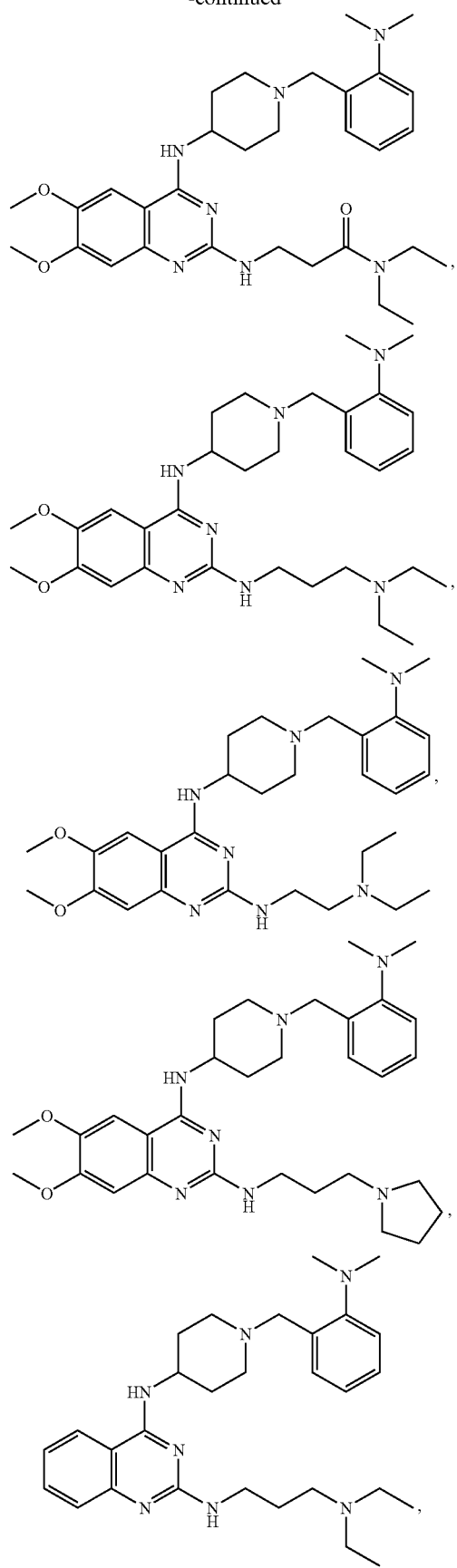
-continued
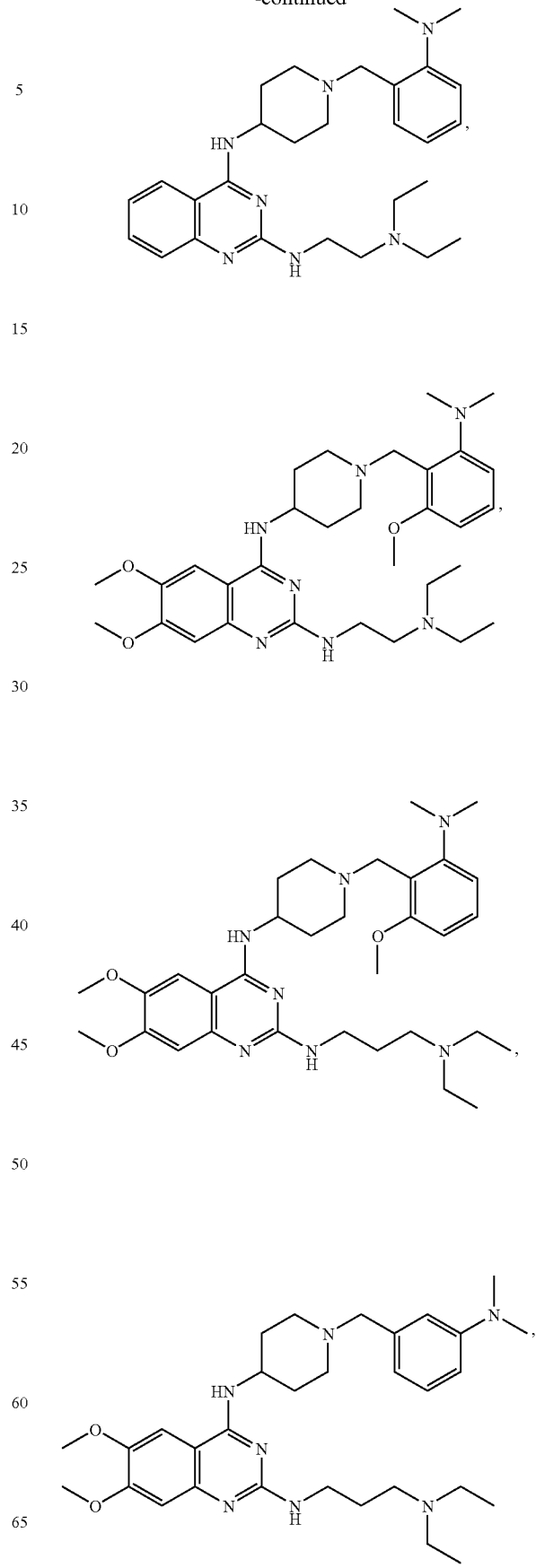

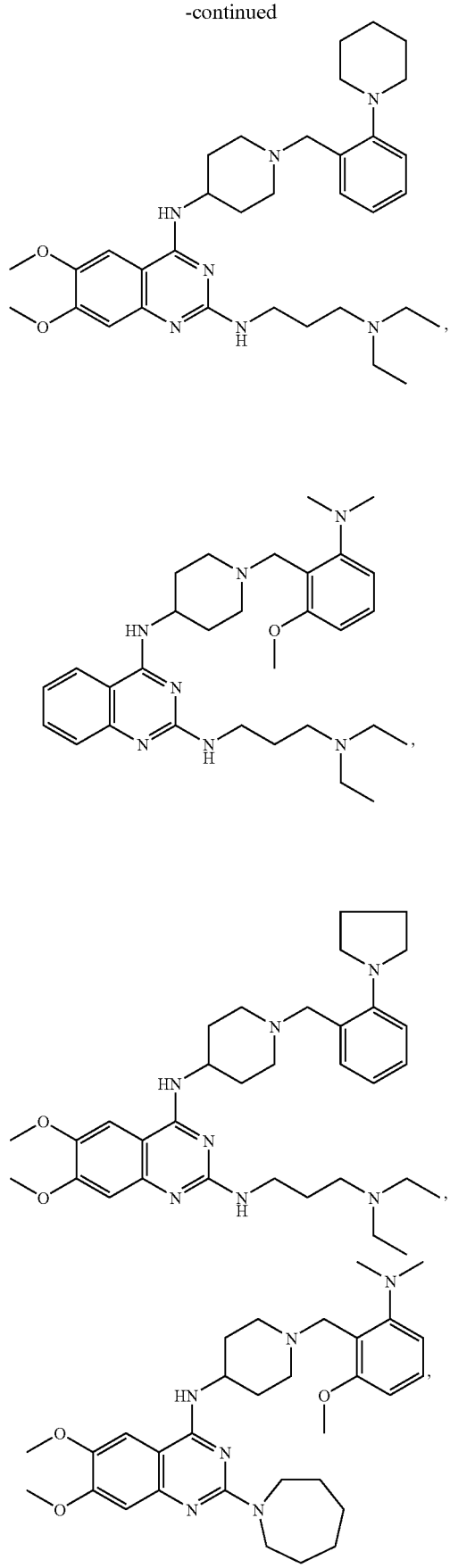
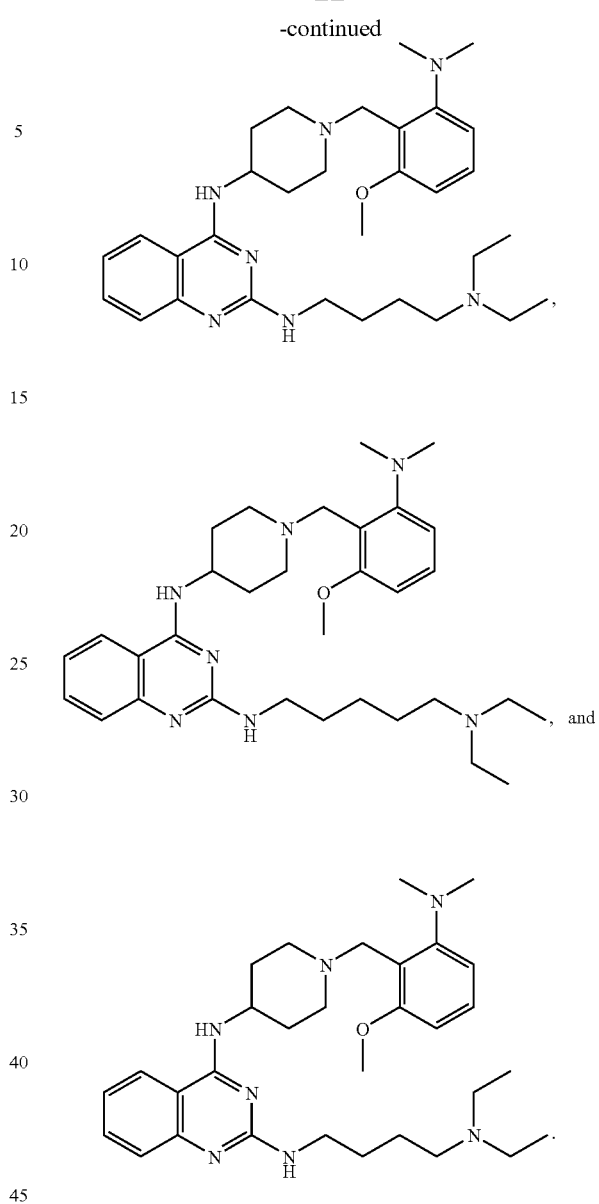
SYNTHETIC EXAMPLES
While there are many methods that may be employed to prepare the compounds disclosed herein, the methods below are some examples of useful methods that may be employed. These examples may be adapted by the person skilled in the art to prepare a wide variety of compounds beyond those depicted in the examples.
General Procedure A
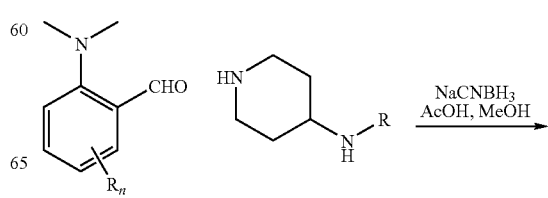

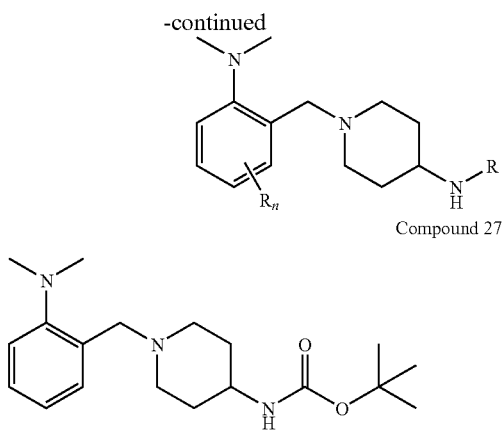

Compound 27

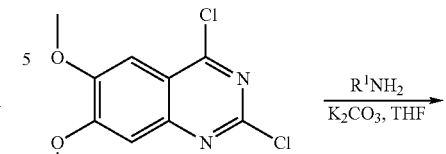

General Procedure C tert-Butyl 1-(2-(Dimethylamino)benzyl)piperin-4-ylcarbamate (Compound 27). General Procedure A To a solution of tert-butyl piperidin-4-ylcarbamate (840 mg, 4.2 mmol) (Aldrich) and 2-(N,N-dimethylamino)benzaldehyde (452 mg, 3.5 mmol) (Aldrich) in MeOH (15 mL) and AcOH (252 mg, 4.2 mmol) was added NaCNBH$_3$ (310 mg, 5 mmol). The solution was stirred at room temperature for 48 h. Approximately 90% of the solvent from the reaction was removed under reduced pressure, and the residue was diluted with CH$_2$Cl$_2$ (75 mL). The solution was washed with 10% aq. KOH, water and brine (20 mL each). The organic layer was separated and dried (Na$_2$SO$_4$), filtered, and the solvent was removed under vacuum. Silica gel flash chromatography with 7N NH$_3$ in MeOH (5%) and CH$_2$Cl$_2$ (95%) as eluent gave the product (Compound 27) as a white solid.

$^1$HNMR (CDCl$_3$): δ 1.40 (br q, J=9.0 Hz, 2H), 1.44 (s, 9H), 1.88 (br d, J=9.0 Hz, 2H), 2.14 (t, J=9.0 Hz, 2H), 2.68 (s, 6H), 2.81 (br d, J=9.0 Hz, 2H), 4.50 (br s, 1H), 7.02 (dt, J=3.0, 9.0 Hz, 1H), 7.06 (dd, J=3.0, 9.0 Hz, 1H), 7.20 (dt, J=3.0, 9.0 Hz, 1H), 7.45 (dd, J=3.0, 9.0 Hz, 1H).

MS (C$_{19}$H$_{31}$N$_3$O$_2$; MWt. 333): Observed M+1=334.

General Procedure B

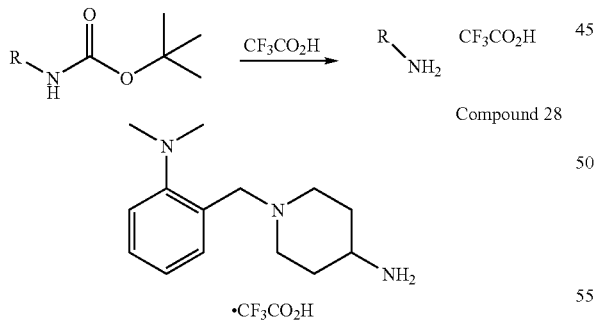

Compound 28

1-(2-(Dimethylamino)bezyl)piperidin-4-amine, trifluoroacetic acid salt (Compound 28). General Procedure B A solution of Compound 27 (250 mg, 0.75 mmol) and CF$_3$CO$_2$H (2 mL) was stirred at ambient for 2 h. All of the solvent was removed under reduced pressure. The crude product as a CF$_3$CO$_2$H salt (Compound 28) was used as is in the next step.

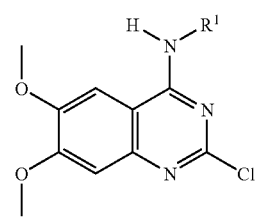

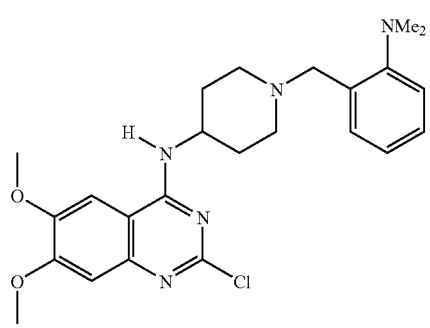

Compound 29

2-Chloro-N-(1-(2-(dimethylamino)benzyl)piperidin-4-yl)-6,7-dimethoxyquinazolin-4-amine (Compound 29). General Procedure C A mixture of Compound 28 (260 mg, 0.75 mmol), 2,4-dichloro-6,7-dimethoxyquinazoline (518 mg, 2 mmol) (Aldrich), K$_2$CO$_3$ (750 mg, 5.6 mmol) and THF (10 mL) was stirred at ambient temperature until the reaction was deemed complete by TLC and/or HNMR analysis. About 50% of the solvent was removed under reduced pressure, and the remaining solvent was diluted with CH$_2$Cl$_2$ (100 mL), and washed with water, and brine (10 mL each), and dried (Na$_2$SO$_4$), filtered, and the solvent was removed under vacuum. The product (Compound 29) was isolated by silica gel chromatography using 7N NH$_3$ in MeOH (5%) and CH$_2$Cl$_2$ (95%) as the eluent.

$^1$HNMR (CDCl$_3$): δ 1.61 (br q, J=9.0 Hz, 2H), 2.09 (br d, J=9.0 Hz, 2H), 2.26 (t, J=12.0 Hz, 2H), 2.70 (s, 6H), 2.91 (br d, J=12.0 Hz, 2H), 3.60 (s, 2H), 3.92 (s, 3H), 3.94 (s, 3H), 4.20-4.30 (m, 1H), 5.60 (br s, 1H), 6.89 (br s, 1H), 7.01 (t, J=9.0 Hz, 1H), 7.05-7.10 (m, 2H), 7.21 (t, J=9.0 Hz, 1H), 7.43 (d, J=9.0 Hz, 1H).

MS (C$_{24}$H$_{30}$ClN$_5$O$_2$; MWt. 455): Observed M+1=456.

General Procedure D

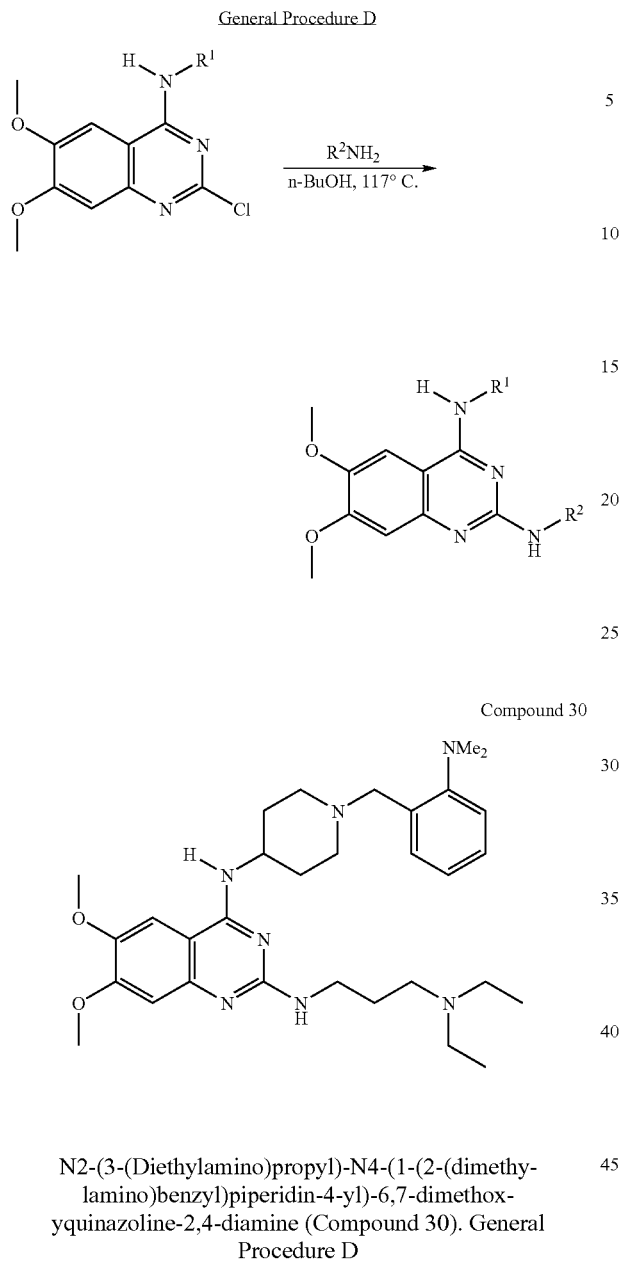

N2-(3-(Diethylamino)propyl)-N4-(1-(2-(dimethylamino)benzyl)piperidin-4-yl)-6,7-dimethoxyquinazoline-2,4-diamine (Compound 30). General Procedure D A mixture of Compound 29 (90 mg, 0.16 mmol), 3-(N,N-diethylamino)propylamine (146 mg, 0.81 mmol) and n-BuOH (3 mL) in a round bottom flask fitted with a reflux condenser was heated to reflux until the reaction was deemed complete by TLC analysis. The product (Compound 30) was purified by silica gel chromatography using 5% (7N NH$_3$-MeOH) and 95% CH$_2$Cl$_2$ solution as the eluent.

$^1$HNMR (CDCl$_3$): δ 1.02 (t, J=9.0 Hz, 6H), 1.58 (br q, J=9.0 Hz, 2H), 1.76 (p, J=6.0 Hz, 2H), 2.10 (br d, J=9.0 Hz, 2H), 2.22 (t, J=9.0 Hz, 2H), 2.46-2.58 (m, 6H), 2.70 (s, 6H), 2.90 (br d, J=12.0 Hz, 2H), 3.49 (q, J=6.0 Hz, 2H), 3.60 (s, 2H), 3.88 (s, 3H), 3.91 (s, 3H), 4.10-4.20 (m, 1H), 5.17 (d, J=9.0 Hz, 1H), 5.30 (br s, 1H), 6.76 (s, 1H), 6.87 (s, 1H), 7.02 (t, J=6.0 Hz, 1H), 7.08 (d, J=6.0 Hz, 1H), 7.19 (d, J=6.0 Hz, 1H), 7.47 (d, J=6.0 Hz, 1H).
MS (C$_{31}$H$_{47}$N$_7$O$_2$; MWt. 549): Observed M+1=550.

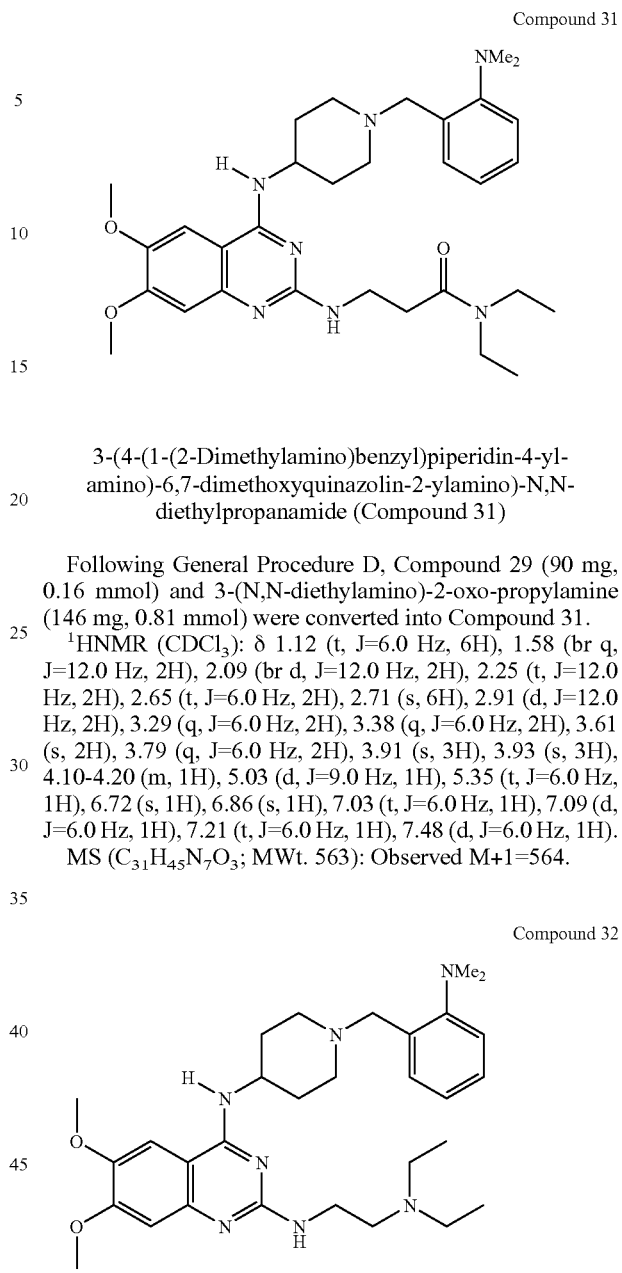

3-(4-(1-(2-Dimethylamino)benzyl)piperidin-4-yl-amino)-6,7-dimethoxyquinazolin-2-ylamino)-N,N-diethylpropanamide (Compound 31)

Following General Procedure D, Compound 29 (90 mg, 0.16 mmol) and 3-(N,N-diethylamino)-2-oxo-propylamine (146 mg, 0.81 mmol) were converted into Compound 31.

$^1$HNMR (CDCl$_3$): δ 1.12 (t, J=6.0 Hz, 6H), 1.58 (br q, J=12.0 Hz, 2H), 2.09 (br d, J=12.0 Hz, 2H), 2.25 (t, J=12.0 Hz, 2H), 2.65 (t, J=6.0 Hz, 2H), 2.71 (s, 6H), 2.91 (d, J=12.0 Hz, 2H), 3.29 (q, J=6.0 Hz, 2H), 3.38 (q, J=6.0 Hz, 2H), 3.61 (s, 2H), 3.79 (q, J=6.0 Hz, 2H), 3.91 (s, 3H), 3.93 (s, 3H), 4.10-4.20 (m, 1H), 5.03 (d, J=9.0 Hz, 1H), 5.35 (t, J=6.0 Hz, 1H), 6.72 (s, 1H), 6.86 (s, 1H), 7.03 (t, J=6.0 Hz, 1H), 7.09 (d, J=6.0 Hz, 1H), 7.21 (t, J=6.0 Hz, 1H), 7.48 (d, J=6.0 Hz, 1H).
MS (C$_{31}$H$_{45}$N$_7$O$_3$; MWt. 563): Observed M+1=564.

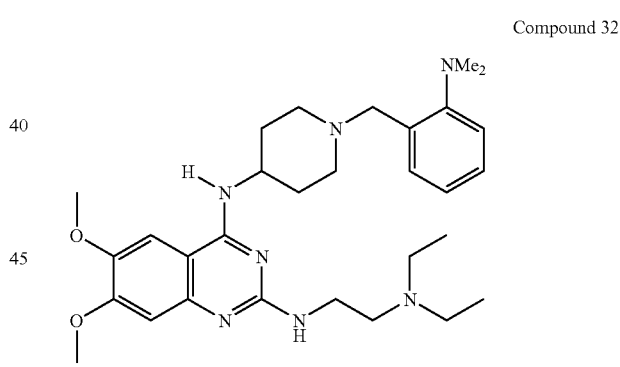

N$^2$-(2-(Diethylamino)ethyl-N4-(1-(2-(dimethylamino)benzyl)piperidin-4-yl)-6,7-dimethoxyquinazoline-2,4-diamine (Compound 32)

Following General Procedure D, Compound 29 (60 mg, 0.11 mmol) and 2-(N,N-diethylamino)-ethylamine (82 mg, 0.73 mmol) were converted into Compound 32.

$^1$HNMR (CDCl$_3$): δ 1.03 (t, J=6.0 Hz, 6H), 1.59 (br q, J=9.0 Hz, 2H), 2.09 (br d, J=9.0 Hz, 2H), 2.25 (t, J=9.0 Hz, 2H), 2.58 (q, J=6.0 Hz, 4H), 2.68 (q, J=6.0 Hz, 2H), 2.71 (s, 6H), 2.92 (d, J=12.0 Hz, 2H), 3.51 (q, J=6.0 Hz, 2H), 3.61 (s, 2H), 3.91 (s, 3H), 3.93 (s, 3H), 4.15-4.25 (m, 1H), 5.07 (d, J=9.0 Hz, 1H), 5.18 (t, J=6.0 Hz, 1H), 6.72 (s, 1H), 6.87 (s, 1H), 7.03 (t, J=6.0 Hz, 1H), 7.09 (d, J=6.0 Hz, 1H), 7.22 (t, J=6.0 Hz, 1H), 7.49 (d, J=6.0 Hz, 1H).
MS (C$_{30}$H$_{45}$N$_7$O$_2$; MWt. 535): Observed M+1=536.

Compound 33

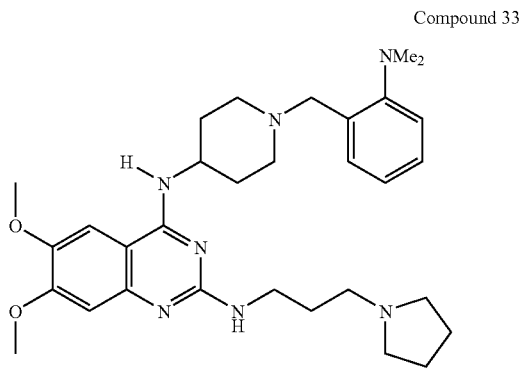

N⁴-(1-(2-Dimethylamino)benzyl)piperidin-4-yl)-6,7-dimethoxy-N²-(3-pyrrolidin-1-yl)quinazoline-2,4-diamine (Compound 33)

Following General Procedure D, Compound 29 (60 mg, 0.11 mmol) and 1-(3-aminopropyl)-pyrrolidine (146 mg, 0.81 mmol) were converted into Compound 33.

¹HNMR (CDCl₃): δ 1.61 (br q, J=6.0 Hz, 2H), 1.76-1.94 (m, 10H), 2.12 (br d, J=6.0 Hz, 2H), 2.26 (t, J=6.0 Hz, 2H), 2.53 (br s, 4H), 2.59 (t, J=6.0 Hz, 2H), 2.72 (s, 6H), 2.94 (d, J=6.0 Hz, 2H), 3.53 (br s, 2H), 3.62 (s, 2H), 3.93 (s, 3H), 3.95 (s, 3H), 4.15-4.25 (m, 1H), 5.05 (br s, 1H), 5.30 (br s, 1H), 6.71 (s, 1H), 6.88 (s, 1H), 7.05 (t, J=6.0 Hz, 1H), 7.11 (d, J=6.0 Hz, 1H), 7.23 (t, J=6.0 Hz, 1H), 7.49 (d, J=6.0 Hz, 1H).

MS ($C_{31}H_{45}N_7O_2$; MWt. 547): Observed M+1=548.

Compound 34

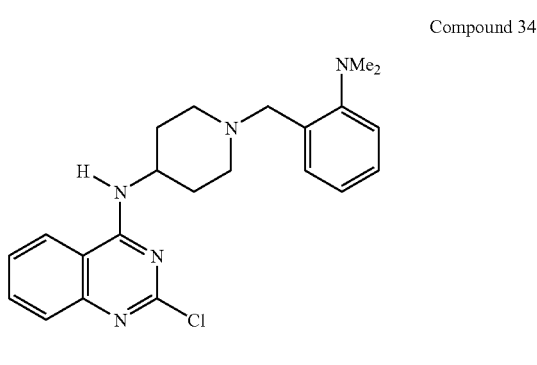

2-Chloro-N-(-1-(2-dimethylamino)benzyl)piperidin-4-yl)quinazolin-4-amine (Compound 34)

Following General Procedure C, Compound 28 (225 mg, 0.68 mmol), and 2,4-dichloro-quinazoline (600 mg, 2.6 mmol), were converted into Compound 34.

¹HNMR (CDCl₃): δ 1.65 (br q, J=6.0 Hz, 2H), 2.11 (br d, J=6.0 Hz, 2H), 2.30 (t, J=6.0 Hz, 2H), 2.71 (s, 6H), 2.91 (br d, J=6.0 Hz, 2H), 3.62 (s, 2H), 4.25-4.35 (m, 1H), 5.98 (br d, J=6.0 Hz, 1H), 7.04 (t, J=6.0 Hz, 1H), 7.10 (d, J=6.0 Hz, 1H), 7.22 (t, J=6.0 Hz, 1H), 7.42 (d, J=6.0 Hz, 1H), 7.47 (d, J=6.0 Hz, 1H), 7.60-7.75 (m, 3H).

MS ($C_{22}H_{26}ClN_5$; MWt. 395): Observed M+1=396.

Compound 35

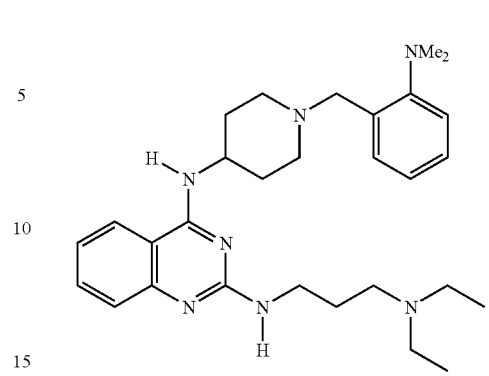

N2-(3-(Diethylamino)propyl)-N4-(1-(2-(dimethylamino)benzyl)piperidin-4-yl)quinazoline-2,4-diamine (Compound 35)

Following General Procedure D, Compound 34 (45 mg, 0.11 mmol) and 3-(N,N-diethylamino)-propylamine (146 mg, 0.81 mmol) were converted into Compound 35.

¹HNMR (CDCl₃): δ 1.04 (t, J=6.0 Hz, 6H), 1.59 (br q, J=6.0 Hz, 2H), 1.77 (p, J=6.0 Hz, 2H), 2.10 (d, J=9.0 Hz, 2H), 2.26 (t, J=9.0 Hz, 2H), 2.50-2.65 (m, 6H), 2.72 (s, 6H), 2.90 (q, J=12.0 Hz, 2H), 3.51 (q, J=6.0 Hz, 2H), 3.61 (s, 2H), 4.15-4.25 (m, 1H), 5.35 (d, J=6.0 Hz, 1H), 7.00-7.15 (m, 3H), 7.21 (d, H=6.0 Hz, 1H), 7.41-7.52 (m, 4H).

MS ($C_{29}H_{43}N_7$; MWt. 489): Observed M+1=490.

Compound 36

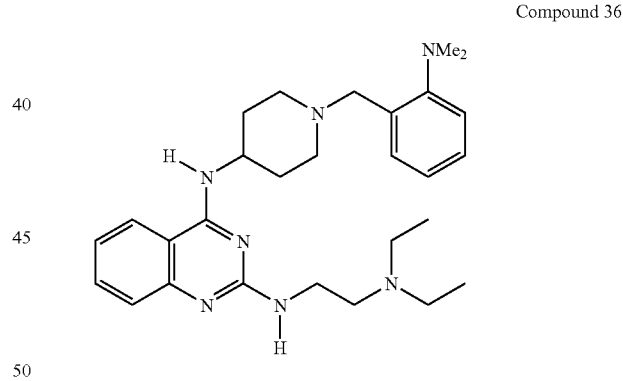

N2-(2-(Diethylamino)ethyl)-N4-(1-(2-(dimethylamino)benzyl)piperidin-4-yl)quinazoline-2,4-diamine (Compound 36)

Following General Procedure D, Compound 34 (45 mg, 0.11 mmol) and 2-(N,N-diethylamino)-ethylamine (146 mg, 0.81 mmol) were converted into Compound 36.

¹HNMR (CDCl₃): δ 1.04 (t, J=6.0 Hz, 6H), 1.59 (br q, J=6.0 Hz, 2H), 2.10 (d, J=9.0 Hz, 2H), 2.27 (t, J=9.0 Hz, 2H), 2.50-2.65 (m, 6H), 2.72 (s, 6H), 2.90 (br d, J=12.0 Hz, 2H), 3.55 (br s, 2H), 3.61 (s, 2H), 4.15-4.25 (m, 1H), 5.35 (m, 1H), 7.00-7.15 (m, 3H), 7.21 (d, H=6.0 Hz, 1H), 7.41-7.52 (m, 4H).

MS ($C_{28}H_{41}N_7$; MWt. 475): Observed M+1=476.

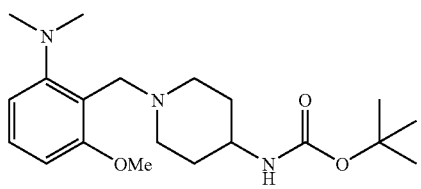

Compound 38 tert-Butyl 1-(2-(Dimethylamino)-6-methoxybenzyl)piperidin-4-yl-carbamate (Compound 38)

Following General Procedure A, 2-(dimethylamino)-6-methoxybenzaldehyde (Ref. Skowronska-Ptasinska et al J. Org. Chem. 1985, 50, 2690) (529 mg, 2.96 mmol) and tert-butyl piperidin-4-ylcarbamate (710 mg, 3.55 mmol) were converted to Compound 38.

$^1$HNMR (CDCl$_3$): δ 1.44 (s, 9H), 1.69 (br q, J=6.0 Hz, 2H), 2.02 (d, J=9.0 Hz, 2H), 2.69 (s, 6H), 3.08 (br s, 2H), 3.34 (s, 2H), 3.59 (br s, 2H), 3.90 (s, 3H), 4.40 (br s, 1H), 6.90 (d, J=9.0 Hz, 1H), 7.00 (d, J=9.0 Hz, 1H), 7.42 (t, J=9.0 Hz, 1H).

MS (C$_{20}$H$_{33}$N$_3$O; MWt. 331): Observed M+1=332.

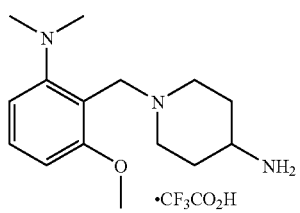

Compound 39

1-(2-(Dimethylamino)-6-methoxybenzyl)piperidin-4-amine 2,2,2-trifluoroacetate (Compound 39)

General Procedure B, Compound 38 (750 mg, 2 mmol) was converted to Compound 39. The crude Compound 39 as its CF$_3$CO$_2$H salt was used as it is in the next step.

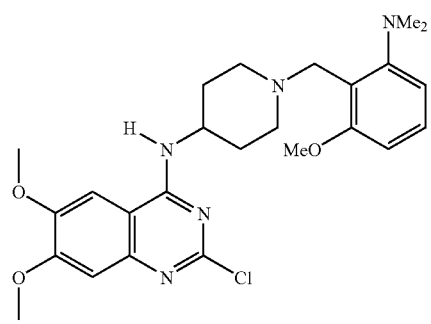

Compound 40

2-Chloro-N-(1-(2-(dimethylamino)-6-methoxybenzyl)piperidin-4-yl)-6,7-dimethoxyquinazolin-4-amine (Compound 40)

Following General Procedure C, Compound 39 (250 mg, 0.7 mmol) and 2,4-dichloro-6,7-dimethoxyquinazoline (518 mg, 2 mmol) were converted into Compound 40.

$^1$HNMR (CDCl$_3$): δ 1.55 (br q, J=9.0 Hz, 2H), 2.05 (br d, J=12.0 Hz, 2H), 2.36 (t, J=12.0 Hz, 2H), 2.76 (s, 6H), 2.96 (br d, J=12.0 Hz, 2H), 3.71 (s, 2H), 3.79 (s, 3H), 3.91 (s, 3H), 3.92 (s, 3H), 4.20-4.30 (m, 1H), 5.70 (br d, J=9.0 Hz, 1H), 6.63 (d, J=9.0 Hz, 1H), 6.76 (d, J=9.0 Hz, 1H), 6.90 (s, 1H), 7.07 (s, 1H), 7.21 (t, J=9.0 Hz, 1H).

MS (C$_{25}$H$_{32}$ClN$_5$O$_3$; MWt. 485): Observed M+1=486.

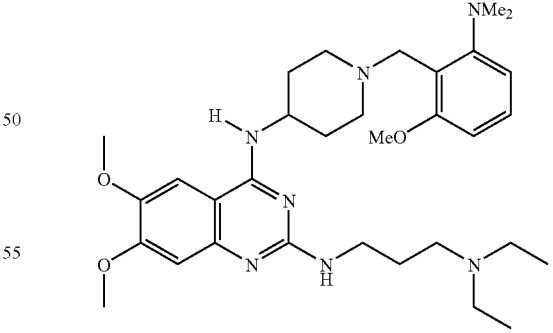

Compound 41

N2-(2-(Diethylamino)ethyl)-N4-(1-(2-(dimethylamino)-6-methoxybenzyl)piperidin-4-yl)-6,7-dimethoxyquinazoline-2,4-diamine (Compound 41)

Following General Procedure D, Compound 40 (45 mg, 0.095 mmol) and 2-(N,N-diethylamino)-ethylamine (146 mg, 0.81 mmol) were converted into Compound 41.

$^1$HNMR (CDCl$_3$): δ 1.04 (t, J=6.0 Hz, 6H), 1.50 (br q, J=9.0 Hz, 2H), 2.05 (br d, J=12.0 Hz, 2H), 2.34 (t, J=9.0 Hz, 2H), 2.59 (q, J=6.0 Hz, 4H), 2.67 (t, J=6.0 Hz, 2H), 2.79 (s, 6H), 2.95 (d, J=12.0 Hz, 2H), 3.52 (q, J=6.0 Hz, 2H), 3.68 (s, 2H), 3.81 (s, 3H), 3.91 (s, 3H), 3.92 (s, 3H), 4.15-4.25 (m, 1H), 5.07 (br s 1H), 5.17 (t, J=6.0 Hz, 1H), 6.64 (d, J=9.0 Hz, 1H), 6.70 (s, 1H), 6.78 (d, J=9.0 Hz, 1H), 6.89 (s, 1H), 7.21 (t, J=6.0 Hz, 1H).

MS (C$_{31}$H$_{47}$N$_7$O$_3$; MWt. 565): Observed M+1=566.

Compound 42

N2-(3-(Diethylamino)propyl)-N4-(1-(2-(dimethylamino)-6-methoxybenzyl)piperidin-4-yl)-6,7-dimethoxyquinazoline-2,4-diamine (Compound 42)

Following General Procedure D, Compound 40 (45 mg, 0.095 mmol) and 3-(N,N-diethylamino)-propylamine (146 mg, 0.81 mmol) were converted into Compound 42.

¹HNMR (CD₃OD): δ 1.05 (t, J=9.0 Hz, 6H), 1.67 (br q, J=9.0 Hz, 2H), 1.76-1.80 (m, 2H), 2.00 (br d, J=9.0 Hz, 2H), 2.29 (t, J=9.0 Hz, 2H), 2.56 (q, J=9.0 Hz, 4H), 2.68 (s, 6H), 3.06 (br d, J=12.0 Hz, 2H), 3.41 (t, J=6.0 Hz, 2H), 3.78 (s, 2H), 3.81 (s, 3H), 3.87 (s, 3H), 3.89 (s, 3H), 4.10-4.20 (m, 1H), 6.76 (d, J=9.0 Hz, 1H), 6.78 (s, 1H), 6.86 (s, 1H), 7.23 (t, J=6.0 Hz, 1H), 7.38 (s, 1H).

MS ($C_{32}H_{49}N_7O_3$; MWt. 579): Observed M+1=580.

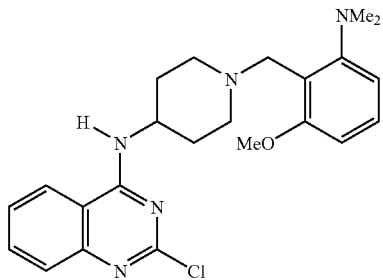

Compound 47

2-Chloro-N-(1-(2-(dimethylamino)-6-methoxybenzyl)piperidin-4-yl)quinazolin-4-amine (Compound 47)

Following General Procedure C, Compound 39 (200 mg, 0.53 mmol) and 2,4-dichloro-quinazoline (500 mg, 2.5 mmol) were converted into Compound 47.

¹HNMR (CDCl₃): δ 1.57 (dq, J=3.0, 12.0 Hz, 2H), 2.07 (br d, J=12.0 Hz, 2H), 2.41 (t, J=12.0 Hz, 2H), 2.77 (s, 6H), 2.96 (br d, J=12.0 Hz, 2H), 3.72 (s, 2H), 3.81 (s, 3H), 4.20-4.35 (m, 1H), 5.81 (br d, J=9.0 Hz, 1H), 6.66 (d, J=9.0 Hz, 1H), 6.79 (d, J=6.0 Hz, 1H), 7.22 (t, J=6.0 Hz, 1H), 7.64 (dt, J=3.0, 6.0 Hz, 1H), 7.60-7.80 (m, 3H).

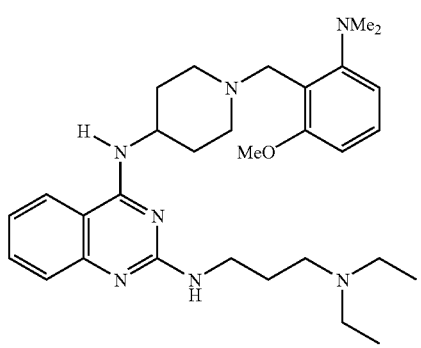

Compound 48

N2-(3-(Diethylamino)propyl)-N4-(1-(2-(dimethylamino)-6-methoxybenzyl)piperidin-4-yl)quinazoline-2,4-diamine (Compound 48)

Following General Procedure D, Compound 47 (120 mg, 0.28 mmol) and 3-(N,N-diethylamino)-propylamine (146 mg, 0.81 mmol) were converted into Compound 48.

¹HNMR (CD₃OD): δ 1.05 (t, J=7.2 Hz, 6H), 1.52 (br q, J=9.0 Hz, 2H), 1.77 (t, J=7.2 Hz, 2H), 2.07 (br d, J=9.0 Hz, 2H), 2.35 (t, J=9.0 Hz, 2H), 2.56 (m, 6H), 2.80 (s, 6H), 2.93 (br d, J=12.0 Hz, 2H), 3.52 (t, J=6.0 Hz, 2H), 3.68 (s, 2H), 3.80 (s, 3H), 4.10-4.20 (m, 1H), 5.37 (d, J=6.0 Hz, 1H), 6.64 (d, J=7.5 Hz, 1H), 6.78 (d, J=7.5 Hz, 1H) 7.21 (t, J=7.5 Hz, 1H), 7.38-7.55 (m, 3H).

MS ($C_{30}H_{45}N_7O_2$; MWt. 519): Observed M+1=520.

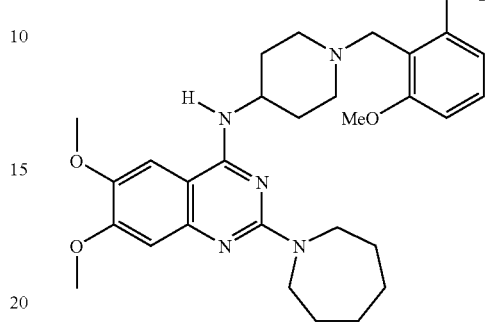

Compound 52

2-(Azepan-1-yl)-N-(1-(2-(dimethylamino)-6-methoxybenzyl)piperidin-4-yl)-6,7-dimethoxyquinazolin-4-amine (Compound 52)

Following General Procedure D, Compound 40 (40 mg, 0.082 mmol) and hexamethylene imine (49 mg, 0.5 mmol) were converted into Compound 52.

¹HNMR (CD₃OD): δ 1.45-1.60 (m, 6H), 1.75-1.90 (m, 4H), 2.20 (br d, J=9.0 Hz, 2H), 2.34 (t, J=9.0 Hz, 2H), 2.80 (s, 6H), 2.95 (br d, J=12.0 Hz, 2H), 3.68 (s, 2H), 3.75-3.85 (m, 7H), 3.90 (s, 3H), 3.92 (s, 3H), 4.05-4.20 (m, 1H), 4.96 (d, J=9.0 Hz, 1H), 6.65 (d, J=6.0 Hz, 1H), 6.70 (s, 1H), 6.79 (d, J=6.0 Hz, 1H), 6.88 (s, 1H), 7.22 (t, J=6.0 Hz, 1H).

MS ($C_{31}H_{44}N_6O_3$; MWt. 548): Observed M+1=549.

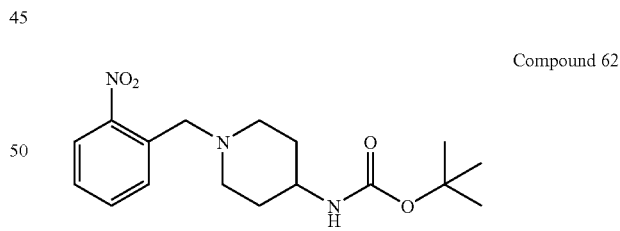

Compound 62 tert-Butyl 1-(2-Nitrobenzyl)piperidin-4-ylcarbamate (Compound 62)

Following General Procedure A, 2-nitrobenzaldehyde (453 mg, 3.0 mmol) and tert-butyl piperidin-4-ylcarbamate (1.5 g, 7.5 mmol) were converted to Compound 62.

¹HNMR (CDCl₃): δ 1.38 (br q, J=9.0 Hz, 2H), 1.44 (s, 9H), 1.85 (br d, J=9.0 Hz, 2H), 2.14 (t, J=9.0 Hz, 2H), 2.69 (br d,

J=9.0 Hz, 2H), 3.75 (s, 2H), 4.40 (br s, 1H), 7.35 (t, J=6.0 Hz, 1H), 7.45-7.60 (m, 2H), 7.79 (d, J=6.0 Hz, 1H).
MS ($C_{12}H_{17}N_3O_2$; MWt. 235): Observed M+1=236.

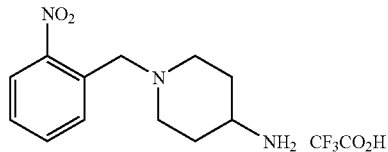

1-(2-Nitrobenzyl)piperidin-4-amine 2,2,2-trifluoroacetic acid salt (Compound 63)

Following General Procedure B, Compound 62 (640 mg, 1.9 mmol) was converted to Compound 63. The crude Compound 63 was used as is in the next step.

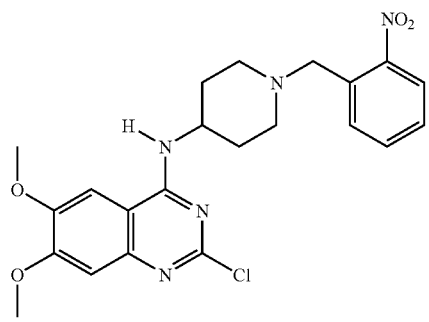

2-Chloro-6,7-dimethoxy-N-(1-(2-nitrobenzyl)piperidin-4-yl)quinazolin-4-amine (Compound 64)

General Procedure C, Compound 63 (335 mg, 0.95 mmol), 2,4-dichloro-6,7-dimethoxyquinazoline (516 mg, 2.0 mmol) were converted into Compound 64.
$^1$HNMR (CDCl$_3$): δ 1.50 (dq, J=3.9, 12.0 Hz, 2H), 2.02 (dd, J=3.0, 6.0 Hz, 2H), 2.23 (dt, J=3.0, 11.4 Hz, 2H), 2.74 (br d, J=12.0 Hz, 2H), 3.77 (s, 2H), 3.91 (s, 3H), 3.96 (s, 3H), 4.20-4.30 (m, 1H), 5.59 (d, J=7.8 Hz, 1H), 6.90 (s, 1H), 7.07 (s, 1H), 7.35-7.43 (m, 1H), 7.46-7.55 (m, 2H), 7.74 (d, J=8.7 Hz, 1H).
MS ($C_{22}H_{24}ClN_5O_4$; MWt. 457): Observed M+1=458.

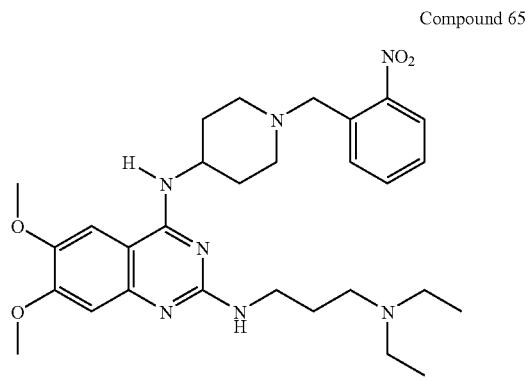

N2-(3-(Diethylamino)propyl)-6,7-dimethoxy-N4-(1-(2-nitrobenzyl)piperidin-4-yl)quinazoline-2,4-diamine (Compound 65)

Following General Procedure D, Compound 64 (200 mg, 0.44 mmol) and 3-(N,N-diethylamino)-propylamine (210 mg, 1.7 mmol) were converted into Compound 65.
$^1$HNMR (CDCl$_3$): δ 1.02 (t, J=7.2 Hz, 6H), 1.52 (dq, J=3.6, 12.0 Hz, 2H), 1.75 (p, J=6.9 Hz, 2H), 2.06 (br d, 12.0 Hz, 2H), 2.22 (dt, J=2.1, 11.4 Hz, 2H), 2.45-2.55 (m, 6H), 2.78 (br d, J=12.0 Hz, 2H), 3.46 (q, J=6.0 Hz, 2H), 3.79 (s, 2H), 3.91 (s, 3H), 3.92 (s, 3H), 4.10-4.22 (m, 1H), 5.05 (d, J=7.5 Hz, 1H), 6.73 (s, 1H), 6.86 (s, 1H), 7.38 (t, J=6.6 Hz, 1H), 7.50-7.60 (m, 2H), 7.77 (dd, J=0.9, 7.8 Hz, 1H).
MS ($C_{29}H_{41}N_7O_4$; MWt. 551): Observed M+1=552.

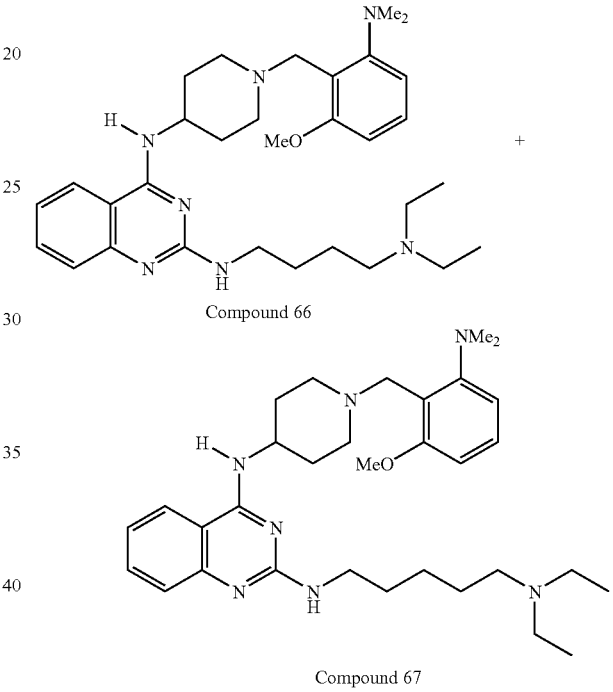

N2-(4-(Diethylamino)butyl)-N4-(1-(2-(dimethylamino)-6-methoxybenzyl)piperidin-4-yl)quinazoline-2,4-diamine (Compound 66) and N2-(5-(Diethylamino)pentyl)-N4-(1-(2-(dimethylamino)-6-methoxybenzyl)piperidin-4-yl)quinazoline-2,4-diamine (Compound 67)

Following General Procedure D, Compound 47 (60 mg, 0.15 mmol) and 4-(N,N-diethylamino)-butylamine and 5-(N,N-diethylamino)-pentylamine (1:1 mixture) (146 mg, 0.81 mmol) were converted into Compounds 66 and 67.
Compound 66: $^1$HNMR (CDCl$_3$): δ 1.04 (t, J=7.5 Hz, 6H), 1.40-1.70 (m, 4H), 2.05 (br d, J=9.0 Hz, 2H), 2.35 (t, J=9.0 Hz, 2H), 2.41 (m, 8H), 2.80 (s, 6H), 2.95 (br d, J=12.0 Hz, 2H), 3.50 (t, J=6.0 Hz, 2H), 3.69 (s, 2H), 3.81 (s, 3H), 4.10-4.20 (m, 1H), 5.32 (d, J=6.0 Hz, 1H), 6.65 (d, J=8.4 Hz, 1H), 6.79 (d, J=8.1 Hz, 1H), 7.02 (t, J=6.9 Hz, 1H), 7.19 (t, J=8.1 Hz, 1H), 7.41-7.55 (m, 3H).
MS ($C_{31}H_{47}N_7O$; M.Wt. 533): Observed M+1=534.
Compound 67: $^1$HNMR (CDCl$_3$): δ 1.04 (t, J=7.5 Hz, 6H), 1.42-1.70 (m, 6H), 2.07 (br d, J=9.0 Hz, 2H), 2.37 (t, J=9.0 Hz, 2H), 2.41-2.62 (m, 8H), 2.80 (s, 6H), 2.93 (br d, J=12.0 Hz, 2H), 3.67 (s, 2H), 3.70 (t, J=6.0 Hz, 2H), 3.81 (s, 3H), 4.10-4.20 (m, 1H), 5.26 (d, J=6.0 Hz, 1H), 6.65 (d, J=8.1 Hz, 1H), 6.79 (d, J=8.1 Hz, 1H), 6.99 (t, J=6.9 Hz, 1H), 7.22 (t, J=8.1 Hz, 1H), 7.39-7.50 (m, 3H).

MS ($C_{32}H_{49}N_7O$; M.Wt. 547): Observed M+1=548.

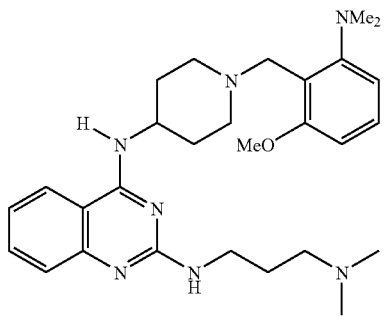

Compound 68

N4-(1-(2-(Dimethylamino)-6-methoxybenzyl)piperidin-4-yl)-N2-(3-(dimethylamino)propyl)quinazoline-2,4-diamine (Compound 68)

Following General Procedure D, Compound 47 (55 mg, 0.13 mmol) and 4-(N,N-dimethylamino)-propylamine (81 mg, 0.8 mmol) were converted into Compound 68. Compound 68 $^1$HNMR (CDCl$_3$): δ 1.43-1.58 (m, 2H), 1.79 (pentane, J=6.9 Hz, 2H), 2.05 (br d, J=9.0 Hz, 2H), 2.24 (s, 6H), 2.34-2.42 (m, 4H), 2.80 (s, 6H), 2.95 (br d, J=12.0 Hz, 2H), 3.50 (q, J=6.6 Hz, 2H), 3.69 (s, 2H), 3.80 (s, 3H), 4.10-4.20 (m, 1H), 5.18 (br s, 1H), 5.35 (d, J=6.0 Hz, 1H), 6.65 (d, J=8.4 Hz, 1H), 6.78 (d, J=8.1 Hz, 1H), 7.03 (t, J=6.9 Hz, 1H), 7.21 (t, J=8.1 Hz, 1H), 7.39-7.55 (m, 3H).

MS ($C_{28}H_{41}N_7O$; M.Wt. 491): Observed M+1=492.

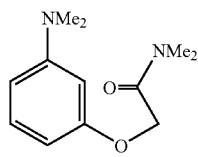

Compound 70

2-(3-(Dimethylamino)phenoxy)-N,N-dimethylacetamide (Compound 70)

To a mixture of 3-N,N-dimethylamino phenol (69) (3.43 g, 25 mmol) and 2-chloro N,N-dimethylacetamide (3.66 g, 30 mmol) in DMSO (30 mL) was added K$_2$CO$_3$ (6.7 g, 50 mmol) and the resulting suspension was stirred at room temperature for 16 h. The reaction was then diluted with dichloromethane (125 mL), and washed with water (2×100 mL), and brine (100 mL), and dried, and filtered, and the solvent was removed under vacuum. The crude product, Compound 70, was obtained as purple, thick oil that was used in the next step without additional purification.

$^1$HNMR (CDCl$_3$): δ 2.93 (s, 6H), 2.97 (s, 3H), 3.09 (s, 3H), 4.66 (s, 2H), 6.28 (dd, J=2.0, 7.1 Hz, 1H), 6.35-6.42 (m, 2H), 7.13 (t, J=7.8 Hz, 1H).

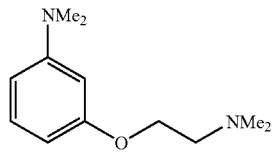

Compound 71

3-(2-(Dimethylamino)ethoxy)-N,N-dimethylaniline (Compound 71)

To AlCl$_3$ (3.29 g, 24.8 mmol) at 0° C. was added anhydrous THF (30 mL). A solution of lithium aluminum hydride in THF (2 M solution, 24.8 mL, 49.6 mmol) was added slowly. The mixture was stirred for 5 min and cooled to −78° C. A solution of Compound 70 (5.2 g, 23.5 mmol) in THF was added slowly. The reaction was warmed to room temperature and stirred for 4 h. Ethyl acetate (5 mL) and MeOH (10 mL) were added very slowly to quench the reaction. A solution of 6 g of K$_2$CO$_3$ in water (25 mL) was added very slowly. The mixture was extracted with CH$_2$Cl$_2$ (2×150 mL), and the organic layers were combined and washed with brine, and dried (MgSO$_4$), and filtered, and the solvent was removed under reduced pressure. The crude product 71 was obtained as a purple thick oil and used in the next step without further purification.

$^1$HNMR (CDCl$_3$): δ 2.33 (s, 6H), 2.71 (t, J=5.7 Hz, 2H), 2.92 (s, 6H), 4.06 (t, J=5.7 Hz, 2H), 6.25-6.40 (m, 3H), 7.13 (t, J=8.1 Hz, 1H).

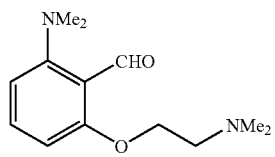

Compound 72

2-(Dimethylamino)-6-(2-(dimethylamino)ethoxy)benzaldehyde (Compound 72)

To a cold (0° C.) solution of Compound 71 (2.8 g, 13.5 mmol) in THF (10 mL) was added TMEDA (1.88 g, 16.2 mmol) followed by n-BuLi (2.5 M solution in hexane, 6.5 mL, 16.2 mmol). The mixture was stirred for 30 min at room temperature then DMF (1.48 g, 20.25 mmol) was added and the solution stirred for 3 h at room temperature. The reaction was then diluted with water (20 mL), and the product was extracted with EtOAc (3×50 mL). The organic layers were combined and washed with brine, and dried (MgSO$_4$), and filtered, and the solvent was removed under reduced pressure. After silica gel chromatography, the product (Compound 72) was obtained as an oil.

$^1$HNMR (CDCl$_3$): δ 2.34 (s, 6H), 2.77 (t, J=5.7 Hz, 2H), 2.89 (s, 6H), 4.13 (t, J=5.7 Hz, 2H), 6.39 (d, J=8.4 Hz, 1H), 6.56 (d, J=8.4 Hz, 1H), 7.31 (t, J=8.4 Hz, 1H), 10.39 (s, 1H).

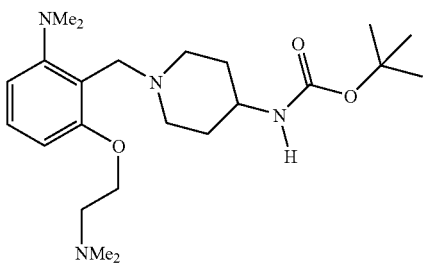

tert-Butyl 1-(2-(Dimethylamino)-6-(2-(dimethylamino)ethoxy)benzyl)piperidin-4-ylcarbamate (Compound 73)

Following General Procedure A, Compound 72 (430 mg, 1.82 mmol) and tert-butyl piperidin-4-ylcarbamate (477 mg, 2.38 mmol) were converted to Compound 73.

$^1$HNMR (CDCl$_3$): δ 1.20-1.40 (m, 2H), 1.43 (s, 9H), 1.83 (br d, J=9.0 Hz, 2H), 2.23 (t, J=8.0 Hz, 2H), 2.34 (s, 6H), 2.72 (t, J=6.0 Hz, 2H), 2.74 (s, 6H), 3.40 (brs, 1H), 3.62 (s, 2H), 4.03 (t, J=6.0 Hz, 2H), 4.40 (brs, 1H), 6.62 (d, J=7.8 Hz, 1H), 6.76 (d, J=8.1 Hz, 1H), 7.17 (t, J=8.1 Hz, 1H).

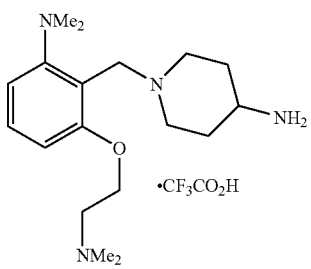

1-(2-(Dimethylamino)-6-(2-(dimethylamino)ethoxy)benzyl)piperidin-4-amine 2,2,2-trifluoroacetate (Compound 74)

Following General Procedure B, Compound 73 (200 mg, 0.48 mmol) was converted to Compound 74. The crude product, Compound 74, was used in the next step without additional purification.

2-Chloro-N-(1-(2-(dimethylamino)-6-(2-(dimethylamino)ethoxy)benzyl)piperidin-4-yl)-6,7-dimethoxyquinazolin-4-amine (Compound 75)

Following General Procedure C, Compound 74 (100 mg), and 2,4-dichloro-6,7-dimethoxyquinazoline (200 mg, 0.77 mmol) were converted into Compound 75.

$^1$HNMR (CDCl$_3$): δ 1.50-1.65 (m, 2H), 2.05 (brs, 2H), 2.35 (s, 6H), 2.30-2.45 (m, 2H), 2.73 (s, 6H), 2.75 (t, J=5.7 Hz, 2H), 2.95 (brd, J=12.3 Hz, 2H), 2.62 (brs, 1H), 3.68 (s, 2H), 3.95 (s, 3H), 3.97 (s, 3H), 4.05 (t, J=5.7 Hz, 2H), 4.20-4.35 (m, 1H), 5.55 (brs, J=7.5 Hz, 1H), 6.65 (d, J=7.5 Hz, 1H), 6.79 (d, J=7.5 Hz, 1H), 6.83 (s, 1H), 7.10 (s, 1H), 7.20 (t, J=7.5 Hz, 1H).

MS (C$_{28}$H$_{39}$ClN$_6$O$_3$; M.Wt. 542): Observed M+1=543.

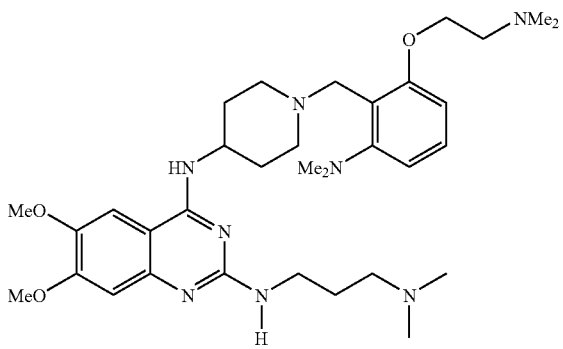

N4-(1-(2-(Dimethylamino)-6-(2-(dimethylamino)ethoxy)benzyl)piperidin-4-yl)-N-2-(3-(dimethylamino)propyl)-6,7-dimethoxyquinazoline-2,4-diamine (Compound 76)

Following General Procedure D, Compound 75 (15 mg, 0.03 mmol) and 4-(N,N-dimethylamino)-propylamine (81 mg, 0.8 mmol) were converted into Compound 76.

$^1$HNMR (CDCl$_3$): δ 1.45-1.55 (m, 2H), 1.75-1.85 (m, 2H), 2.05-2.15 (m, 2H), 2.25 (s, 6H), 2.42 (s, 6H), 2.30-2.45 (m, 4H), 2.75 (s, 6H), 2.70-2.80 (m, 2H), 2.95 (brd, J=8.0 Hz, 2H), 3.50 (q, J=5.7 Hz, 2H), 3.68 (s, 2H), 3.92 (s, 3H), 3.94 (s, 3H), 4.07 (t, J=6.0 Hz, 2H), 4.10-4.20 (m, 1H), 5.07 (brs, 1H), 6.66 (d, J=8.1 Hz, 1H), 6.80 (d, J=8.1 Hz, 1H), 6.86 (s, 1H), 7.21 (t, J=8.1 Hz, 1H).

MS (C$_{33}$H$_{52}$8$_6$O$_3$; M.Wt. 608): Observed M−1=607.

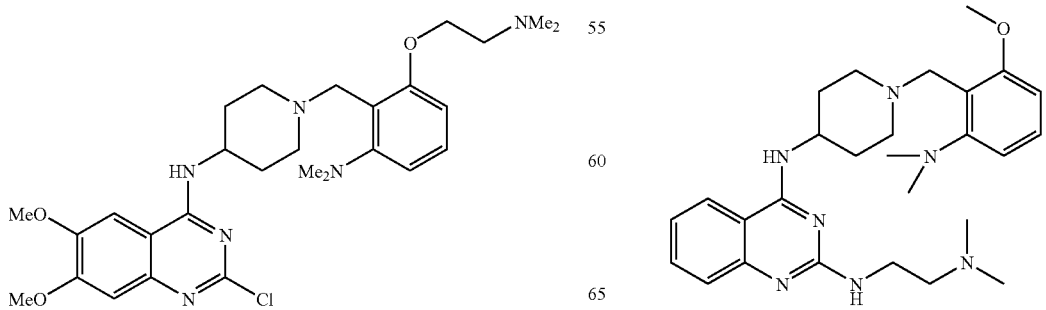

N~2~-[2-(Dimethylamino)ethyl]-N~4~-{1-[2-(dimethylamino)-6-methoxybenzyl]piperidin-4-yl}quinazoline-2,4-diamine (Compound 77)

Following General Procedure D, Compound 47 (57.2 mg, 0.14 mmol) and N,N-dimethylethylenediamine (0.050 mL, 0.42 mmol) were converted to Compound 77.

$^1$HNMR (CD$_3$OD): δ ppm 1.68 (dd, J=11.87, 3.37 Hz, 2H), 1.99 (dd, J=12.01, 2.34 Hz, 2H), 2.31 (s, 8H), 2.59 (t, J=6.89 Hz, 2H), 2.68 (s, 7H), 3.07 (d, J=12.01 Hz, 2H), 3.56 (t, J=6.89 Hz, 2H), 3.75-3.87 (m, 6H), 4.11-4.24 (m, 1H), 6.76 (d, J=8.20 Hz, 1H), 6.86 (d, J=7.33 Hz, 1H), 7.06 (dd, J=15.24, 1.17 Hz, 1H), 7.18-7.25 (m, 1H), 7.28 (d, J=5.27 Hz, 1H), 7.45-7.45 (m, 1H), 7.89 (dd, J=8.50, 1.17 Hz, 1H).

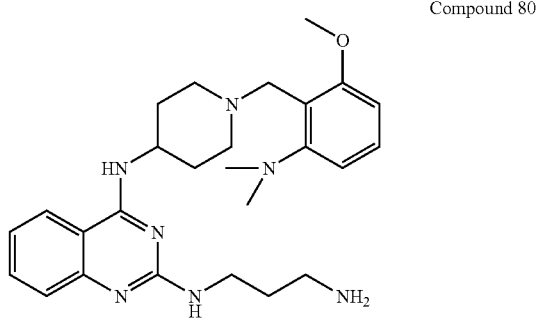

Compound 80

N~2~-(3-Aminopropyl)-N~4~-{1-[2-(dimethylamino)-6-methoxybenzyl]piperidin-4-yl}quinazoline-2,4-diamine (Compound 80)

Following General Procedure B, Compound 225 (0.12 g, 0.21 mmol) was converted into Compound 80.

$^1$HNMR (CDCl$_3$): δ ppm 1.74 (m, 2H), 1.88 (m, 2H), 1.99 (m, 2H), 2.34-2.51 (m, 2H), 2.73 (s, 6H), 2.91 (br. s., 2H), 3.02 (m, 2H), 3.55 (br. s., 2H), 3.78 (m, 5H), 4.17 (br. s., 1H), 6.64 (d, J=8.20 Hz, 1H), 6.79 (d, J=7.62 Hz, 1H), 7.06 (d, J=7.03 Hz, 1H), 7.24 (d, J=8.50 Hz, 2H), 7.33 (d, J=7.62 Hz, 1H), 7.43 (d, J=7.03 Hz, 1H), 7.68 (d, J=7.64 Hz, 1H).

MS (C$_{26}$H$_{37}$N$_7$O; MWt. 463): Observed M+1=464.

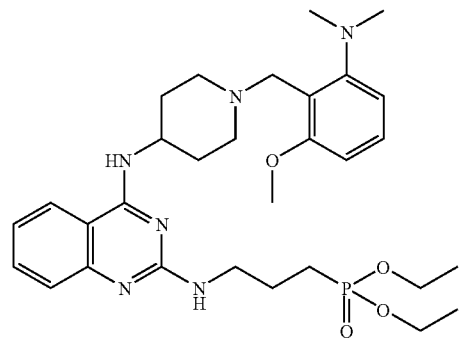

Compound 81

Diethyl 3-(4-(1-(2-(Dimethylamino)-6-methoxybenzyl)piperidin-4-ylamino)quinazolin-2-ylamino)propylphosphonate (Compound 81)

Following General Procedure D, Compound 47 (50 mg, 0.12 mmol) and diethyl 3-aminopropylphosphonate (69 mg, 0.36 mmol) in n-BuOH (3 mL) were heated to 117° C. for 24 h with a reflux condenser. The product (Compound 81) was purified by preparative silica gel TLC plate 1000µ using 5% (7N NH$_3$-MeOH) and 95% CH$_2$Cl$_2$ solution as eluent.

1H NMR (CD$_3$OD): δ 1.29 (s, 9H), 1.73 (dd, J=11.7, 4.1 Hz, 2H), 1.83-1.98 (m, 4H), 1.99-2.14 (m, 2H), 2.44 (t, J=12.0 Hz, 2H), 3.12 (d, J=10.5 Hz, 2H), 3.49 (t, J=6.5 Hz, 2H), 3.84 (s, 3H), 3.89 (s, 2H), 3.99-4.12 (m, 4H), 4.12-4.24 (m, 1H), 6.79 (d, J=8.5 Hz, 1H), 6.89 (d, J=7.3 Hz, 1H), 7.08 (dd, J=15.2, 1.17 Hz, 1H), 7.27 (t, J=8.2 Hz, 2H), 7.47-7.57 (m, 1H), 7.90 (d, J=7.3 Hz, 1H)

MS (C$_{30}$H$_{40}$N$_6$O$_4$P; MWt. 584): Observed M+1=585

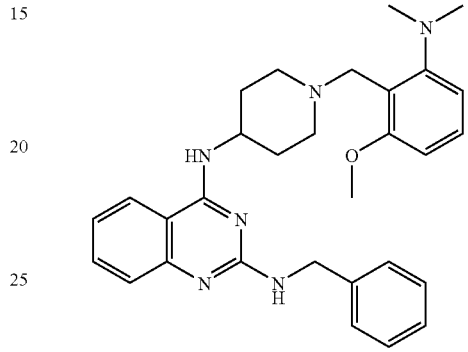

Compound 82

N2-Benzyl-N4-(1-(2-(dimethylamino)-6-methoxybenzyl)piperidin-4-yl)quinazoline-2,4-diamine (Compound 82)

Employing General Procedure D, Compound 47 (50 mg, 0.12 mmol) and phenylmethanamine (36 mg, 0.36 mmol) were converted into Compound 82, which was purified by basic alumina flash column chromatography using 3% MeOH and 97% CH$_2$Cl$_2$ solution as eluent.

1H NMR (CD$_3$OD): δ 1.50-1.66 (m, 2H), 1.84 (d, J=14.0 Hz, 2H), 2.16-2.30 (m, 2H), 2.68 (s, 6H), 2.98 (d, J=13.2 Hz, 2H), 3.78 (s, 2H), 3.83 (s, 3H), 3.94-4.06 (m, 1H), 4.60 (s, 2H), 6.78 (d, J=7.9 Hz, 1H), 6.87 (d, J=7.3 Hz, 1H), 7.05 (td, J=7.6, 1.3 Hz, 1H), 7.17 (d, J=7.0 Hz, 1H), 7.20-7.37 (m, 6H), 7.49 (ddd, J=8.4, 6.8, 1.5 Hz, 1H), 7.86 (d, J=8.2 Hz, 1H)

MS (C$_{30}$H$_{36}$N$_6$O$_6$; MWt. 496): Observed M+1=497

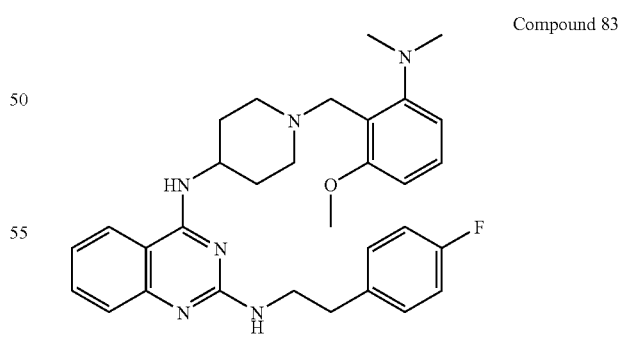

Compound 83

N4-(1-(2-(Dimethylamino)-6-methoxybenzyl)piperidin-4-yl)-N2-(4-fluorophenethyl)quinazoline-2,4-diamine (Compound 83)

Following General Procedure D, Compound 47 (50 mg, 0.12 mmol) and 2-(4-fluorophenyl)ethanamine (50 mg, 0.36 mmol) were converted into Compound 83.

1H NMR (CD$_3$OD): δ 1.73 (dd, 3H), 2.04 (d, J=12.6 Hz, 2H), 2.42 (t, J=11.0 Hz, 2H), 2.68 (s, 6H), 2.90 (t, J=7.5 Hz, 3H), 3.12 (d, J=12.3 Hz, 2H), 3.62 (t, J=7.9 Hz, 2H), 3.83 (s, 3H), 3.90 (s, 2H), 4.21 (dd, J=15.5, 7.6 Hz, 1H), 6.80 (d, J=8.2 Hz, 1H), 6.89 (d, J=8.2 Hz, 1H), 6.94-7.04 (m, 2H), 7.09 (t, J=7.6 Hz, 1H), 7.22-7.34 (m, 4H), 7.52 (t, J=7.6 Hz, 1H), 7.91 (d, J=7.6 Hz, 1H)

MS (C$_{31}$H$_{37}$FN$_6$O; MWt. 528): Observed M+1=529

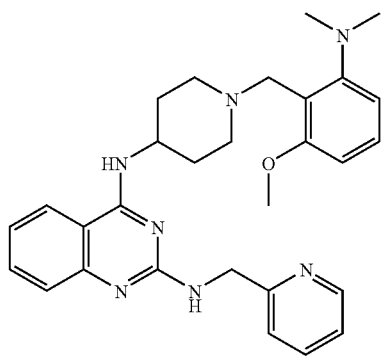

Compound 84

N4-(1-(2-(Dimethylamino)-6-methoxybenzyl)piperidin-4-yl)-N2-(pyridin-2-ylmethyl)quinazoline-2,4-diamine (Compound 84)

Following General Procedure D, Compound 47 (50 mg, 0.12 mmol) and pyridin-2-ylmethanamine (36 mg, 0.36 mmol) were converted into Compound 84.

1H NMR (CD$_3$OD): δ 1.42-1.61 (m, 2H), 1.61-1.77 (m, 2H), 2.14 (t, J=12.8 Hz, 2H), 2.68 (s, 6H), 2.93 (d, J=11.3 Hz, 2H), 3.76 (br. s., 2H), 3.84 (s, 3H), 4.70 (s, 2H), 6.79 (d, J=8.2 Hz, 1H), 6.88 (d, J=7.0 Hz, 1H), 7.07 (ddd, J=8.2, 6.9, 1.3 Hz, 1H), 7.18-7.35 (m, 3H), 7.40 (d, J=7.9 Hz, 1H), 7.51 (ddd, J=845, 6.9, 1.5 Hz, 1H), 7.72 (td, J=7.8, 1.8 Hz, 1H), 7.86 (dd, J=8.5, 1.2 Hz, 1H), 8.40 (d, J=5.3 Hz, 1H)

MS (C$_{29}$H$_{35}$N$_7$O; MWt. 497): Observed M+1=498

General Procedure E

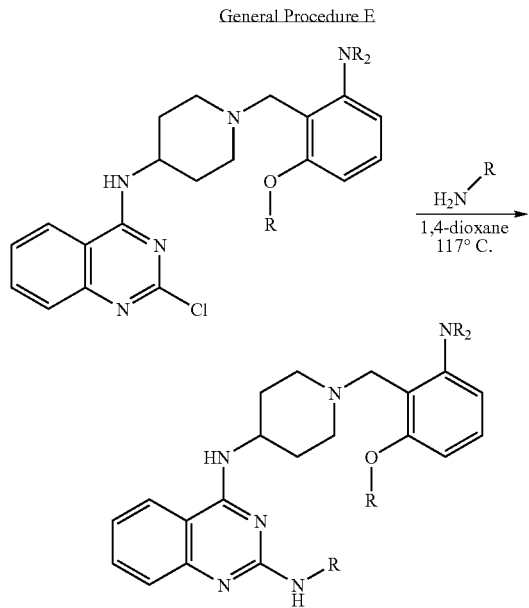

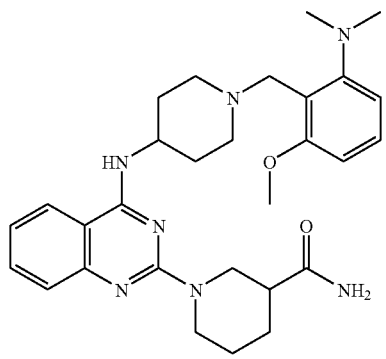

Compound 85

1-(4-(1-(2-(Dimethylamino)-6-methoxybenzyl)piperidin-4-ylamino)quinazolin-2-yl)piperidine-3-carboxamide (Compound 85). General Procedure E.

Compound 47 (50 mg, 0.12 mmol) and piperidine-3-carboxamide (45 mg, 0.36 mmol) in 1,4-dioxane (5 mL) were heated to 117° C. for 24 h in a sealed tube. The product (AGN-219171) was purified by basic alumina flash column chromatography using 3% MeOH and 97% CH$_2$Cl$_2$ solution as eluent.

1H NMR (CD$_3$OD): δ 1.50-1.90 (m, 6H), 2.02-2.10 (m, 2H), 2.26-2.53 (m, 4H), 2.69 (s, 6H), 2.97-3.22 (m, 4H), 3.80 (s, 2H), 3.83 (s, 3H), 4.58-4.71 (m, 1H), 4.71-4.82 (m, 1H), 6.77 (d, J=7.9 Hz, 1H), 6.87 (d, J=8.2 Hz, 1H), 7.07 (t, J=7.6 Hz, 1H), 7.25 (t, J=8.2 Hz, 1H), 7.33-7.38 (m, 1H), 7.48 (d, J=8.5 Hz, 1H), 7.87 (d, J=7.9 Hz, 1H)

MS (C$_{29}$H$_{39}$N$_7$O$_2$; MWt. 517): Observed M+1=518

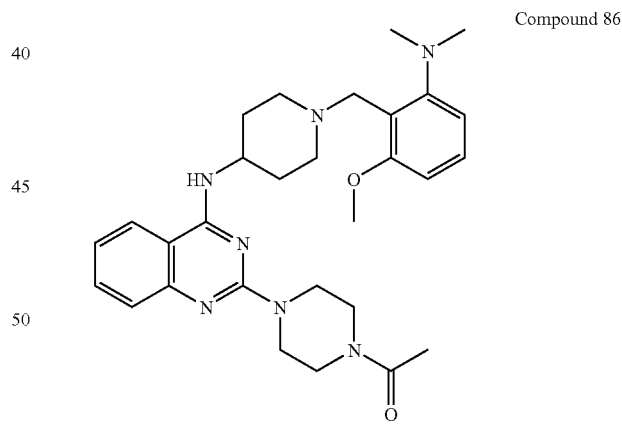

Compound 86

1-(4-(4-(1-(2-(Dimethylamino)-6-methoxybenzyl)piperidin-4-ylamino)quinazolin-2-yl)piperazin-1-yl)ethanone (Compound 86)

Following General Procedure E, Compound 47 (50 mg, 0.12 mmol) and 1-(piperazin-1-yl)ethanone (45 mg, 0.36 mmol) were converted into Compound 86.

1H NMR (CD$_3$OD): δ 1.62-1.78 (m, 2H), 1.95-2.06 (m, 2H), 2.16 (s, 3H), 2.29-2.42 (m, 2H), 2.69 (s, 6H), 3.02-3.12 (m, 2H), 3.59-3.69 (m, 3H), 3.83 (s, 3H), 3.88-3.95 (m, 2H), 4.06-4.20 (m, 1H), 6.78 (d, J=8.2 Hz, 1H), 6.87 (d, J=8.2 Hz,

1H), 7.10 (t, J=8.2 Hz, 1H), 7.25 (t, J=8.2 Hz, 1H), 7.38 (d, J=7.6 Hz, 1H), 7.47-7.56 (m, 1H), 7.90 (d, J=8.2 Hz, 1H)

MS ($C_{29}H_{39}N_7O_2$; MWt. 517): Observed M+1=518

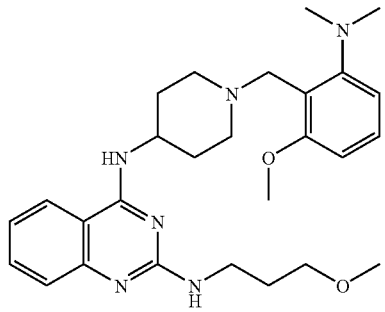

Compound 87

N4-(1-(2-(Dimethylamino)-6-methoxybenzyl)piperidin-4-yl)-N2-(3-methoxypropyl)quinazoline-2,4-diamine (Compound 87)

Following General Procedure E, Compound 47 (50 mg, 0.12 mmol) and 3-methoxypropan-1-amine (33 mg, 0.36 mmol) were converted into Compound 87, which was purified by silica gel flash column chromatography using 5% (7N $NH_3$-MeOH) and 95% $CH_2Cl_2$ solution as eluent.

1H NMR ($CD_3OD$): δ 1.67-1.83 (m, 2H), 1.82-1.94 (m, 2H), 1.99-2.12 (m, 2H), 2.37-2.53 (m, 2H), 2.69 (s, 6H), 3.06-3.19 (m, 2H), 3.34 (s, 2H), 3.51 (d, J=12.0 Hz, 2H), 3.84 (s, 3H), 3.90 (s, 1H), 4.12-4.28 (m, 1H), 6.80 (d, J=8.5 Hz, 1H), 6.89 (d, J=7.3 Hz, 1H), 7.09 (t, J=7.0 Hz, 1H), 7.27 (t, J=8.2 Hz, 2H), 7.46-7.56 (m, 1H), 7.90 (d, J=8.2 Hz, 1H)

MS ($C_{27}H_{38}N_6O_2$; MWt. 478): Observed M+1=479

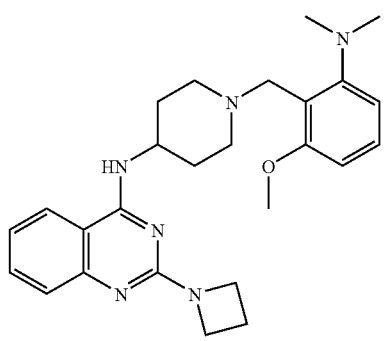

Compound 88

2-(Azetidin-1-yl)-N-(1-(2-(dimethylamino)-6-methoxybenzyl)piperidin-4-yl)quinazolin-4-amine (Compound 88)

Following General Procedure E, Compound 47 (50 mg, 0.12 mmol) and azetidine (25 mg, 0.36 mmol) were converted into Compound 88.

1H NMR ($CD_3OD$): δ 1.66-1.82 (m, 2H), 2.05 (dd, J=11.0, 4.5 Hz, 2H), 2.27-2.41 (m, 3H), 2.41-2.54 (m, 2H), 2.69 (s, 6H), 3.04-3.18 (m, 2H), 3.84 (s, 3H), 3.90 (br. s., 2H), 4.11-4.20 (m, 4H), 6.79 (d, J=8.5 Hz, 1H), 6.89 (d, J=7.3 Hz, 1H), 7.10 (dd, J=15.2, 1.2 Hz, 1H), 7.27 (t, J=8.2 Hz, 1H), 7.38 (d, J=7.6 Hz, 1H), 7.52 (ddd, J=8.4, 7.0, 1.3 Hz, 1H), 7.90 (d, J=8.8 Hz, 1H)

MS ($C_{29}H_{36}N_6O$; MWt. 446): Observed M+1=447

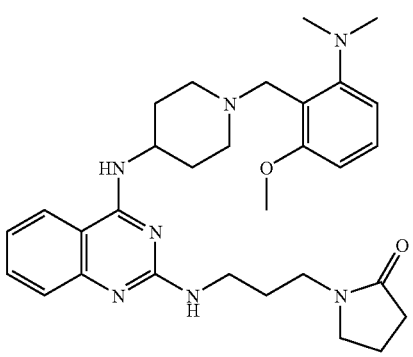

Compound 89

1-(3-(4-(1-(2-(Dimethylamino)-6-methoxybenzyl) piperidin-4-ylamino)quinazolin-2-ylamino)propyl) pyrrolidin-2-one (Compound 89)

Employing General Procedure E, Compound 47 (50 mg, 0.12 mmol) and 1-(3-aminopropyl)-2-pyrrolidinone (50 mg, 0.36 mmol) were converted into Compound 89.

1H NMR ($CD_3OD$): δ 1.62-1.91 (m, 4H), 1.94-2.10 (m, 4H), 2.27-2.42 (m, 4H), 2.68 (s, 6H), 3.02-3.24 (m, 2H), 3.28-3.30 (m, 2H), 3.32-3.49 (m, 4H), 3.80 (s, 2H), 3.82 (s, 3H), 4.07-4.25 (m, 1H), 6.76 (d, J=8.5 Hz, 1H), 6.86 (d, J=7.3 Hz, 1H), 7.05 (t, J=7.5 Hz, 1H), 7.16-7.35 (m, 1H), 7.49 (ddd, J=8.4, 7.0, 1.3 Hz, 1H), 7.88 (d, J=8.5 Hz, 1H)

MS ($C_{30}H_{41}N_7O_2$; MWt. 531): Observed M+1=532

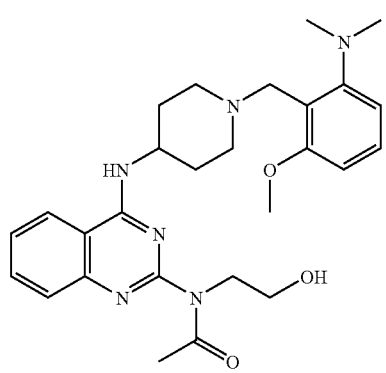

Compound 90

N-(4-(1-(2-(Dimethylamino)-6-methoxybenzyl)piperidin-4-ylamino)quinazolin-2-yl)-N-(2-hydroxyethyl)acetamide (Compound 90)

Employing General Procedure E, Compound 47 (50 mg, 0.12 mmol) and N-Acetyl-ethylenediamine (36 mg, 0.36 mmol) were converted into Compound 90.

1H NMR ($CD_3OD$): δ 1.60-1.78 (m, 2H), 1.93 (s, 3H), 1.94-2.06 (m, 2H), 2.39 (t, J=11.6 Hz, 2H), 2.68 (s, 6H), 3.07 (d, J=12.3 Hz, 2H), 3.40 (t, J=5.9 Hz, 2H), 3.50-3.58 (m, 2H), 3.82 (s, 3H), 3.83 (s, 2H), 4.10-4.25 (m, 1H), 6.76 (d, J=8.2 Hz, 1H), 6.86 (d, J=8.2 Hz, 1H), 7.07 (t, J=7.6 Hz, 1H), 7.24 (t, J=8.2 Hz, 1H), 7.31 (d, J=8.5 Hz, 1H), 7.49 (dd, J=15.4, 1.3 Hz, 1H), 7.89 (d, J=8.2 Hz, 1H)

MS ($C_{27}H_{36}N_6O_3$; MWt. 492): Observed M+1=493

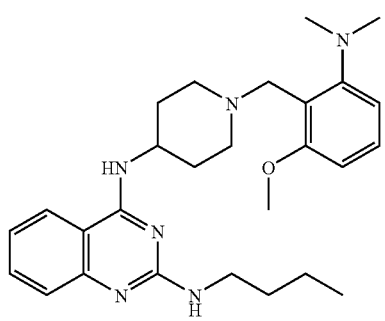

Compound 91

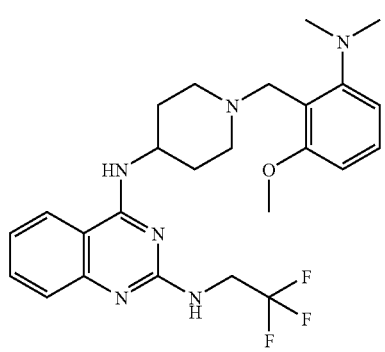

Compound 93

N2-Butyl-N4-(1-(2-(dimethylamino)-6-methoxybenzyl)piperidin-4-yl)quinazoline-2,4-diamine (Compound 91)

Employing General Procedure E, Compound 47 (50 mg, 0.12 mmol) and N-Butylamine (22 mg, 0.36 mmol) were converted into Compound 91.

1H NMR (CD$_3$OD): δ 0.92-1.02 (m, 3H), 1.38-1.47 (m, 2H), 1.56-1.65 (m, 2H), 1.97-2.05 (m, 2H), 2.31 (t, J=12.2 Hz, 2H), 2.69 (s, 6H), 3.07 (d, J=12.2 Hz, 2H), 3.40 (t, J=7.2 Hz, 2H), 3.81 (s, 2H), 3.83 (s, 3H), 4.10-4.20 (m, 1H), 6.77 (d, J=8.3 Hz, 1H), 6.87 (d, J=8.1 Hz, 1H), 7.05 (t, J=7.6 Hz, 1H), 7.25 (t, J=8.2 Hz, 1H), 7.27-7.33 (m, 1H), 7.49 (dd, J=15.4, 1.2 Hz, 1H), 7.87 (d, J=8.1 Hz, 1H)

MS (C$_{27}$H$_{38}$N$_6$O; MWt. 462): Observed M+1=463

N4-(1-(2-(Dimethylamino)-6-methoxybenzyl)piperidin-4-yl)-N2-(2,2,2-trifluoroethyl)quinazoline-2,4-diamine (Compound 93)

Employing General Procedure E, Compound 47 (50 mg, 0.12 mmol) and 2,2,2-Trifluoroethylamine (35 mg, 0.36 mmol) were converted into Compound 93.

1H NMR (CD$_3$OD): δ 1.65-1.77 (m, 2H), 2.04 (d, J=12.2 Hz, 2H), 2.37 (t, J=12.5 Hz, 2H), 2.69 (s, 6H), 3.09 (d, J=11.3 Hz, 2H), 3.35 (s, 2H), 3.83 (s, 3H), 4.19 (q, J=9.5 Hz, 2H), 6.78 (d, J=8.3 Hz, 1H), 6.88 (d, J=7.8 Hz, 1H), 7.13 (t, J=7.6 Hz, 1H), 7.26 (t, J=8.2 Hz, 1H), 7.34 (d, J=8.1 Hz, 1H), 7.54 (t, J=7.7 Hz, 1H), 7.94 (d, J=8.1 Hz, 1H)

MS (C$_{25}$H$_{31}$F$_3$N$_6$O; MWt. 488): Observed M+1=489

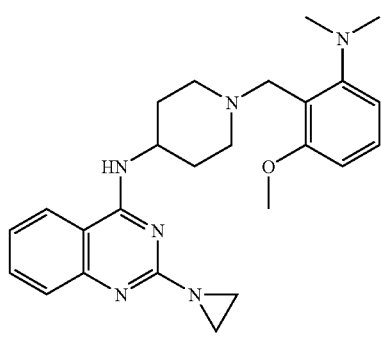

Compound 92

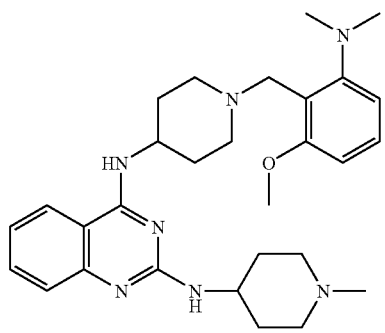

Compound 94

2-(Aziridin-1-yl)-N-(1-(2-(dimethylamino)-6-methoxybenzyl)piperidin-4-yl)quinazolin-4-amine (Compound 92)

Employing General Procedure E, Compound 47 (50 mg, 0.12 mmol) and ethyleneimine (15 mg, 0.36 mmol) were converted into Compound 92.

1H NMR (CD3OD): δ 1.96-2.13 (m, 2H), 2.32 (d, J=11.5 Hz, 2H), 2.71-2.74 (m, 2H), 2.75 (s, 6H), 3.15-3.29 (m, 2H), 3.44-3.52 (m, 2H), 3.94 (s, 3H), 3.98 (s, 2H), 4.44-4.55 (m, 2H), 6.94 (d, J=8.315 Hz, 1H), 7.04 (d, J=8.1 Hz, 1H), 7.17 (t, J=7.5 Hz, 1H), 7.37-7.48 (m, 2H), 7.58 (t, J=7.705 Hz, 1H), 7.98 (d, J=8.1 Hz, 1H)

MS (C$_{25}$H$_{32}$N$_6$O; MWt. 432): Observed M+1=433

N4-(1-(2-(Dimethylamino)-6-methoxybenzyl)piperidin-4-yl)-N2-(1-methylpiperidin-4-yl)quinazoline-2,4-diamine (Compound 94)

Employing General Procedure E, Compound 47 (50 mg, 0.12 mmol) and 4-amino-1-methyl-piperidine (35 mg, 0.36 mmol) were converted into Compound 94.

1HNMR (CD$_3$OD): δ 1.55-1.77 (m, 4H), 1.95-2.10 (m, 4H), 2.13-2.26 (m, 2H), 2.32 (s, 3H), 2.34-2.38 (m, 1H), 2.65 (s, 2H), 2.69 (s, 6H), 2.88 (dd, J=12.3, 2.6 Hz, 2H), 3.09 (d, J=12.0 Hz, 2H), 3.83 (s, 3H), 3.84 (s, 2H), 4.04-4.17 (m, 1H), 6.78 (d, J=7.9 Hz, 1H), 6.87 (d, J=8.2 Hz, 1H), 7.07 (t, J=7.6 Hz, 2H), 7.21-7.33 (m, 2H), 7.46-7.53 (m, 1H), 7.88 (d, J=8.2 Hz, 1H)

MS (C$_{29}$H$_{41}$N$_7$O; MWt. 503): Observed M+1=504

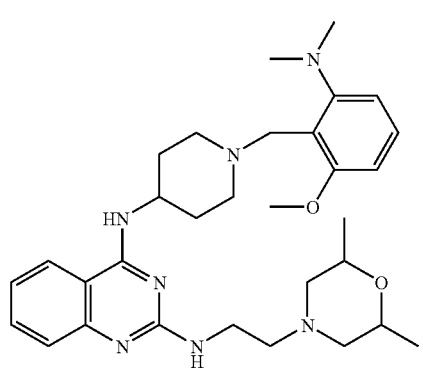

Compound 95

N4-(1-(2-(Dimethylamino)-6-methoxybenzyl)piperidin-4-yl)-N2-(2-(2,6-dimethylmorpholino)ethyl)quinazoline-2,4-diamine (Compound 95)

Employing General Procedure E, Compound 47 (50 mg, 0.12 mmol) and 2(2,6-dimethylmorpholin-4-yl)-ethanamine (50 mg, 0.36 mmol) were converted into Compound 95.

1H NMR (CD$_3$OD): δ 1.14 (s, 3H), 1.16 (s, 3H), 1.64-1.75 (m, 2H), 1.78 (d, J=10.6 Hz, 2H), 2.01 (d, J=11.4 Hz, 2H), 2.36 (t, J=12.8 Hz, 2H), 2.60 (t, J=6.6 Hz, 2H), 2.69 (s, 6H), 2.87 (d, J=10.6 Hz, 2H), 3.08 (d, J=12.6 Hz, 2H), 3.58 (t, J=6.6 Hz, 2H), 3.62-3.77 (m, 2H), 3.81 (s, 2H), 3.83 (s, 3H), 4.11-4.27 (m, 1H), 6.77 (d, J=8.5 Hz, 1H), 6.87 (d, J=8.2 Hz, 1H), 7.07 (t, J=7.9 Hz, 1H), 7.25 (t, J=8.4 Hz, 2H), 7.50 (t, J=8.2 Hz, 1H), 7.89 (d, J=8.2 Hz, 1H)

MS (C$_{31}$H$_{45}$N$_7$O$_2$; MWt. 547): Observed M+1=548

Compound 96

N2-(3-(Dimethylamino)-2,2-dimethylpropyl)-N4-(1-(2-(dimethylamino)-6-methoxybenzyl)piperidin-4-yl)quinazoline-2,4-diamine (Compound 96)

Employing General Procedure E, Compound 47 (50 mg, 0.12 mmol) and N,N,2,2-tetramethyl-1,3-propanediamine (42 mg, 0.36 mmol) were converted into Compound 96.

1H NMR (CD$_3$OD): δ 1.00 (s, 6H), 1.65-1.78 (m, 2H), 2.03 (dd, J=8.9, 3.1 Hz, 2H), 2.32-2.43 (m, 4H), 2.68 (s, 6H), 3.10 (d, J=14.9 Hz, 2H), 3.83 (s, 3H), 3.84 (s, 2H), 6.78 (d, J=8.2 Hz, 1H), 6.87 (d, J=7.6 Hz, 1H), 7.08 (t, J=7.5 Hz, 1H), 7.21-7.28 (m, 1H), 7.29 (d, J=4.7 Hz, 1H), 7.52 (t, J=7.6 Hz, 1H), 7.90 (d, J=9.1 Hz, 1H)

MS (C$_{30}$H$_{45}$N$_7$O$_2$; MWt. 519): Observed M+1=520

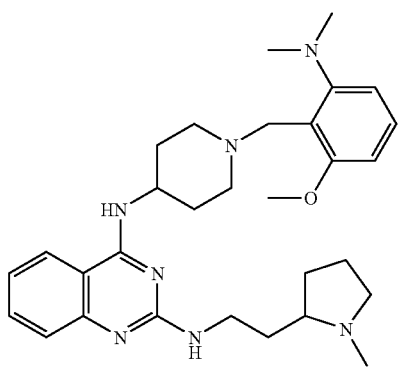

Compound 97

N4-(1-(2-(Dimethylamino)-6-methoxybenzyl)piperidin-4-yl)-N2-(2-(1-methylpyrrolidin-2-yl)ethyl)quinazoline-2,4-diamine (Compound 97)

Employing General Procedure E, Compound 47 (50 mg, 0.12 mmol) and 2-(2-Aminoethyl)-1-methylpyrrolidine (40 mg, 0.36 mmol) were converted into Compound 97.

1H NMR (CD$_3$OD): δ 1.50-1.66 (m, 2H), 1.66-1.84 (m, 3H), 1.97-2.16 (m, 4H), 2.18-2.33 (m, 5H), 2.34 (s, 3H), 2.68 (s, 6H), 3.02-3.16 (m, 3H), 3.36-3.58 (m, 2H), 3.83 (s, 3H), 3.84 (s, 2H), 4.12-4.26 (m, 1H), 6.78 (d, J=8.2 Hz, 1H), 6.88 (d, J=7.3 Hz, 1H), 7.07 (dd, J=15.2, 1.2 Hz, 1H), 7.25 (t, J=8.1 Hz, 2H), 7.46-7.55 (m, 1H), 7.89 (d, J=8.5 Hz, 1H)

MS (C$_{30}$H$_{43}$N$_7$O; MWt. 517): Observed M+1=518

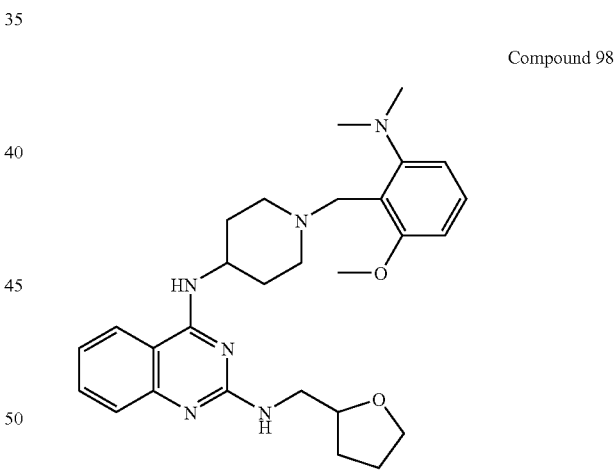

Compound 98

N4-(1-(2-(Dimethylamino)-6-methoxybenzyl)piperidin-4-yl)-N2-((tetrahydrofuran-2-yl)methyl)quinazoline-2,4-diamine (Compound 98)

Employing General Procedure E, Compound 47 (50 mg, 0.12 mmol) and (tetrahydrofuran-2-yl)methanamine (33 mg, 0.36 mmol) were converted into Compound 98.

1H NMR (CD$_3$OD): δ 1.70 (dd, J=10.3, 2.9 Hz, 3H), 1.83-2.09 (m, 4H), 2.37 (t, J=13.0 Hz, 2H), 2.69 (s, 6H), 3.09 (d, J=12.3 Hz, 2H), 3.42-3.63 (m, 2H), 3.71-3.81 (m, 1H), 3.83 (s, 3H), 3.84 (s, 2H), 3.85-3.96 (m, 1H), 4.05-4.23 (m, 2H), 6.78 (d, J=8.2 Hz, 1H), 6.87 (d, J=8.2 Hz, 1H), 7.07 (t, J=7.5

Hz, 1H), 7.20-7.34 (m, 2H), 7.50 (ddd, J=8.4, 7.0, 1.3 Hz, 1H), 7.89 (d, J=8.2 Hz, 1H)
MS (C$_{28}$H$_{38}$N$_6$O$_2$; MWt. 490): Observed M+1=491

1H), 7.10 (t, J=7.5 Hz, 1H), 7.25 (t, J=8.2 Hz, 1H), 7.32 (d, J=8.2 Hz, 1H), 7.52 (dd, J=15.4, 1.3 Hz, 1H), 7.91 (d, J=8.5 Hz, 1H)
MS (C$_{26}$H$_{33}$N$_7$O; MWt. 459): Observed M+1=460

Compound 99

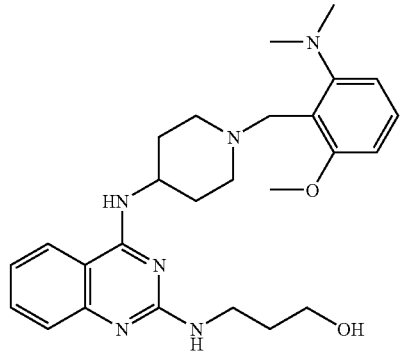

3-(4-(1-(2-(Dimethylamino)-6-methoxybenzyl)piperidin-4-ylamino)quinazolin-2-ylamino)propan-1-ol (Compound 99)

Employing General Procedure E, Compound 47 (50 mg, 0.12 mmol) and 3-Amino-1-propanol (25 mg, 0.36 mmol) were converted into Compound 99.
1H NMR (CD$_3$OD): δ 1.68-1.78 (m, 2H), 1.82 (t, J=6.2 Hz, 1H), 1.98-2.10 (m, 2H), 2.39-2.54 (m, 2H), 2.69 (s, 6H), 3.05-3.19 (m, 2H), 3.53 (t, J=6.6 Hz, 2H), 3.65 (t, J=6.2 Hz, 2H), 3.84 (s, 3H), 3.90 (s, 2H), 4.13-4.26 (m, 1H), 6.80 (d, J=8.5 Hz, 1H), 6.89 (d, J=8.2 Hz, 1H), 7.08 (t, J=7.6 Hz, 1H), 7.28 (t, J=8.6 Hz, 2H), 7.51 (dd, J=8.5, 5.6 Hz, 1H), 7.90 (d, J=8.5 Hz, 1H)
MS (C$_{26}$H$_{36}$N$_6$O$_2$; MWt. 495): Observed M+1=496

Compound 101

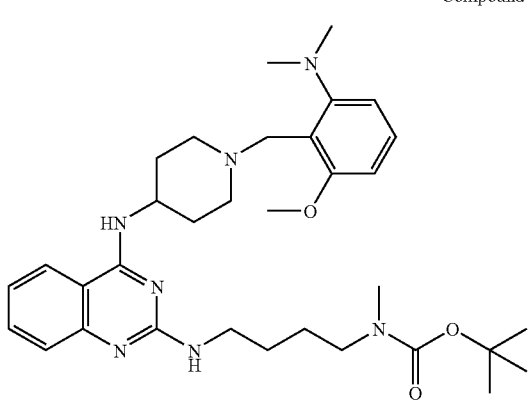

tert-Butyl 4-(4-(1-(2-(Dimethylamino)-6-methoxybenzyl)piperidin-4-ylamino)quinazolin-2-ylamino)butyl(methyl)carbamate (Compound 101)

Employing General Procedure E, Compound 47 (70 mg, 0.17 mmol) and tert-butyl 4-aminobutyl(methyl)carbamate (85 mg, 0.51 mmol) were converted into Compound 101.
1H NMR (CD$_3$OD): δ 1.45 (s, 9H), 1.58-1.68 (m, 6H), 1.77-1.95 (m, 4H), 2.18 (d, J=7.6 Hz, 2H), 2.71 (s, 5H), 2.85 (s, 6H), 3.19-3.26 (m, 2H), 3.45-3.55 (m, 2H), 3.88 (s, 3H), 4.22 (br. s., 0H), 4.37 (br. s., 0H), 6.87 (d, J=8.8 Hz, 1H), 6.97 (d, J=8.5 Hz, 1H), 7.22 (t, J=7.6 Hz, 1H), 7.31-7.46 (m, 2H), 7.62 (t, J=8.8 Hz, 1H), 8.01 (d, J=8.5 Hz, 1H)
MS (C$_{33}$H$_{49}$N$_7$O$_3$; MWt. 591): Observed M+1=592

Compound 100

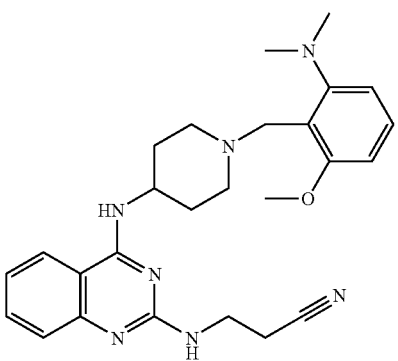

3-(4-(1-(2-(Dimethylamino)-6-methoxybenzyl)piperidin-4-ylamino)quinazolin-2-ylamino)propanenitrile (Compound 100)

Employing General Procedure E, Compound 47 (50 mg, 0.12 mmol) and 3-aminopropanenitrile (32 mg, 0.36 mmol) were converted into Compound 100.
1H NMR (CD$_3$OD): δ 1.62-1.79 (m, 2H), 1.95-2.07 (m, 2H), 2.32-2.44 (m, 2H), 2.69 (s, 6H), 2.79 (t, J=6.7 Hz, 2H), 3.09 (d, J=12.6 Hz, 2H), 3.70 (t, J=6.7 Hz, 2H), 3.83 (s, 7H), 4.11-4.23 (m, 1H), 6.77 (d, J=8.2 Hz, 1H), 6.87 (d, J=8.2 Hz, General Procedure F:

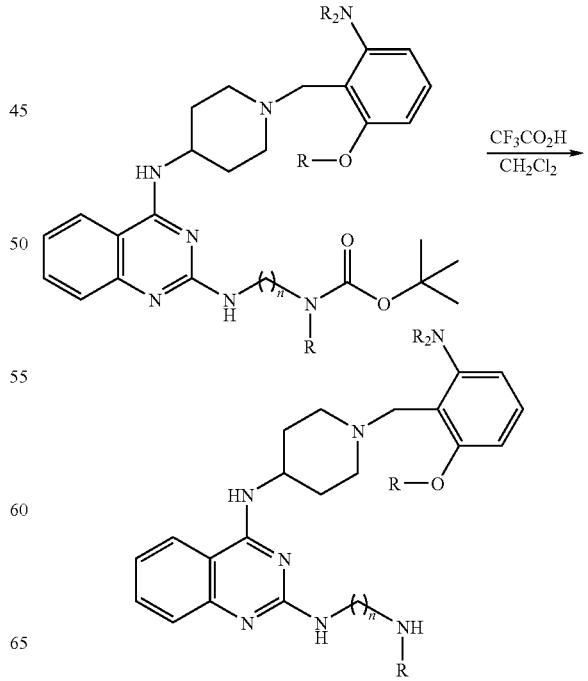

Compound 102

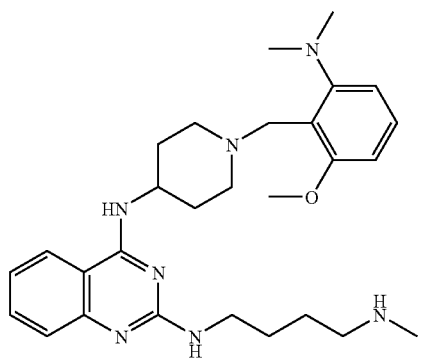

N4-(1-(2-(Dimethylamino)-6-methoxybenzyl)piperidin-4-yl)-N2-(4-(methylamino)butyl)quinazoline-2,4-diamine (Compound 102). General Procedure F A solution of Compound 101 (39 mg, 0.07 mmol) and trifluoroacetic acid (0.2 ml, 0.35 mmol) in dichloromethane (3 mL) was stirred at room temperature for 2 h. The product (Compound 102) was purified by basic alumina flash column chromatography using 3% MeOH and 97% $CH_2Cl_2$ solution as eluent.

1H NMR ($CD_3OD$): δ 1.62-1.78 (m, 6H), 2.01 (d, J=11.7 Hz, 2H), 2.29-2.42 (m, 2H), 2.46 (s, 3H), 2.69 (s, 9H), 3.08 (d, J=12.0 Hz, 2H), 3.42-3.49 (m, 2H), 3.83 (s, 5H), 4.10-4.22 (m, 1H), 6.77 (d, J=8.5 Hz, 1H), 6.87 (d, J=8.2 Hz, 1H), 7.07 (t, J=7.0 Hz, 1H), 7.21-7.27 (m, 1H), 7.27-7.34 (m, 1H), 7.50 (dd, J=15.5, 1.5 Hz, 1H), 7.88 (d, J=8.2 Hz, 1H)

Compound 103

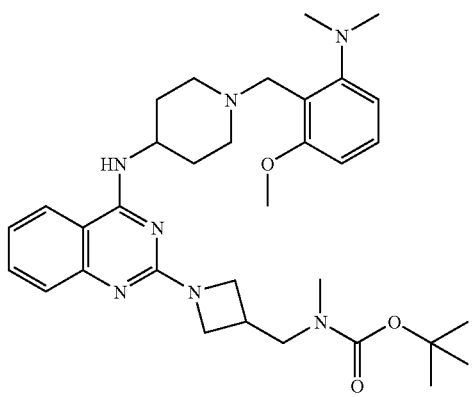

tert-Butyl (1-(4-(1-(2-(Dimethylamino)-6-methoxybenzyl)piperidin-4-ylamino)quinazolin-2-yl)azetidin-3-yl)methyl(methyl)carbamate (Compound 103)

Following General Procedure E, Compound 47 (80 mg, 0.19 mmol) and 3-(N'-Boc-methylaminomethyl)azatidine (94 mg, 0.48 mmol) were converted into Compound 103.

1H NMR ($CD_3OD$): δ 1.47 (s, 9H), 1.59-1.75 (m, 2H), 1.96-2.05 (m, 2H), 2.29 (t, J=11.4 Hz, 2H), 2.68 (s, 6H), 2.90 (s, 3H), 3.05 (d, J=12.3 Hz, 2H), 3.55 (d, J=7.3 Hz, 2H), 3.78 (s, 2H), 3.82 (s, 3H), 3.87 (dd, J=8.6, 5.4 Hz, 2H), 4.06-4.23 (m, 3H), 6.76 (d, J=8.2 Hz, 1H), 6.86 (d, J=7.6 Hz, 1H), 7.08 (dd, J=15.2, 1.2 Hz, 1H), 7.24 (t, J=8.1 Hz, 1H), 7.38 (d, J=8.5 Hz, 1H), 7.46-7.56 (m, 1H), 7.90 (d, J=8.2 Hz, 1H)
MS ($C_{33}H_{47}N_7O_3$; MWt. 589): Observed M+1=590

Compound 104

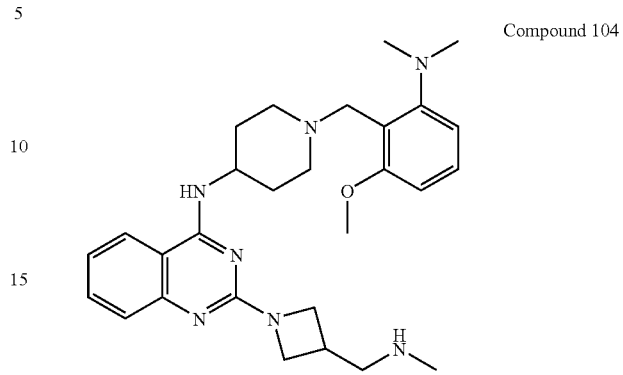

N-(1-(2-(Dimethylamino)-6-methoxybenzyl)piperidin-4-yl)-2-(3-((methylamino)methyl)azetidin-1-yl)quinazolin-4-amine (Compound 104)

Following General Procedure F, Compound 103 (28 mg, 0.05 mmol) and TFA (0.2 mL) were converted into Compound 104.

1H NMR ($CD_3OD$): δ 1.58-1.76 (m, 3H), 1.95-2.05 (m, 2H), 2.30 (td, J=12.3, 2.1 Hz, 2H), 2.41 (s, 3H), 2.68 (s, 6H), 2.84 (s, 3H), 3.05 (d, J=12.6 Hz, 2H), 3.78 (s, 2H), 3.80-3.85 (m, 2H), 3.82 (s, 3H), 4.06-4.19 (m, 1H), 4.23 (t, J=8.2 Hz, 2H), 6.77 (d, J=8.2 Hz, 1H), 6.86 (d, J=7.6 Hz, 1H), 7.08 (dd, J=15.2, 1.2 Hz, 1H), 7.24 (t, J=8.2 Hz, 1H), 7.37 (d, J=7.9 Hz, 1H), 7.50 (ddd, J=8.4, 7.0, 1.3 Hz, 1H), 7.89 (d, J=8.2 Hz, 1H)
MS ($C_{28}H_{39}N_7O$; MWt. 489): Observed M+1=490

Compound 105

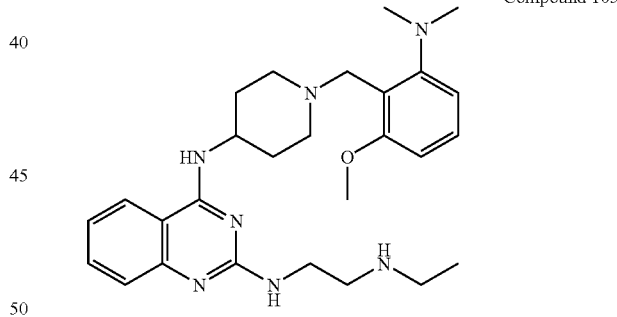

N4-(1-(2-(Dimethylamino)-6-methoxybenzyl)piperidin-4-yl)-N2-(2-(ethylamino)ethyl)quinazoline-2,4-diamine (Compound 105)

Following General Procedure E, Compound 47 (50 mg, 0.12 mmol) and N-ethylethylenediamine (30 mg, 0.36 mmol) were converted into Compound 105.

1H NMR ($CD_3OD$): δ 1.14 (t, 3H), 1.57-1.77 (m, 2H), 1.98 (d, J=11.4 Hz, 2H), 2.31 (t, J=12.0 Hz, 2H), 2.68 (s, 6H), 2.69-2.76 (m, 2H), 2.86 (t, J=6.3 Hz, 2H), 3.06 (d, J=12.3 Hz, 2H), 3.56 (t, J=6.2 Hz, 2H), 3.79 (s, 2H), 3.82 (s, 3H), 4.09-4.24 (m, 1H), 6.76 (d, J=8.5 Hz, 1H), 6.86 (d, J=8.2 Hz, 1H), 7.07 (t, J=7.5 Hz, 1H), 7.24 (t, J=8.2 Hz, 1H), 7.31 (d, J=8.20 Hz, 1H), 7.50 (t, J=7.2 Hz, 1H), 7.88 (d, J=7.6 Hz, 1H)
MS ($C_{27}H_{39}N_7O$; MWt. 477): Observed M+1=478

Compound 106

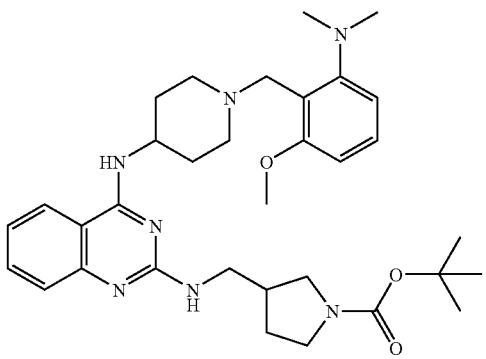

tert-Butyl 3-((4-(1-(2-(Dimethylamino)-6-methoxybenzyl)piperidin-4-ylamino)quinazolin-2-ylamino)methyl)pyrrolidine-1-carboxylate (Compound 106)

Following General Procedure E, Compound 47 (100 mg, 0.24 mmol) and 3-Aminomethyl-pyrrolidine-1-carboxylic acid tert-butyl ester (120 mg, 0.60 mmol) were converted into Compound 106.

1H NMR (CD$_3$OD): δ 1.43 (s, 9H), 1.66-1.83 (m, 2H), 1.98-2.17 (m, 3H), 2.21-2.36 (m, 2H), 2.49-2.65 (m, 1H), 2.73 (s, 6H), 3.06-3.23 (m, 3H), 3.41-3.59 (m, 6H), 3.92 (s, 3H), 4.44 (br. s., 2H), 4.47-4.56 (m, 1H), 6.92 (d, J=8.5 Hz, 1H), 7.02 (d, J=8.2 Hz, 1H), 7.27 (t, J=7.6 Hz, 1H), 7.37-7.47 (m, 3H), 7.67 (t, J=7.3 Hz, 1H), 8.10 (d, J=7.6 Hz, 1H)

MS (C$_{33}$H$_{47}$N$_7$O$_3$; MWt. 589): Observed M+1=590

Compound 108

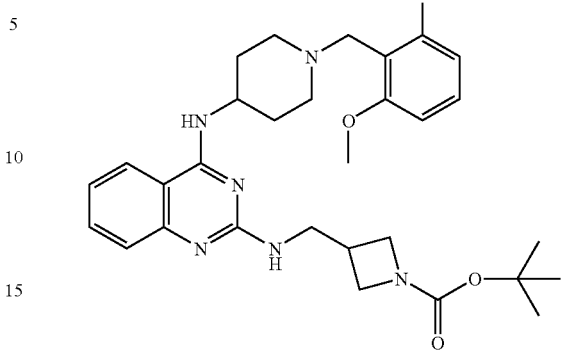

tert-Butyl 3-((4-(1-(2-(Dimethylamino)-6-methoxybenzyl)piperidin-4-ylamino)quinazolin-2-ylamino)methyl)azetidine-1-carboxylate (Compound 108)

Following General Procedure E, Compound 47 (80 mg, 0.19 mmol) and tert-Butyl 3-(aminomethyl)azetidine-1-carboxylate (88 mg, 0.48 mmol) were converted into Compound 108.

1H NMR (CD$_3$OD): δ 1.42 (s, 9H), 2.00-2.18 (m, 2H), 2.23-2.35 (m, 2H), 2.70 (s, 1H), 2.74 (s, 6H), 2.86-2.99 (m, 1H), 3.16-3.28 (m, 2H), 3.50 (dd, J=10.9, 4.4 Hz, 2H), 3.69-3.78 (m, 4H), 3.93 (s, 3H), 4.04 (t, J=8.5 Hz, 2H), 4.49 (s, 1H), 4.52-4.61 (m, 1H), 6.94 (d, J=8.2 Hz, 1H), 7.04 (d, J=8.2 Hz, 1H), 7.30 (t, J=7.8 Hz, 1H), 7.39-7.50 (m, 2H), 7.69 (t, J=7.2 Hz, 1H), 8.13 (d, J=8.5 Hz, 1H)

MS (C$_{32}$H$_{45}$N$_7$O$_3$; MWt. 575): Observed M+1=576

Compound 107

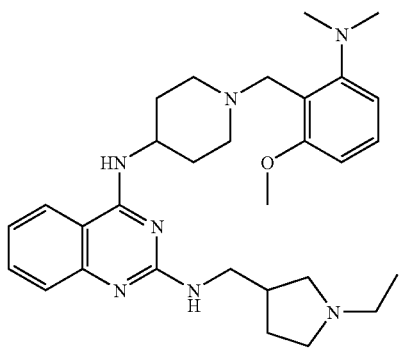

N4-(1-(2-(Dimethylamino)-6-methoxybenzyl)piperidin-4-yl)-N2-((1-ethylpyrrolidin-3-yl)methyl)quinazoline-2,4-diamine (Compound 107)

Following General Procedure E, Compound 47 (50 mg, 0.12 mmol) and C-(1-Ethyl pyrrolidine-3-yl-methylamine (42 mg, 0.36 mmol) were converted into Compound 107.

1H NMR (CD$_3$OD): δ 1.12 (t, J=7.2 Hz, 3H), 1.51-1.78 (m, 4H), 1.94-2.07 (m, 3H), 2.23-2.38 (m, 3H), 2.45-2.60 (m, 3H), 2.68 (s, 6H), 2.69-2.76 (m, 2H), 2.86 (dd, J=9.4, 8.2 Hz, 1H), 3.06 (d, J=10.0 Hz, 2H), 3.40 (t, J=7.8 Hz, 1H), 3.78-3.81 (m, 2H), 3.82 (s, 3H), 4.05-4.23 (m, 1H), 6.76 (d, J=8.2 Hz, 1H), 6.86 (d, J=7.1 Hz, 1H), 6.99-7.11 (m, 1H), 7.17-7.55 (m, 3H), 7.83-7.91 (m, 1H)

MS (C$_{30}$H$_{43}$N$_7$O; MWt. 517): Observed M+1=518

Compound 109

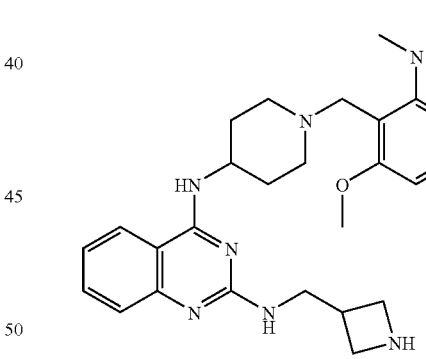

N2-(Azetidin-3-ylmethyl)-N4-(1-(2-(dimethylamino)-6-methoxybenzyl)piperidin-4-yl)quinazoline-2,4-diamine (Compound 109)

Following General Procedure F, Compound 108 (90 mg, 0.16 mmol) and TFA (0.2 mL) were converted into Compound 109.

1H NMR (CD$_3$OD): δ 1.57-1.76 (m, 2H), 1.98 (d, J=10.3 Hz, 2H), 2.28 (t, J=12.3 Hz, 2H), 2.65 (s, 1H), 2.68 (s, 6H), 2.98-3.16 (m, 3H), 3.47-3.73 (m, 5H), 3.78 (s, 2H), 3.82 (s, 3H), 4.06-4.19 (m, 1H), 6.76 (d, J=8.2 Hz, 1H), 6.86 (d, J=8.2 Hz, 1H), 7.06 (t, J=7.3 Hz, 1H), 7.17-7.36 (m, 2H), 7.49 (t, J=7.5 Hz, 1H), 7.87 (d, J=8.2 Hz, 1H)

MS (C$_{27}$H$_{37}$N$_7$O; MWt. 475): Observed M+1=476

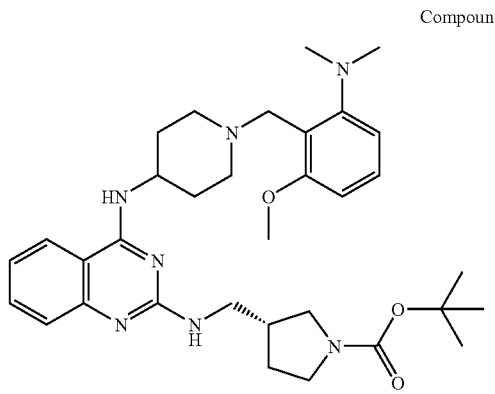

Compound 110

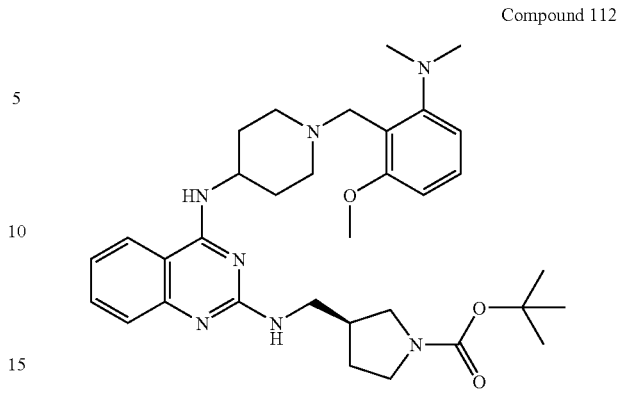

Compound 112

(R)-tert-Butyl 3-((4-(1-(2-(Dimethylamino)-6-methoxybenzyl)piperidin-4-ylamino)quinazolin-2-ylamino)methyl)pyrrolidine-1-carboxylate (Compound 110)

Following General Procedure E, Compound 47 (80 mg, 0.19 mmol) and (R)-3-(Aminomethyl)-1-N-Boc-pyrrolidine (94 mg, 0.48 mmol) were converted into Compound 110.

1H NMR (CD$_3$OD): δ 1.45 (s, 9H), 1.69-1.84 (m, 2H), 1.94-2.16 (m, 3H), 2.20-2.33 (m, 2H), 2.50-2.65 (m, 1H), 2.73 (s, 6H), 3.05-3.21 (m, 3H), 3.39-3.58 (m, 6H), 3.92 (s, 3H), 4.43 (s, 2H), 4.45-4.54 (m, 1H), 6.92 (d, J=8.5 Hz, 1H), 7.01 (d, J=8.2 Hz, 1H), 7.26 (t, J=7.5 Hz, 1H), 7.38-7.47 (m, 2H), 7.66 (t, J=7.9 Hz, 1H), 8.10 (d, J=8.5 Hz, 1H)

MS (C$_{33}$H$_{47}$N$_7$O$_3$; MWt. 589): Observed M+1=590.

(S)-tert-Butyl 3-((4-(1-(2-(Dimethylamino)-6-methoxybenzyl)piperidin-4-ylamino)quinazolin-2-ylamino)methyl)pyrrolidine-1-carboxylate (Compound 112)

Following General Procedure E, Compound 47 (80 mg, 0.19 mmol) and (S)-3-(Aminomethyl)-1-N-Boc-pyrrolidine (94 mg, 0.48 mmol) were converted into Compound 112.

1H NMR (CD$_3$OD): δ 1.43 (s, 9H), 1.73 (dd, J=6.0, 5.42 Hz, 1H), 1.98 (dd, J=19.1, 4.4 Hz, 3H), 2.23 (d, J=14.1 Hz, 2H), 2.51-2.66 (m, 1H), 2.71 (s, 1H), 2.72 (s, 6H), 2.88-3.06 (m, 2H), 3.09-3.21 (m, 1H), 3.33-3.42 (m, 1H), 3.42-3.54 (m, 5H), 3.90 (s, 3H), 4.30 (br. s., 2H), 4.33-4.46 (m, 1H), 6.89 (d, J=8.5 Hz, 1H), 6.99 (d, J=7.9 Hz, 1H), 7.18 (t, J=7.6 Hz, 1H), 7.31-7.45 (m, 2H), 7.60 (dd, J=15.5, 1.2 Hz, 1H), 8.00 (d, J=7.9 Hz, 1H)

MS (C$_{33}$H$_{47}$N$_7$O$_3$; MWt. 589): Observed M+1=590

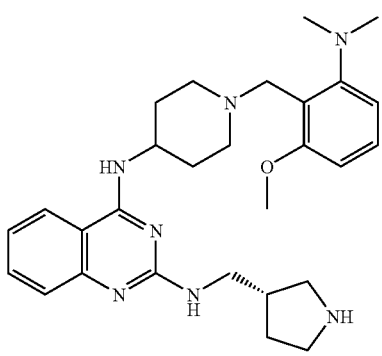

Compound 111

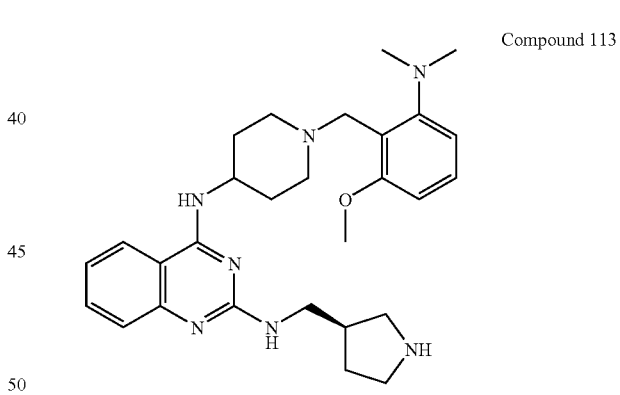

Compound 113

(S)—N-4-(1-(2-(Dimethylamino)-6-methoxybenzyl)piperidin-4-yl)-N2-(pyrrolidin-3-ylmethyl)quinazoline-2,4-diamine (Compound III)

Following General Procedure F, Compound 110 (90 mg, 0.16 mmol) and TFA (0.2 mL) were converted into Compound 111.

1H NMR (CD$_3$OD): δ 1.50-1.76 (m, 2H), 1.89-2.05 (m, 2H), 2.29 (t, J=11.6 Hz, 2H), 2.45-2.59 (m, 1H), 2.70-2.77 (m, 1H), 2.85-2.97 (m, 2H), 2.96-3.11 (m, 5H), 3.40 (t, J=7.9 Hz, 2H), 3.79 (s, 2H), 3.81 (s, 3H), 4.06-4.20 (m, 1H), 6.76 (d, J=8.2 Hz, 1H), 6.85 (d, J=7.9 Hz, 1H), 7.06 (t, J=7.3 Hz, 1H), 7.18-7.35 (m, 2H), 7.49 (t, J=7.2 Hz, 1H), 7.88 (d, J=8.2 Hz, 1H)

MS (C$_{28}$H$_{39}$N$_7$O; MWt. 489): Observed M+1=490

(R)—N-4-(1-(2-(Dimethylamino)-6-methoxybenzyl)piperidin-4-yl)-N2-(pyrrolidin-3-ylmethyl)quinazoline-2,4-diamine (Compound 113)

Following General Procedure F, Compound 112 (80 mg, 0.16 mmol) and TFA (0.2 mL) were converted into Compound 113.

1H NMR (CD$_3$OD): δ 1.50-1.74 (m, 2H), 1.87-2.06 (m, 2H), 1.87-2.07 (m, 2H), 2.28 (t, J=11.4 Hz, 2H), 2.41-2.55 (m, 1H), 2.63 (br. s., 1H), 2.67 (s, 6H), 2.74-3.11 (m, 7H), 3.33-3.47 (m, 2H), 3.78 (s, 2H), 3.81 (s, 3H), 4.06-4.19 (m, 1H), 6.75 (d, J=8.2 Hz, 1H), 6.85 (d, J=8.2 Hz, 1H), 7.05 (t, J=7.5 Hz, 1H), 7.18-7.34 (m, 2H), 7.49 (t, J=7.6 Hz, 1H), 7.88 (d, J=7.9 Hz, 1H)

MS (C$_{28}$H$_{39}$N$_7$O; MWt. 489): Observed M+1=490

Compound 114

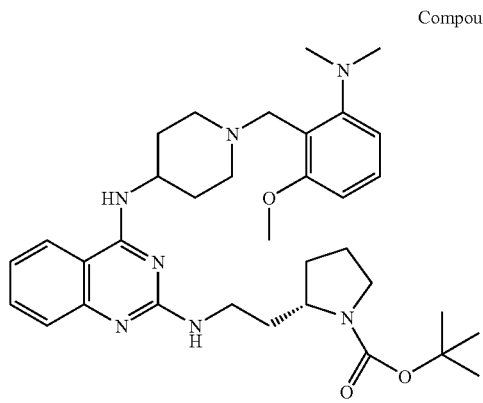

(S)-tert-Butyl 2-(2-(4-(1-(2-(Dimethylamino)-6-methoxybenzyl)piperidin-4-ylamino)quinazolin-2-ylamino)ethyl)pyrrolidine-1-carboxylate (Compound 114)

Following General Procedure E, Compound 47 (80 mg, 0.19 mmol) and (R)-2-(2-Amino-ethyl)-1-N-Boc-pyrrolidine (100 mg, 0.48 mmol) were converted into Compound 114.

1H NMR (CD$_3$OD): δ 1.45 (s, 9H), 1.64-2.11 (m, 12H), 2.36-2.49 (m, 2H), 2.69 (s, 6H), 3.13 (d, J=9.1 Hz, 2H), 3.34-3.39 (m, 1H), 3.47-3.57 (m, 1H), 3.84 (s, 3H), 3.88-3.93 (m, 2H), 4.13-4.30 (m, 1H), 6.80 (d, J=8.5 Hz, 1H), 6.89 (d, J=8.5 Hz, 1H), 7.08 (t, J=7.0 Hz, 1H), 7.23-7.35 (m, 2H), 7.51 (t, J=7.8 Hz, 1H), 7.90 (d, J=7.6 Hz, 1H)

MS (C$_{34}$H$_{49}$N$_7$O$_3$; MWt. 603): Observed M+1=604

Compound 116

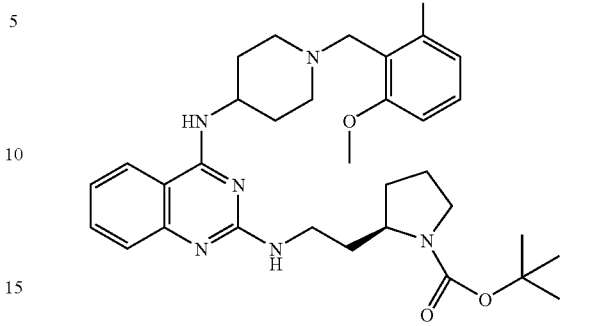

(R)-tert-Butyl 2-(2-(4-(1-(2-(Dimethylamino)-6-methoxybenzyl)piperidin-4-ylamino)quinazolin-2-ylamino)ethyl)pyrrolidine-1-carboxylate (Compound 116)

Following General Procedure E, Compound 47 (80 mg, 0.19 mmol) and (S)-2-(2-Amino-ethyl)-1-N-Boc-pyrrolidine (100 mg, 0.48 mmol) were converted into Compound 116.

1H NMR (CD$_3$OD): δ 1.45 (s, 9H), 1.58-2.09 (m, 12H), 2.31-2.47 (m, 2H), 2.68 (s, 6H), 3.10 (d, J=12.3 Hz, 2H), 3.32-3.39 (m, 1H), 3.46-3.57 (m, 1H), 3.83 (s, 3H), 3.90 (s, 2H), 4.14-4.24 (m, 1H), 6.78 (d, J=8.5 Hz, 1H), 6.88 (d, J=7.3 Hz, 1H), 7.07 (dd, J=15.2, 1.2 Hz, 1H), 7.22-7.33 (m, 2H), 7.50 (ddd, J=8.5, 7.03, 1.5 Hz, 1H), 7.89 (d, J=7.0 Hz, 1H)

MS (C$_{34}$H$_{49}$N$_7$O$_3$; MWt. 603): Observed M+1=604

Compound 115

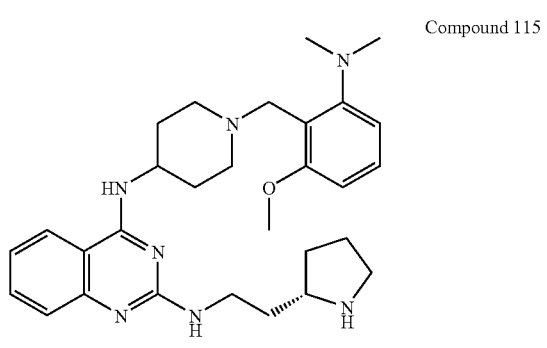

(S)—N-4-(1-(2-(Dimethylamino)-6-methoxybenzyl)piperidin-4-yl)-N2-(2-(pyrrolidin-2-yl)ethyl)quinazoline-2,4-diamine (Compound 115)

Following General Procedure F, Compound 114 (57 mg, 0.10 mmol) and TFA (0.2 mL) were converted into Compound 115.

1H NMR (CD$_3$OD): δ 1.26-1.45 (m, 2H), 1.59-1.86 (m, 6H), 1.91-2.04 (m, 3H), 2.28 (t, J=12.0 Hz, 2H), 2.68 (s, 6H), 2.73-2.86 (m, 1H), 2.92-3.11 (m, 3H), 3.38-3.61 (m, 2H), 3.78 (s, 2H), 3.81 (s, 3H), 4.11-4.22 (m, 1H), 6.76 (d, J=8.2 Hz, 1H), 6.85 (d, J=7.9 Hz, 1H), 7.05 (t, J=7.62 Hz, 1H), 7.18-7.34 (m, 2H), 7.49 (t, J=7.6 Hz, 1H), 7.87 (d, J=7.9 Hz, 1H)

MS (C$_{29}$H$_{41}$N$_7$O; MWt. 503): Observed M+1=504

Compound 117

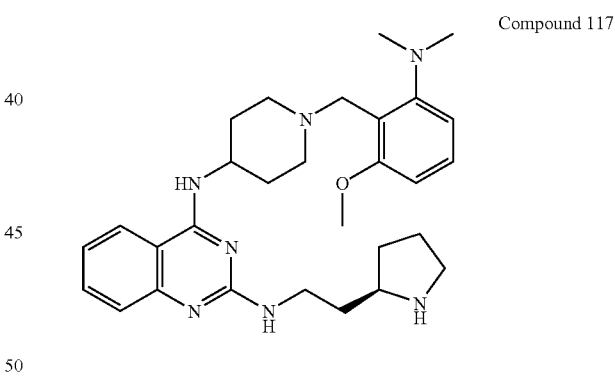

(R)—N-4-(1-(2-(Dimethylamino)-6-methoxybenzyl)piperidin-4-yl)-N2-(2-(pyrrolidin-2-yl)ethyl)quinazoline-2,4-diamine (Compound 117)

Following General Procedure F, Compound 116 (65 mg, 0.10 mmol) and TFA (0.2 mL) were converted into Compound 117

1H NMR (CD$_3$OD): δ 1.32-1.48 (m, 2H), 1.59-1.90 (m, 6H), 1.91-2.04 (m, 3H), 2.29 (t, J=11.3 Hz, 2H), 2.68 (s, 6H), 2.77-2.90 (m, 1H), 2.96-3.17 (m, 3H), 3.38-3.62 (m, 2H), 3.79 (s, 2H), 3.82 (s, 3H), 4.16 (dt, J=14.0, 6.92 Hz, 1H), 6.76 (d, J=8.2 Hz, 1H), 6.86 (d, J=8.2 Hz, 1H), 7.06 (t, J=7.3 Hz, 1H), 7.19-7.34 (m, 2H), 7.49 (t, J=7.6 Hz, 1H), 7.88 (d, J=7.9 Hz, 1H)

MS (C$_{29}$H$_{41}$N$_7$O; MWt. 503): Observed M+1=504

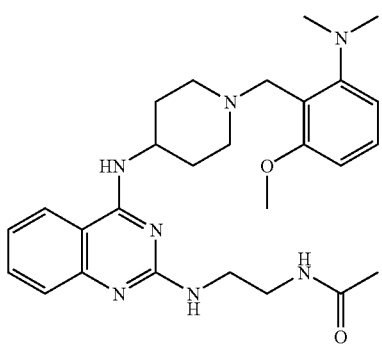

Compound 118

N-(2-(4-(1-(2-(Dimethylamino)-6-methoxybenzyl)piperidin-4-ylamino)quinazolin-2-ylamino)ethyl)acetamide (Compound 118)

Following General Procedure E, Compound 47 (50 mg, 0.12 mmol) and N-acetylethylene-diamine (32 mg, 0.36 mmol) were converted into Compound 118.

1H NMR (CD$_3$OD): δ 1.93 (s, 3H), 1.95 (s, 3H), 2.00-2.17 (m, 2H), 2.23-2.35 (m, 2H), 3.25 (s, 1H), 3.40-3.53 (m, 3H), 3.60 (t, J=6.0 Hz, 2H), 3.90 (s, 2H), 3.93 (s, 3H), 4.50 (s, 2H), 4.58-4.71 (m, 1H), 6.93 (d, J=8.2 Hz, 1H), 7.03 (d, J=8.20 Hz, 1H), 7.28 (t, J=7.6 Hz, 1H), 7.43 (q, J=7.8 Hz, 2H), 7.68 (t, J=7.8 Hz, 1H), 8.11 (d, J=8.2 Hz, 1H)

MS (C$_{27}$H$_{37}$N$_7$O$_2$; MWt. 491): Observed M+1=492

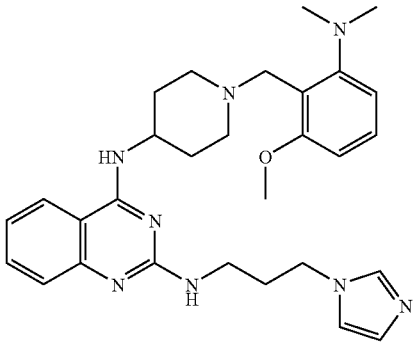

Compound 120

N2-(3-(1H-Imidazol-1-yl)propyl)-N4-(1-(2-(dimethylamino)-6-methoxybenzyl)piperidin-4-yl)quinazoline-2,4-diamine (Compound 120)

Following General Procedure E, Compound 47 (50 mg, 0.12 mmol) and 1-(3-Amimopropyl) imidazole (38 mg, 0.36 mmol) were converted into Compound 120.

1H NMR (CD$_3$OD): δ 1.59-1.77 (m, 2H), 1.98 (d, J=12.9 Hz, 2H), 2.11 (quin, J=6.8 Hz, 2H), 2.23-2.37 (m, 2H), 2.67 (s, 6H), 3.05 (d, J=12.3 Hz, 2H), 3.42 (t, J=6.7 Hz, 2H), 3.80 (s, 2H), 3.81 (s, 3H), 4.12 (t, J=7.0 Hz, 3H), 6.76 (d, J=8.2 Hz, 1H), 6.85 (d, J=7.9 Hz, 1H), 6.95 (s, 1H), 7.06 (t, J=7.6 Hz, 1H), 7.14 (s, 1H), 7.23 (t, J=8.2 Hz, 1H), 7.31 (d, J=8.2 Hz, 1H), 7.49 (t, J=7.8 Hz, 1H), 7.65 (s, 1H), 7.88 (d, J=8.2 Hz, 1H)

MS (C$_{29}$H$_{38}$N$_8$O; MWt. 514): Observed M+1=515

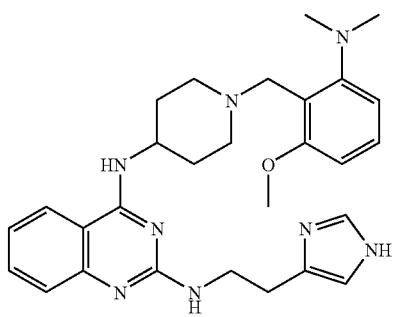

Compound 119

N2-(2-(1H-Imidazol-4-yl)ethyl)-N4-(1-(2-(dimethylamino)-6-methoxybenzyl)piperidin-4-yl)quinazoline-2,4-diamine (Compound 119)

Following General Procedure E, Compound 47 (50 mg, 0.12 mmol) and Histamine (36 mg, 0.36 mmol) were converted into Compound 119.

1H NMR (CD$_3$OD): δ 1.60-1.77 (m, 2H), 1.99 (d, J=8.5 Hz, 2H), 2.26-2.39 (m, 2H), 2.67 (s, 6H), 2.91 (t, J=7.2 Hz, 2H), 3.06 (d, J=12.3 Hz, 2H), 3.67 (t, J=7.2 Hz, 2H), 3.80 (s, 2H), 3.81 (s, 3H), 4.05-4.24 (m, 1H), 6.76 (d, J=8.5 Hz, 1H), 6.85 (s, 1H), 6.87 (s, 1H), 7.06 (t, J=7.2 Hz, 1H), 7.19-7.34 (m, 2H), 7.49 (t, J=7.2 Hz, 1H), 7.58 (s, 1H), 7.88 (d, J=8.2 Hz, 1H)

MS (C$_{28}$H$_{36}$N$_8$O; MWt. 500): Observed M+1=501

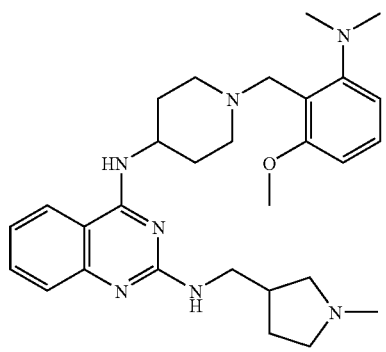

Compound 121

N4-(1-(2-(Dimethylamino)-6-methoxybenzyl)piperidin-4-yl)-N2-((1-methylpyrrolidin-3-yl)methyl)quinazoline-2,4-diamine (Compound 121)

Following General Procedure E, Compound 47 (50 mg, 0.12 mmol) and (1-methylpyrrolidin-3-yl)methanamine (36 mg, 0.36 mmol) were converted into Compound 121.

1H NMR (CD$_3$OD): δ 1.52-1.76 (m, 3H), 1.99 (d, J=8.5 Hz, 2H), 2.24-2.33 (m, 2H), 2.34 (s, 3H), 2.49-2.65 (m, 2H), 2.68 (s, 6H), 2.78 (t, J=8.8 Hz, 1H), 3.06 (d, J=12.0 Hz, 2H), 3.31 (s, 3H), 3.39 (d, J=7.0 Hz, 2H), 3.79 (s, 2H), 3.80-3.83 (m, 3H), 4.05-4.21 (m, 1H), 6.76 (d, J=7.9 Hz, 1H), 6.85 (d, J=7.9 Hz, 1H), 7.05 (t, J=7.33 Hz, 1H), 7.23 (t, J=8.2 Hz, 1H), 7.29 (d, J=8.5 Hz, 1H), 7.49 (t, J=7.2 Hz, 1H), 7.88 (d, J=7.9 Hz, 1H)

MS (C$_{29}$H$_{41}$N$_7$O; MWt. 503): Observed M+1=504

Compound 122

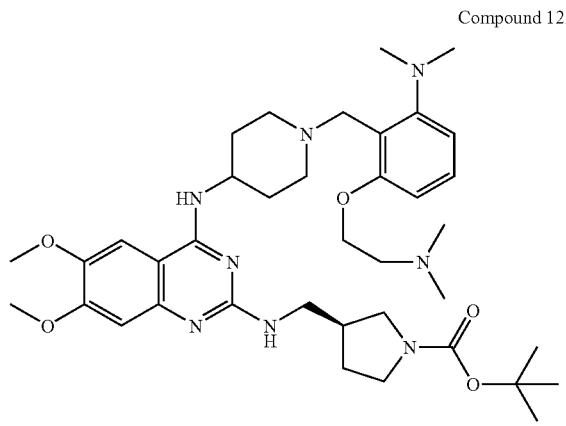

(S)-tert-Butyl 3-((4-(1-(2-(Dimethylamino)-6-(2-(dimethylamino)ethoxy)benzyl)piperidin-4-ylamino)-6,7-dimethoxyquinazolin-2-ylamino)methyl)pyrrolidine-1-carboxylate (Compound 122)

Following General Procedure D, Compound 75 (96 mg, 0.17 mmol) and (S)-tert-butyl 3-(aminomethyl)pyrrolidine-1-carboxylate (90 mg, 0.51 mmol) were converted into Compound 122.

1H NMR (CD$_3$OD): δ 1.44 (s, 9H), 1.69-1.83 (m, 1H), 2.01-2.20 (m, 2H), 2.25-2.37 (m, 1H), 2.50 (s, 6H), 2.58-2.68 (m, 1H), 2.72 (s, 6H), 2.80-2.98 (m, 4H), 3.03-3.28 (m, 4H), 3.42-3.60 (m, 6H), 3.94 (s, 3H), 3.94 (s, 3H), 4.20-4.31 (m, 2H), 4.50 (s, 2H), 6.87-7.01 (m, 2H), 7.04 (d, J=7.6 Hz, 1H), 7.40 (t, J=8.2 Hz, 0H), 7.64 (s, 1H)

MS (C$_{38}$H$_{58}$N$_8$O$_5$; MWt. 606): Observed M+1=607

Compound 123

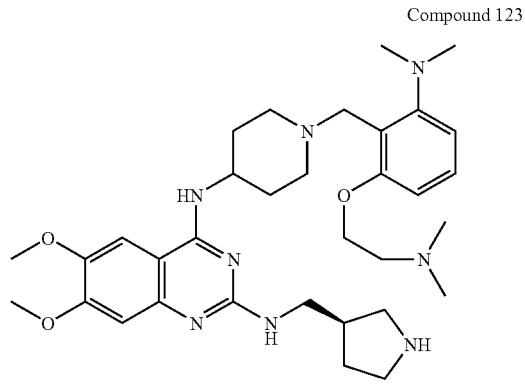

(R)—N-4-(1-(2-(Dimethylamino)-6-(2-(dimethylamino)ethoxy)benzyl)piperidin-4-yl)-6,7-dimethoxy-N2-(pyrrolidin-3-ylmethyl)quinazoline-2,4-diamine (Compound 123)

Employing General Procedure F, Compound 122 (59 mg, 0.08 mmol) and TFA (0.2 mL) were converted into Compound 123.

1H NMR (CD$_3$OD): δ 1.50-1.75 (m, 4H), 1.88-2.04 (m, 3H), 2.25-2.36 (m, 2H), 2.37 (s, 6H), 2.44-2.60 (m, 1H), 2.68 (s, 6H), 2.70-3.14 (m, 8H), 3.37 (dd, J=9.8, 7.2 Hz, 2H), 3.81 (s, 2H), 3.87 (s, 3H), 3.88 (s, 3H), 4.11 (t, J=5.7 Hz, 2H), 6.71-6.82 (m, 2H), 6.86 (d, J=7.9 Hz, 1H), 7.23 (t, J=8.2 Hz, 1H), 7.38 (s, 1H)

MS (C$_{33}$H$_{50}$N$_8$O$_3$; MWt. 503): Observed M+1=504

Compound 124

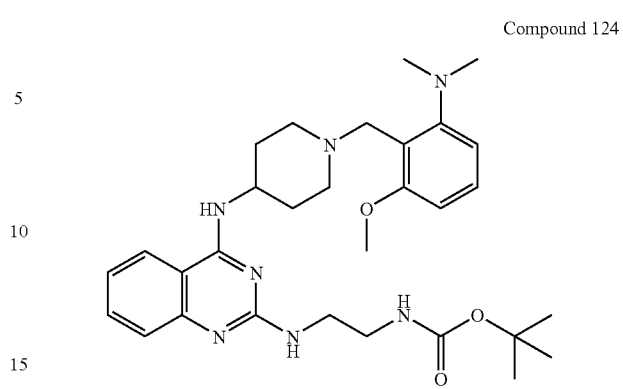

tert-Butyl 2-(4-(1-(2-(dimethylamino)-6-methoxybenzyl)piperidin-4-ylamino)quinazolin-2-ylamino)ethylcarbamate (Compound 124)

Employing General Procedure E, Compound 47 (80 mg, 0.19 mmol) and ter-butyl-N-(2-aminoethyl) carbamate (75 mg, 0.48 mmol) were converted into compound 124.

1H NMR (CD$_3$OD): δ 1.42 (s, 9H), 2.03-2.20 (m, 2H), 2.26-2.39 (m, 2H), 2.74 (s, 6H), 3.33-3.38 (m, 4H), 3.46-3.62 (m, 4H), 3.93 (s, 3H), 4.50 (s, 2H), 4.67 (br. s., 1H), 6.94 (d, J=8.5 Hz, 1H), 7.04 (d, J=8.2 Hz, 1H), 7.34 (s, 1H), 7.46 (t, J=8.4 Hz, 2H), 7.72 (t, J=7.6 Hz, 1H), 8.17 (d, J=8.2 Hz, 1H)

MS (C$_{30}$H$_{43}$N$_7$O$_3$; MWt. 549): Observed M+1=550

Compound 125

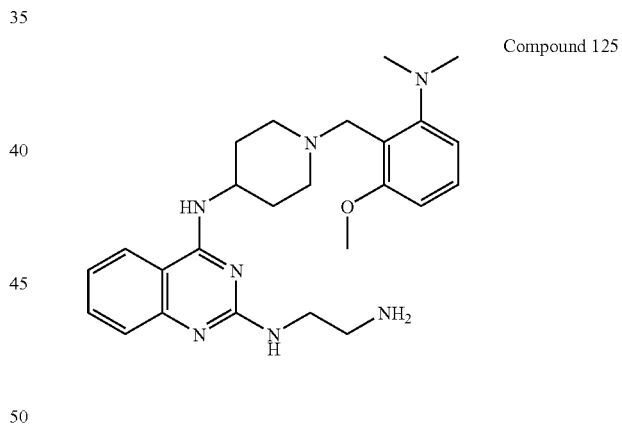

N2-(2-Aminoethyl)-N4-(1-(2-(dimethylamino)-6-methoxybenzyl)piperidin-4-yl)quinazoline-2,4-diamine (Compound 125)

Employing General Procedure F, Compound 124 (103 mg, 0.19 mmol) and TFA (0.3 mL) were converted into Compound 125.

1H NMR (CD$_3$OD): δ 1.59-1.77 (m, 2H), 1.98 (d, J=13.8 Hz, 2H), 2.29 (t, J=11.4 Hz, 2H), 2.67 (s, 6H), 2.85 (t, J=6.0 Hz, 2H), 3.04 (d, J=11.4 Hz, 2H), 3.49 (t, J=5.9 Hz, 2H), 3.77 (s, 2H), 3.81 (s, 3H), 4.07-4.24 (m, 1H), 6.75 (d, J=8.2 Hz, 1H), 6.84 (d, J=7.9 Hz, 1H), 7.06 (t, J=7.3 Hz, 1H), 7.23 (t, J=8.1 Hz, 1H), 7.32 (d, J=7.9 Hz, 1H), 7.49 (t, J=7.5 Hz, 1H), 7.88 (d, J=7.6 Hz, 1H)

MS (C$_{25}$H$_{35}$N$_7$O; MWt. 449): Observed M+1=450

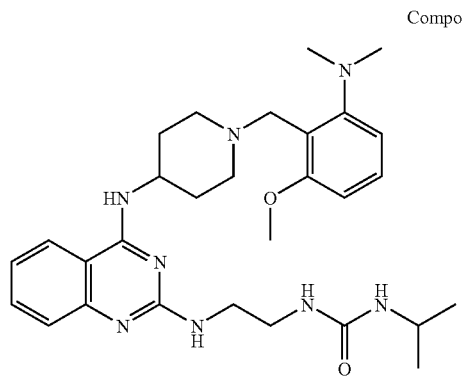

Compound 126

1-(2-(4-(1-(2-(Dimethylamino)-6-methoxybenzyl) piperidin-4-ylamino)quinazolin-2-ylamino)ethyl)-3-isopropylurea (Compound 126)

A solution of Compound 125 (15 mg, 0.03 mmol) and isopropyl isocyanate (2.8 mg, 0.03 mmol) in dichloromethane (2 mL) was stirred at room temperature for 1 h. The product (Compound 126) was purified by Neutral alumina Prep TLC plate using 10% MeOH and 90% CH$_2$Cl$_2$ solution as eluent.

1H NMR (CD$_3$OD): δ 1.07 (s, 3H), 1.09 (s, 3H), 1.59-1.77 (m, 2H), 2.01 (d, J=11.7 Hz, 2H), 2.36 (t, J=12.0 Hz, 2H), 2.68 (s, 6H), 3.07 (d, J=12.0 Hz, 2H), 3.32-3.39 (m, 2H), 3.51 (t, J=5.9 Hz, 2H), 3.72-3.81 (m, 1H), 3.81 (s, 2H), 3.83 (s, 3H), 4.05-4.24 (m, 1H), 6.77 (d, J=7.9 Hz, 1H), 6.86 (d, J=8.2 Hz, 1H), 7.07 (t, J=7.0 Hz, 1H), 7.25 (t, J=8.2 Hz, 1H), 7.31 (d, J=8.2 Hz, 1H), 7.50 (t, J=7.6 Hz, 1H), 7.88 (d, J=7.9 Hz, 1H)

MS (C$_{29}$H$_{42}$N$_8$O$_2$; MWt. 534): Observed M+1=535

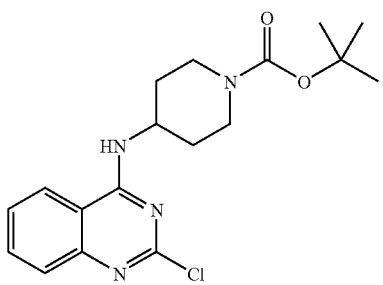

Compound 127 tert-Butyl 4-(2-Chloroquinazolin-4-ylamino)piperidine-1-carboxylate (Compound 127).

To a solution of 2,4-dichloroquinazoline (2 g, 10.05 mmol) in THF (50 ml) at 0° C. was added tert-butyl 4-aminopiperidine-1-carboxylate (2.2 g, 11.05 mmol), followed by TEA (2.8 ml, 20.1 mmol) and catalyst DMAP (3 mg). The reaction mixtures was then warmed up to room temperature and stirred for 20 hours. The product was extracted with EtOAc (×2). The organic layers were combined and washed with water, and brine, and dried (MgSO$_4$) and concentrated under vacuum. The product was isolated after silica gel column chromatography using 20% EtOAc and 80% hexane as eluent.

$^1$H NMR (300 MHz, CD$_3$OD) δ 8.16 (d, J=7.62 Hz, 1H), 7.71-7.86 (m, 1H), 7.60 (d, J=7.91 Hz, 1H), 7.45-7.56 (m, 1H), 4.37-4.53 (m, J=3.96, 4.25, 11.43, 11.43 Hz, 1H), 4.17

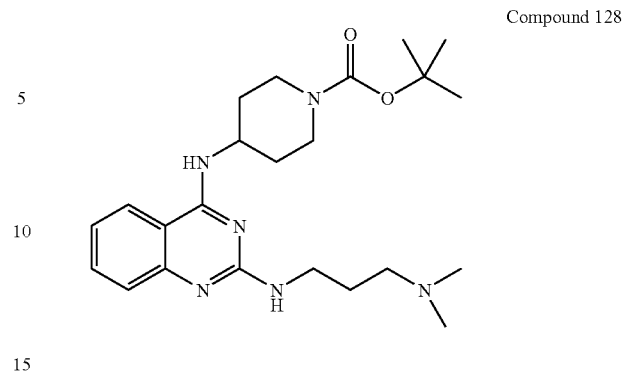

Compound 128 tert-Butyl 4-(2-(3-(Dimethylamino)propylamino)quinazolin-4-ylamino)piperidine-1-carboxylate (Compound 128).

tert-Butyl 4-(2-chloroquinazolin-4-ylamino)piperidine-1-carboxylate (3.34 g. 9.21 mmol) and 3-(N,N-dimethyl amino)propylamine (2.9 ml, 23.03 mmol) in dioxane (15 ml) in a sealed-tube were heated to 120° C. overnight. The solvent was removed and the crude product was purified by silica gel column chromatography using 10% NH$_3$ ca. 7 N MeOH in CH$_2$Cl$_2$ and 90% CH$_2$Cl$_2$ solution as eluent to produce the title compound as a pure white solid.

$^1$H NMR (300 MHz, CD$_3$OD) δ 7.84-7.97 (m, 1H), 7.52 (ddd, J=1.47, 7.03, 8.50 Hz, 1H), 7.33 (d, J=8.20 Hz, 1H), 7.01-7.16 (m, 1H), 4.27-4.48 (m, 1H), 4.15 (d, J=13.48 Hz, 2H), 3.47 (t, J=6.89 Hz, 2H), 2.94 (t, J=14.51 Hz, 2H), 2.41-2.59 (m, 2H), 2.31 (s, 6H), 2.06 (d, J=9.67 Hz, 2H), 1.76-1.95 (m, 2H), 1.49-1.72 (m, 2H), 1.48 (s, 9H).

MS (C$_{23}$H$_{36}$N$_6$O$_2$; MWt. 428): Observed M+1=429.

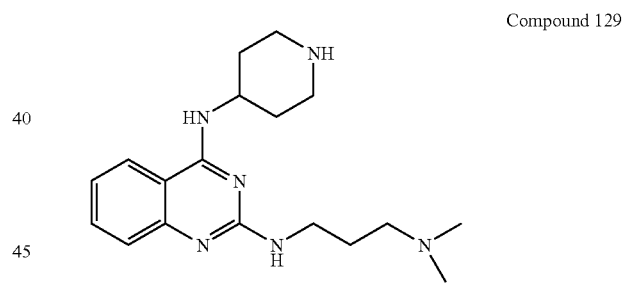

Compound 129

N2-(3-(Dimethylamino)propyl)-N4-(piperidin-4-yl) quinazoline-2,4-diamine (Compound 129).

tert-Butyl 4-(2-(3-(dimethylamino)propylamino)quinazolin-4-ylamino)piperidine-1-carboxylate (3.3 g, 7.71 mmol) in CH$_2$Cl$_2$ (20 ml) at 0° C. was added CF$_3$COOH (4 ml, 53.9 mmol) and the reaction was stirred at room temperature overnight. The reaction mixture was then neutralized with 7 N NH$_3$-MeOH. The resulting white solid was filtered away. The filtrate was concentrated and purified by silica gel column chromatography using 10% NH$_3$ ca. 7 N MeOH in CH$_2$Cl$_2$ and 90% CH$_2$Cl$_2$ solution as eluent to obtain the title compound as a pure white solid.

$^1$H NMR (300 MHz, CD$_3$OD) δ 8.11 (d, J=8.20 Hz, 1H), 7.70 (t, J=7.18 Hz, 1H), 7.43 (d, J=8.50 Hz, 1H), 7.30 (t, J=7.77 Hz, 1H), 4.37-4.67 (m, 1H), 3.43-3.69 (m, 4H), 3.00-3.25 (m, 4H), 2.80 (s, 6H), 2.22-2.44 (m, 2H), 1.80-2.15 (m, 4H).

MS (C$_{18}$H$_{28}$N$_6$; MWt. 328): Observed M+1=329.

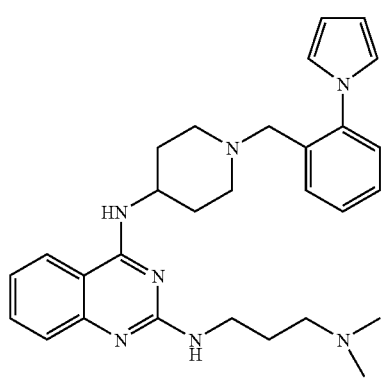

Compound 130

N4-(1-(2-(1H-Pyrrol-1-yl)benzyl)piperidin-4-yl)-N2-(3-(dimethylamino)propyl)quinazoline-2,4-diamine (Compound 130)

N2-(3-(Dimethylamino)propyl)-N4-(piperidin-4-yl) quinazoline-2,4-diamine (62 mg, 0.189 mmol), 2-(1H-pyrrol-1-yl)benzaldehyde (32 mg, 0.189 mmol), NaCNBH$_3$ (12 mg, 0.190 mmol) and ZnCl$_2$ (13 mg, 0.09 mmol) in MeOH (1 ml) was stirred at room temperature overnight. The solvent was removed under reduced pressure, and the crude product was purified by silica gel chromatography using 5% NH$_3$ ca. 7 N MeOH in CH$_2$Cl$_2$ and 90% CH$_2$Cl$_2$ solution as eluent to produce the title compound as a brown oil.

$^1$H NMR (300 MHz, CD$_3$OD) δ 7.88 (d, J=7.91 Hz, 1H), 7.53-7.65 (m, 1H), 7.42-7.53 (m, 1H), 7.18-7.43 (m, 4H), 7.05 (t, J=7.62 Hz, 1H), 6.91 (t, J=2.05 Hz, 2H), 6.25 (t, J=1.90 Hz, 2H), 3.96-4.26 (m, 1H), 3.37-3.50 (m, 4H), 2.85 (d, J=11.72 Hz, 2H), 2.34-2.52 (m, 2H), 2.24 (s, 6H), 1.92-2.11 (m, 4H), 1.54-1.90 (m, 4H).

MS (C$_{29}$H$_{37}$N$_7$; MWt. 483): Observed M+1=484.

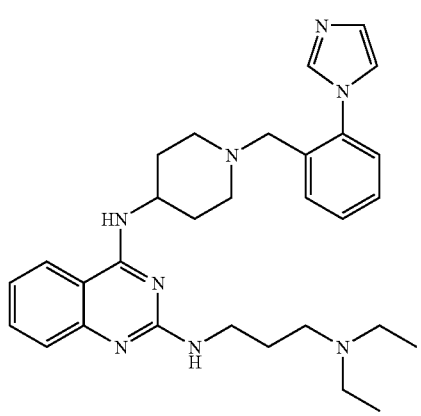

Compound 131

N4-(1-(2-(1H-Imidazol-1-yl)benzyl)piperidin-4-yl)-N2-(3-(diethylamino)propyl)quinazoline-2,4-diamine (Compound 131)

To a solution of 57 mg (0.160 mmol) N2-(3-(diethylamino)propyl)-N4-(piperidin-4-yl)quinazoline-2,4-diamine (prepared analogously to Compound 129) and 2-(1H-imidazol-1-yl)benzaldehyde (28 mg, 0.160 mmol) in MeOH (1 ml) was added NaCNBH$_3$ (10 mg, 0.160 mmol) and ZnCl$_2$ (11 mg, 0.08 mmol), The solution was stirred at room temperature overnight. Solvent was removed under reduced pressure. The crude product was purified by silica gel chromatography using 5% NH$_3$ ca. 7 N MeOH in CH$_2$Cl$_2$ and 90% CH$_2$Cl$_2$ solution as eluent to produce the title compound as a brown oil.

$^1$H NMR (300 MHz, CDCl$_3$) δ 7.79-7.85 (m, 1H), 7.45-7.57 (m, 3H), 7.35-7.45 (m, 3H), 7.26-7.33 (m, 1H), 7.21-7.25 (m, 1H), 7.17-7.21 (m, 1H), 7.08 (td, J=1.32, 7.55 Hz, 1H), 5.58 (bs, 1H), 4.03-4.23 (m, J=3.66, 7.40, 7.40 Hz, 1H), 3.53 (t, J=6.59 Hz, 2H), 3.29 (s, 2H), 2.69-2.84 (m, 2H), 2.60 (q, J=7.03 Hz, 6H), 1.98-2.23 (m, 4H), 1.72-1.87 (m, 2H), 1.41-1.65 (m, 2H), 1.06 (t, J=7.18 Hz, 6H).

MS (C$_{30}$H$_{40}$N$_8$; MWt. 512): Observed M+1=513.

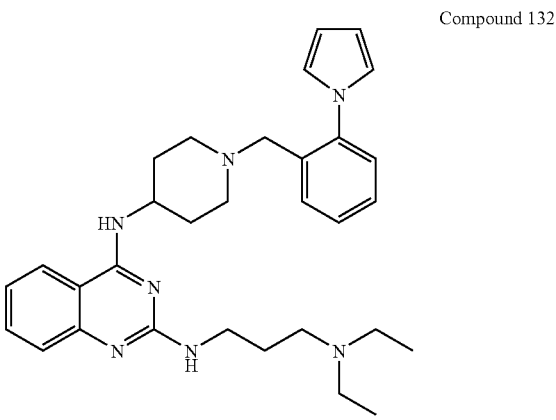

Compound 132

N4-(1-(2-(1H-Pyrrol-1-yl)benzyl)piperidin-4-yl)-N2-(3-(diethylamino)propyl)quinazoline-2,4-diamine (Compound 132)

A solution of 56 mg (0.155 mmol) N2-(3-(diethylamino)propyl)-N4-(piperidin-4-yl)quinazoline-2,4-diamine (prepared analogously to Compound 129) 2-(1H-pyrrol-1-yl)benzaldehyde (27 mg, 0.157 mmol), NaCNBH$_3$ (10 mg, 0.160 mmol) and ZnCl$_2$ (11 mg, 0.08 mmol) in MeOH (1 ml) was stirred at room temperature overnight to obtain the target compound.

$^1$H NMR (300 MHz, CDCl$_3$) δ 7.24-7.59 (m, 7H), 7.04 (ddd, J=1.32, 6.81, 8.28 Hz, 1H), 6.95 (t, J=2.05 Hz, 2H), 6.31 (t, J=2.20 Hz, 2H), 5.54 (br. s., 1H), 5.29 (d, J=7.03 Hz, 1H), 4.01-4.28 (m, 1H), 3.45-3.56 (m, 2H), 3.34 (s, 2H), 2.74-2.88 (m, 2H), 2.43-2.63 (m, 6H), 2.02-2.23 (m, 4H), 1.69-1.85 (m, 2H), 1.47-1.65 (m, 2H), 1.04 (t, J=7.03 Hz, 6H).

MS (C$_{31}$H$_{41}$N$_7$; MWt. 511): Observed M+1=512.

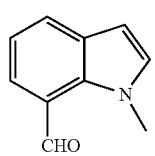

Compound 132

1-Methyl-1H-indole-7-carbaldehyde (Compound 132)

A solution of 1H-indole-7-carbaldehyde (500 mg, 3.444 mmol) and dimethylsulfate (478 mg, 3.789 mmol) in DMF (3 ml) was cannulated into a suspension of NaH (99 mg, 95% in mineral oil, 4.133 mmol) in DMF (2 ml) at 0° C. The reaction was stirred and allowed to warmed up to room temperature for 1 hour. The reaction was quenched with water and the product was extracted with EtOAC (×2). The organic layers were combined and washed with water, and brine, and dried (MgSO$_4$) and the solution was concentrated to produce a light pink solid, which was used in the next step without further purification.

$^1$H NMR (300 MHz, CDCl$_3$) δ 10.22 (s, 1H), 7.88 (dd, J=1.17, 7.91 Hz, 1H), 7.70 (dd, J=1.17, 7.33 Hz, 1H), 7.22 (t, J=7.62 Hz, 2H), 7.08 (d, J=3.22 Hz, 1H), 6.58 (d, J=3.22 Hz, 1H), 4.14 (s, 3H).

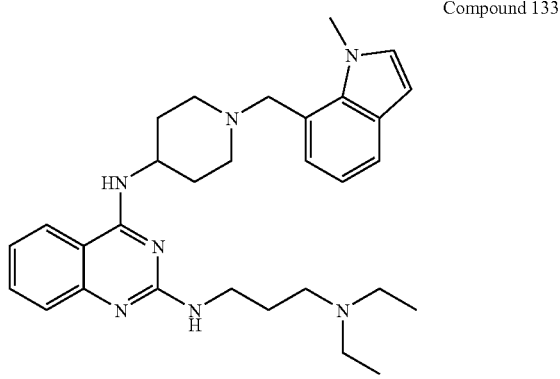

Compound 133

N2-(3-(Diethylamino)propyl)-N4-(1-((1-methyl-1H-indol-7-yl)methyl)piperidin-4-yl)quinazoline-2,4-diamine (Compound 133)

A solution of N2-(3-(diethylamino)propyl)-N4-(piperidin-4-yl)quinazoline-2,4-diamine (56 mg, 0.157 mmol), 1-methyl-1H-indole-7-carbaldehyde (27 mg, 0.157 mmol), NaCNBH$_3$ (10 mg, 0.160 mmol) and ZnCl$_2$ (11 mg, 0.08 mmol) in MeOH (1 ml) was stirred at room temperature overnight to obtain the target compound.

$^1$H NMR (300 MHz, CDCl$_3$) δ 7.41-7.58 (m, 4H), 6.93-7.09 (m, 4H), 6.47 (d, J=2.93 Hz, 1H), 5.78 (br. s., 1H), 5.43 (br. s., 1H), 4.05-4.31 (m, 4H), 3.80 (s, 2H), 3.54 (t, J=6.59 Hz, 2H), 2.91 (d, J=11.72 Hz, 2H), 2.47-2.70 (m, 6H), 2.01-2.31 (m, 4H), 1.72-1.89 (m, J=6.74, 6.94, 6.94, 6.94 Hz, 2H), 1.41-1.63 (m, 2H), 1.01-1.16 (m, 6H).

MS (C$_{30}$H$_{41}$N$_7$; MWt. 499): Observed M+1=500.

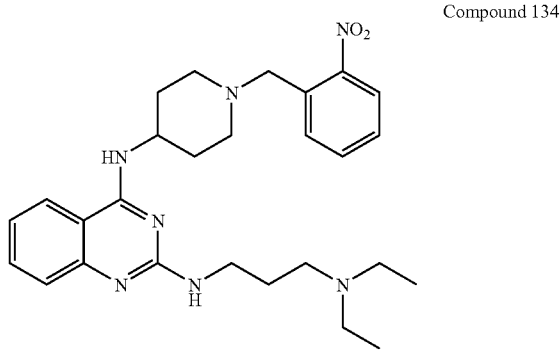

Compound 134

(4-(2-(3-(Diethylamino)propylamino)quinazolin-4-ylamino)piperidin-1-yl)(2-nitrophenyl)methanone (Compound 134)

A solution of N2-(3-(diethylamino)propyl)-N4-(piperidin-4-yl)quinazoline-2,4-diamine (55 mg, 0.154 mmol) and 2-nitrobenzoyl chloride (57 mg, 0.309 mmol) and TEA (43 ul, 0.309 mmol) in CH$_2$Cl$_2$ was stirred at room temperature for 1 hour. The crude reaction was directly loaded on the silica gel column and isolated the product using 10% NH$_3$ ca. 7 N MeOH in CH$_2$Cl$_2$ and 90% CH$_2$Cl$_2$ solution as eluent to gain a yellow oil.

$^1$H NMR (300 MHz, CD$_3$OD) δ 8.26 (d, 1H), 7.78-7.99 (m, 2H), 7.64-7.77 (m, 1H), 7.44-7.58 (m, 2H), 7.32 (d, J=8.50 Hz, 1H), 7.02-7.14 (m, 1H), 4.40-4.63 (m, J=11.43, 11.43 Hz, 1H), 3.39-3.57 (m, 2H), 3.03-3.19 (m, 2H), 2.50-2.71 (m, 7H), 1.61-2.33 (m, 7H), 1.05 (t, J=7.18 Hz, 6H).

MS (C$_{27}$H$_{35}$N$_7$O$_3$; MWt. 505): Observed M+1=506.

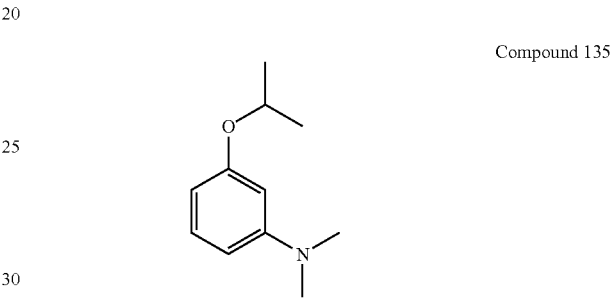

Compound 135

3-Isopropoxy-N,N-dimethylaniline (Compound 135)

To a solution of 3-(dimethylamino)phenol (2.0 g, 14.60 mmol) in acetone (40.0 mL) were added K$_2$CO$_3$ (20.2 g, 146.0 mmol) and 2-iodopropane (2.20 mL, 21.90 mmol), and the reaction was refluxed for 18 h, then cooled to room temperature, and filtered through Celite. The solvent was removed under vacuum, and the residue was purified by silica gel chromatography using ethyl acetate (20%) and hexanes (80%) as eluent to produce Compound 135 as yellow oil.

$^1$HNMR (CDCl$_3$): δ ppm 1.34 (d, J=6.15 Hz, 6H), 2.93 (s, 6H), 4.56 (m, 1H), 6.28-6.39 (m, 3H), 7.13 (t, J=8.50 Hz, 1H).

General Procedure G

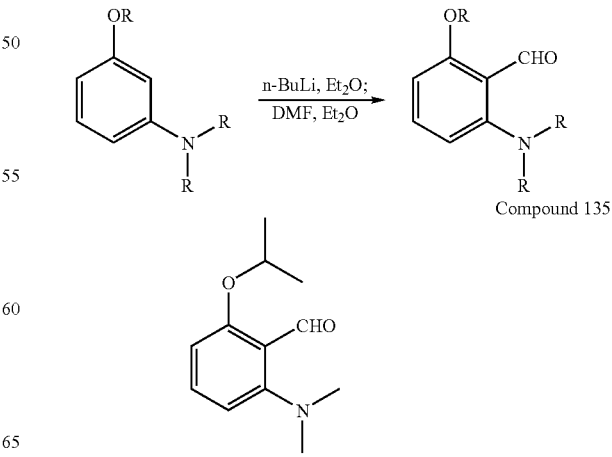

Compound 135

2-(Dimethylamino)-6-isopropoxybenzaldehyde (Compound 135). General Procedure G To a solution of compound A (1.59 g, 8.85 mmol) in Et$_2$O (10.0 mL) at room temperature under argon was added a 2.5M of n-BuLi solution (4.0 mL, 9.74 mmol). The reaction was refluxed for 20 h, and then cooled to room temperature. A solution of DMF (1.40 mL, 17.70 mmol) in Et$_2$O (5.0 mL) was added, and the reaction was stirred for 3 h, and then quenched with water. The product was extracted with EtOAc, and washed with brine, and dried over MgSO$_4$, and filtered. The solvent was removed under vacuum, and the residue was purified by silica gel chromatography with 7N NH$_3$ in MeOH (5%) and CH$_2$Cl$_2$ (95%) as eluent to afford the product as fluorescent green oil.

$^1$HNMR (CDCl$_3$): δ ppm 1.36 (d, J=6.15 Hz, 6H), 2.87 (s, 6H), 4.52-4.69 (m, 1H), 6.39 (3, J=8.20 Hz, 1H), 6.51 (d, J=8.20 Hz, 1H), 722-7.30 (m, 1H), 10.36 (s, 1H).

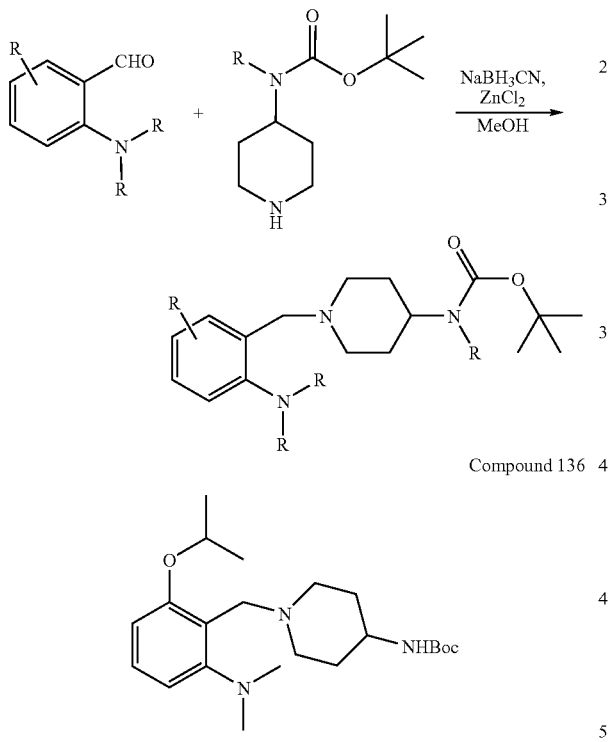

Compound 136 tert-Butyl 1-(2-(dimethylamino)-6-isopropoxybenzyl)piperidin-4-ylcarbamate (Compound 136). General Procedure H To a solution of compound 135 (0.117 g, 0.57 mmol) and 4-(N-Boc amino)piperidine (0.14 g, 0.68 mmol) in MeOH (5.0 mL) was added a solution of NaBH$_3$CN (0.036 g, 0.57 mmol) and ZnCl$_2$ (0.039 g, 0.29 mmol) in MeOH (5.0 mL), and the reaction was stirred for 18 h. The solvent was then removed, and the residue was purified by silica gel flash chromatography with 7N NH$_3$ in MeOH (5%) and CH$_2$Cl$_2$ (95%) as eluent to afford Compound 136 as a yellow oil.

$^1$HNMR (CD$_3$OD): δ ppm 1.32 (d, J=6.15, 6H), 1.42 (m, 11H), 1.72-1.86 (m, 2H), 2.29 (t, J=11.28 Hz, 2H), 2.67 (s, 6H), 3.00 (d, J=12.60 Hz, 2H), 3.20-3.30 (m, 1H), 3.76 (s, 2H), 4.50-4.66 (m, 1H), 6.73 (d, J=8.20 Hz, 1H), 6.80 (d, J=8.20 Hz, 1H), 7.19 (t, J=8.20 Hz, 1H).

MS (C$_{22}$H$_{37}$N$_3$O$_3$; MWt. 391): Observed M+1=392.

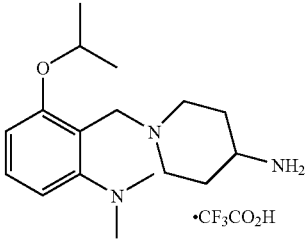

Compound 137

1-(2-(Dimethylamino)-6-isopropoxybenzyl)piperidin-4-amine (Compound 137)

Following General Procedure B, Compound 136 (110 mg, 0.28 mmol) and CF$_3$CO$_2$H (0.50 mL) were coverted into Compound 137.

$^1$HNMR (CD$_3$OD): δ ppm 1.32 (d, J=6.15 Hz, 6H), 1.48 (td, J=11.79, 3.37 Hz, 2H), 1.84 (d, J=12.60 Hz, 2H), 2.27-2.43 (m, 2H), 2.68 (s, 6H), 2.72-2.82 (m, 1H), 3.01-3.14 (m, 2H), 3.82 (s, 2H), 4.53-4.68 (m, 1H), 6.75 (d, J=8.20 Hz, 1H), 6.82 (d, J=7.33 Hz, 1H), 7.21 (t, J=8.06 Hz, 1H).

MS (C$_{17}$H$_{29}$N$_3$O; MWt. 291): Observed M+1=292.

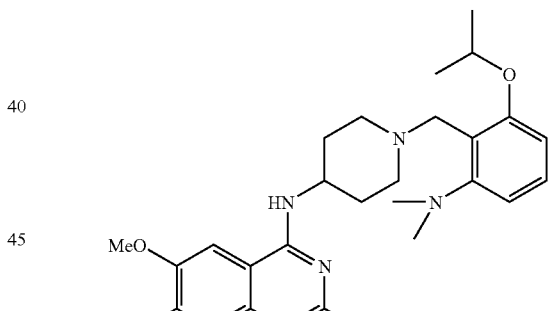

Compound 138

2-Chloro-N-(1-(2-(dimethylamino)-6-isopropoxybenzyl)piperidin-4-yl)-6,7-dimethoxyquinazolin-4-amine (Compound 138)

Following General Procedure C, Compound 137 (41 mg, 0.14 mmol) and 2,4-dicholoro-6,7-dimethoxyquinazoline (0.55 mg, 0.21 mmol), were converted into Compound 138.

$^1$HNMR (CD$_3$OD): δ ppm 1.35 (d, J=5.86 Hz, 6H), 1.68 (dd, J=12.16, 3.66 Hz, 2H), 1.98 (dd, J=12.01, 2.05 Hz, 2H), 2.26-2.41 (m, 2H), 2.71 (s, 6H), 3.12 (d, J=12.01 Hz, 2H), 3.78 (s, 2H), 3.92 (d, J=1.17 Hz, 6H), 4.16 (m, 1H), 4.53-4.67 (m, 1H), 6.74 (d, J=8.20 Hz, 1H), 6.82 (d, J=7.03 Hz, 1H), 6.92 (s, 1H), 7.20 (t, J=8.20 Hz, 1H), 7.49 (s, 1H).

MS (C$_{27}$H$_{36}$ClN$_5$O$_3$; MWt. 513): Observed M+1=514.

Compound 139

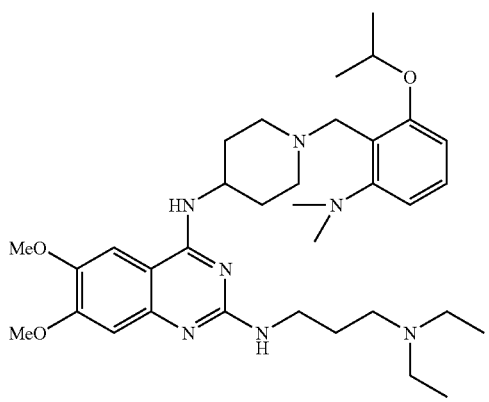

N~2~-[3-(Diethylamino)propyl]-N~4~-{1-[2-(dimethylamino)-6-isopropoxybenzyl]piperidin-4-yl}-6,7-dimethoxyquinazoline-2,4-diamine (Compound 139)

Following General Procedure D, Compound 138 (29 mg, 0.056 mmol) and 3-(diethylamino)propylamine (26 mL, 0.17 mmol) were converted into Compound 139.

$^1$HNMR (CD$_3$OD): δ ppm 1.30 (d, J=5.86 Hz, 6H), 1.40 (d, J=5.86 Hz, 6H), 1.91-1.97 (m, 2H), 2.00-2.17 (m, 4H), 2.27-2.41 (m, 2H), 2.76 (s, 6H), 2.82 (d, J=7.62 Hz, 1H), 3.04-3.13 (m, 1H), 3.20 (d, J=7.03 Hz, 6H), 3.49-3.67 (m, 4H), 3.83-3.90 (m, 1H), 8.94 (d, J=4.69 Hz, 6H), 4.51 (s, 2H), 6.90-7.03 (m, 3H), 7.43 (t, J=8.20 Hz, 1H), 7.61 (s, 1H).

MS (C$_{34}$H$_{53}$N$_7$O$_3$; MWt. 607): Observed M+1=608.

Compound 140

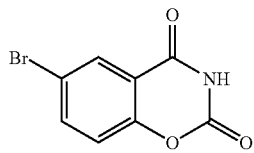

6-Bromo-2H-benzo[e][1,3]oxazine-2,4(3H)-dione (Compound 140)

A mixture of methyl-2-amino-5-bromobenzoate and urea was stirred at 200° C. for 1 h, then cooled to room temperature and washed with H$_2$O. The product, Compound 140, was collected under suction as a brown solid.

$^1$HNMR (CD$_3$OD): δ ppm 7.11 (d, J=8.50 Hz, 1H), 7.74 (d, J=2.64 Hz, 1H), 8.10 (s, 1H).

Compound 141

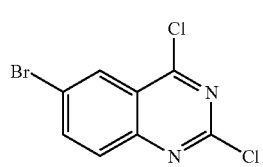

6-Bromo-2,4-dichloroquinazoline (Compound 141)

A mixture of Compound 140 (2.55 g, 10.58 mmol), POCl$_3$ (16.0 mL), and N,N-dimethylaniline (0.60 mL) was refluxed for 16 h, then cooled to room temperature. The solvent was removed to afford 5.6 g of a yellow solid, which was boiled with aqueous NaOH 1N, cooled and kept at 20° C. for 30 min, then acidified with concentrated HCl. The solid G was collected and washed with water, and used for the next step without further purification.

$^1$HNMR (CD$_3$OD): δ ppm 8.19 (d, J=2.05 Hz, 1H), 8.22 (d, J=2.34 Hz, 1H), 8.51 (d, J=2.05 Hz, 1H).

Compound 142

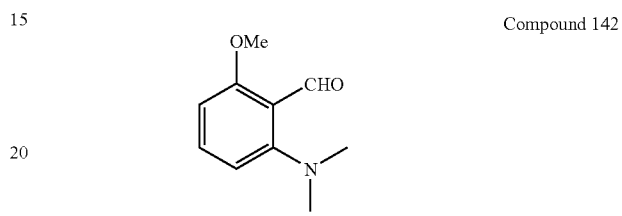

2-(Dimethylamino)-6-methoxybenzaldehyde (Compound 142)

Following General Procedure G, 3-dimethylaminoanisole (1.0 g, 6.62 mmol) was converted into Compound 142.

$^1$HNMR (CDCl$_3$): δ ppm 2.90 (s, 6H), 3.87 (s, 3H), 6.42 (d, J=8.20 Hz, 1H), 6.57 (d, J=8.50 Hz, 1H), 7.33 (t, J=8.35 Hz, 1H), 10.32 (s, 1H).

Compound 143

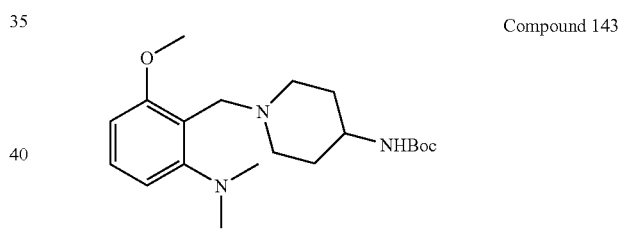

tert-Butyl 1-(2-(dimethylamino)-6-methoxybenzyl)piperidin-4-ylcarbamate (Compound 143)

Following General Procedure H, Compound 142 (0.53 g, 2.96 mmol) and 4-(N-Boc amino)-piperidine (0.71 g, 3.55 mmol) were converted into Compound 143.

$^1$HNMR (CD$_3$OD): δ ppm 1.44 (s, 9H), 1.64-1.86 (m, 2H), 2.04 (dd, J=14.21, 3.08 Hz, 2H), 2.69 (s, 6H), 3.07 (d, J=1.47 Hz, 2H), 3.51-3.66 (m, 1H), 3.90 (s, 3H), 4.40 (s, 2H), 6.90 (d, J=8.50 Hz, 1H), 7.00 (d, J=8.21 Hz, 1H), 7.42 (t, J=8.35 Hz, 1H).

Compound 144

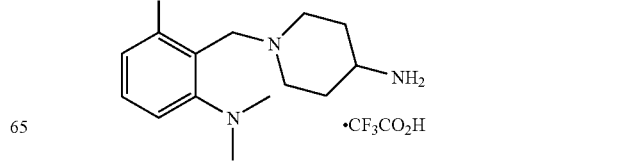

1-(2-(Dimethylamino)-6-methoxybenzyl)piperidin-4-amine 2,2,2-trifluoroacetate (Compound 144)

Following General Procedure B, Compound 143 (0.32 g, 0.96 mmol) was converted into Compound 144.

¹HNMR (CD$_3$OD): δ ppm 1.88-2.08 (m, 2H), 2.26 (d, J=11.43 Hz, 2H), 2.94 (s, 6H), 2.97-3.11 (m, 2H), 3.40-3.54 (m, 3H), 4.14 (s, 3H), 6.75 (d, J=7.62 Hz, 1H), 6.84 (d, J=1.17 Hz, 1H), 7.25 (t, J=7.77 Hz, 1H).

Compound 145

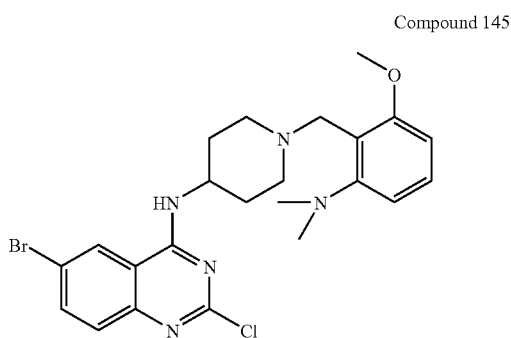

6-Bromo-2-chloro-N-(1-(2-(dimethylamino)-6-methoxybenzyl)piperidin-4-yl)quinazolin-4-amine (Compound 145)

Following General Procedure C, Compound 141 (2.60 g, 4.71 mmol) and Compound 144 (0.74 g, 2.84 mmol) were converted into Compound 145.

¹HNMR (CD$_3$OD): δ ppm 1.77-1.99 (m, 2H), 2.15 (m, 2H), 2.70 (m, 8H), 3.35 (s, 1H), 3.86 (s, 3H), 4.12 (br. s., 2H), 4.22-4.41 (m, 1H), 6.79-6.87 (m, 1H), 6.91-7.00 (m, 1H), 7.33 (s, 2H).

MS (C$_{23}$H$_{27}$BrClN$_5$O; MWt. 504): Observed M=504; M+2=506.

Compound 146

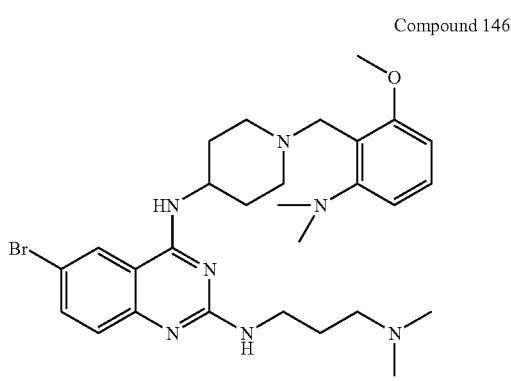

6-Bromo-N~4~-{1-[2-(dimethylamino)-6-methoxybenzyl]piperidin-4-yl}-N~2~-[3-(dimethylamino)propyl]quinazoline-2,4-diamine (Compound 146)

Following General Procedure D, Compound 145 (30 mg, 0.060 mmol) and 3-(dimethylamino)propylamine (25 mL, 0.18 mmol) were converted into Compound 146.

¹HNMR (CDCl$_3$): δ ppm 0.94 (t, J=7.33 Hz, 2H), 1.32-1.49 (m, 2H), 1.51-1.71 (m, 4H), 1.80 (m, 2H), 2.04 (d, J=10.55 Hz, 4H), 2.26 (s, 6H), 2.40 (d, J=7.62 Hz, 4H), 2.79 (s, 6H), 2.98 (d, J=12.60 Hz, 2H), 3.45-3.58 (m, 2H), 3.65 (t, J=6.59 Hz, 2H), 3.74 (s, 2H), 3.82 (s, 3H), 4.13 (br.s., 1H), 6.66 (d, J=7.91 Hz, 1H), 6.80 (d, J=7.62 Hz, 1H), 7.18-7.36 (m, 2H).

MS (C$_{28}$H$_{40}$BrN$_7$O; MWt. 570): Observed M=570; M+2=572.

Compound 147

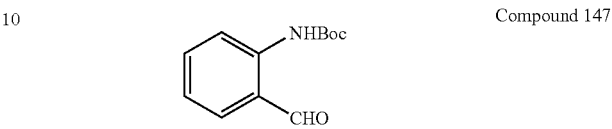

tert-Butyl-2-formylphenylcarbamate (Compound 147)

A mixture of Boc-2-aminobenzylalcohol (0.95 g, 4.26 mmol), TPAP (0.10 g), and NMO (1.0 g, 8.52 mmol) in CH$_2$Cl$_2$ was stirred at room temperature for 18 h, then filtered through Celite. The solvent was removed, and the residue was purified by silica gel flash chromatography with EtOAc (35%) and hexanes (65%) as eluent to produce Compound 147 as a yellow oil.

¹HNMR (CDCl$_3$): δ ppm 1.46 (s, 9H), 7.04 (dd, J=14.92, 0.98 Hz, 1H), 7.48 (dd, J=15.77, 1.35 Hz, 1H), 7.53 (dd, J=7.58, 1.71 Hz, 1H), 8.37 (d, J=8.56 Hz, 1H), 9.81 (s, 1H).

Compound 148

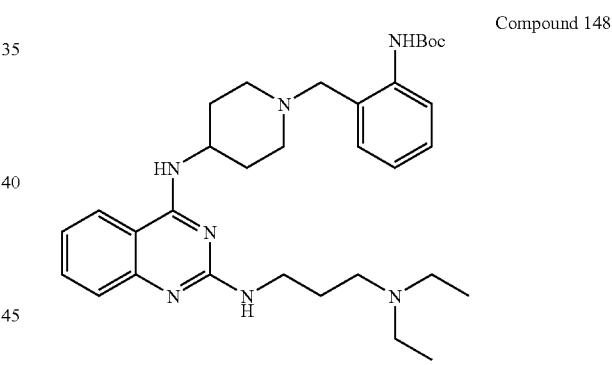

tert-Butyl 2-((4-(2-(3-(diethylamino)propylamino)quinazolin-4-ylamino)piperidin-1-yl)methyl)phenylcarbamate (Compound 148)

Following General Procedure H, Compound 147 (0.54 g, 2.45 mmol) and compound N (0.96 g, 2.70 mmol) were converted into Compound 148.

¹HNMR (CD$_3$OD): d ppm 1.33 (t, J=7.33 Hz, 6H), 1.54 (s, 9H), 1.85 (dd, J=11.43 Hz, 2.34 Hz, 2H), 2.13 (dd, J=7.18, 3.96 Hz, 3H), 2.38 (br. s., 2H), 3.03 (br. s., 2H), 3.27-3.38 (m, 4H), 3.68 (t, J=6.59 Hz, 2H), 4.39 (dd, J=15.38, 7.18 Hz, 1H), 7.03 (d, J=7.33 Hz, 1H), 7.20 (d, J=7.03 Hz, 1H), 7.28 (dd, J=15.53, 1.47 Hz, 1H), 7.39 (t, J=7.76 Hz, 1H), 7.47 (d, J=8.50 Hz, 1H), 7.77 (dd, J=15.68, 1.32 Hz, 1H), 8.19 (d, J=8.20 Hz, 1H).

MS (C$_{32}$H$_{47}$N$_7$O$_2$; MWt. 561): Observed M+1=562.

75

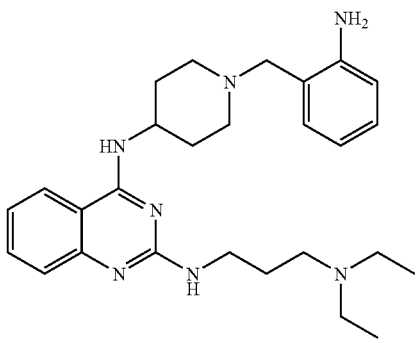

Compound 149

N~4~-[1-(2-Aminobenzyl)piperidin-4-yl]-N~2~-[3-(diethylamino)propyl]quinazoline-2,4-diamine (Compound 149)

Following General Procedure F, Compound 148 (1.188 g, 2.12 mmol) was converted into Compound 149.

¹HNMR (CD₃OD): δ ppm 1.33 (t, J=7.33 Hz, 6H), 1.93 (s, 2H), 2.13 (t, J=8.35 Hz, 2H), 2.21-2.38 (m, 2H), 3.25-3.33 (m, 4H), 3.53 (d, J=12.60 Hz, 2H), 3.68 (t, J=6.01 Hz, 2H), 4.24 (s, 2H), 4.60 (br. s., 1H), 6.69 (t, J=7.47 Hz, 1H), 6.81 (d, J=7.91 Hz, 1H), 7.14 (t, J=7.76 Hz, 1H), 7.22 (d, J=6.74 Hz, 1H), 7.34 (t, J=7.76 Hz, 1H), 7.72 (t, J=7.76 Hz, 1H), 8.22 (d, J=7.91 Hz, 1H).

MS ($C_{27}H_{39}N_7$; MWt. 461): Observed M+1=462.

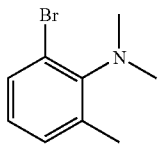

Compound 150

2-Bromo-N,N,6-trimethylaniline (Compound 150)

To a solution of 2-bromo-6-methylaniline (0.5 g, 2.69 mmol) in acetonitrile (30.0 mL) at ambient temperature was added a 37% aqueous solution of formaldehyde (4.0 mL, 53.6 mmol), followed by NaBH₃CN (1.40 g, 22.1 mmol). The pH of the reaction was adjusted to pH 5-6 with glacial acetic acid, and the reaction was stirred for 4 h, then the solvent was removed. The residue was dissolved in EtOAc, and basified with NaOH 2N, dried over MgSO₄, and filtered. The solvent was removed, and the residue was purified by silica gel flash chromatography with EtOAc (15%) and hexanes (85%) as eluent to produce Compound 150 as a clear oil.

¹HNMR (CDCl₃): δ ppm 2.23 (s, 3H), 2.76 (s, 6H), 6.78 (t, J=7.76 Hz, 1H), 7.00 (d, J=7.33 Hz, 1H), 7.27 (d, J=7.91 Hz, 1H).

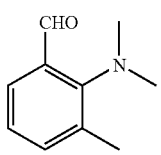

Compound 151

76

2-(Dimethylamino)-3-methylbenzaldehyde (Compound 151)

To a solution of Compound 150 (0.17 g, 0.81 mmol) in Et₂O (5.0 mL) at −78° C. under Argon atmosphere was added dropwise a solution of 1.7M t-BuLi in pentane (1.0 mL, 1.79 mmol), and the reaction was stirred for 1 h. DMF (0.25 mL, 3.24 mmol) was added, and the cooling bath was removed. After 1h15, the reaction was cooled to 0° C., and saturated NH₄Cl was added. The mixture was extracted with EtOAc, washed with brine, dried over MgSO₄, and filtered. The solvent was removed, and the residue was purified by silica gel flash chromatography with EtOAc (15%) and hexanes (85%) as eluent to produce Compound 151 as a yellow oil.

¹HNMR (CDCl₃): δ ppm 2.27 (s, 3H), 2.33 (s, 6H), 6.94 (d, J=1.47 Hz, 1H), 7.06-7.11 (m, 1H), 7.57 (dd, J=7.91, 1.76 Hz, 1H), 10.29 (s, 1H).

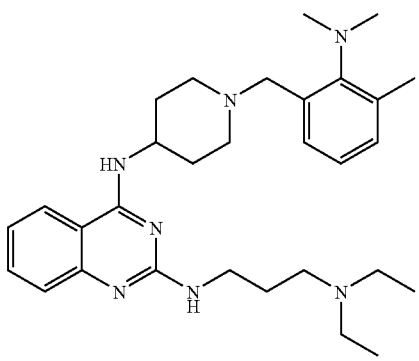

Compound 152

N~2~-[3-(Diethylamino)propyl]-N~4~-{1-[2-(dimethylamino)-3-methylbenzyl]piperidin-4-yl}quinazoline-2,4-diamine (Compound 152)

Following General Procedure H, compound 151 (46.7 mg, 0.14 mmol) and N2-(3-(diethylamino)propyl)-N4-(piperidin-4-yl)quinazoline-2,4-diamine (53 mg, 0.14 mmol) were converted into Compound 152.

¹HNMR (CD₃OD): δ ppm 1.07 (t, J=7.18 Hz, 6H), 1.61-1.91 (m, 4H), 2.03 (d, J=2.05 Hz, 2H), 2.13-2.24 (m, 2H), 2.30 (s, 3H), 2.62 (q, J=7.33 Hz, 4H), 2.76-2.85 (m, 6H), 2.98 (d, J=12.01 Hz, 1H), 3.45 (t, J=6.74 Hz, 2H), 3.63 (s, 2H), 4.21 (dd, J=15.53, 7.33 Hz, 1H), 6.97-7.12 (m, 3H), 7.28 (dd, J=11.87, 7.47 Hz, 2H), 7.50 (m, 1H), 7.91 (dd, J=8.20, 1.17 Hz, 1H).

MS ($C_{30}H_{45}N_7$; MWt. 503): Observed M+1=504.

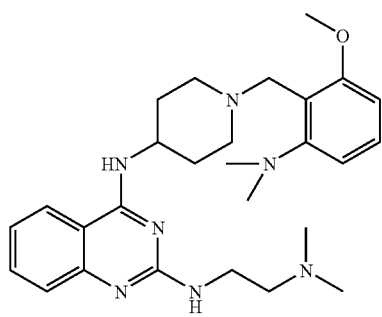

Compound 153

N~2~-[2-(Dimethylamino)ethyl]-N~4~-{1-[2-(dimethylamino)-6-methoxybenzyl]piperidin-4-yl}quinazoline-2,4-diamine (Compound 153)

Following General Procedure D, Compound 47 (57.2 mg, 0.14 mmol) and N,N-dimethylethylenediamine (0.050 mL, 0.42 mmol) were converted into Compound 153.

$^1$HNMR (CD$_3$OD): δ ppm 1.68 (dd, J=11.87, 3.37 Hz, 2H), 1.99 (dd, J=12.01, 2.34 Hz, 2H), 2.31 (s, 8H), 2.59 (t, J=6.89 Hz, 2H), 2.68 (s, 7H), 3.07 (d, J=12.01 Hz, 2H), 3.56 (t, J=6.89 Hz, 2H), 3.75-3.87 (m, 6H), 4.11-4.24 (m, 1H), 6.76 (d, J=8.20 Hz, 1H), 6.86 (d, J=7.33 Hz, 1H), 7.06 (dd, J=15.24, 1.17 Hz, 1H), 7.18-7.25 (m, 1H), 7.28 (d, J=5.27 Hz, 1H), 7.45-7.45 (m, 1H), 7.89 (dd, J=8.50, 1.17 Hz, 1H).

MS (C$_{27}$H$_{39}$N$_7$O; MWt. 477): Observed M+1=478.

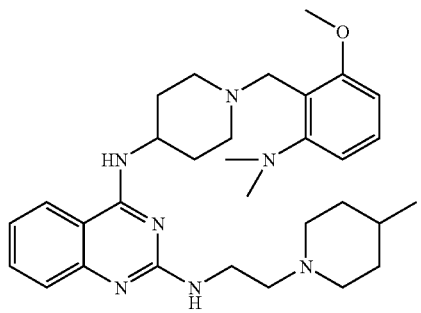

Compound 154

N~4~-{1-[2-(Dimethylamino)-6-methoxybenzyl]piperidin-4-yl}-N~2~-[2-(4-methylpiperazin-1-yl)ethyl]quinazoline-2,4-diamine (Compound 154)

Following General Procedure D, Compound 47 (67.0 mg, 0.16 mmol) and 2-(4-methyl-piperazin-1-yl)-ethylamine (62 mg, 0.48 mmol) were converted into Compound 154.

$^1$HNMR (CD$_3$OD): δ ppm 1.71 (dd, J=12.16, 3.37 Hz, 2H), 1.94-2.09 (m, 2H), 2.28 (s, 3H), 2.37 (t, J=12.16 Hz, 1H), 2.44-2.71 (m, 14H), 3.10 (d, J=12.31 Hz, 2H), 3.57 (t, J=6.59 Hz, 2H), 3.78-3.90 (m 5H), 4.12-4.28 (m, 1H), 6.78 (d, J=8.20 Hz, 1H), 6.87 (d, J=8.20 Hz, 1H), 7.08 (dd, J=15.24, 1.17 Hz, 1H), 7.25 (t, J=8.20 Hz, 2H), 7.50 (m, 1H), 7.90 (d, J=7.33 Hz, 1H).

MS (C$_{30}$H$_{44}$N$_8$O; MWt. 532): Observed M+1=533.

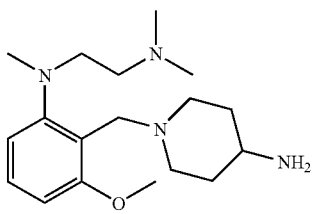

Compound 155

N1-(2-((4-Aminopiperidin-1-yl)methyl)-3-methoxyphenyl)-N1,N2,N2-trimethylethane-1,2-diamine (Compound 155)

Following General Procedure F, tert-butyl 1-(2-((2-(dimethylamino)ethyl)(methyl)amino)-6-methoxybenzyl)piperidin-4-ylcarbamate (0.43 g, 1.02 mmol) was converted into Compound 155.

$^1$HNMR (CD$_3$OD): δ ppm 2.01 m, 2H), 2.22 (m, 2H), 2.68 (s, 3H), 2.91 (s, 6H), 3.26 (m, 2H), 3.34-3.42 (m, 2H), 3.42-3.60 (m, 2H), 8.94 (s, 3H), 4.51 (s, 2H), 6.99 (d, J=8.20 Hz, 1H), 7.06 (d, J=7.62 Hz, 1H), 7.51 (t, J=8.20 Hz, 1H).

MS (C$_{18}$H$_{32}$N$_4$O; MWt. 320): Observed M+1=321.

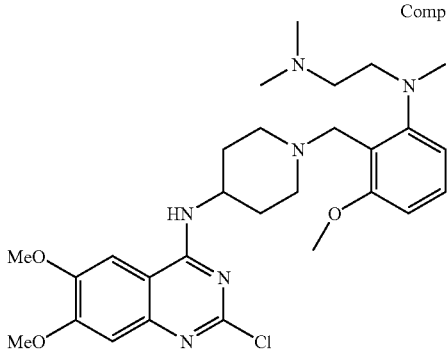

Compound 156

N1-(2-((4-(2-Chloro-6,7-dimethoxyquinazolin-4-ylamino)piperidin-1-yl)methyl)-3-methoxyphenyl)-N1,N2,N2-trimethylethane-1,2-diamine (Compound 156)

Following General Procedure C, compound 155 (0.16 g, 0.51 mmol) and 2,4-dichloro-6,7-dimethoxyquinazoline (0.16 g, 0.61 mmol) were converted into Compound 156 as a yellow solid.

$^1$HNMR (CD$_3$OD): δ ppm 1.62-1.86 (m, 2H), 2.01 (d, J=10.55 Hz, 2H), 2.28 (s, 5H), 2.34-2.48 (m, 4H), 2.68 (d, J=6.15 Hz, 6H), 8.00-8.16 (m, 4H), 3.35 (s, 1H), 3.75-3.87 (m, 5H), 4.10-4.22 (m, 1H), 6.80 (d, J=8.50 Hz, 1H), 7.27 (t, J=8.20 Hz, 1H), 7.47 (s, 1H).

MS (C$_{28}$H$_{39}$ClN$_6$O$_3$; MWt. 542): Observed M+1=543; M+Na=565.

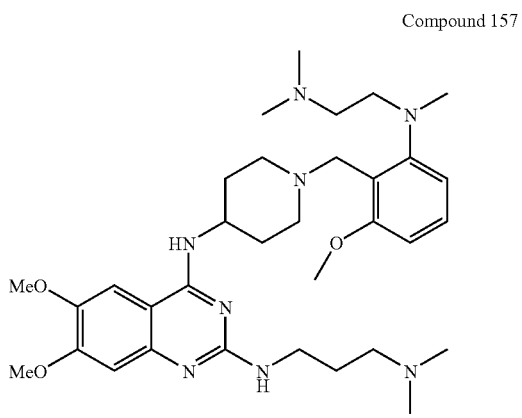

Compound 157

N~4~-[1-(2-{[2-(Dimethylamino)ethyl](methyl)amino}-6-methoxybenzyl)piperidin-4-yl]-N~2~-[3-(dimethylamino)propyl]-6,7-dimethoxyquinazoline-2,4-diamine (Compound 157)

Following General Procedure D, Compound 156 (0.13 g, 0.24 mmol) and 3-(dimethylamino)propylamine (0.15 mL, 1.20 mmol) were converted into Compound 157.

$^1$HNMR (CD$_3$OD): δ ppm 0.81-0.96 (m, 1H), 1.28 (s, 3H), 1.58-1.90 (m, 4H), 2.01 (d, J=10.84 Hz, 2H), 2.18-2.29 (m, 13H), 2.33 (d, J=12.31 Hz, 1H), 2.39-2.58 (m, 4H), 2.71 (s, 3H), 2.99-3.12 (m, 2H), 3.38-3.50 (m, 2H), 3.77 (s, 2H), 3.83 (d, J=2.05 Hz, 5H), 3.86-3.91 (m, 6H), 3.91-3.98 (m, 3H), 4.11-4.24 (m, 1H), 6.74-6.83 (m, 2H), 6.89 (d, J=8.20 Hz, 1H), 6.98 (s, 1H), 7.26 (t, J=8.20 Hz, 1H), 7.56 (s, 1H).

MS (C$_{33}$H$_{52}$N$_8$O$_3$; MWt. 608): Observed M+1=609; M+Na=631; 2M+1=1217.

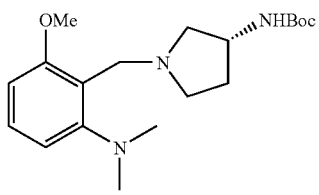

Compound 158

(R)-tert-Butyl 1-(2-(dimethylamino)-6-methoxybenzyl)pyrrolidin-3-ylcarbamate (Compound 158)

Following General Procedure H, Compound 142 (0.14 g, 0.78 mmol) and (S)-(−)-3-(Boc amino)pyrrolidine (0.18 g, 0.94 mmol) were converted into the Compound 158 as an amber oil.

$^1$HNMR (CD$_3$OD): d ppm 1.42 (s, 9H), 1.72 (dd, J=12.16, 4.83 Hz, 1H), 2.27 (d, J=7.91 Hz, 1H), 2.67 (s, 6H), 2.82 (d, J=8.50 Hz, 2H), 3.07 (d, J=7.33 Hz, 2H), 3.84 (s, 3H), 3.96-4.17 (m, 3H), 6.79 (d, J=8.20 Hz, 1H), 6.88 (d, J=8.20 Hz, 1H), 7.29 (t, J=8.20 Hz, 1H).

MS (C$_{19}$H$_{31}$N$_3$O$_3$; MWt. 349): Observed M+1=350.

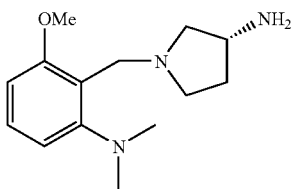

Compound 159

(R)-1-(2-(Dimethylamino)-6-methoxybenzyl)pyrrolidin-3-amine (Compound 159)

Following General Procedure F, Compound 158 (0.43 g, 1.02 mmol) was converted into Compound 159.

$^1$HNMR (CD$_3$OD): d ppm 2.14-2.31 (m, 1H), 2.53-2.71 (m, 1H), 2.88 (s, 6H), 3.41-3.75 (m, 3H), 3.84 (dd, J=12.89, 8.50 Hz, 1H), 3.92 (s, 3H), 3.98 (s, 1H), 4.08-4.24 (m, 1H), 7.01 (d, J=8.20 Hz, 1H), 7.14 (d, J=7.62 Hz, 1H), 7.52 (t, J=8.35 Hz, 1H).

MS (C$_{14}$H$_{23}$N$_3$O; MWt. 249): Observed M+1=250.

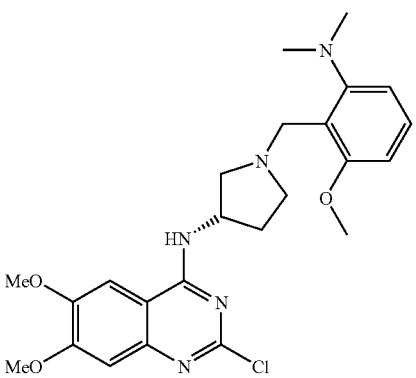

Compound 160

(S)-2-Chloro-N-(1-(2-(dimethylamino)-6-methoxybenzyl)pyrrolidin-3-yl)-6,7-dimethoxyquinazolin-4-amine (Compound 160)

Following General Procedure C, Compound 159 (0.14 g, 0.56 mmol) and 2,4-dichloro-6,7-dimethoxyquinazoline (0.17 g, 0.67 mmol) were converted into Compound 160 as a yellow solid.

$^1$HNMR (CD$_3$OD): δ ppm 1.66-1.85 (m, 1H), 2.25-2.43 (m, 1H), 2.49-2.72 (m, 8H), 2.74-3.02 (m, 4H), 3.77 (s, 3H), 3.86 (m, 8H), 4.64-4.79 (m, 1H), 6.69 (d, J=8.20 Hz, 1H), 7.17 (t, J=8.20 Hz, 1H), 7.26 (s, 1H).

MS (C$_{24}$H$_{30}$ClN$_5$O$_3$; MWt. 471): Observed M+1=472; M+Na=494.

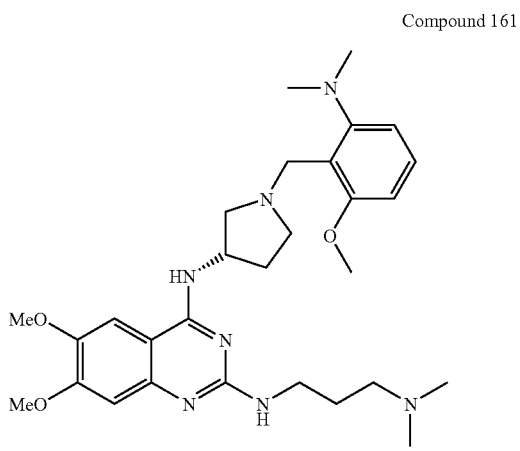

Compound 161

N~4~-{1-[2-(Dimethylamino)-6-methoxybenzyl]
pyrrolidin-3-yl}-N~2~-[3-(dimethylamino)propyl]-6,
7-dimethoxyquinazoline-2,4-diamine (Compound 161)

Following General Procedure E, Compound 160 (0.25 g 0.53 mmol) and 3-(dimethylamino)propylamine (0.20 mL, 1.60 mmol) were converted into Compound 161.

$^1$HNMR (CDCl$_3$): δ ppm 1.57-1.85 (m, 3H), 2.20 (s, 6H), 2.27-2.52 (m, 5H), 2.65-2.83 (m, 8H), 2.95 (m, 1H), 3.41-3.55 (m, 2H), 3.77 (s, 3H), 3.82 (s, 3H), 3.86 (s, 3H), 4.69-4.84 (m, 1H), 5.04 (t, J=5.57 Hz, 1H), 5.84 (d, J=7.91 Hz, 1H), 6.62 (d, J=8.20 Hz, 1H), 6.69-6.76 (m, 2H), 6.82 (s, 1H), 7.18 (t, J=8.20 Hz, 1H).

MS (C$_{29}$H$_{43}$N$_7$O$_3$; MWt. 537): Observed M+1=538; M+Na=560; 2M+1=1075; 2M+Na=1097.

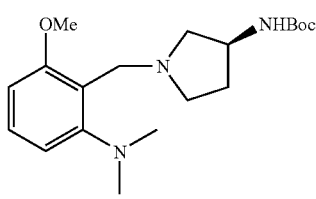

Compound 162

(S)-tert-Butyl 1-(2-(dimethylamino)-6-methoxybenzyl)pyrrolidin-3-ylcarbamate (Compound 162)

Following General Procedure H, Compound 142 (0.14 g, 0.78 mmol) and (R)-(+)-3-(Boc amino)pyrrolidine (0.18 g, 0.94 mmol) were converted into the Compound 162 as a brown oil.

$^1$HNMR (CD$_3$OD): δ ppm 1.42 (s, 9H), 1.64-1.82 (m, 1H), 2.19-2.37 (m, 1H), 2.67 (s, 7H), 2.76-2.92 (m, 2H), 3.09 (d, J=7.62 Hz, 2H), 3.84 (s, 3H), 3.98-4.10 (m, 1H), 4.12 (br. s., 2H), 6.80 (d, J=8.50 Hz, 1H), 6.89 (d, J=8.20 Hz, 1H), 7.30 (t, J=8.20 Hz, 1H).

MS (C$_{19}$H$_{31}$N$_3$O$_3$; MWt. 349): Observed M+1=350.

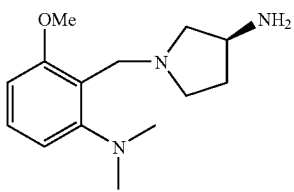

Compound 163

(S)-1-(2-(Dimethylamino)-6-methoxybenzyl)pyrrolidin-3-amine (Compound 163)

Following General Procedure F, Compound 162 (0.20 g, 0.56 mmol) was converted into Compound 163.

$^1$HNMR (CD$_3$OD): δ ppm 2.11-2.32 (m, 1H), 2.54-2.74 (m, 1H), 2.90 (s, 6H), 3.43-3.75 (m, 3H), 3.79-3.90 (m, 1H), 3.93 (s, 3H), 4.10-4.24 (m, 1H), 4.64 (s, 2H), 7.03 (d, J=8.20 Hz, 1H), 7.15 (d, J=7.91 Hz, 1H), 7.53 (t, J=8.35 Hz, 1H).

MS (C$_{14}$H$_{23}$N$_3$O; MWt. 249): Observed M+1=250.

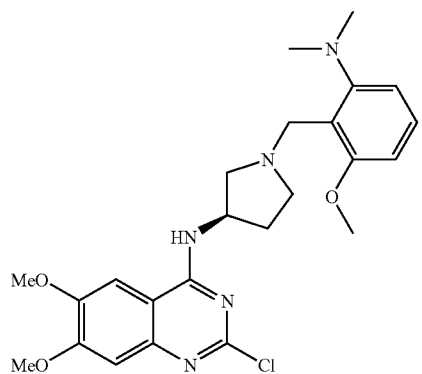

Compound 164

(R)-2-Chloro-N-(1-(2-(dimethylamino)-6-methoxybenzyl)pyrrolidin-3-yl)-6,7-dimethoxyquinazolin-4-amine (Compound 164)

Following General Procedure C, Compound 163 (0.14 g, 0.56 mmol) and 2,4-dichloro-6,7-dimethoxyquinazoline (0.17 g, 0.67 mmol) were converted into Compound 164 as a yellow solid.

$^1$HNMR (CD$_3$OD): δ ppm 1.52-1.70 (m, 1H), 1.71-1.88 (m, 1H), 2.12-2.27 (m, 1H), 2.28-2.42 (m, 1H), 2.48-2.71 (m, 10H), 2.74-3.05 (m, 3H), 3.79 (d, J=2.64 Hz, 6H), 3.88 (d, 5H), 4.25-4.39 (m, 1H), 4.66-4.79 (m, 1H), 6.71 (d, J=8.20 Hz, 1H), 7.18 (t, J=8.06 Hz, 1H), 7.32 (s, 1H).

MS (C$_{24}$H$_{30}$ClN$_5$O$_3$; MWt. 471): Observed M+1=472; M+K=510.

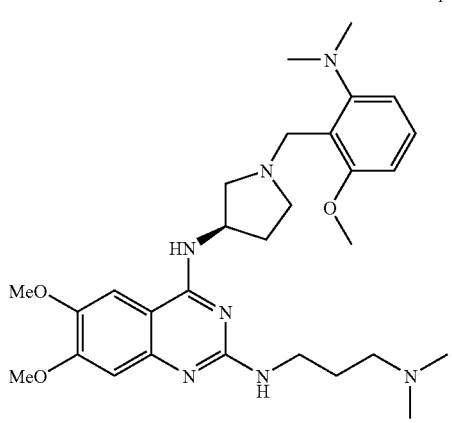

Compound 165

N~4~-{1-[2-(Dimethylamino)-6-methoxybenzyl]pyrrolidin-3-yl}-N~2~-[3-(dimethylamino)propyl]-6,7-dimethoxyquinazoline-2,4-diamine (Compound 165)

Following General Procedure E, Compound 164 (0.25 g 0.54 mmol) and 3-(dimethylamino)propylamine (0.20 mL, 1.62 mmol) were converted into Compound 165.

$^1$HNMR (CDCl$_3$): δ ppm 1.58-1.85 (m, 4H), 2.11-2.24 (m, 8H), 2.26-2.41 (m, 6H), 2.51 (d, J=5.57 Hz, 1H), 2.63-2.75 (m, 8H), 2.89-3.07 (m, 2H), 3.38 (s, 3H), 3.46 (d, J=7.98 Hz, 2H), 3.58-3.74 (m, 3H), 3.72-3.81 (m, 4H), 3.81-3.95 (m, 8H), 4.81 (br. s., 1H), 5.06 (br. s., 1H), 6.26 (d, J=7.62 hz, 1H), 6.63 (d, J=8.50 Hz, 1H), 6.70-6.86 (m, 3H), 7.19 (t, J=8.20 Hz, 1H).

MS (C$_{29}$H$_{43}$N$_7$O$_3$; MWt. 537): Observed M+1=538; M+Na=560; 2M+1=1075; 2M+Na=1097.

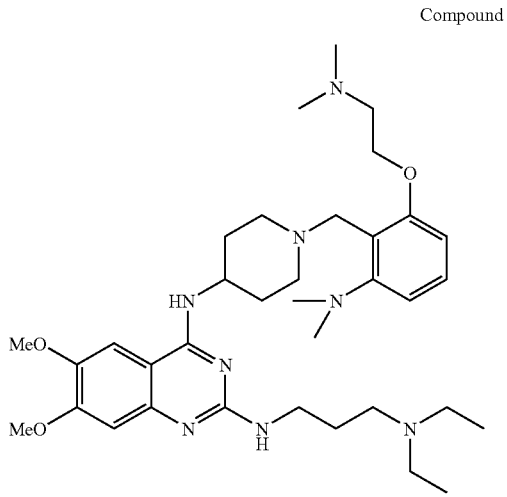

Compound 166

N~2~-[3-(Diethylamino)propyl]-N~4~-(1-{2-(dimethylamino)-6-[2-(dimethylamino)ethoxy]benzyl}piperidin-4-yl)-6,7-dimethoxyquinazoline-2,4-diamine (AGN-219816)

Following General Procedure E, Compound 75 (35 mg 0.065 mmol) and 3-(diethylamino)propylamine (30 μL, 019 mmol) were converted into Compound 166.

$^1$HNMR (CD$_3$OD): δ ppm 1.04 (t, J=7.18 Hz, 6H), 1.41-1.71 (m, 3H), 1.71-1.86 (m, 2H), 2.04 (d, J=9.67 Hz, 2H), 2.25-2.41 (m, 8H), 2.44-2.65 (m, 6H), 2.75 (d, J=11.43 Hz, 2H), 2.95 (d, J=12.01 Hz, 2H), 3.33-3.44 (m, 1H), 3.45-3.56 (m, 2H), 3.67 (s, 2H), 4.06 (t, J=5.71 Hz, 2H), 4.10-4.24 (m, 1H), 5.02 (d, J=7.62 Hz, 1H), 5.32 (br. s., 1H), 6.65 (d, J=8.20 Hz, 1H), 6.69 (s, 1H), 6.79 (d, J=7.91 Hz, 1H), 6.86 (s, 1H), 7.20 (t, J=8.06 Hz, 1H), MS (C$_{35}$H$_{56}$N$_8$O$_3$; MWt. 636): Observed M+1=637; M+Na=659; 2M+1=1273.

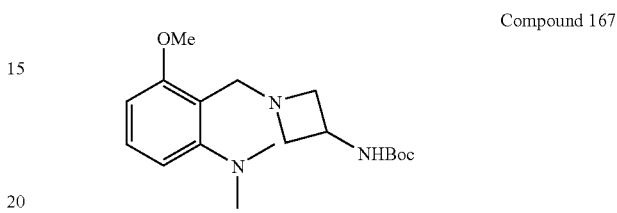

Compound 167 tert-Butyl 1-(2-(dimethylamino)-6-methoxybenzyl)azetidin-3-ylcarbamate (Compound 167)

Following General Procedure H, Compound 142 (0.21 g, 1.19 mmol) and 3-N-Boc amino azetidine (0.25 g, 1.42 mmol) were converted into the Compound 167 as a yellow oil.

$^1$HNMR (CDCl$_3$): δ ppm 1.41 (s, 9H), 2.66 (s, 6H), 2.69-2.83 (m, 2H), 3.42 (s, 5H), 3.75-3.89 (m, 5H), 3.91-4.05 (m, 2H), 4.16-4.39 (m, 1H), 5.43 (br. s., 1H), 6.64 (d, J=8.50 Hz, 1H), 6.76 (d, J=8.20 Hz, 1H), 7.21 (t, J=8.20 Hz, 1H).

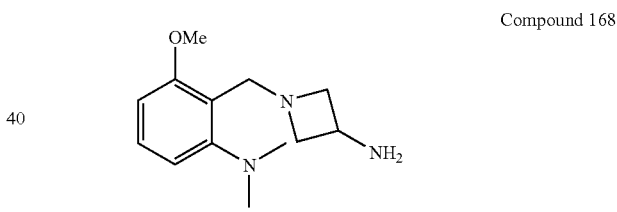

Compound 168

1-(2-(Dimethylamino)-6-methoxybenzyl)azetidin-3-amine (Compound 168)

Following General Procedure F, Compound 167 (0.31 g, 0.92 mmol) was converted into Compound 168.

$^1$HNMR (CD$_3$OD): δ ppm 3.26 (s, 6H), 3.93 (s, 1H), 3.95 (s, 3H), 4.28-4.43 (m, 1H), 4.57 (t, J=5.71 Hz, 2H), 4.64 (d, J=8.20 Hz, 2H), 4.74 (s, 2H), 7.19 (d, J=8.50 Hz, 1H), 7.36 (d, J=8.20 Hz, 1H), 7.64 (t, J=8.35 Hz, 1H).

MS (C$_{13}$H$_{22}$N$_3$O; MWt. 235): Observed M+1=236.

General Procedure I

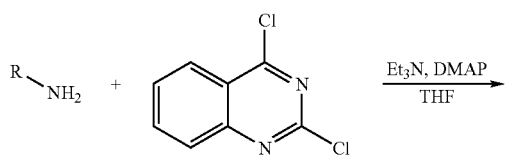

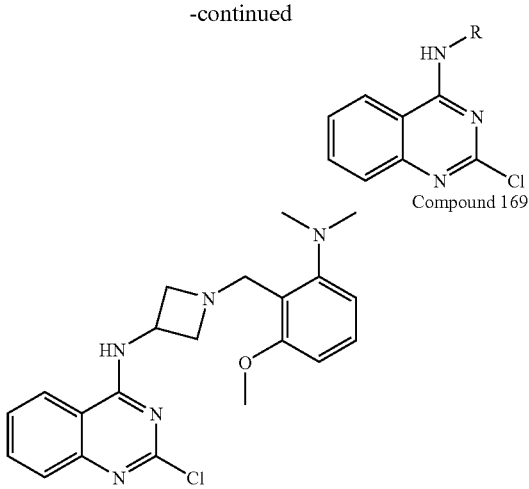

Compound 169

2-Chloro-N-(1-(2-(dimethylamino)-6-methoxybenzyl)azetidin-3-yl)quinazolin-4-amine (Compound 169). General Procedure I.

To a solution of Compound 168 (0.22 g, 0.92 mmol) in THF (10.0 mL) at 0° C. was added 2,4-dichloroquinazoline (0.22 g, 1.10 mmol), followed by Et$_3$N (0.65 mL, 4.60 mmol) and DMAP (catalytic amount), and the reaction was allowed to warm up slowly to ambient temperature and stirred for 18 h, then quenched with 7N NH$_3$ in MeOH. The solvent was removed, and the residue was purified by preparative thin layer chromatography with 7N NH$_3$ in MeOH (2%), hexanes (8%) and CH$_2$Cl$_2$ (90%) to afford the compound EE as a yellow solid.

$^1$HNMR (CD$_3$OD): δ ppm 2.67 (s, 6H), 3.35 (s, 2H), 3.37-3.43 (m, 2H), 3.73-3.87 (m, 5H), 3.90 (s, 2H), 4.62-4.78 (m, 1H), 6.75 (d, J=8.20 Hz, 1H), 6.84 (d, J=7.33 Hz, 1H), 7.22 (t, J=8.06 Hz, 1H), 7.52 (ddd, J=8.35, 7.03, 1.32 Hz, 1H), 7.62 (t, J=8.35 Hz, 1H), 7.78 (ddd, J=8.50, 7.03, 1.47 Hz, 1H), 8.16 (d, J=7.62 Hz, 1H).

MS (C$_{21}$H$_{24}$ClN$_5$O; MWt. 397): Observed M+1=398; M+Na=420.

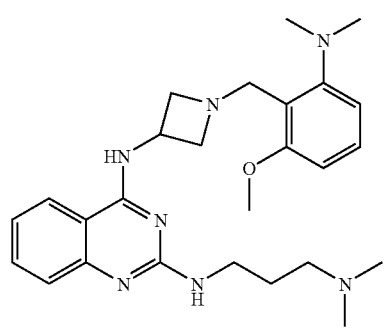

Compound 170

N~4~-{1-[2-(Dimethylamino)-6-methoxybenzyl]azetidin-3-yl}-N~2~-[3-(dimethylamino)propyl]quinazoline-2,4-diamine (Compound 170)

Following General Procedure D, Compound 169 (13.3 mg, 0.034 mmol) and 3-(dimethylamino)propylamine (13 µL, 0.11 mmol) were converted into Compound 170.

$^1$HNMR (CD$_3$OD): δ ppm 1.75-1.91 (m, 2H), 2.26 (s, 6H), 2.37-2.49 (m, 1H), 2.60 (s, 6H), 2.79 (dd, J=7.33, 4.98 Hz, 2H), 3.76 (s, 3H), 4.00 (t, J=10.55 Hz, 1H), 4.46 (dd, J=10.99, 7.18 Hz, 1H), 6.70 (d, J=8.20 Hz, 1H), 6.79 (d, J=8.20 Hz, 1H), 7.04 (t, J=7.62 Hz, 1H), 7.12-7.29 (m, 2H), 7.46 (dd, J=15.53, 1.47 Hz, 1H), 7.85 (dd, J=7.91, 1.76 Hz, 1H).

MS (C$_{26}$H$_{37}$N$_7$O; MWt. 463): Observed M+1=464; M+Na=486; 2M+Na=949.

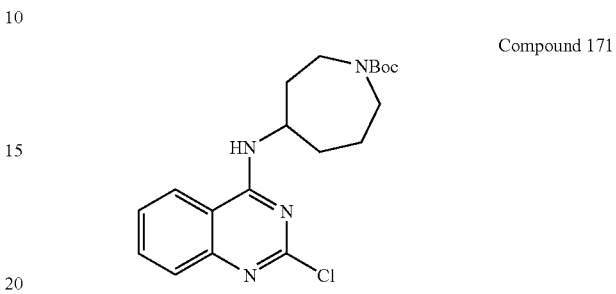

Compound 171 tert-Butyl 4-(2-chloroquinazolin-4-ylamino)azepane-1-carboxylate (Compound 171)

Following General Procedure 1,1-N-Boc-hexahydro-1H-azepin-4H-amine (0.20 g, 0.94 mmol) and 2,4-dichloroquinazoline (0.22 g, 1.12 mmol) were converted into Compound 171 as a yellow solid.

$^1$HNMR (CDCl$_3$): δ ppm 1.43 (s, 9H), 1.57-2.49 (m, 6H), 2.93-3.37 (m, 2H), 3.44 (s, 1H), 3.54-3.75 (m, 1H), 4.46 (br. s., 1H), 6.64 (br. s., 1H), 7.29-7.41 (m, 1H), 7.59-7.70 (m, 2H), 7.81-7.96 (m, 1H).

MS (C$_{19}$H$_{25}$ClN$_4$O$_2$; MWt. 376): Observed M+Na=399; 2M+Na=775.

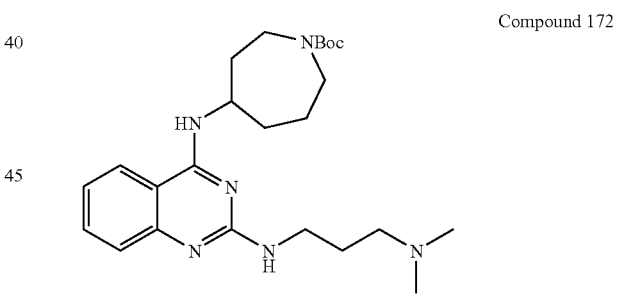

Compound 172 tert-Butyl 4-(2-(3-(dimethylamino)propylamino)quinazolin-4-ylamino)azepane-1-carboxylate (Compound 172)

Following General Procedure D, Compound 171 (0.16 g, 0.42 mmol) and 3-(dimethylamino)propylamine (0.16 mL, 1.26 mmol) were converted into the Compound 172 as a yellow solid.

$^1$HNMR (CD$_3$OD): δ ppm 0.78-0.96 (m, 6H), 1.24-1.41 (m, 4H), 1.44 (s, 9H), 1.47-1.56 (m, 4H), 1.61-1.88 (m, 5H), 2.19 (s, 6H), 2.30-2.41 (m, 2H), 2.81 (br. s., 3H), 3.44-3.54 (m, 2H), 3.54-3.64 (m, 5H), 4.32 (br. s., 1H), 5.65 (br. s., 1H), 6.90-7.06 (m, 1H), 7.34-7.54 (m, 3H).

MS (C$_{24}$H$_{38}$N$_6$O$_2$; MWt. 442): Observed M+1=443.

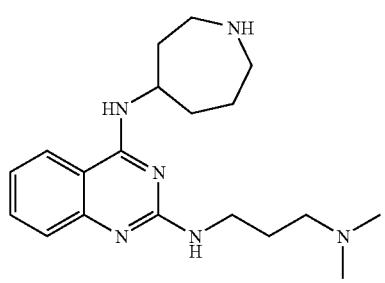
Compound 173

N4-(Azepan-4-yl)-N2-(3-(dimethylamino)propyl) quinazoline-2,4-diamine (Compound 173)

Following General Procedure F, Compound 172 (0.20 g, 0.45 mmol) was converted into compound 173.

$^1$HNMR (CD$_3$OD): δ ppm 1.87-2.54 (m, 8H), 2.92 (s, 6H), 3.33-3.42 (m, 2H), 3.44-3.56 (m, 1H), 3.63-3.78 (m, 2H), 4.66 (br. s., 2H), 7.27-7.53 (m, 2H), 7.77 (t, J=7.62 Hz, 1H), 8.25 (d, J=8.20 Hz, 1H).

MS (C$_{19}$H$_{30}$N$_6$; MWt. 342): Observed M+1=343.

Compound 174

N~4~-{1-[2-(Dimethylamino)-6-methoxybenzyl] azepan-4-yl}-N~2~-[3-(dimethylamino)propyl] quinazoline-2,4-diamine (Compound 174)

Following General Procedure H, Compound 142 (76 mg, 0.42 mmol) and Compound 173 (0.15 g, 0.42 mmol) were converted into Compound 174 as a yellow oil.

$^1$HNMR (CD$_3$OD): δ ppm 1.71-1.95 (m, 4H), 1.98-2.22 (m, 3H), 2.28 (s, 6H), 2.42-2.53 (m, 1H), 2.62-2.74 (m, 6H), 2.94-3.12 (m, 2H), 3.16-3.29 (m, 1H), 3.46 (t, J=6.74 Hz, 2H), 3.87 (s, 3H), 4.06-4.22 (m, 2H), 4.42-4.59 (m, 1H), 6.83 (d, J=8.50 Hz, 1H), 6.92 (d, J=8.20 Hz, 1H), 7.09 (t, J=7.62 Hz, 1H), 7.25-7.39 (m, 2H), 7.52 (t, J=7.62 Hz, 1H), 7.85 (d, J=8.50 Hz, 1H).

MS (C$_{27}$H$_{43}$N$_7$O; MWt. 505): Observed M+1=506; 2M+1=1011.

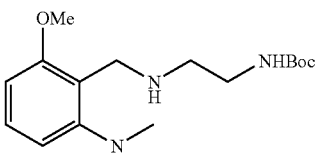
Compound 175 tert-Butyl 2-(2-(dimethylamino)-6-methoxybenzylamino)ethylcarbamate (Compound 175)

Following General Procedure H, Compound 142 (0.21 g, 1.16 mmol) and N-Boc-ethylenediamine (0.25 g, 1.40 mmol) were converted into the Compound 175 as a yellow oil.

$^1$HNMR (CDCl$_3$): δ ppm 1.40 (s, 9H), 2.66 (s, 8H), 3.20 (d, J=5.57 Hz, 2H), 3.35 (s, 1H), 3.79 (s, 3H), 3.85 (s, 2H), 5.34 (br. s., 1H), 6.60 (d, J=8.20 Hz, 1H), 6.73 (d, J=8.20 Hz, 1H), 7.15 (t, J=8.06 Hz, 1H).

MS (C$_{17}$H$_{29}$N$_3$O$_3$; MWt. 323): Observed M+1324; M+Na=346.

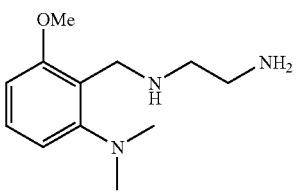
Compound 176

N1-(2-(Dimethylamino)-6-methoxybenzyl)ethane-1, 2-diamine (Compound 176)

Following General Procedure F, compound II (0.36 g, 1.11 mmol) was converted into compound JJ.

$^1$HNMR (CD$_3$OD): δ ppm 3.13 (s, 6H), 3.39-3.49 (m, 2H), 3.50-3.60 (m, 2H), 3.97 (s, 3H), 4.53 (s, 2H), 7.15 (d, J=8.20 Hz, 1H), 7.29 (d, J=7.62 Hz, 1H), 7.61 (t, J=8.35 Hz, 1H).

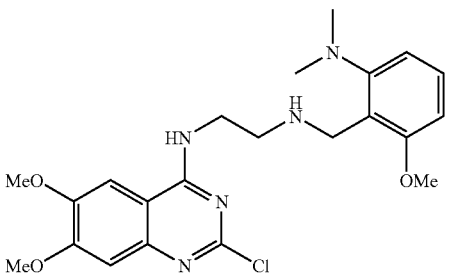
Compound 177

N1-(2-Chloro-6,7-dimethoxyquinazolin-4-yl)-N2-(2-(dimethylamino)-6-methoxybenzyl)ethane-1,2-diamine (Compound 177)

Following General Procedure C, Compound 176 (0.25 g, 1.11 mmol) and 2,4-dichloro-6,7-dimethoxyquinazoline (0.34 g, 1.33 mmol) were converted into Compound 177 as a yellow solid.

¹HNMR (CD₃OD): δ ppm 2.58 (s, 6H), 2.86 (t, J=6.01 Hz, 2H), 3.66 (s, 3H), 3.72 (t, J=6.01 Hz, 2H), 3.90-3.98 (m, 8H), 6.59 (d, J=8.50 Hz, 1H), 6.76 (d, J=7.33 Hz, 1H), 6.99 (s, 1H), 7.12 (t, J=8.20 Hz, 1H), 7.43 (s, 1H).

MS (C$_{22}$H$_{28}$ClN$_5$O$_3$; MWt. 445): Observed M+1=446; M+Na=468; 2M+1=891; 2M+Na=912.

¹HNMR (CD₃OD): δ ppm 1.31-1.50 (m, 11H), 1.58-1.79 (m, 2H), 2.02 (br. s., 2H), 2.38 (s, 9H), 2.69 (s, 6H), 2.82 (t, J=5.71 Hz, 2H), 3.06-3.20 (m, 2H), 3.24-3.36 (m, 2H), 3.44-3.55 (m, 2H), 3.88 (d, J=4.40 Hz, 8H), 4.08-4.22 (m, 4H), 6.73-6.83 (m, 2H), 6.89 (d, J=7.33 Hz, 1H), 7.25 (t, J=8.20 Hz, 1H), 7.39 (s, 1H).

MS (C$_{35}$H$_{54}$N$_8$O$_5$; MWt. 666): Observed M+1=667; M+Na=689.

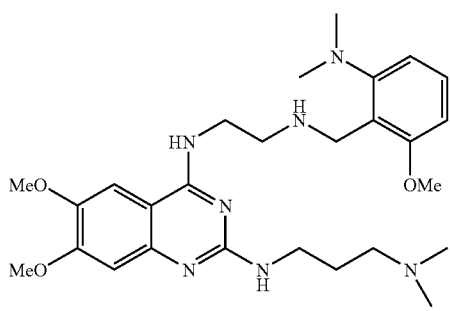

Compound 178

N~4~-(2-{[2-(Dimethylamino)-6-methoxybenzyl]amino}ethyl)-N~2~-[3-(dimethylamino)propyl]-6,7-dimethoxyquinazoline-2,4-diamine (Compound 178)

Following General Procedure D, Compound 177 (26.3 mg, 0.059 mmol) and 3-(dimethylamino)propylamine (25 μL, 0.30 mmol) were converted into Compound 178 as a yellow solid.

¹HNMR (CD₃OD): δ ppm 1.54-1.89 (m, 4H), 2.24 (s, 14H), 2.32-2.48 (m, 6H), 2.55 (s, 6H), 2.68 (t, J=7.03 Hz, 2H), 2.87 (t, J=5.71 Hz, 2H), 3.39 (t, J=6.74 Hz, 2H), 3.60 (s, 3H), 3.72 (t, J=5.86 Hz, 2H), 3.89 (d, J=10.26 Hz, 8H), 6.62 (d, J=7.91 Hz, 1H), 6.72-6.86 (m, 2H), 7.15 (t, J=8.20 Hz, 1H), 7.29 (s, 1H).

MS (C$_{27}$H$_{41}$N$_7$O$_3$; MWt. 511): Observed M+1=512; M+Na=534.

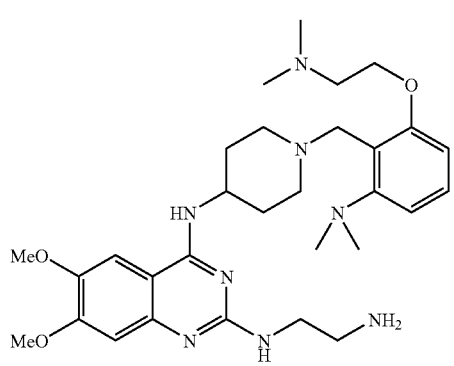

Compound 180

N~2~-(2-Aminoethyl)-N~4~-(1-{2-(dimethylamino)-6-[2-(dimethylamino)ethoxy]benzyl}piperidin-4-yl)-6,7-dimethoxyquinazoline-2,4-diamine (Compound 180)

Following General Procedure F, Compound 179 (43 mg, 0.065 mmol) was converted into Compound 180 as a yellow solid.

¹HNMR (CD₃OD): δ ppm 1.60-1.74 (m, 2H), 1.97 (d, J=2.34 Hz, 2H), 2.24-2.42 (m, 10H), 2.69 (s, 6H), 2.78-2.90 (m, 2H), 3.08 (d, J=12.31 Hz, 2H), 3.47 (t, J=6.15 Hz, 2H), 3.80 (s, 3H), 3.88 (d, J=4.98 Hz, 8H), 4.05-4.19 (m, 4H), 6.87 (d, J=8.70 Hz, 1H), 7.23 (t, J=8.06 Hz, 1H), 7.38 (s, 1H).

MS (C$_{30}$H$_{46}$N$_8$O$_3$; MWt. 566): Observed M+1=567; M+Na=589.

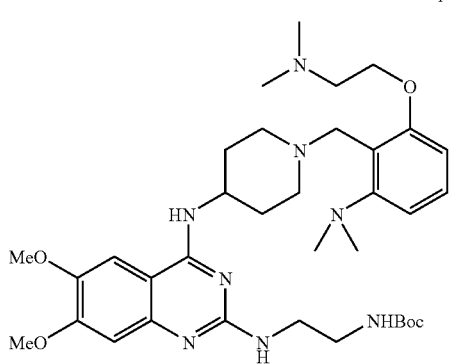

Compound 179 tert-Butyl 2-(4-(1-(2-(dimethylamino)-6-(2-(dimethylamino)ethoxy)benzyl)piperidin-4-ylamino)-6,7-dimethoxyquinazolin-2-ylamino)ethylcarbamate (Compound 179)

Following General Procedure D, Compound 75 (0.10 g, 0.19 mmol) and t-butyl-N-(2-aminoethyl)carbamate (90 μL, 0.55 mmol) were converted into Compound 179 as a yellow solid.

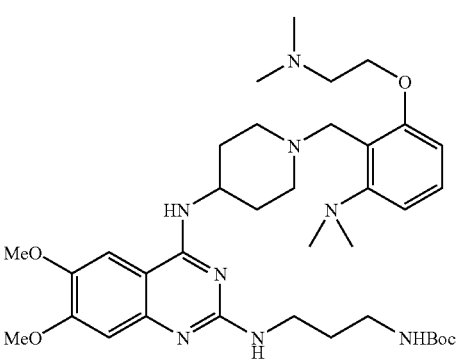

Compound 181 tert-Butyl 3-(4-(1-(2-(dimethylamino)-6-(2-(dimethylamino)ethoxy)benzyl)piperidin-4-ylamino)-6,7-dimethoxyquinazolin-2-ylamino)propylcarbamate (Compound 181)

Following General Procedure D, Compound 75 (0.12 g, 0.22 mmol) and N-Boc-1,3-propanediamine (0.14 mL, 0.78 mmol) were converted into Compound 181 as a yellow solid.

¹HNMR (CDCl₃): δ ppm 1.45 (s, 9H), 1.55 (dd, J=11.72, 2.93 Hz, 2H), 1.67-1.81 (m, 2H), 1.99 (d, J=6.45 Hz, 3H), 2.35 (s, 8H), 2.67-2.80 (m, 12H), 2.94 (d, J=11.72 Hz, 2H), 3.12-3.26 (m, 3H), 3.54 q, J=6.25 Hz, 2H), 3.67 (s, 2H), 4.05 (t, J=5.57 Hz, 2H), 4.11-4.24 (m, 1H), 4.82 (br. s., 1H), 5.14 (d, J=7.91 Hz, 1H), 6.65 (d, J=8.20 Hz, 1H), 6.72 (s, 1H), 6.79 (d, J=7.91 Hz, 1H), 6.84-6.92 (m, 1H), 7.20 (t, J=8.20 Hz, 1H).

MS (C₃₆H₅₆N₈O₅; MWt. 680): Observed M+1=681; M+Na=703.

Compound 182

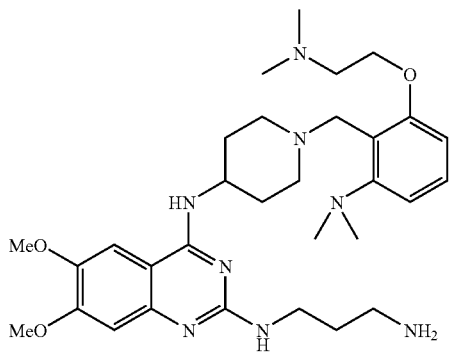

N~2~-(3-Aminopropyl)-N~4~-(1-{2-(dimethylamino)-6-[2-(dimethylamino)ethoxy]benzyl}piperidin-4-yl)-6,7-dimethoxyquinazoline-2,4-diamine (Compound 182)

Following General Procedure F, Compound 181 (0.138 g, 0.20 mmol) was converted into Compound 182 as a yellow solid.

¹HNMR (CD₃OD): δ ppm 1.53-1.86 (m, 4H), 1.99 (d, J=11.72 Hz, 2H), 2.31 (dd, J=9.52, 2.49 Hz, 2H), 2.37 (s, 6H), 2.69 (s, 6H), 2.73 (t, J=6.89 Hz, 1H), 2.82 (t, J=5.71 Hz, 2H), 3.07 (d, J=12.01 Hz, 2H), 3.47 (t, J=6.59 Hz, 2H), 3.79 (s, 2H), 4.11 (t, J=5.71 Hz, 2H), 6.86 (d, J=7.91 Hz, 1H), 7.22 (t, J=8.20 Hz, 1H), 7.37 (s, 1H).

MS (C₃₁H₄₈N₈O₃; MWt. 580): Observed M+1=581.

Compound 183

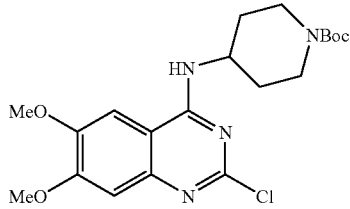

tert-Butyl 4-(2-chloro-6,7-dimethoxyquinazolin-4-ylamino)piperidine-1-carboxylate (Compound 183)

following General Procedure C, 2,4-dichloro-6,7-dimethoxyquinazoline (6.95 g, 26.8 mmol) and 4-amino-1-Boc-piperidine (5.0 g, 25.0 mmol) were converted into Compound 183 which is a yellow solid.

¹HNMR (CDCl₃): δ ppm 1.47 (s, 11H), 2.13 (d, J=2.64 Hz, 2H), 2.88-3.06 (m, 2H), 3.97 (s, 3H), 4.06 (s, 3H), 4.11-4.24 (m, 2H), 4.35-4.53 (m, 1H), 5.50 (d, J=7.62 Hz, 1H), 7.13 (s, 2H).

MS (C₂₀H₂₇ClN₄O₄; MWt. 422): Observed M+Na=445; 2M+Na=867.

Compound 184

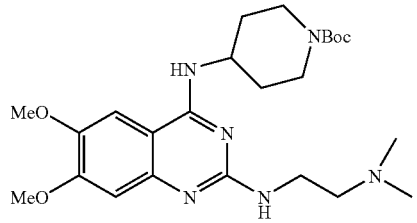

tert-Butyl 4-(2-(2-(dimethylamino)ethylamino)-6,7-dimethoxyquinazolin-4-ylamino)piperidine-1-carboxylate (Compound 184)

Following General Procedure D, Compound 183 (2.3 g, 5.45 mmol) and N,N-dimethylethylenediamine (2.0 mL, 19.08 mmol) were converted into the Compound 184 as a yellow solid.

¹HNMR (CDCl₃): δ ppm 1.44 (s, 9H), 1.78-2.13 (m, 4H), 2.52 (s, 6H), 2.74-3.02 (m, 4H), 3.70-3.83 (m, 2H), 3.90 (s, 3H), 4.02 (s, 3H), 4.15 (d, J=11/72 Hz, 2H), 4.35-4.53 (m, 1H), 6.86 (br. s., 1H), 7.89 (s, 2H), 8.41 (br. s., 1H).

MS (C₂₄H₃₈N₆O₄; MWt. 474): Observed M+1=475.

Compound 185

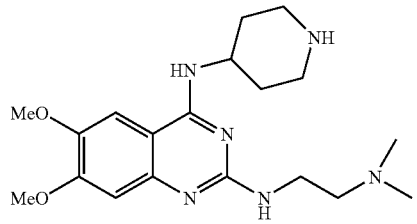

N2-(2-(Dimethylamino)ethyl)-6,7-dimethoxy-N4-(piperidin-4-yl)quinazoline-2,4-diamine (Compound 185)

Following General Procedure F, Compound 184 (0.10 g, 0.21 mmol) was converted into compound the Compound 185 as a yellow solid.

¹HNMR (CD₃OD): δ ppm 1.61 (dd, J=11.87 Hz, 2H), 2.08 (d, J=11.72 Hz, 2H), 2.32 (s, 6H), 2.59 (t, J=6.74 Hz, 2H), 2.74 (t, J=12.45 Hz, 2H), 3.14 (d, J=12.60 Hz, 2H), 3.31 (dd, J=3.08, 1.61 Hz, 2H), 3.55 (t, J=6.59 Hz, 2H), 3.90 (s, 6H), 4.32 (t, J=3.81 Hz, 1H), 6.79 (s, 1H), 7.42 (s, 1H).

MS (C₁₉H₃₀N₆O₂; 374): Observed M+1=375.

General Procedure J

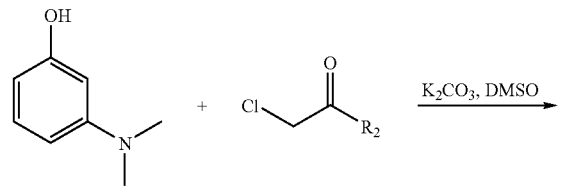

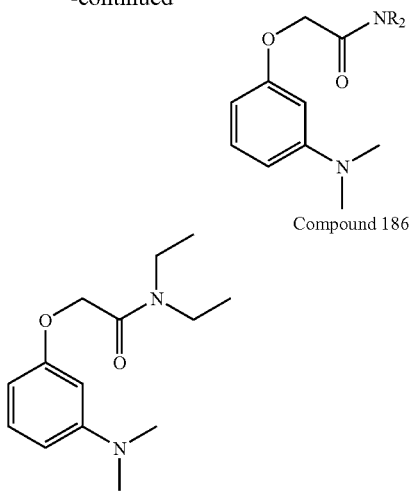

Compound 186

2-(3-(Dimethylamino)phenoxy)-N,N-diethylacetamide (Compound 186). General Procedure J To a solution of m-dimethylaminophenol (1.0 g, 7.3 mmol) in DMSO (10.0 mL) was added slowly $K_2CO_3$ (1.6 g, 11.68 mmol), followed by N-(2-chloroacetyl)-diethylamine (1.2 mL, 8.76 mmol) under Argon atmosphere. The reaction was stirred at ambient temperature for 18 h, then diluted with $CH_2Cl_2$, washed with water (3×), brine, dried over $MgSO_4$, and filtered. The solvent was removed to afford the Compound 186 as a dark oil.

$^1$HNMR (CDCl$_3$): δ ppm 0.85-1.10 (m, 6H), 2.71 (s, 6H), 3.04-3.30 (m, 4H), 4.45 (s, 2H), 6.10 (d, J=8.20 Hz, 1H), 6.17 (d, J=2.64 Hz, 2H), 6.91 (t, J=8.50 Hz, 1H).

General Procedure K

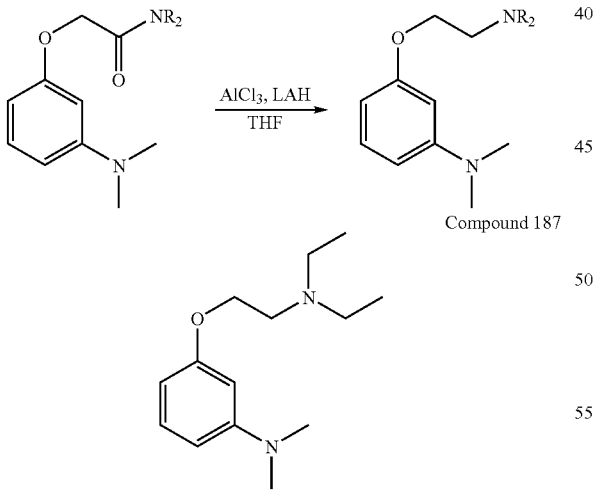

Compound 187

3-(2-(Diethylamino)ethoxy)-N,N-dimethylaniline (Compound 187). General Procedure K AlCl$_3$ (1.10 g, 8.27 mmol) was added to THF at 0° C., then the mixture was cooled to −78° C. under Argon atmosphere. A 2.0M solution of LAH in THF (8.0 mL, 16.54 mmol) was added slowly dropwise, followed by a solution of Compound 186 (1.88 g, 7.52 mmol) in THF (20.0 mL) slowly, then the reaction was stirred at ambient temperature for 1 h, then cooled to −78° C. EtOAc (1.0 mL) was added dropwise, followed by MeOH (2.0 mL). The mixture was stirred at ambient temperature for 3 h, then an aqueous solution of $K_2CO_3$ (1.0 g/10.0 mL) was added slowly in shaking the reaction. $CH_2Cl_2$ was added, then the mixture was filtered through Celite. The mother liquid was dried over MgSO$_4$, and filtered, then the solvent was removed to afford the Compound 187 as a dark oil.

$^1$HNMR (CDCl$_3$): δ ppm 1.07 (t, J=7.03 Hz, 6H), 2.52-2.68 (m, 4H), 2.87 (t, J=6.59 Hz, 2H), 2.92 (s, 6H), 4.05 (t, J=6.59 Hz, 2H), 6.23-6.40 (m, 3H), 7.13 (t, J=8.50 Hz, 1H).

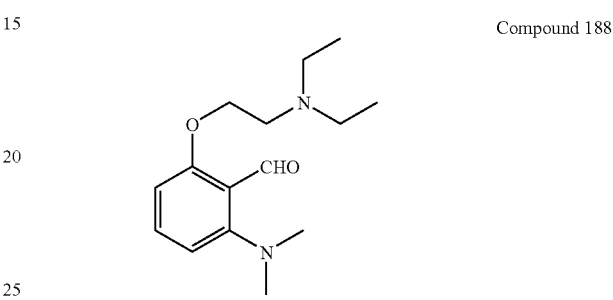

Compound 188

2-(2-(Diethylamino)ethoxy)-6-(dimethylamino)benzaldehyde (Compound 188)

Following General Procedure G, Compound 187 (1.23 g, 5.21 mmol) was converted into Compound 188 as a yellow oil.

$^1$HNMR (CDCl$_3$): δ ppm 1.05 (t, J=7.03 Hz, 6H), 2.62 (q, J=7.03 Hz, 4H), 2.81-2.97 (m, 8H), 4.00-4.19 (m, 2H), 6.39 (d, J=8.20 Hz, 1H), 6.54 (d, J=8.50 Hz, 1H), 7.30 (t, J=8.35 Hz, 1H), 10.37 (s, 1H).

MS ($C_{15}H_{24}N_2O_2$; MWt. 264): Observed M+1=265.

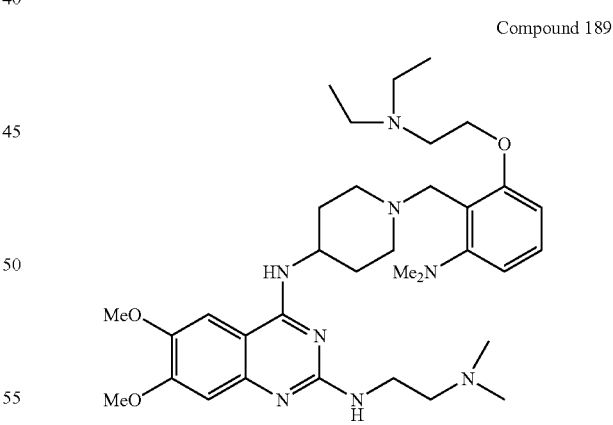

Compound 189

N~4~-(1-{2-[2-(Diethylamino)ethoxy]-6-(dimethylamino)benzyl}piperidin-4-yl)-N~2~-[2-(dimethylamino)ethyl]-6,7-dimethoxyquinazoline-2,4-diamine (Compound 189)

Following General Procedure H, Compound 185 (34.6 mg, 0.093 mmol) and Compound 188 (58.2 mg, 0.22 mmol) were converted into the final product AGN-221250 as a yellow solid.

¹HNMR (CD₃OD): δ ppm 1.11 (t, J=7.18 Hz, 6H), 2.31 (s, 8H), 2.55-2.63 (m, 2H), 2.64-2.76 (m, 10H), 2.93 (q, J=5.37 Hz, 2H), 3.11 (d, J=12.31 Hz, 2H), 3.54 (t, J=6.89 Hz, 2H), 4.04-4.26 (m, 3H), 6.73-6.81 (m, 2H), 6.87 (d, J=8.20 Hz, 1H), 7.24 (t, J=8.06 Hz, 1H), 7.39 (s, 1H).

MS (C$_{34}$H$_{54}$N$_8$O$_3$; MWt. 622): Observed M+1=623.

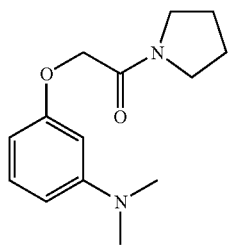

Compound 190

2-(3-(Dimethylamino)phenoxy)-1-(pyrrolidin-1-yl) ethanone (Compound 190)

Following General Procedure J, m-dimethylaminophenol (1.0 g, 7.19 mmol) and 2-chloro-1-pyrrolidin-1-yl-ethanone (1.06 g, 7.19 mmol) were converted into the Compound 190 as a dark oil.

¹HNMR (CDCl$_3$): δ ppm 1.87 (t, J=6.45 Hz, 2H), 2.85 (s, 6H), 3.44 (m, 6H), 4.53 (s, 2H), 6.22 (dd, J=6.74, 1.76 Hz, 1H), 6.26-6.36 (m, 2H), 7.05 (t, J=8.35 Hz, 1H).

MS (C$_{14}$H$_{20}$N$_2$O$_2$; MWt. 248): Observed M+Na=271; 2M+Na=519.

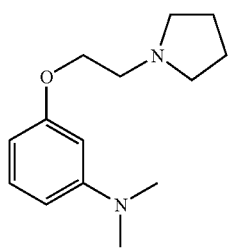

Compound 191

N,N-Dimethyl-3-(2-(pyrrolidin-1-yl)ethoxy)aniline (Compound 191)

Following General Procedure K, Compound 190 (1.68 g, 6.76 mmol) was converted into the Compound 191 as a dark oil.

¹HNMR (CDCl$_3$): δ ppm 1.72-1.87 (m, 4H), 2.58-2.68 (m, 4H), 2.85-2.97 (m, 8H), 4.11 (t, J=6.15 Hz, 2H), 6.25-6.40 (m, 3H), 7.12 (t, J=8.50 Hz, 1H).

MS (C$_{14}$H$_{22}$N$_2$O; MWt. 234): Observed M+1=235, M+Na=257, 2M+Na=491.

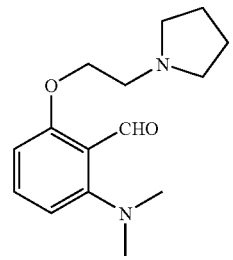

Compound 192

2-(Dimethylamino)-6-(2-(pyrrolidin-1-yl)ethoxy) benzaldehyde (Compound 192)

Following General Procedure K, Compound 191 (1.20 g, 5.12 mmol) was converted into Compound 192 as a dark oil.

¹HNMR (CDCl$_3$): δ ppm 1.77-1.88 (m, 4H), 2.56-2.72 (m, 4H), 2.82-3.00 (m, 8H), 4.18 (t, J=6.01 Hz, 2H), 6.41 (d, J=7.91 Hz, 1H), 6.57 (d, J=8.50 Hz, 1H, 7.28-7.37 (m, 1H), 10.38 (s, 1H).

MS (C$_{15}$H$_{22}$N$_2$O$_2$; MWt. 262): Observed M+1=263, M+Na=285; 2M+Na=547.

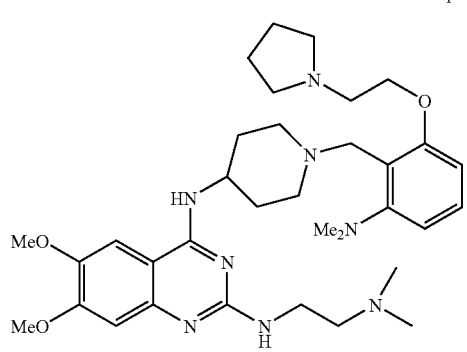

Compound 193

N~2~-[2-(Dimethylamino)ethyl]-N~4~-{1-[2-(dimethylamino)-6-(2-pyrrolidin-1-ylethoxy)benzyl]piperidin-4-yl}-6,7-dimethoxyquinazoline-2,4-diamine (Compound 193)

Following General Procedure H, compound 185 (0.12 g, 0.32 mmol) and Compound 192 (87.4 mg, 0.33 mmol) were converted into the final product Compound 193 as a yellow solid.

¹HNMR (CD₃OD): δ ppm 1.66 (dd, J=12.01, 3.22 Hz, 2H), 1.76-1.89 (m, 4H), 1.93-2.06 (m, 2H), 2.30 (s, 7H), 2.51-2.64 (m, 2H), 2.68 (s, 8H), 3.08 (d, J=12.31 Hz, 2H), 3.53 (t, J=6.89 Hz, 2H), 3.80 (s, 2H), 4.14 (m, 4H), 3.87 (d, 6H), 4.14 (m, 4H), 6.71-6.81 (m, 2H), 6.86 (d, J=7.62 Hz, 1H), 7.23 (t, J=8.06 Hz, 1H), 7.38 (s, 1H).

MS (C$_{34}$H$_{52}$N$_8$O$_3$; MWt. 620): Observed M+1=621, M+Na=643.

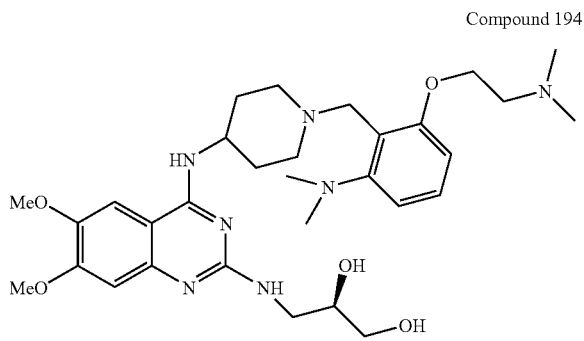

Compound 194

3-({4-[(1-{2-(Dimethylamino)-6-[2-(dimethylamino)ethoxy]benzyl}piperidin-4-yl)amino]-6,7-dimethoxyquinazolin-2-yl}amino)propane-1,2-diol (Compound 194)

Following General Procedure D, Compound 75 (50.0 mg, 0.10 mmol) and (R)-(+)-3-amino-1,2-propanediol (32.0 mg, 0.35 mmol) were converted into Compound 194.

$^1$HNMR (CD$_3$OD): δ ppm 1.97-2.19 (m, 2H), 2.27 (d, J=3.22 Hz, 2H), 2.50 (s, 6H), 2.64-2.75 (m, 7H), 2.94 (br. s., 2H), 3.14-3.27 (m, 2H), 3.40-3.63 (m, 4H), 3.63-3.77 (m, 1H), 3.78-3.88 (m, 1H), 3.92 (d, J=1.76 Hz, 6H), 4.28 (t, J=5.13 Hz, 1H), 4.49 (s, 2H), 6.84 (s, 1H), 6.95 (d, J=8.21 Hz, 1H), 7.04 (d, J=7.91 Hz, 1H), 7.43 (t, J=8.20 Hz, 1H), 7.53 (s, 1H).

MS (C$_{31}$H$_{47}$N$_7$O$_5$; MWt. 597): Observed M+1=598.

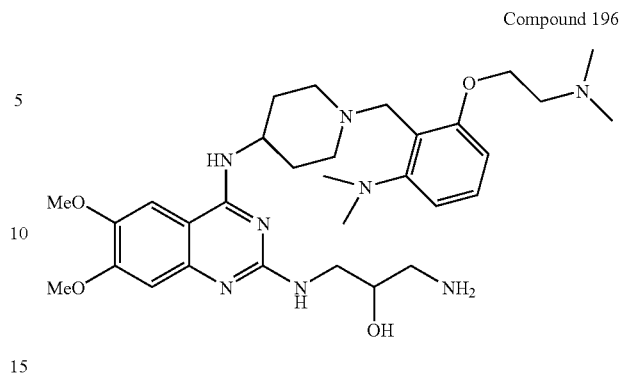

Compound 196

1-Amino-3-({4-[(1-{2-(dimethylamino)-6-[2-(dimethylamino)ethoxy]benzyl}piperidin-4-yl)amino]-6,7-dimethoxyquinazolin-2-yl}amino)propan-2-ol (Compound 196)

Following General Procedure D, Compound 75 (50.0 mg, 0.10 mmol) and 1,3-diamino-2-hydroxypropane (30.0 mg, 0.34 mmol) were converted into Compound 196 as a yellow solid.

$^1$HNMR (CD$_3$OD): δ ppm 1.57-1.79 (m, 3H), 2.00 (br. s., 2H), 2.38 (s, 8H), 2.64-2.72 (m, 7H), 2.83 (t, J=5.57 hz, 2H), 3.06 (dd, J=8.96, 2.49 Hz, 2H), 3.42 (dd, J=14.07, 6.15 Hz, 1H), 3.50-3.59 (m, 1H), 3.66 (m, 1H), 3.76 (dd, J=8.79, 2.05 Hz, 1H), 3.81 (s, 2H), 3.88 (d, J=4.10 Hz, 6H), 4.13 (t, J=5.71 Hz, 3H), 6.72-6.82 (m, 2H), 6.87 (d, J=7.33 Hz, 1H), 7.23 (t, J=8.20 Hz, 1H), 7.39 (s, 1H).

MS (C$_{31}$H$_{48}$N$_8$O$_4$; MWt. 596): Observed M+1=597, M+Na=619.

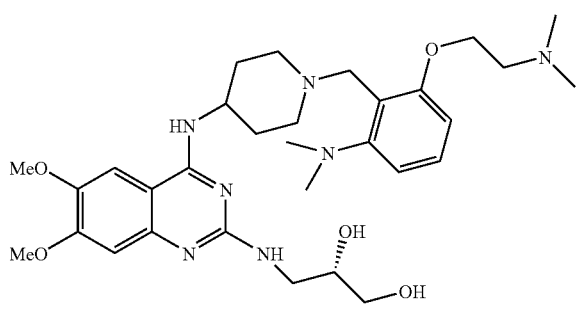

Compound 195

3-({4-[(1-{2-(Dimethylamino)-6-[2-(dimethylamino)ethoxy]benzyl}piperidin-4-yl)amino]-6,7-dimethoxyquinazolin-2-yl}amino)propane-1,2-diol (Compound 195)

Following General Procedure D, Compound 75 (0.26 g, 0.48 mmol) and (S)-(−)-3-amino-1,2-propanediol (0.13 g, 1.44 mmol) were converted into the Compound 195.

$^1$HNMR (CDCl$_3$): δ ppm 1.52-1.72 (m, 2H), 1.99 (dd, J=1.17 Hz, 2H), 2.22-2.40 (m, 8H), 2.72 (s, 6H), 2.76 (t, J=5.57 Hz, 2H), 2.97 (d, J=12.01 Hz, 2H), 3.48-3.67 (m, 4H), 3.69 (s, 2H), 3.77-3.86 (m, 1H), 3.92 (s, 6H), 4.06 (t, J=5.42 Hz, 2H), 4.11-4.27 (m, 1H), 5.13 (br. s., 1H), 5.42 (d, J=7.91 Hz, 1H), 6.66 (d, J=7.62 Hz, 1H), 6.75-6.87 (m, 3H), 7.21 (t, J=8.20 Hz, 1H).

MS (C$_{31}$H$_{47}$N$_7$O$_5$; MWt. 597): Observed M+1=598, M+Na=620.

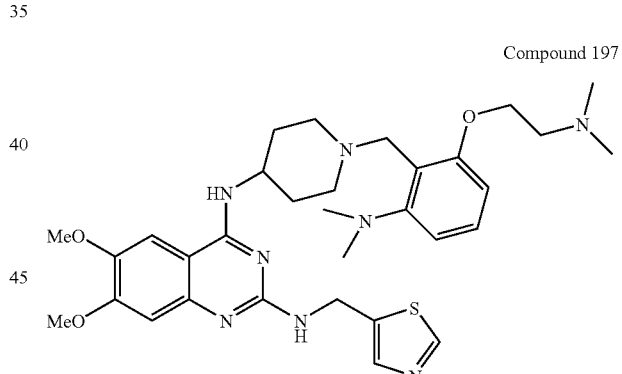

Compound 197

N~4~-(1-{2-(Dimethylamino)-6-[2-(dimethylamino)ethoxy]benzyl}piperidin-4-yl)-6,7-dimethoxy-N~2~-(1,3-thiazol-5-ylmethyl)quinazoline-2,4-diamine (Compound 197)

Following General Procedure D, Compound 75 (67.0 mg, 0.12 mmol) and thiazol-5-yl-methylamine hydrochloride (65.0 mg, 0.43 mmol) were converted into Compound 197 as a yellow solid.

$^1$HNMR (CDCl$_3$): δ ppm 1.46-1.65 (m, 2H), 2.02 (d, J=9.38 Hz, 2H), 2.44 (br. s., 2H), 2.68-2.79 (m, 8H), 2.95 (d, J=12.01 Hz, 2H), 3.67 (s, 2H), 3.95 (d, J=5.27 Hz, 8H), 4.06 (t, J=5.71 Hz, 2H), 4.12-4.25 (m, 1H), 4.88 (d, J=5.86 Hz, 2H), 5.05-5.24 (m, 1H), 6.65 (d, J=7.62 Hz, 1H), 6.74 (s, 1H), 6.80 (d, J=7.33 Hz, 1H), 6.89 (s, 1H), 7.20 (t, J=8.20 Hz, 1H), 7.82 (s, 1H), 8.67 (s, 1H).

MS (C₃₂H₄₄N₈O₃S; MWt. 620): Observed M+1=621, M+Na=643.

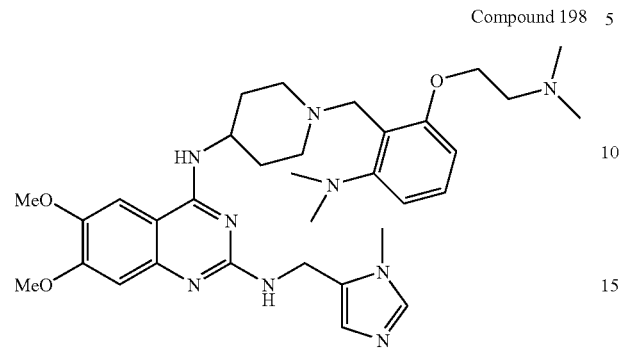

Compound 198

N~4~-(1-{2-(Dimethylamino)-6-[2-(dimethylamino)ethoxy]benzyl}piperidin-4-yl)-6,7-dimethoxy-N~2~-[(1-methyl-1H-imidazol-5-yl)methyl]quinazoline-2,4-diamine (Compound 198)

Following General Procedure D, Compound 75 (49.0 mg, 0.090 mmol) and (1-methyl-1H-imidazol-5-yl)methylamine (35.0 mg, 0.32 mmol) were converted into Compound 198 as a yellow solid.

¹HNMR (CDCl₃): δ ppm 2.05 (d, J=7.33 Hz, 2H), 2.37 (s, 6H), 2.47-2.60 (m, 2H), 2.70 (s, 4H), 2.78 (t, J=5.27 Hz, 2H), 3.08-3.24 (m, 2H), 3.68 (s, 3H), 3.81-3.97 (m, 5H), 4.00 (s, 2H), 4.09 (t, J=5.27 Hz, 2H), 4.33 (br. s., 1H), 4.63 (d, J=4.98 Hz, 1H), 6.70 (d, J=7.91 Hz, 1H), 6.83-6.91 (m, 2H), 6.98 (s, 1H), 7.21-7.31 (m, 2H), 7.39 (s, 1H).

MS (C₃₃H₄₇N₉O₃; MWt. 617): Observed M+1=618.

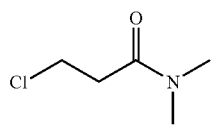

Compound 199

3-Chloro-N,N-dimethylpropanamide (Compound 199)

To a mixture of K₂CO₃ (24.0 g, 171 mmol) in THF (50.0 mL) in a closed round bottom flask at ambient temperature was added dimethylamine, then the mixture was cooled to −78° C. 3-Chloropropionyl chloride (3.3 mL, 34.2 mmol) as added slowly, then the reaction was stirred at ambient temperature for 18 h. The reaction was filtered, and the solvent was removed to afford the Compound 199 as a light orange oil.

¹HNMR (CDCl₃): δ ppm 2.83 (t, J=7.02 Hz, 2H), 3.01 (s, 6H), 3.84 (t, J=7.03 Hz, 2H).

MS (C₅H₁₀ClNO; MWt. 135): Observed M+1=136.

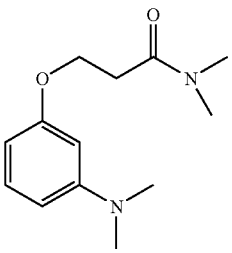

Compound 200

3-(3-(Dimethylamino)phenoxy)-N,N-dimethylpropanamide (Compound 200)

Following General Procedure J, m-dimethylaminophenol (1.45 g, 10.6 mmol) and Compound 199 (1.45 g, 10.6 mmol) were converted into Compound 200 as a dark oil.

¹HNMR (CDCl₃): δ ppm 2.90-2.99 (m, 2H), 3.02 (s, 6H), 3.09 (s, 6H), 5.67 (d, 2H), 6.27 (d, J=2.05 Hz, 1H), 6.33 (d, J=2.06 Hz, 1H), 6.51-6.68 (m, 2H).

MS (C₁₃H₂₀N₂O₂; MWt. 236): Observed: M+1=237, M+Na=259.

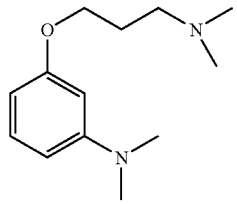

Compound 201

3-(3-(Dimethylamino)propoxy)-N,N-dimethylaniline (Compound 201)

Following General Procedure K, compound 200 (0.37 g, 1.57 mmol) was converted into the Compound 201 as a dark brown oil.

¹HNMR (CDCl₃): δ ppm 1.98 (dd, J=8.06, 6.59 Hz, 2H), 2.30 (s, 6H), 2.46-2.59 (m, 2H), 2.92 (s, 6H), 4.00 (t, J=6.30 Hz, 2H), 6.27 (d, J=1.76 Hz, 2H), 6.35 (dd, J=9.08, 1.76 Hz, 2H), 7.12 (t, J=8.50 Hz, 1H).

MS (C₁₃H₂₂N₂O; MWt. 222): Observed M+1=223.

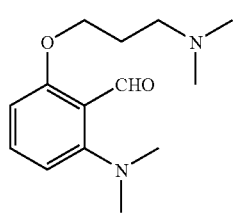

Compound 202

2-(Dimethylamino)-6-(3-(dimethylamino)propoxy) benzaldehyde (Compound 202)

Following General Procedure G, compound 201(1.20 g, 5.12 mmol) was converted into the compound 202 as a dark oil.

¹HNMR (CD₃OD): δ ppm 1.98 (m, 2H), 2.30 (s, 6H), 2.46 (m, 2H), 2.92 (s, 6H), 4.02 (t, J=6.30 Hz, 2H), 6.40 (d, 1H), 6.58 (d, 1H), 7.30 (m, 1H), 10.40 (s, 1H).

MS ($C_{14}H_{22}N_2O_2$; MWt. 250): Observed M+1=251, M+Na=273.

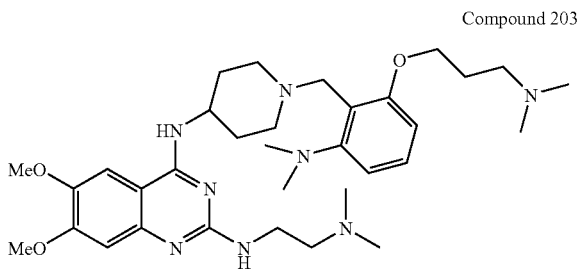

Compound 203

N~4~-(1-{2-(Dimethylamino)-6-[3-(dimethylamino) propoxy]benzyl}piperidin-4-yl)-N~2~-[2-(dimethylamino)ethyl]-6,7-dim ethoxyquinazoline-2,4-diamine (Compound 203)

Following General Procedure H, Compound 185 (34.6 mg, 0.093 mmol) and Compound 202 (58.2 mg, 0.22 mmol) were converted into Compound 203 as a yellow solid.

¹HNMR (CDCl₃): δ ppm 1.39-1.59 (m, 2H), 1.73 (br. s., 4H), 1.91-2.13 (m, 2H), 2.28 (s, 8H), 2.52 (dd, J=14.94, 7.91 Hz, 2H), 2.79 (s, 6H), 2.92-3.05 (m, 2H), 3.51-3.61 (m, 2H), 3.69 (s, 2H), 3.98-4.08 (m, 2H), 4.10-4.25 (m, 1H), 4.95 (d, J=7.91 Hz, 1H), 5.17 (t, J=5.13 Hz, 1H), 6.61-6.74 (m, 2H), 6.78 (d, J=8.20 Hz, 1H), 6.88 (s, 1H), 7.19 (t, J=8.21 Hz, 1H).

MS ($C_{33}H_{52}N_8O_3$; MWt. 608): Observed M+1=609.

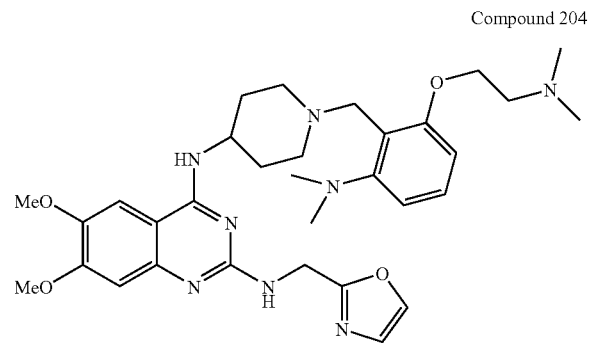

Compound 204

N~4~-(1-{2-(Dimethylamino)-6-[2-(dimethylamino) ethoxy]benzyl}piperidin-4-yl)-6,7-dimethoxy-N2(1,3-oxazol-2-ylmethyl)quinazoline-2,4-diamine (compound 204)

Following General Procedure D, Compound 75 (0.16 g, 0.29 mmol) and oxazol-2-yl-methylamine hydrochloride (77.0 mg, 0.58 mmol) were converted into the Compound 204 as a yellow solid.

¹HNMR (CDCl₃): δ ppm 1.49-1.72 (m, 2H), 1.99 (d, J=9.67 Hz, 2H), 2.36 (s, 8H), 2.66-2.82 (m, 8H), 2.82-3.05 (m, 4H), 3.72 (s, 2H), 3.94 (d, J=2.05 Hz, 6H), 4.07 (t, J=5.57 hz, 2H), 4.13-4.28 (m, 1H), 4.81 (d, J=4.98 Hz, 2H), 5.24-5.48 (m, 1H), 6.67 (d, J=7.91 Hz, 1H), 6.80 (d, J=2.93 Hz, 2H), 6.88 (s, 1H), 7.06 (s, 1H), 7.22 (t, J=8.21 Hz, 1H), 7.58 (s, 1H).

MS ($C_{32}H_{44}N_8O_4$; MWt. 604): Observed M+1=605.

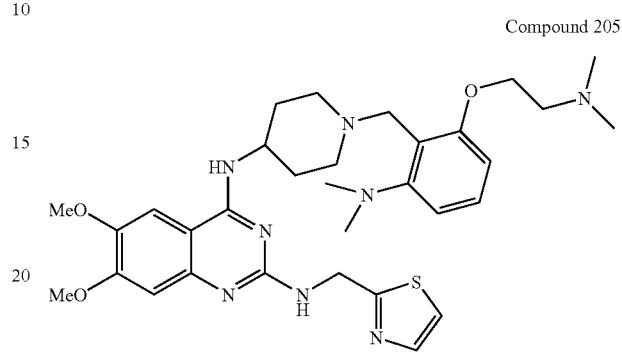

Compound 205

N~4~-(1-{2-(Dimethylamino)-6-[2-(dimethylamino) ethoxy]benzyl}piperidin-4-yl)-6,7-dimethoxy-N~2~-(1,3-thiazol-2-ylmethyl)quinazoline-2,4-diamine (Compound 205)

Following General Procedure D, Compound 75 (0.25 g, 0.47 mmol) and C-thiazol-2-yl-methylamine dihydrochloride (0.11 g, 0.58 mmol) were converted into the Compound 205 as a yellow solid.

¹HNMR (CDCl₃): δ ppm 1.41-1.70 (m, 2H), 1.91 (m, 2H), 2.35 (s, 8H), 2.65-2.80 (m, 9H), 2.94 (d, J=12.01 Hz, 2H), 3.45 (s, 2H), 3.70 (s, 2H), 3.93 (s, 6H), 4.06 (t, J=5.57 Hz, 2H), 4.16 (dd, J=10.99, 4.25 Hz, 1H), 4.99 (br. s., 2H), 6.66 (d, J=8.20 Hz, 1H), 6.81 (d, J=8.20 Hz, 1H), 6.85-6.91 (m, 2H), 7.14-7.25 (m, 2H), 7.70 (s, 1H).

MS ($C_{32}H_{44}N_8O_3S$; MWt. 620): Observed M+1=621.

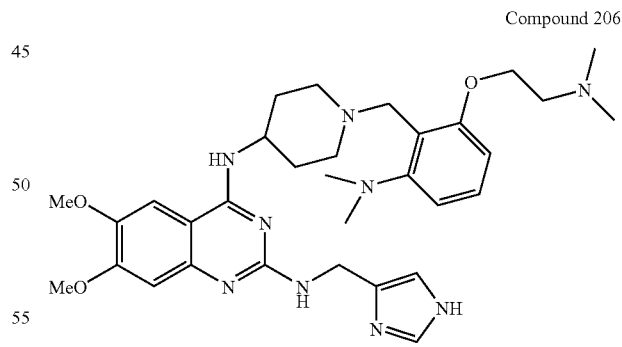

Compound 206

N~4~-(1-{2-(Dimethylamino)-6-[2-(dimethylamino) ethoxy]benzyl}piperidin-4-yl)-N~2~-(1H-imidazol-4-ylmethyl)-6,7-dimethoxyquinazoline-2,4-diamine (Compound 206)

Following General Procedure D, Compound 75 (55.0 mg, 0.10 mmol) and (1H-imidazol-4-yl)methylamine dihydrochloride (61.0 mg, 0.36 mmol) were converted into Compound 206 as a yellow solid.

$^1$HNMR (CDCl$_3$): δ ppm 1.61-1.85 (m, 2H), 2.00 (d, J=9.96 Hz, 2H), 2.24-2.47 (m, 8H), 2.71 (s, 6H), 2.76 (t, J=5.27 Hz, 2H), 3.03 (d, J=11.43 Hz, 2H), 3.77 (s, 2H), 3.95 (s, 6H), 4.06 (t, J=5.42 Hz, 2H), 4.21 (br. s., 1H), 4.57 (br. s., 2H), 6.67 (d, J=8.20 Hz, 1H), 6.83 (d, J=7.91 Hz, 1H), 6.90 (d, J=12.60 Hz, 2H), 7.01 (br. s., 1H), 7.18-7.28 (m, 1H), 7.50 (s, 1H).

MS (C$_{32}$H$_{45}$N$_9$O$_3$; MWt. 603): Observed M+1=604.

Compound 207

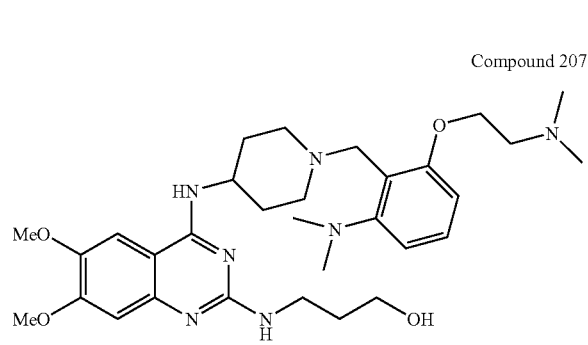

3-({4-[(1-{2-(Dimethylamino)-6-[2-(dimethylamino)ethoxy]benzyl}piperidin-4-yl)amino]-6,7-dimethoxyquinazolin-2-yl}amino)propan-1-ol (Compound 207)

Following General Procedure D, Compound 75 (0.25 g, 0.10 mmol) and 3-amino-1-propanol (0.12 mL, 1.61 mmol) were converted into compound 207 as a yellow oil.

$^1$HNMR (CD$_3$OD): δ ppm 1.73-1.93 (m, 2H), 2.13 (d, J=11.72 Hz, 2H), 2.40 (s, 6H), 2.70 (s, 6H), 2.83 (t, J=5.27 Hz, 2H), 3.20-3.28 (m, 2H), 3.52 (t, J=6.74 Hz, 2H), 3.66 (t, J=6.01 hz, 2H), 3.89 (d, J=3.52 Hz, 6H), 4.10 (s, 2H), 4.18 (t, J=5.42 Hz, 2H), 4.24-4.35 (m, 1H), 6.76-6.89 (m, 2H), 6.94 (d, J=7.91 Hz, 1H), 7.32 (t, J=8.20 Hz, 1H), 7.43 (s, 1H).

MS (C$_{31}$H$_{47}$N$_7$O$_4$; MWt. 581): Observed M+1=582.

Compound 208

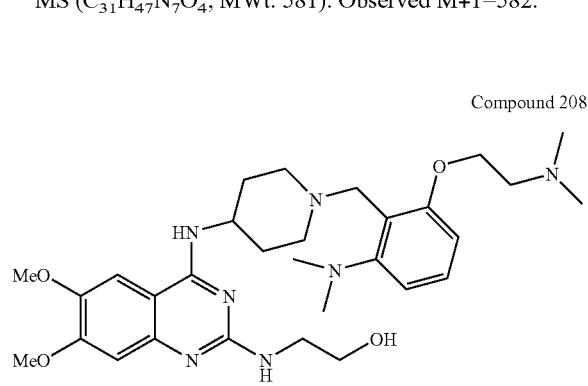

2-({4-[(1-{2-(Dimethylamino)-6-[2-(dimethylamino)ethoxy]benzyl}piperidin-4-yl)amino]-6,7-dimethoxyquinazolin-2-yl}amino)ethanol (Compound 208)

Following General Procedure D, Compound 75 (70.0 mg, 0.13 mmol) and ethanolamine (30.0 μL, 0.45 mmol) were converted into Compound 208 as a yellow oil.

$^1$HNMR (CD$_3$OD): δ ppm 1.69-1.90 (m, 2H), 2.07 (d, J=1.47 Hz, 2H), 2.36 (s, 6H), 2.53-2.66 (m, 2H), 2.70 (s, 6H), 2.84 (t, J=5.57 Hz, 2H), 3.15-3.26 (m, 4H), 3.35-3.46 (m, 1H), 3.54 (t, J=5.42 Hz, 2H), 3.64 (t, J=5.86 Hz, 1H), 3.73 (t, J=5.57 Hz, 2H), 3.89 (d, J=3.81 Hz, 6H), 4.02 (s, 2H), 4.16 (t, J=5.42 Hz, 2H), 4.21-4.31 (m, 1H), 6.77-6.88 (m, 2H), 6.92 (d, J=7.91 Hz, 1H), 7.30 (t, J=8.20 Hz, 1H), 7.42 (s, 1H).

MS (C$_{30}$H$_{45}$N$_7$O$_4$; MWt. 567): Observed M+1=568, M+Na=590.

Compound 209

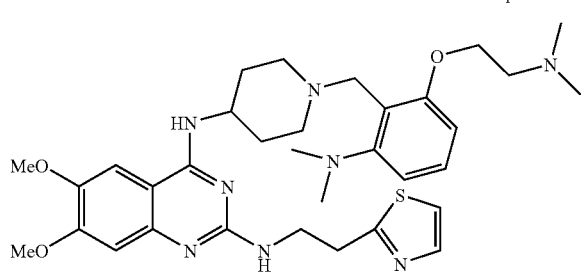

N~4~-(1-{2-(Dimethylamino)-6-[2-(dimethylamino)ethoxy]benzyl}piperidin-4-yl)-6,7-dimethoxy-N~2~-[2-(1,3-thiazol-2-yl)ethyl]quinazoline-2,4-diamine (Compound 209)

Following General Procedure D, Compound 75 (73.0 mg, 0.14 mmol) and 2-thiazol-2-yl-ethylamine hydrochloride (44.0 mg, 0.27 mmol) were converted into Compound 209 as a yellow solid.

$^1$HNMR (CDCl$_3$): δ ppm 1.65-1.89 (m, 2H), 2.07 (d, J=5.27 Hz, 2H), 2.29-2.49 (m, 8H), 2.64-2.84 (m, 8H), 3.04 (d, J=11.72 Hz, 2H), 3.37 (t, J=6.89 Hz, 2H), 3.85 (d, J=5.86 Hz, 2H), 3.93 (s, 3H), 3.98 (s, 3H), 4.07 (t, J=5.57 Hz, 2H), 4.22 (br. s., 1H), 6.67 (d, J=8.50 Hz, 1H), 6.81 (d, J=8.20 Hz, 1H), 6.87 (s, 1H), 7.15-7.31 (m, 3H), 7.69 (d, J=3.22 Hz, 1H).

MS (C$_{33}$H$_{46}$N$_8$O$_3$S; MWt. 634): Observed M+1=635.

Compound 210

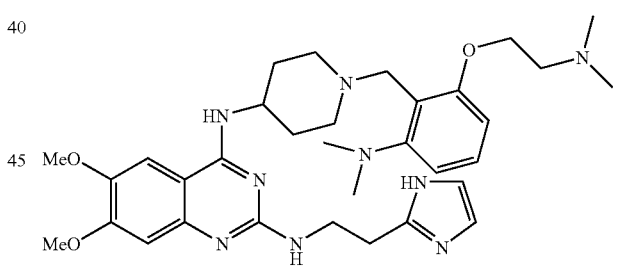

N~4~-(1-{2-(Dimethylamino)-6-[2-(dimethylamino)ethoxy]benzyl}piperidin-4-yl)-N~2~-[2-(1H-imidazol-2-yl)ethyl]-6,7-dimethoxyquinazoline-2,4-diamine (Compound 210)

Following General Procedure D, Compound 75 (0.10 g, 0.19 mmol) and 2-(1H-imidazol-2-yl)ethylamine dihydrochloride (0.12 g, 0.66 mmol) were converted into Compound 210 as a yellow solid.

$^1$HNMR (CD$_3$OD): δ ppm 2.06-2.32 (m, 4H), 2.61 (s, 6H), 2.72 (s, 6H), 3.01-3.17 (m, 4H), 3.34-3.45 (m, 2H), 3.45-3.57 (m, 2H), 3.85 (t, J=6.74 Hz, 2H), 3.92 (s, 6H), 4.26-4.38 (m, 2H), 4.47-4.60 (m, 3H), 6.89 (s, 1H), 6.92-7.01 (m, 3H), 7.06 (d, J=8.20 Hz, 1H), 7.45 (t, J=8.35 Hz, 1H), 7.60 (s, 1H).

MS (C$_{33}$H$_{47}$N$_9$O$_3$; MWt. 617): Observed M+1=618, M+Na=640.

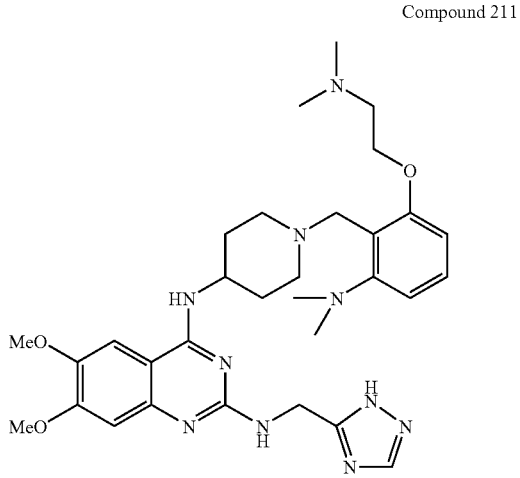

Compound 211

N~4~-(1-{2-(Dimethylamino)-6-[2-(dimethylamino)ethoxy]benzyl}piperidin-4-yl)-6,7-dimethoxy-N2 (1H-1,2,4-triazol-5-ylmethyl)quinazoline-2,4-diamine (Compound 211)

Following General Procedure D, Compound 75 (0.27 g, 0.50 mmol) and 2H-[1,2,4]triazol-3-yl-methylamine hydrochloride (67.0 mg, 0.50 mmol) were converted into Compound 211 as a light yellow solid.

$^1$HNMR (CD$_3$OD): δ ppm 1.52-1.73 (m, 2H), 1.77-1.95 (m, 2H), 2.30-2.49 (m, 8H), 2.69 (s, 6H), 2.82 (t, J=5.57 Hz, 2H), 3.07 (d, J=12.31 Hz, 2H), 3.81-3.94 (m, 8H), 3.93-4.04 (m, 1H), 4.14 (t, J=5.57 Hz, 2H), 4.73 (s, 2H), 6.75-6.83 (m, 2H), 6.89 (d, J=7.33 Hz, 1H), 7.26 (t, J=8.20 Hz, 1H), 7.36 (s, 1H), 8.02 (s, 1H).

MS (C$_{31}$H$_{44}$N$_{10}$O$_3$; MWt. 604): Observed M+1=605.

Compound 212

N~4~-(1-{2-(Dimethylamino)-6-[2-(dimethylamino)ethoxy]benzyl}piperidin-4-yl)-6,7-dimethoxy-N~2~-(1,3-oxazol-5-ylmethyl)quinazoline-2,4-diamine (Compound 212)

Following General Procedure D, Compound 75 (0.34 g, 0.62 mmol) and oxazol-5-yl-methylamine hydrochloride (0.13 g, 0.93 mmol) were converted into Compound 212.

$^1$HNMR (CD$_3$OD): δ ppm 1.63-1.91 (m, 2H), 1.97-2.08 (m, 2H), 2.39 (s, 8H), 2.44-2.64 (m, 2H), 2.69 (s, 6H), 2.83 (t, J=5.42 Hz, 2H), 3.13-3.25 (m, 2H), 3.81-3.93 (m, 8H), 4.00 (br. s., 3H), 4.11-4.23 (m, 4H), 4.70 (s, 2H), 6.75-6.87 (m, 2H), 6.87-6.99 (m, 2H), 7.29 (t, J=8.20 Hz, 1H), 7.39 (s, 1H), 8.07 (s, 1H).

MS (C$_{32}$H$_{44}$N$_8$O$_4$; MWt. 604): Observed M+1=605.

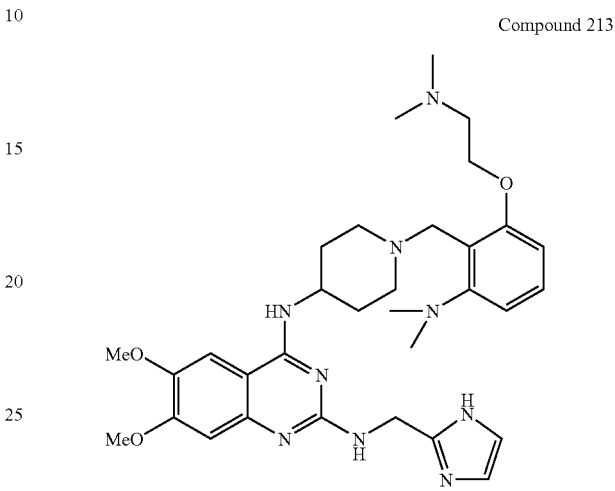

Compound 213

N~4~-(1-{2-(Dimethylamino)-6-[2-(dimethylamino)ethoxy]benzyl}piperidin-4-yl)-N~2~-(1H-imidazol-2-ylmethyl)-6,7-dimethoxyquinazoline-2,4-diamine (Compound 213)

Following General Procedure D, Compound 75 (0.37 g, 0.68 mmol) and C-(1H-imidazol-2-yl)methylamine dihydrochloride (0.14 g, 0.82 mmol) were converted into Compound 213.

$^1$HNMR (CD$_3$OD): δ ppm 1.68-2.02 (m, 4H), 2.42 (s, 6H), 2.70 (s, 6H), 2.79-2.92 (m, 4H), 3.23 (d, J=12.01 Hz, 2H), 3.83-3.94 (m, 8H), 4.11-4.27 (m, 5H), 4.65 (s, 2H), 6.81-6.94 (m, 4H), 6.97 (d, J=7.62 Hz, 1H), 7.36 (t, J=8.20 Hz, 1H), 7.42 (s, 1H).

MS (C$_{32}$H$_{45}$N$_9$O$_3$; MWt. 603): Observed M+1=604.

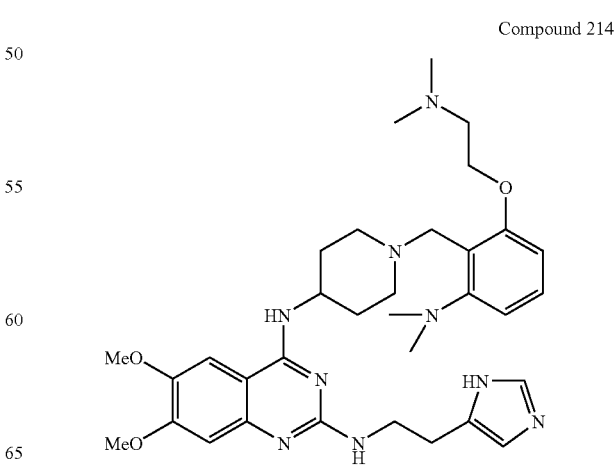

Compound 214

N~4~-(1-{2-(Dimethylamino)-6-[2-(dimethylamino)ethoxy]benzyl}piperidin-4-yl)-N~2~-[2-(1H-imidazol-5-yl)ethyl]-6,7-dimethoxyquinazoline-2,4-diamine (Compound 214)

Following General Procedure D, Compound 75 (0.24 g, 0.45 mmol) and histamine (0.15 g, 1.34 mmol) were converted into Compound 214.

$^1$HNMR (CD$_3$OD): δ ppm 1.68-1.88 (m, 2H), 2.00-2.14 (m, 2H), 2.38 (s, 6H), 2.59 (t, 2H), 2.69 (s, 6H), 2.82 (t, J=5.42 Hz, 2H), 2.91 (t, J=7.03 Hz, 2H), 3.19 (d, J=12.60 Hz, 2H), 3.67 (t, J=7.03 Hz, 2H), 3.88 (d, 6H), 4.00 (s, 2H), 4.11-4.20 (m, 2H), 4.21-4.30 (m, 1H), 6.76-6.96 (m, 4H), 7.29 (t, J=8.20 Hz, 1H), 7.42 (s, 1H), 7.58 (s, 1H).

MS (C$_{33}$H$_{47}$N$_9$; MWt. 617): Observed M+1=618, M+Na=640.

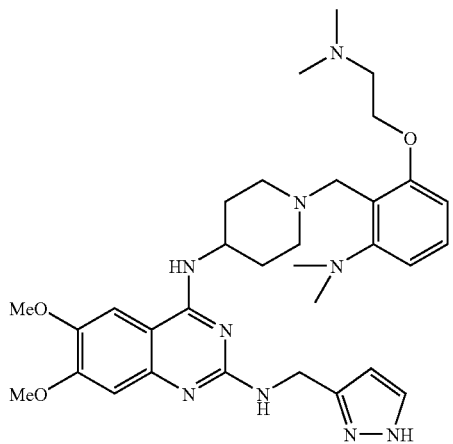

Compound 216

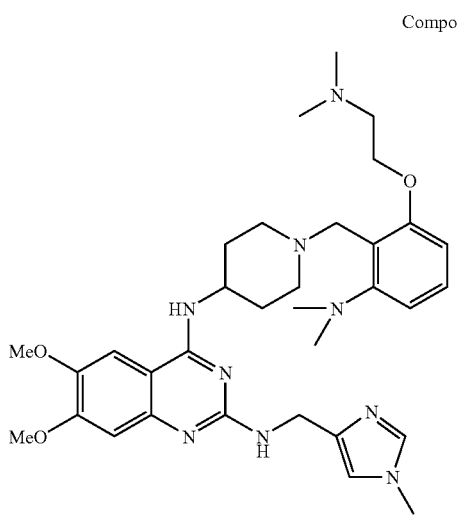

Compound 215

N~4~-(1-{2-(Dimethylamino)-6-[2-(dimethylamino)ethoxy]benzyl}piperidin-4-yl)-6,7-dimethoxy-N~2~-(1H-pyrazol-3-ylmethyl)quinazoline-2,4-diamine (Compound 216)

Following General Procedure D, Compound 75 (0.23 g, 0.43 mmol) and C-(1H-pyrazol-3-yl)methylamine (0.11 g, 1.11 mmol) were converted into the Compound 216 as a yellow solid.

$^1$HNMR (CD$_3$OD): δ ppm 1.68-1.85 (m, 2H), 2.01 (d, J=10.55 Hz, 2H), 2.38 (s, 6H), 2.54-2.73 (m, 8H), 2.82 (t, J=5.42 Hz, 2H), 3.71 (d, J=12.31 Hz, 2H), 3.88 (d, J=2.34 Hz, 6H), 4.04 (s, 2H), 4.11-4.27 (m, 3H), 4.65 (s, 2H), 6.24 (d, J=2.05 Hz, 1H), 6.78-6.88 (m, 2H), 2.92 (d, J=7.62 Hz, 1H), 7.30 (t, J=8.20 Hz, 1H), 7.41 (s, 1H), 7.49 (d, J=2.05 Hz, 1H).

MS (C$_{32}$H$_{45}$N$_9$O$_3$; MWt. 603): Observed M+1=604; M+Na=626.

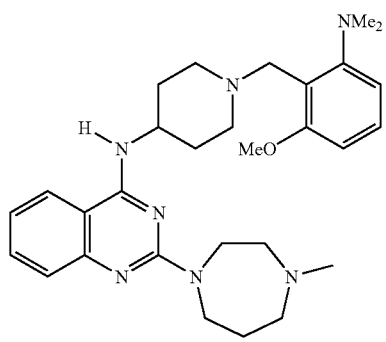

Compound 217

N~4~-(1-{2-(Dimethylamino)-6-[2-(dimethylamino)ethoxy]benzyl}piperidin-4-yl)-6,7-dimethoxy-N~2~-[(1-methyl-1H-imidazol-4-yl)methyl]quinazoline-2,4-diamine (Compound 215)

Following General Procedure D, Compound 75 (0.23 g, 0.43 mmol) and (1-methyl-1H-imidazol-4-yl)methylamine (0.14 g, 1.28 mmol) were converted into the Compound 215 as a yellow solid.

$^1$HNMR (CD$_3$OD): δ ppm 1.58-1.78 (m, 2H), 1.88-2.04 (m, 2H), 2.26-2.48 (m, 8H), 2.68 (s, 6H), 2.80 (t, J=5.57 Hz, 2H), 3.09 (d, J=12.60 Hz, 2H), 3.64 (s, 3H), 3.88 (d, J=3.81 Hz, 6H), 4.08-4.20 (m, 3H), 4.51 (s, 2H), 6.71-6.96 (m, 4H), 7.25 (t, J=8.20 Hz, 1H), 7.39 (s, 1H), 7.50 (s, 1H).

MS (C$_{33}$H$_{47}$N$_9$O$_3$; MWt. 617): Observed M+1=618, M+Na=640.

N-(1-(2-(Dimethylamino)-6-methoxybenzyl)piperidin-4-yl)-2-(4-methyl-1,4-diazepan-1-yl)quinazolin-4-amine (Compound 217)

Following General Procedure D, Compound 47 (50 mg, 0.12 mmol) and 1-methyl-1,4-diazepane (50 mg, 0.44 mmol) were converted into Compound 217.

$^1$HNMR (CDCl$_3$): δ 1.52 (br q, J=9.0 Hz, 2H), 1.77 (t, J=7.2 Hz, 2H), 2.00-2.15 (m, 4H), 2.30-2.45 (m, 2H), 2.37 (s, 3H), 2.55-2.62 (m, 2H), 2.70-2.78 (m, 2H), 2.80 (s, 6H), 2.93

(br d, J=12.0 Hz, 2H), 3.68 (s, 2H), 3.81 (s, 3H), 3.91 (t, J=6.0 Hz, 2H), 4.00 (t, J=5.1 Hz, 2H), 4.05-4.20 (m, 1H), 5.30 (d, J=7.2 Hz, 1H), 6.65 (d, J=8.1 Hz, 1H), 6.79 (d, J=8.1 Hz, 1H) 6.99 (dt, J=1.5, 6.6 Hz, 1H), 7.22 (t, J=8.1 Hz, 1H), 7.40-7.51 (m, 3H).

MS ($C_{29}H_{41}N_7O$; MWt. 503): Observed M+1=504.

Compound 218

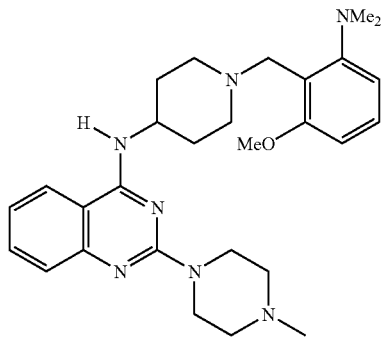

N-(1-(2-(Dimethylamino)-6-methoxybenzyl)piperidin-4-yl)-2-(4-methyl-piperazin-1-yl)quinazolin-4-amine (Compound 218)

Following General Procedure D, compound 47 (17 mg, 0.04 mmol) and 1-methylpiperazine (50 mg, 0.5 mmol) were converted into compound AGN 218795.

$^1$HNMR (CDCl$_3$): δ 1.52 (br q, J=9.0 Hz, 2H), 2.05 (br d, J=12.6 Hz, 2H), 2.35 (s, 3H), 2.39 (br t, J=9.9 Hz, 2H), 2.47 (t, J=4.8 Hz, 4H), 2.80 (s, 6H), 2.94 (br, 2H), 3.70 (s, 2H), 3.82 (s, 3H), 3.92 (t, J=4.2 Hz, 4H), 4.05-4.10 (m, 1H), 5.31 (d, J=7.2 Hz, 1H), 6.66 (d, J=8.1 Hz, 1H), 6.79 (d, J=8.1 Hz, 1H), 7.04 (t, J=6.6 Hz, 1H), 7.22 (t, J=8.1 Hz, 1H), 7.40-7.56 (m, 3H).

MS ($C_{28}H_{39}N_7O$; MWt. 489): Observed M+1=490.

Compound 219

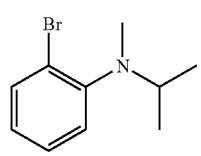

2-Bromo-N-isopropyl-N-methylaniline (Compound 219)

To a solution of 2-bromo-N-methylaniline (2.07 g, 11.22 mmol), in dichloroethane (45 mL) was added acetone (1.31 g, 22.5 mmol), AcOH (4.04 g, 67.32 mmol) and Na(OAc)$_3$BH (7.14 g, 33.66 mmol) sequentially at RT. The mixture was stirred for 72 h. The reaction was cooled with ice bath, and 2M NaOH (100 mL) was added slowly, then stirred for 5 min. The organic layer was separated, washed with brine dried and solvent removed. The crude product contained a mixture of 2:1 ratio of Compound 219 and starting material. This mixture was used as is in the next step.

MS ($C_{10}H_{14}BrN$; MWt. 227): Observed M+1=228.

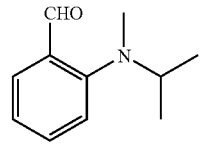

Compound 220

2-(N-Isopropyl-N-methylamino)benzaldehyde (Compound 220)

To a cold (−78° C.) solution of 2-bromo-N-isopropyl-N-methylaniline (Compound 220) (and 2-bromo-N-methylaniline ~50%) (1.2 g, 2.66 mmol), in THF (10 mL) was added n-BuLi in hexane (2.5 M soln., 3.6 mL, 2.92 mmol). The reaction was stirred for 5 min at −78° C., and DMF (700 mg, 9.6 mmol) was added. The cooling bath was removed and the reaction was stirred at RT for 30 min. The reaction was then quenched by adding EtOAc (75 mL), and the solution was washed with water, and brine; and dried, and the solvent was removed in vacuo. The crude material was purified by silica gel chromatography eluting with 0-10% EtOAc in hexane. The title compound was obtained as pale yellow oil.

$^1$HNMR (CDCl$_3$): δ 1.17 (d, J=6.9 Hz, 6H), 2.44 (s, 3H), 3.48 (sept, J=6.9 Hz, 1H), 7.02 (t, J=7.5 Hz, 1H), 7.09 (d, J=7.5 Hz, 1H), 7.46 (t, J=7.5 Hz, 1H), 7.79 (d, J=7.5 Hz, 1H), 10.21 (s, 1H).

MS ($C_{10}H_{14}BrN$; MWt. 227): Observed M+1=228.

Compound 221

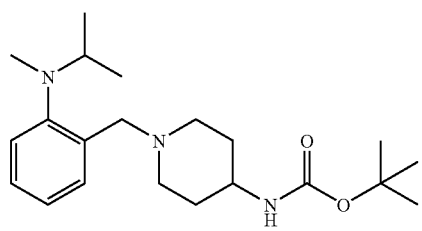

tert-Butyl 1-(2-(N-isopropyl-N-methylamino)benzyl)piperidin-4-ylcarbamate (Compound 221)

To a solution of tert-butyl piperidin-4-ylcarbamate (262 mg, 1.31 mmol) (Aldrich) and 2-(N-isopropyl-N-methylamino)benzaldehyde (150 mg, 0.85 mmol) in CH$_2$Cl$_2$ (6 mL) was added Na(OAc)$_3$BH (288 mg, 1.36 mmol) followed by AcOH (0.1 mL). This mixture was stirred for 3 h at RT. The reaction was quenched by adding 2M NaOH—H$_2$O (5 mL) and stirred for 5 min. The mixture was then extracted with CH$_2$Cl$_2$ (2×25 mL), and the organic layer was washed with brine, and dried, and the solvent was removed. The crude material was purified by silica gel column chromatography eluting with 5% NH$_3$-MeOH in CH$_2$Cl$_2$ gave Compound 221.

$^1$HNMR (CDCl$_3$): δ 1.05 (d, J=6.9 Hz, 6H), 1.36-1.50 (m, 2H), 1.44 (s, 9H), 1.89 (br d, J=12.6 Hz, 2H), 2.14 (t, J=12.6 Hz, 2H), 2.58 (s, 3H), 2.80 (br d, J=11.4 Hz, 2H), 3.26 (sept, J=6.9 Hz, 1H), 3.55 (s, 2H), 4.42 (br s, 1H), 7.02 (t, J=7.5 Hz, 1H), 7.09 (d, J=7.5 Hz, 1H), 7.18 (t, J=7.5 Hz, 1H), 7.46 (d, J=7.5 Hz, 1H).

MS ($C_{21}H_{35}N_3O_2$; MWt. 361): Observed M+1=362.

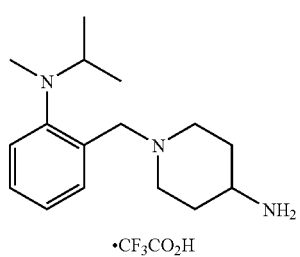

Compound 222

·CF₃CO₂H

Compound A-3 (50 mg, 0.14 mmol) and CF₃CO₂H (2 mL) were stirred at RT for 2 h. Then, all the CF₃CO₂H was removed on rotavapor and the crude product (compound A-4) was used as it is in the next step.

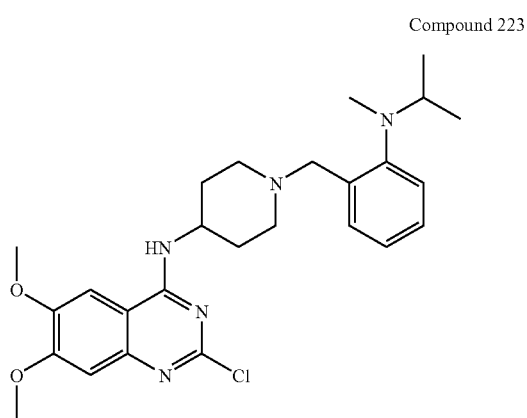

Compound 223

N-(1-(2-(Isopropyl(methyl)aminobenzyl)piperidin-4-yl)-2-chloro-6,7-dimethoxyquinazolin-4-amine (Compound A-5)

Following General Procedure C, Compound 222 (400 mg), and 2,4-dichloro-6,7-dimethoxyquinazoline (360 mg, 1.44 mmol) were converted into Compound 223.

¹HNMR (CDCl₃): δ 1.07 (d, J=6.6 Hz, 6H), 1.61 (br q, J=12.0 Hz, 2H), 2.20 (br d, J=10.5 Hz, 2H), 2.27 (br t, J=10.5 Hz, 2H), 2.60 (S, 3H), 2.90 (br d, J=12.3, 2H), 3.30 (sept, J=6.6 Hz, 1H), 3.59 (s, 2H), 3.95 (s, 3H), 3.97 (s, 3H), 4.20-4.28 (m, 1H), 5.38-5.45 (br s, 1H), 6.82 (br s, 1H), 7.03 (dt, J=1.5, 7.2 Hz, 1H), 7.09 (dd, J=1.5, 7.2 Hz, 1H), 7.11 (s, 1H), 7.47 (dd, J=1.5, 7.2 Hz, 1H).

MS (C₂₆H₃₄ClN₅O₂; M.Wt. 483): Observed M+1=484.

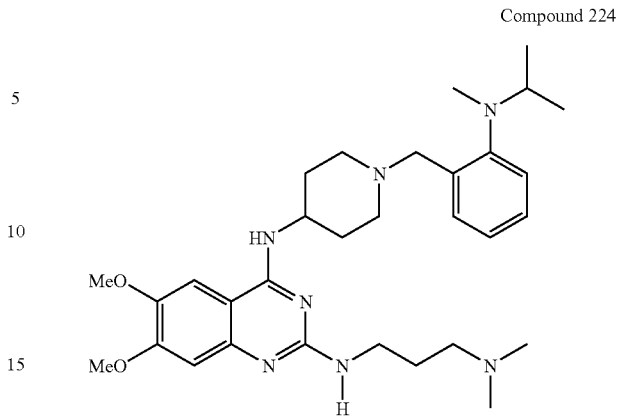

Compound 224

N2-(3-(Dimethylamino)propyl)-N4-(1-(2-(isopropyl (methyl)amino)benzyl)piperidin-4-yl)-6,7-dimethox-yquinazoline-2,4-diamine (Compound 224)

Following General Procedure D, Compound 223 (90 mg, 0.19 mmol) and 3-(N,N-dimethylamino)-propylamine (220 mg, 2.16 mmol) were converted into Compound 224.

¹HNMR (CDCl₃): δ 1.06 (d, J=6.3 Hz, 6H), 1.55 (br q, J=12.0 Hz, 2H), 1.78 (pent, J=7.5 Hz, 2H), 2.12 (br d, J=12.0 Hz, 2H), 2.18-2.24 (m, 2H), 2.22 (s, 6H), 2.37 (t, J=6.9 Hz, 2H), 2.59 (s, 3H), 2.95 (br d, J=12.0 Hz, 2H), 3.30 (sept, J=6.3 Hz, 1H), 3.49 (q, J=6.0 Hz, 2H), 3.58 (s, 2H), 3.88 (s, 3H), 3.91 (s, 3H), 4.10-4.23 (m, 1H), 5.05 (br t, J=6.0 Hz, 1H), 5.24 (br d, J=6.0 Hz, 1H), 6.78 (s, 1H), 6.86 (s, 1H), 7.02 (dt, J=1.4, 7.4 Hz, 1H), 7.08 (dd, J=1.4, 7.4 Hz, 1H), 7.19 (dt, J=1.4, 7.4 Hz, 1H), 7.47 (dd, J=1.4, 7.4 Hz, 1H).

MS (C₃₁H₄₇N₇O₂; M.Wt. 549): Observed M+1=550.

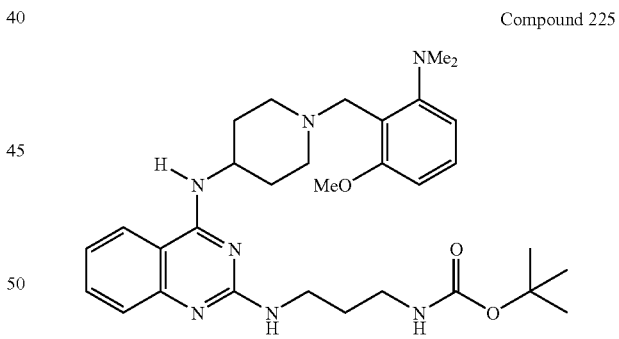

Compound 225 tert-Butyl-3-(4-(1-(2-(dimethylamino)-6-methoxy-benzyl)piperidin-4-ylamino)quinazolin-2-ylamino) propylcarbamate (Compound 225)

Following General Procedure D, Compound 47 (104 mg, 0.25 mmol) and tert-butyl 3-aminopropylcarbamate (300 mg, 1.8 mmol) were converted into Compound 225.

¹HNMR (CDCl₃): δ 1.49 (s, 9H), 1.45-1.55 (m, 2H), 1.70-1.78 (m, 2H), 2.03 (br d, J=7.5 Hz, 2H), 2.37 (br t, J=7.5 Hz, 2H), 2.80 (s, 6H), 2.94 (br d, J=7.2 Hz, 2H), 3.20 (, br d, J=3.3 Hz, 2H), 3.59 (br q, J=3.3 Hz, 2H), 3.70 (s, 2H), 3.81 (s, 3H), 4.09-4.20 (m, 1H), 4.95-5.02 (br s, 1H), 5.35-5.42 (br s, 1H), 6.66 (d, J=5.1 Hz, 1H), 6.79 (d, J=5.1 Hz, 1H), 7.07 (t, J=4.8 Hz, 1H), 7.23 (t, J=5.1 Hz, 1H), 7.45 (d, J=4.8 Hz, 1H), 7.47-7.55 (m, 2H).
MS ($C_{31}H_{45}N_7O_3$; MWt. 563): Observed M+1=564

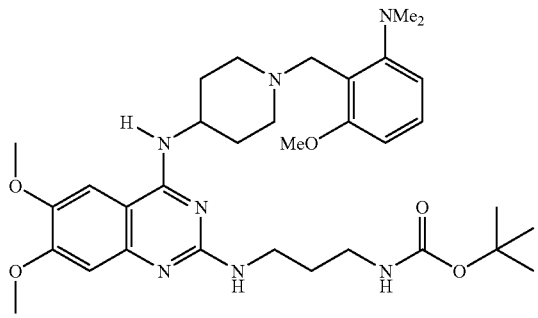

Compound 226 tert-Butyl-3-(4-(1-(2-(dimethylamino)-6-methoxy-benzyl)piperidin-4-ylamino)6,7-dimethoxyquinazo-lin-2-ylamino)propylcarbamate (Compound 226)

Following General Procedure D, Compound 40 (120 mg, 0.25 mmol) and tert-butyl 3-aminopropylcarbamate (300 mg, 1.8 mmol) were converted into Compound 226.
$^1$HNMR (CDCl$_3$): δ 1.46 (s, 9H), 1.45-1.60 (m, 2H), 1.70-1.85 (m, 3H), 2.05 (br d, J=7.5 Hz, 2H), 2.35 (br t, J=7.5 Hz, 2H), 2.80 (s, 6H), 3.03 (br d, J=7.2 Hz, 2H), 3.22 (br q, J=6.0 Hz, 2H), 3.60 (br q, J=6.0 Hz, 2H), 3.70 (s, 2H), 3.81 (s, 3H), 3.92 (s, 3H), 3.96 (s, 3H), 4.09-4.20 (m, 1H), 4.98 (br d, J=6.0 Hz, 1H), 6.65 (d, J=8.1 Hz, 1H), 6.68 (s, 1H), 6.80 (d, J=8.1 Hz, 1H), 6.88 (s, 1H), 7.22 (t, J=8.1 Hz, 1H).
MS ($C_{33}H_{49}N_7O_5$; MWt. 623): Observed M+1=624

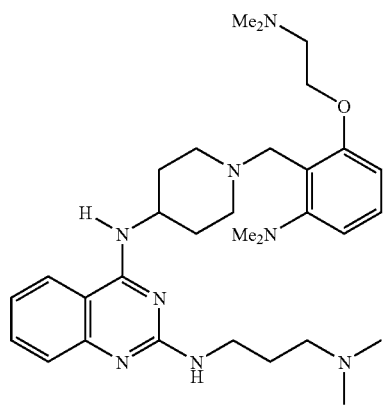

Compound 227 tert-Butyl-3-(4-(1-(2-(dimethylamino)-6-methoxy-benzyl)piperidin-4-ylamino)6,7-dimethoxyquinazo-lin-2-ylamino)propylcarbamate (Compound 227)

Compound 226 (6 mg, 0.0096 mmol) was mixed with CF$_3$CO$_2$H (0.5 mL) and stirred for 2 h at RT. Then all the solvent was removed on rotavapor and the crude mixture was diluted with CH$_2$Cl$_2$ (2 mL). To this mixture was added K$_2$CO$_3$ (100 mg), and the reaction was stirred for 30 min. Then water (0.1 mL) was added and the mixture was stirred for an additional 10 min. The product was extracted with CH$_2$Cl$_2$ (20 mL), and the solvent was dried, and filtered, and the solvent removed under reduced pressure to obtain Compound 227 as a thick oil.

$^1$HNMR (CDCl$_3$): δ 1.45-1.70 (m, 4H), 1.70-1.85 (m, 2H), 2.05 (br d, J=7.5 Hz, 2H), 2.35 (br t, J=7.5 Hz, 2H), 2.80 (s, 6H), 2.95 (br d, J=7.2 Hz, 2H), 3.55 (br q, J=6.0 Hz, 2H), 3.69 (s, 2H), 3.81 (s, 3H), 3.92 (s, 3H), 3.94 (s, 3H), 4.05-4.20 (m, 1H), 4.95-5.02 (br s, 1H), 6.66 (d, J=8.1 Hz, 1H), 6.68 (s, 1H), 6.79 (d, J=8.1 Hz, 1H), 6.86 (s, 1H), 7.22 (t, J=8.1 Hz, 1H).
MS ($C_{28}H_{41}N_7O_3$; MWt. 523): Observed M−1=522.

Compound 228

N4-(1-(2-(Dimethylamino)-6-(2-(dimethylamino)ethoxy)benzyl)piperidin-4-yl)-N2-(3-(dimethylamino)propyl)quinazoline-2,4-diamine (Compound 228)

Following General Procedure A, compound 72 (118 mg, 0.5 mmol) and Compound 129 (150 mg, 0.46 mmol) were converted to Compound 228.
$^1$HNMR (CD$_3$OD): δ 2.10-2.28 (m, 5H), 2.47 (br d, J=7.2 Hz, 2H), 2.87 (s, 6H), 2.99 (s, 8H), 3.07 (s, 6H), 3.55-3.64 (br s, 4H), 3.77 (t, J=4.5 Hz, 2H), 3.77-3.85 (br s, 4H), 4.50 (t, J=4.5 Hz, 2H), 7.08 (d, J=8.1 Hz, 1H), 7.21 (d, J=8.1 Hz, 1H), 7.47 (t, J=7.8 Hz, 1H), 7.50 (d, J=7.8 Hz, 1H), 7.56 (t, J=8.1 Hz, 1H), 7.83 (d, J=7.8 Hz, 1H), 8.25 (d, J=8.4 Hz, 1H).
MS ($C_{31}H_{48}N_8O$; MWt. 548): Observed M+1=549

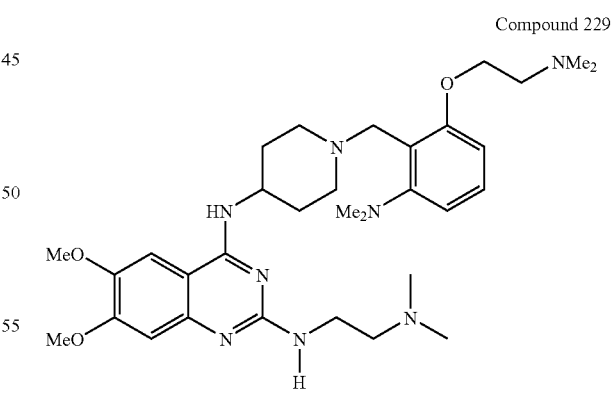

Compound 229

N4-(1-(2-(Dimethylamino)-6-(2-(dimethylamino)ethoxy)benzyl)piperidin-4-yl)-N2-(2-(dimethylamino)ethyl)-6,7-dimethoxyquinazoline-2,4-diamine (Compound 229)

Following General Procedure D, compound 75 (100 mg, 0.18 mmol) and 2(N,N-dimethyl amino)-ethylamine (176 mg, 2 mmol) were converted into Compound 229.

¹HNMR (CDCl₃): δ 1.55 (br q, J=7.5 Hz, 2H), 2.05 (br d, J=7.5 Hz, 2H), 2.28 (s, 6H), 2.34 (s, 6H), 235-2.40 (m, 2H), 2.54 (t, J=6.3 Hz, 2H), 2.70-2.80 (m, 2H), 2.77 (s, 6H), 2.98 (br d, J=7.5 Hz, 2H), 3.54 (q, J=5.4 Hz, 2H), 3.68 (s, 2H), 3.90 (s, 3H), 3.92 (s, 3H), 4.07 (t, J=6.3 Hz, 2H), 4.10-4.23 (m, 1H), 5.15-5.21 (m, 2H), 6.65 (d, J=8.1 Hz, 1H), 6.76 (s, 1H), 6.79 (d, J=8.1 Hz, 1H), 6.88 (s, 1H), 7.20 (t, J=8.1 Hz, 1H).

MS ($C_{32}H_{50}N_8O_3$; M.Wt. 594): Observed M+1=594.

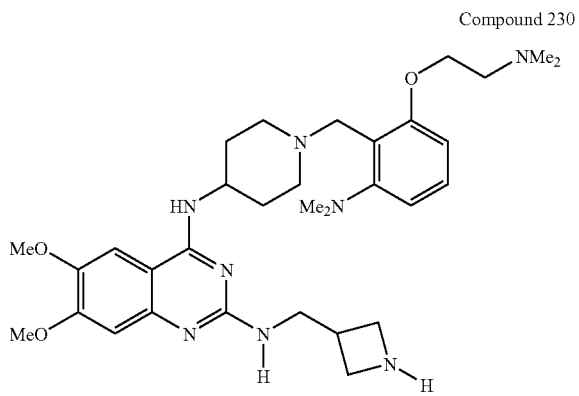

Compound 230

N2-(Azetidin-3-ylmethyl)-N4-(1-(2-(dimethylamino)-6-(2-(dimethylamino)ethoxy)benzyl)piperidin-4-yl)-6,7-dimethoxyquinazoline-2,4-diamine (Compound 230)

Following General Procedure D, Compound 75 (100 mg, 0.18 mmol) and tert-butyl 3-(aminomethyl)azetidine-1-carboxylate (62 mg, 0.31 mmol) were converted into the carbamate product. The crude carbamate product was treated with $CF_3CO_2H$ and purified using neutral alumina prep TLC, eluting with 5% $NH_3$-MeOH and 95% $CH_2Cl_2$ to isolate the title compound.

¹HNMR (CDCl₃): δ 1.58 (br q, J=7.5 Hz, 2H), 2.05 (br d, J=7.5 Hz, 2H), 2.30-2.43 (m, 5H), 2.38 (s, 6H), 2.65-2.75 (m, 2H), 2.70 (s, 6H), 2.98 (br d, J=7.5 Hz, 2H), 3.50 (t, J=4.5 Hz, 2H), 3.72 (s, 2H), 3.72-3.80 (m 2H), 3.93 (s, 3H), 3.96 (s, 3H), 4.07 (t, J=4.5 Hz, 2H), 4.08-4.23 (m, 1H), 5.20 (br, 2H), 6.68 (d, J=7.8 Hz, 1H), 6.75 (s, 1H), 6.83 (d, J=7.8 Hz, 1H), 6.88 (s, 1H), 7.20 (t, J=7.8 Hz, 1H).

MS ($C_{32}H_{48}N_8O_3$; M.Wt. 592): Observed M+1=593.

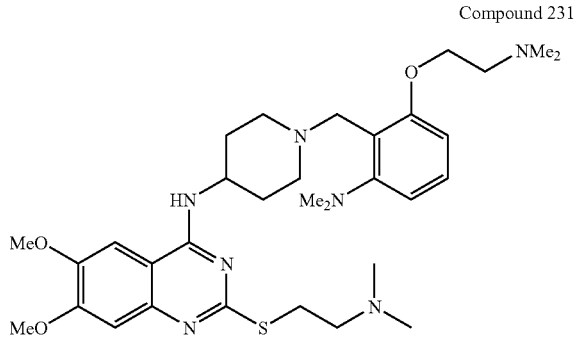

Compound 231

N-(1-(2-(Dimethylamino)-6-(2-(dimethylamino)ethoxy)benzyl)piperidin-4-yl)-2-(2-(dimethylamino)ethylthio)-6,7-dimethoxyquinazolin-4-amine (Compound 231)

In to a teflon screw capped pressure tube was placed 2-(dimethyalmino)-ethanethiol hydrochloride (35 mg, 0.24 mmol), t-BuOK (55 mg, 0.5 mmol) and anhydrous t-BuOH (3 mL) under nitrogen atmosphere. The pressure tube was capped and heated to 70° C. for 20 min. Then the cap was removed under positive nitrogen flow, and Compound 75 (50 mg, 0.095 mmol) was added, the pressure tube was capped under positive nitrogen flow. The reaction was heated to 140° C. for 16 h. The solvent was removed under reduced pressure, and the product was purified by silica gel chromatography (eluted with 5% $NH_3$-MeOH and 95% $CH_2Cl_2$). The title compound was isolated as a pale yellow oil.

¹HNMR (CDCl₃): δ 1.65 (br q, J=7.5 Hz, 2H), 2.05 (br d, J=7.5 Hz, 2H), 2.34 (s, 6H), 2.36 (s, 6H), 2.45-2.55 (br m, 2H), 2.70-2.85 (m, 4H), 2.72 (s, 6H), 2.95 (br d, J=8.4 Hz, 2H), 3.31 (t, J=5.6 Hz, 2H), 3.69 (s, 2H), 3.96 (s, 3H), 3.98 (s, 3H), 4.06 (t, J=5.6 Hz, 2H), 4.20-4.30 (br m, 1H), 5.35-5.42 (br d, 1H), 6.66 (d, J=7.2 Hz, 1H), 6.80 (s, 1H), 6.81 (d, J=8.1 Hz, 1H), 7.03 (s, 1H), 7.21 (t, J=8.1 Hz, 1H).

MS ($C_{32}H_{49}N_7O_3S$; M.Wt. 611): Observed M+1=612.

Biological Methods

Measurement of Intracellular $Ca^{+2}$ Responses for CXCR4 Compounds

HEK-Gqi5 cells stably expressing the human CXCR4 receptor were utilized for these studies. The growth media for the CXCR4 receptor expressing cell line was DMEM high glucose medium supplemented with 10% fetal bovine serum (FBS), 1% antibiotic-antimycotic, 50 ug/ml hygromycin B, and 400 μg/ml geneticin. Ten thousand cells per well were plated into 384-well poly-D-lysine coated plates one day prior to use. On the day of the experiment, the cells were washed twice with Hank's Balanced Salt Solution supplemented with 20 mM hepes (HBSS/hepes buffer). The cells were then dye loaded with 2 uM Fluo-4 diluted in the HBSS/Hepes buffer and incubated at 37° C. for 40 minutes. Extracellular dye was removed by washing the cell plates four times prior to placing the plates in the FLIPR (Fluorometric Imaging Plate Reader, Molecular Devices). Ligands were diluted in HBSS/Hepes buffer and prepared in 384-well microplates. The positive control, stromal-cell derived factor-1 (SDF-1α), was diluted in HBSS/Hepes buffer with 4 mg/ml fatty acid free bovine serum albumin. Two drug additions were made by the FLIPR. The first drug addition was the test drug in concentrations ranging from 2.44 nM to 40,000 nM. After this addition, fluorescent measurements were taken. Any calcium release in response to this drug addition represents agonist activity of the compounds. The second drug addition was SDF-1α at a final concentration of 1.9 nM ($EC_{65}$). Fluorescence measurements were also taken after this second drug addition and were used to determine the ability of the test compounds to antagonize the SDF-1α response. Results were expressed as $EC_{50}$ and efficacy values, as well as $IC_{50}$ and percent antagonism values. As controls, SDF-1α (CXCR4 agonist) and AMD3100 (CXCR4 antagonist) dose-response curves were also determined in each study.

| Compound Number | Structure | CXCR4 IC$_{50}$ (% Inh) |
|---|---|---|
| 30 | 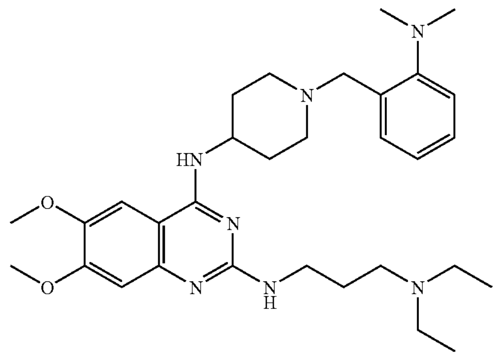 | 270 nM (100) |
| 31 | 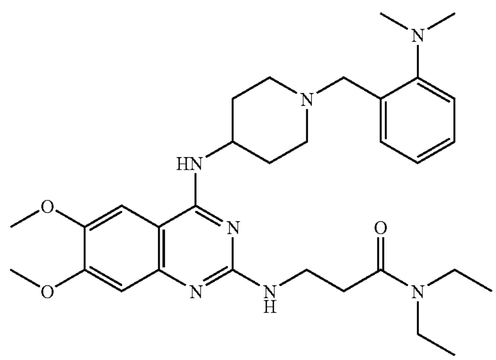 | 2.4 µM (92) |
| 32 | 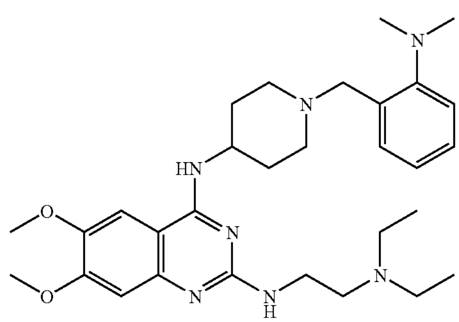 | 343 nM (90) |
| 33 | 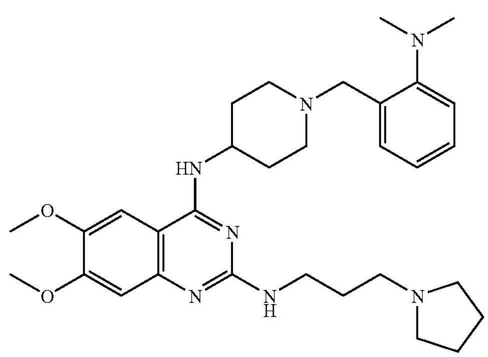 | 617 nM (93) |

-continued

| Compound Number | Structure | CXCR4 IC$_{50}$ (% Inh) |
|---|---|---|
| 35 | 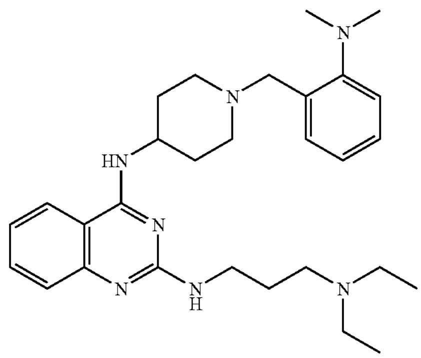 | 330 nM (90) |
| 36 | 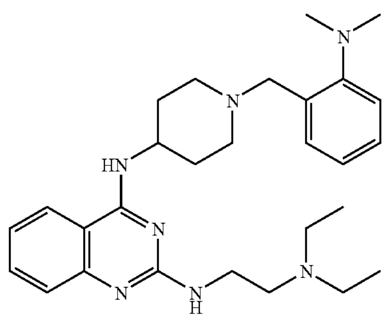 | 800 nM (90) |
| 41 | 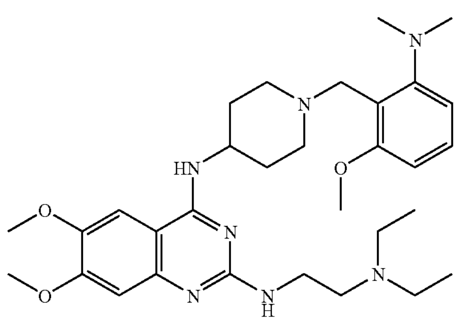 | 360 nM (100) |
| 42 | 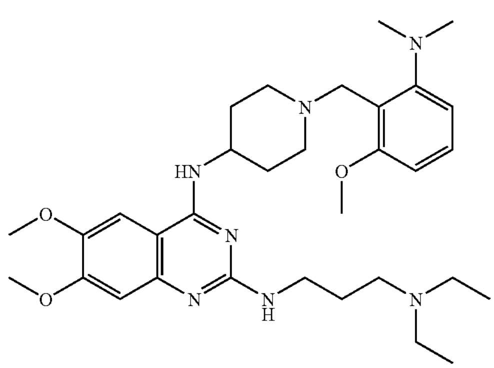 | 179 nM (98) |

-continued

| Compound Number | Structure | CXCR4 IC$_{50}$ (% Inh) |
|---|---|---|
| 48 | 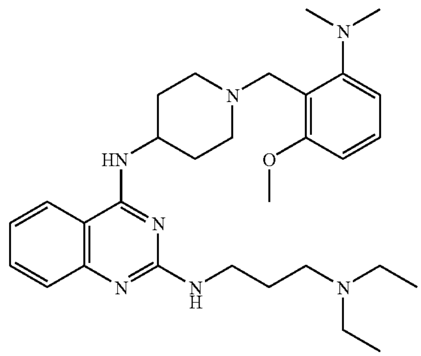 | 150 nM (100) |
| 50 | 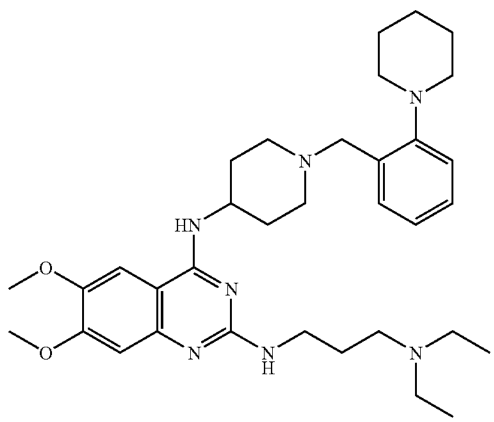 | 6.7 μM (86) |
| 51 | 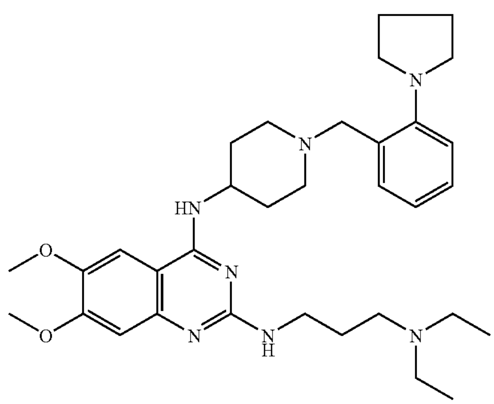 | 1.1 μM (92) |
| 52 | 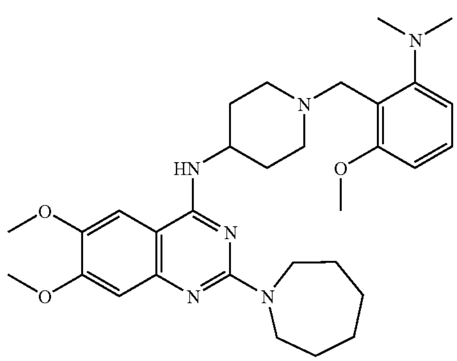 | 730 nM (90) |

-continued

| Compound Number | Structure | CXCR4 IC$_{50}$ (% Inh) |
|---|---|---|
| 65 | 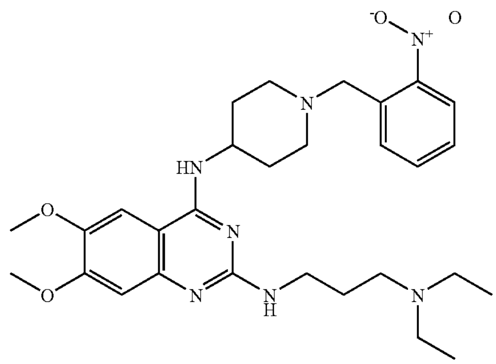 | 4.9 µM (93) |
| 66 | 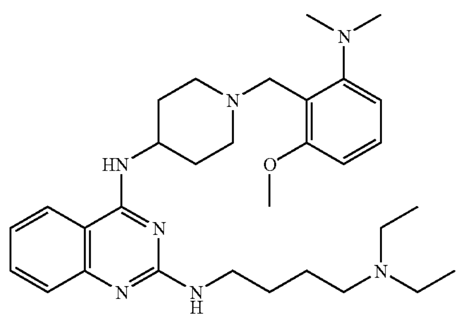 | 200 nM (93) |
| 67 | 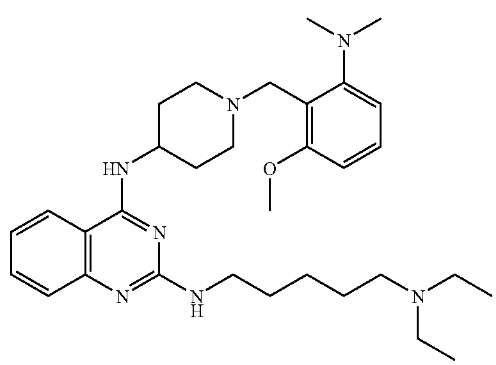 | 1.9 µM (88) |
| 68 | 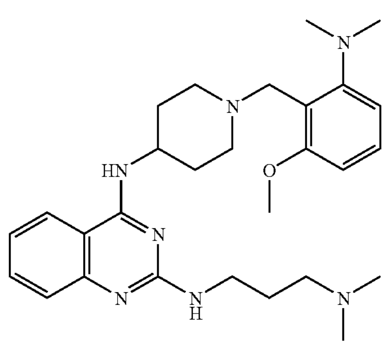 | 41 nM (95) |

-continued
| Compound Number | Structure | CXCR4 IC$_{50}$ (% Inh) |
|---|---|---|
| 76 | 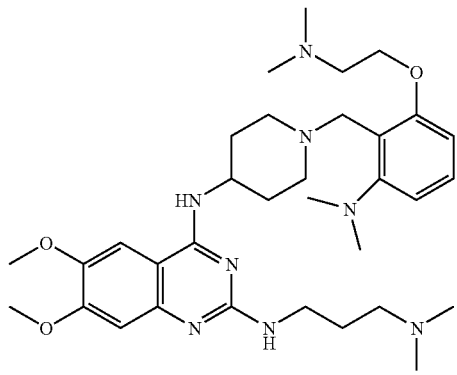 | 19 nM (94) |
| 77 | 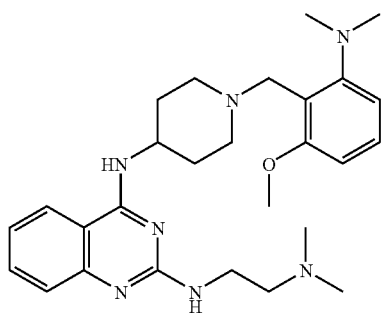 | 118 nM (98) |
| 78 | 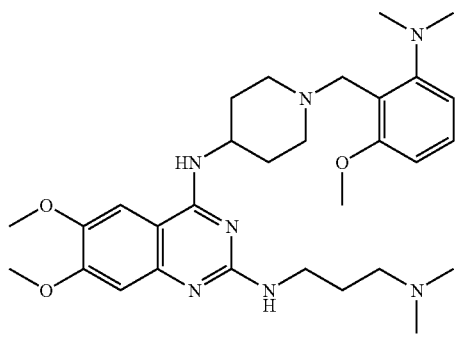 | 283 nM (100) |
| 80 | 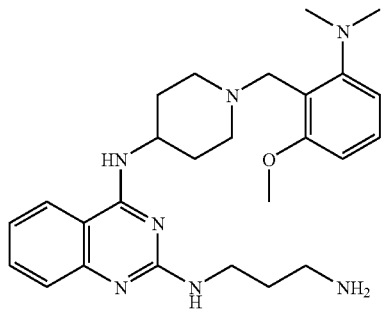 | 130 nM (94) |

-continued

| Compound Number | Structure | CXCR4 IC$_{50}$ (% Inh) |
| --- | --- | --- |
| 81 | 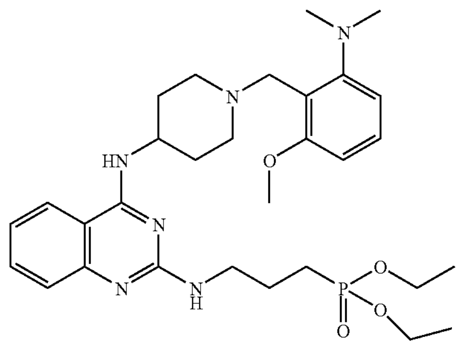 | 1.6 μM (99) |
| 82 | 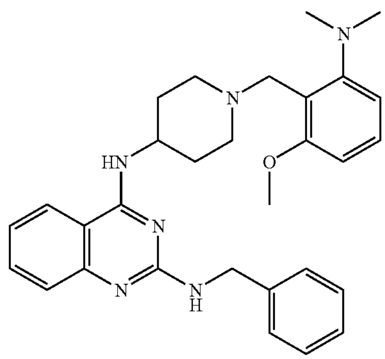 | ND |
| 83 | 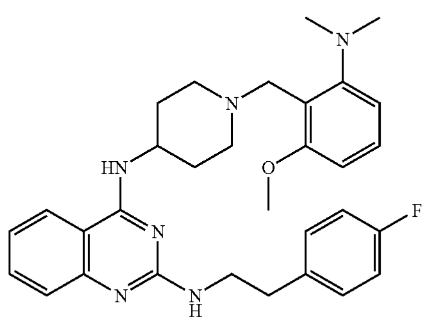 | ND |
| 84 | 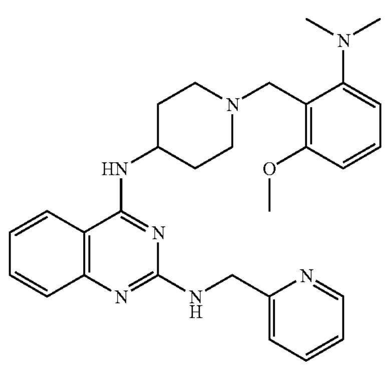 | 574 nM (95) |

-continued
| Compound Number | Structure | CXCR4 IC$_{50}$ (% Inh) |
|---|---|---|
| 85 | 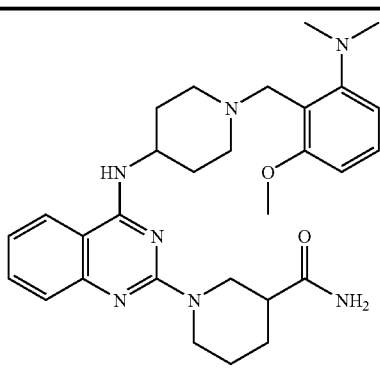 | 4.9 μM (93) |
| 86 | 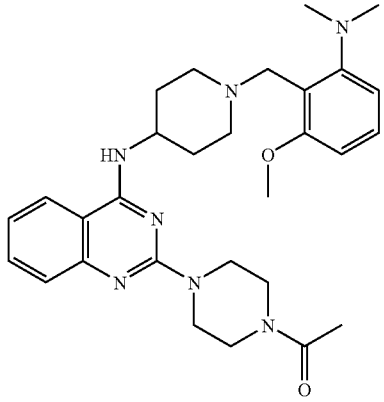 | 3.5 μM (86) |
| 87 | 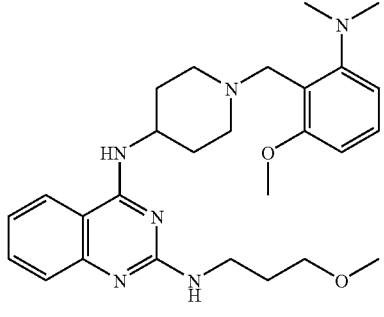 | 810 nM (96) |
| 88 | 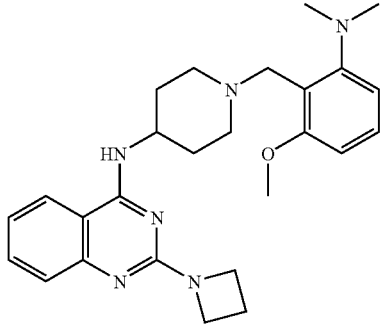 | 1.9 μM (94) |

-continued
| Compound Number | Structure | CXCR4 IC$_{50}$ (% Inh) |
|---|---|---|
| 89 | 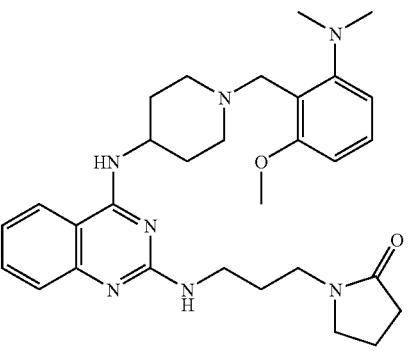 | 1.4 μM (92) |
| 90 | 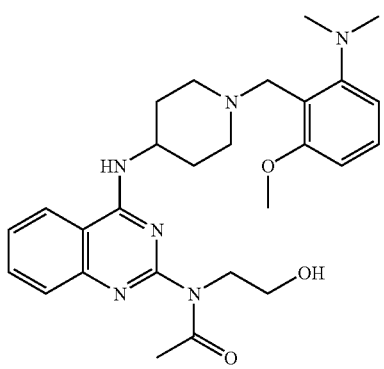 | 1.5 μM (93) |
| 91 | 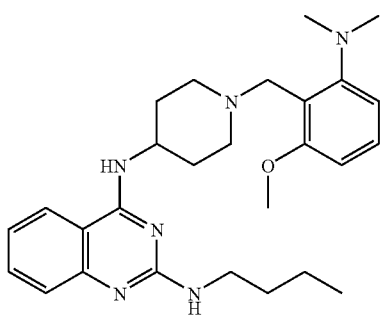 | 2.0 μM (80) |
| 92 | 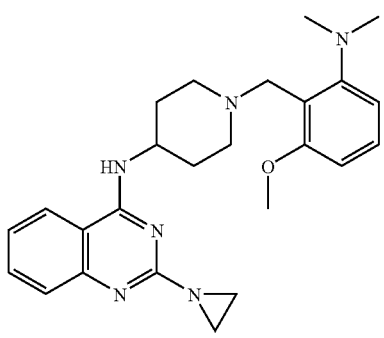 | 2.1 μM (75) |

-continued
| Compound Number | Structure | CXCR4 IC$_{50}$ (% Inh) |
|---|---|---|
| 93 | 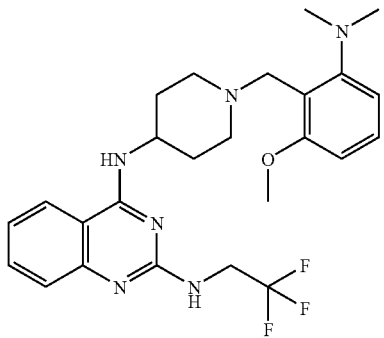 | 4.3 µM (79) |
| 94 | 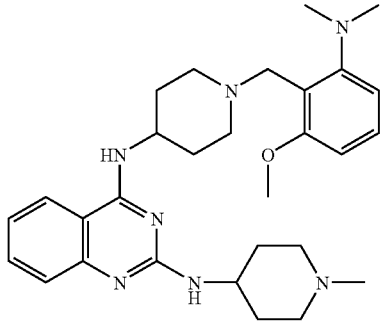 | 790 nM (96) |
| 95 | 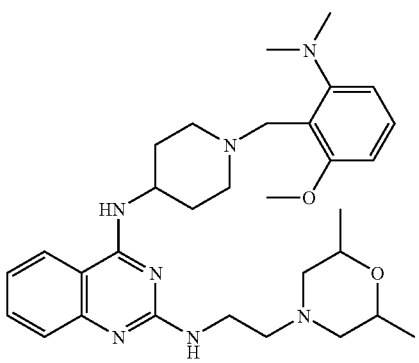 | 605 nM (98) |
| 96 | 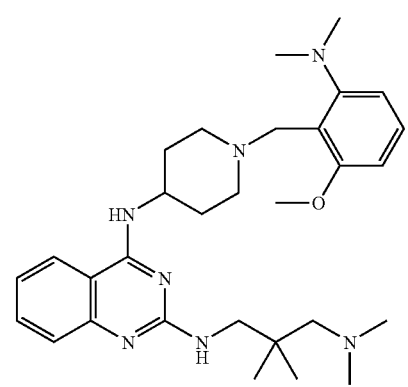 | 240 nM (100) |

-continued
| Compound Number | Structure | CXCR4 IC$_{50}$ (% Inh) |
|---|---|---|
| 97 | 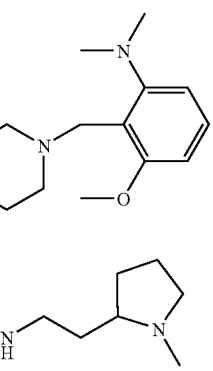 | 140 nM (100) |
| 98 | 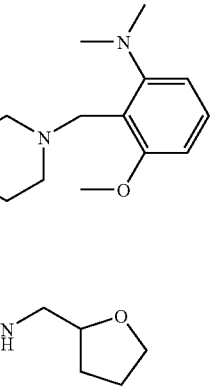 | 624 nM (98) |
| 99 | 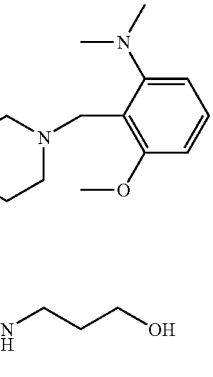 | 611 nM (100) |
| 100 | 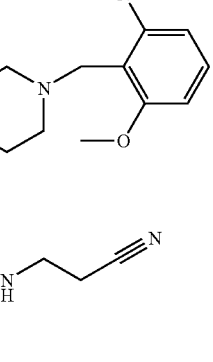 | 1.9 μM (100) |

-continued

| Compound Number | Structure | CXCR4 IC$_{50}$ (% Inh) |
|---|---|---|
| 101 | 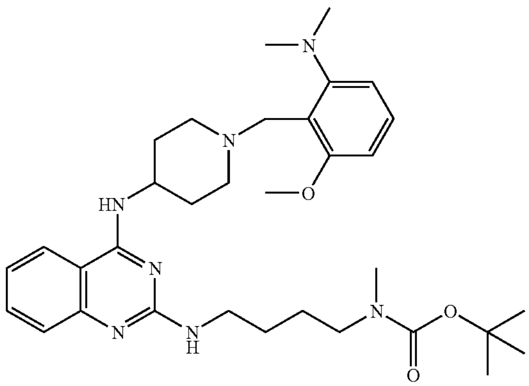 | ND |
| 102 | 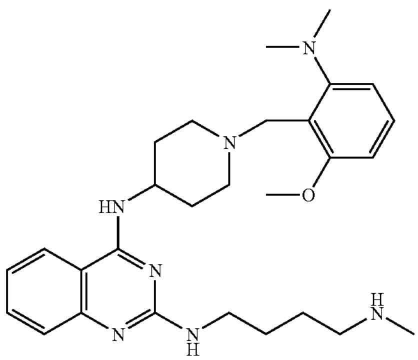 | 215 nM (97) |
| 103 | 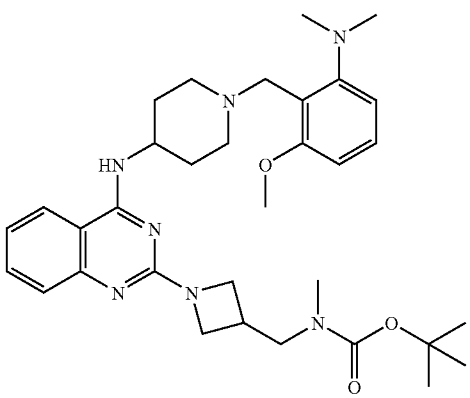 | 4.1 μM (82) |
| 104 | 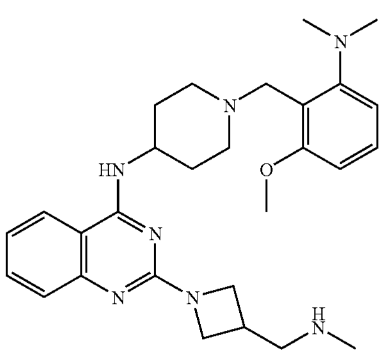 | 1.0 μM (97) |

-continued

| Compound Number | Structure | CXCR4 IC$_{50}$ (% Inh) |
|---|---|---|
| 105 | 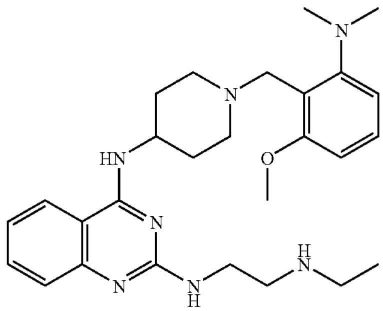 | 771 nM (98) |
| 106 | 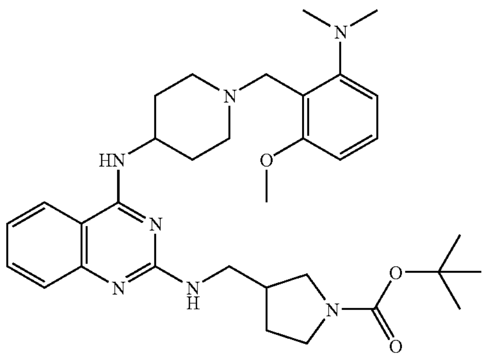 | 2.3 μM (73) |
| 107 | 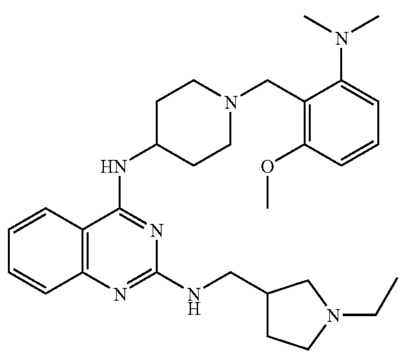 | 653 nM (96) |
| 108 | 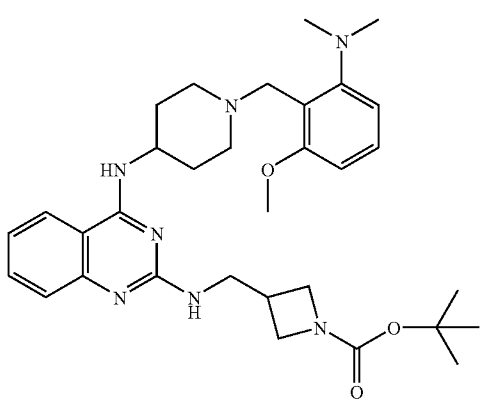 | 2.0 μM (89) |

-continued
| Compound Number | Structure | CXCR4 IC$_{50}$ (% Inh) |
|---|---|---|
| 109 | 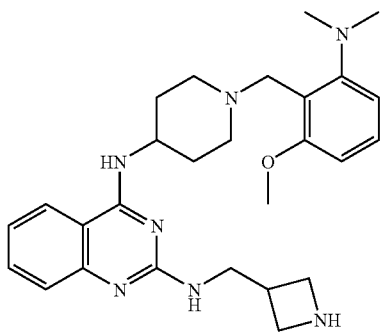 | 155 nM (98) |
| 110 | 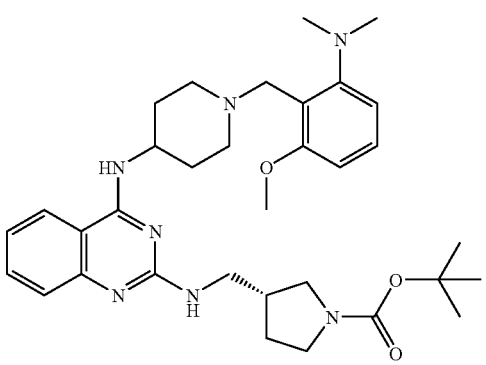 | 2.2 μM (81) |
| 111 | 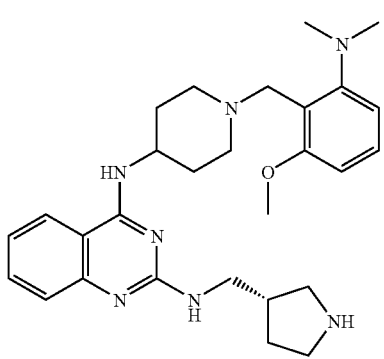 | 224 μM (98) |
| 112 | 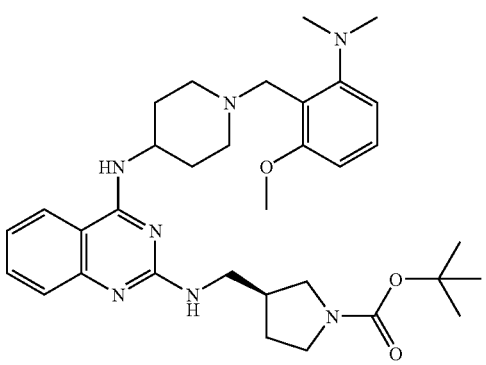 | 2.1 μM (77) |

-continued

| Compound Number | Structure | CXCR4 IC$_{50}$ (% Inh) |
|---|---|---|
| 113 | 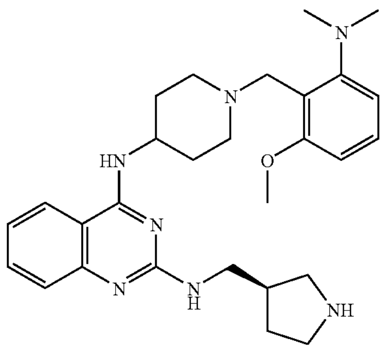 | 129 nM (99) |
| 114 | 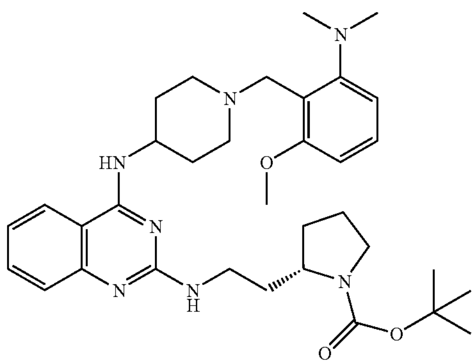 | 2.1 µM (75) |
| 115 | 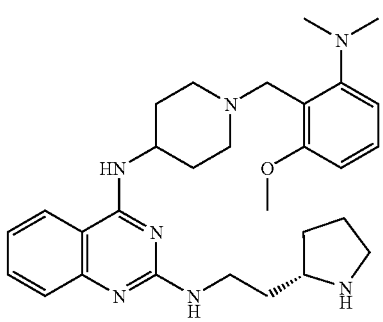 | 234 nM (95) |
| 116 | 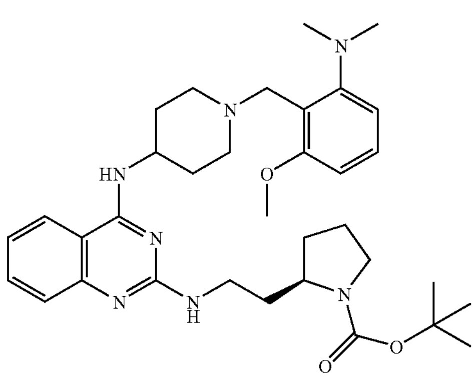 | 2.2 µM (83) |

-continued

| Compound Number | Structure | CXCR4 IC$_{50}$ (% Inh) |
|---|---|---|
| 117 | 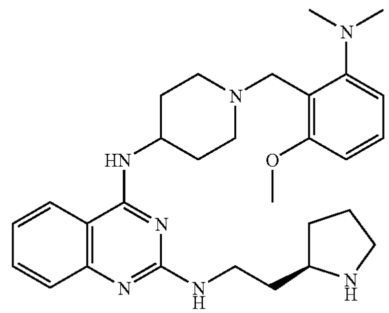 | 319 nM (95) |
| 118 | 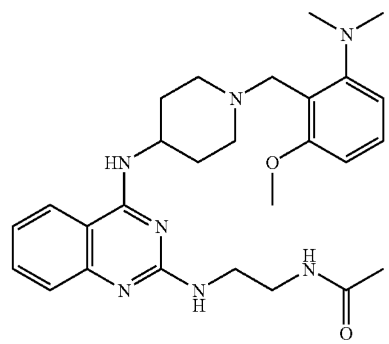 | 762 nM (97) |
| 119 | 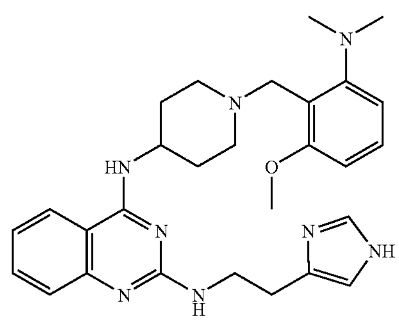 | 387 nM (96) |
| 120 | 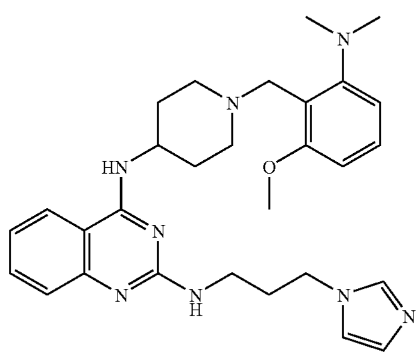 | 1.7 μM (95) |

-continued

| Compound Number | Structure | CXCR4 IC₅₀ (% Inh) |
|---|---|---|
| 121 | 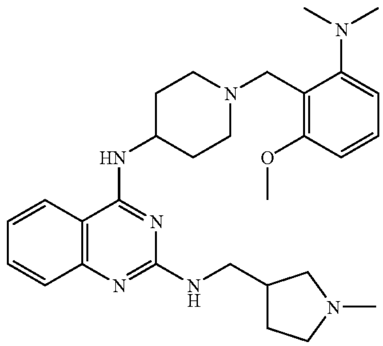 | 380 nM (97) |
| 123 | 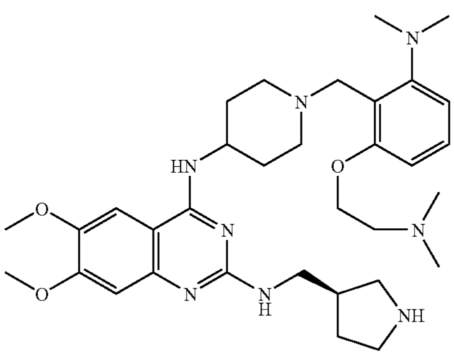 | 84 nM (96) |
| 125 | 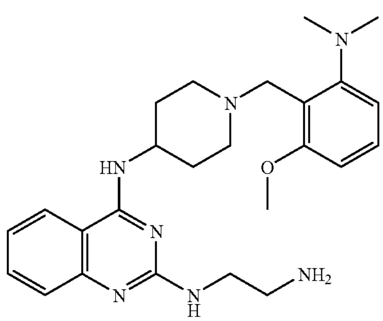 | 268 nM (97) |
| 126 | 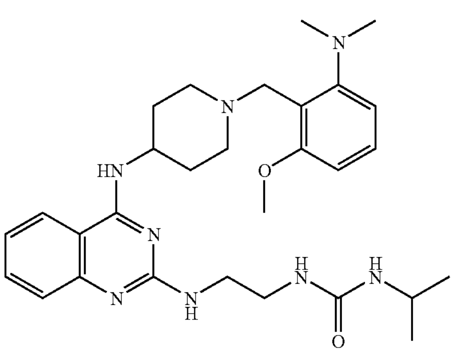 | 2.9 μM (96) |

-continued
| Compound Number | Structure | CXCR4 IC$_{50}$ (% Inh) |
|---|---|---|
| 130 | 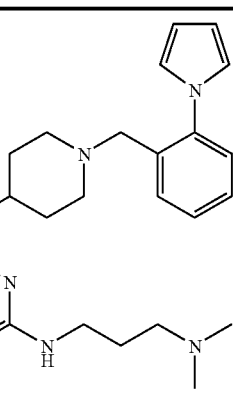 | 978 nM (75) |
| 131 | 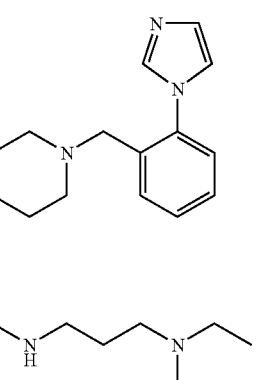 | 6.6 μM (74) |
| 132 | 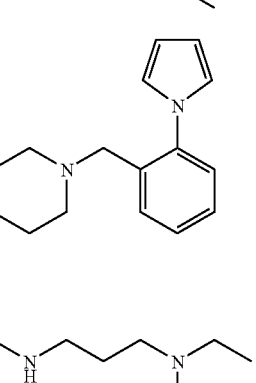 | 1.4 μM (84) |
| 133 | 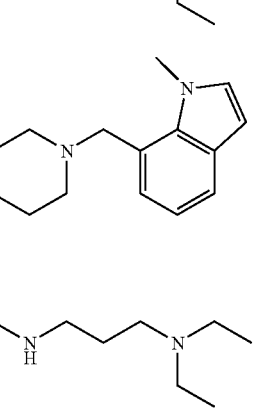 | 2.2 μM (63) |

-continued

| Compound Number | Structure | CXCR4 IC$_{50}$ (% Inh) |
|---|---|---|
| 134 | 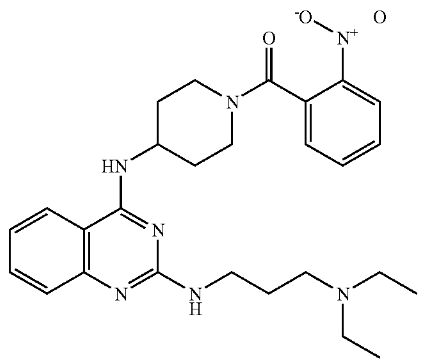 | NA |
| 139 | 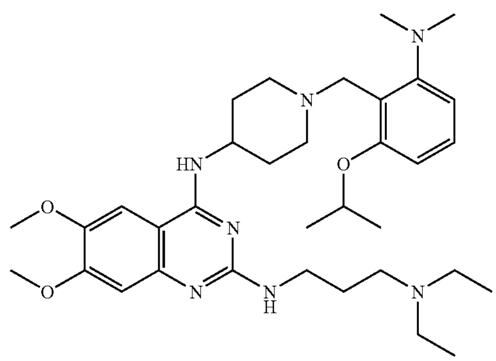 | 1.4 µM (93) |
| 146 | 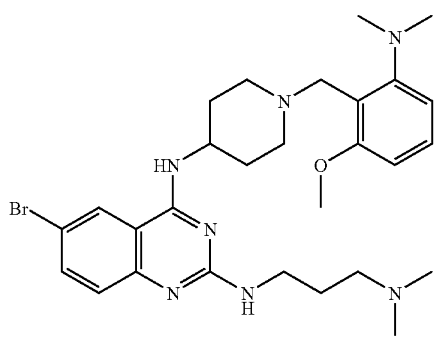 | 1.2 µM (96) |
| 149 | 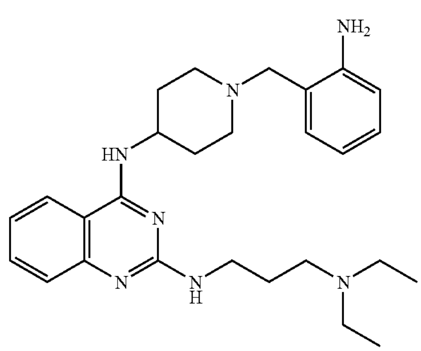 | >10 µM (68) |

-continued
| Compound Number | Structure | CXCR4 IC$_{50}$ (% Inh) |
|---|---|---|
| 152 | 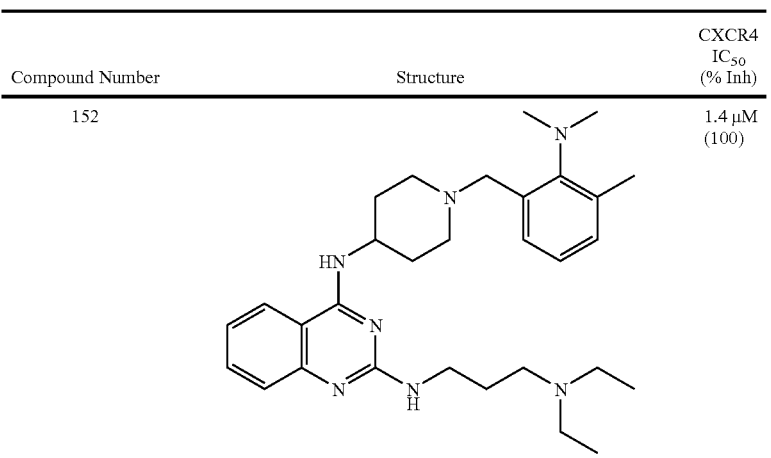 | 1.4 μM (100) |
| 153 | 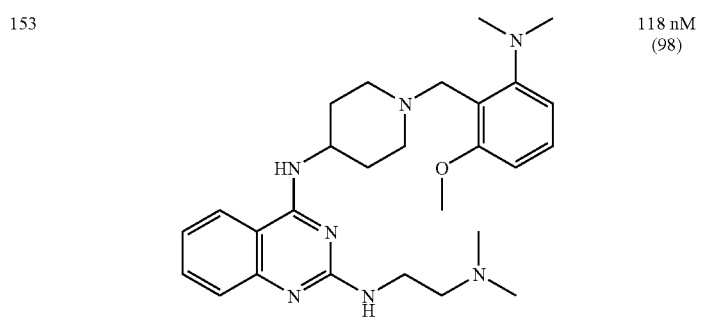 | 118 nM (98) |
| 154 | 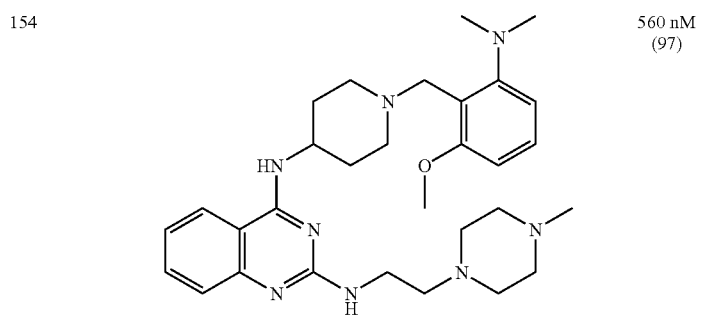 | 560 nM (97) |
| 157 | 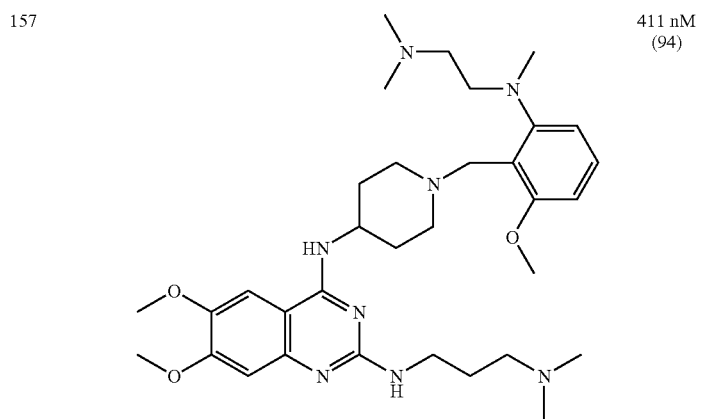 | 411 nM (94) |

-continued

| Compound Number | Structure | CXCR4 IC$_{50}$ (% Inh) |
|---|---|---|
| 161 | 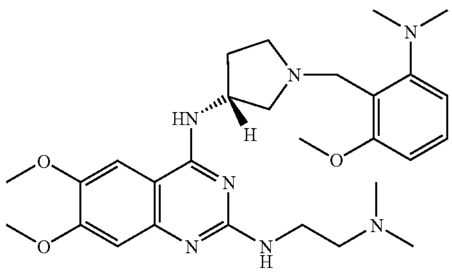 | 1.9 µM (92) |
| 165 | 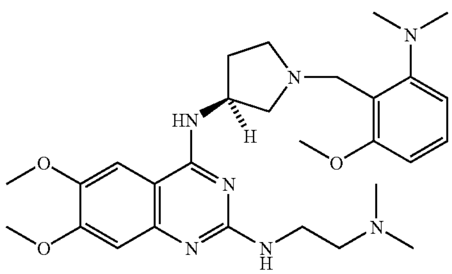 | 538 nM (97) |
| 166 | 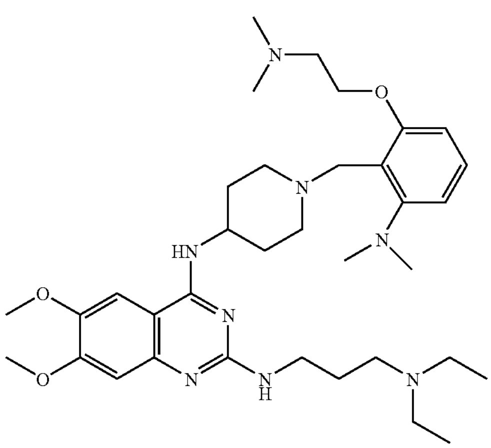 | 49 nM (94) |
| 170 | 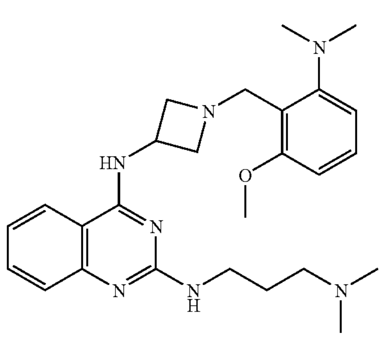 | NA |

| Compound Number | Structure | CXCR4 IC$_{50}$ (% Inh) |
|---|---|---|
| 174 | 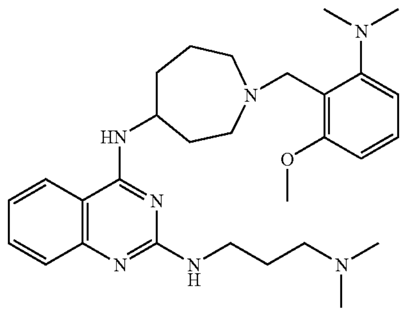 | 770 nM (97) |
| 178 | 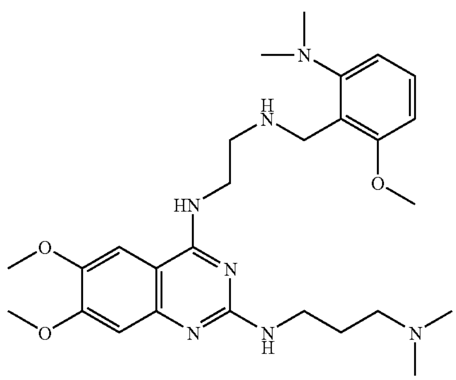 | >10 μM (49) |
| 180 | 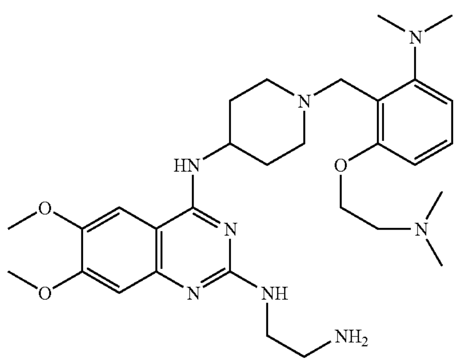 | 116 nM (94) |
| 182 | 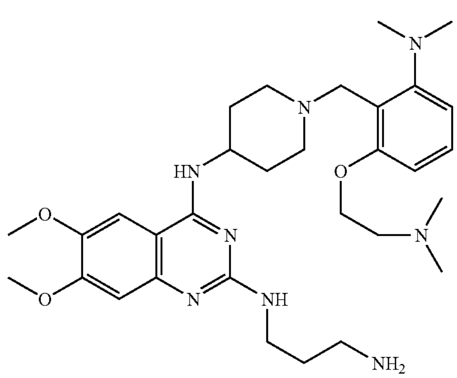 | 47 nM (94) |

-continued
| Compound Number | Structure | CXCR4 IC$_{50}$ (% Inh) |
|---|---|---|
| 189 | 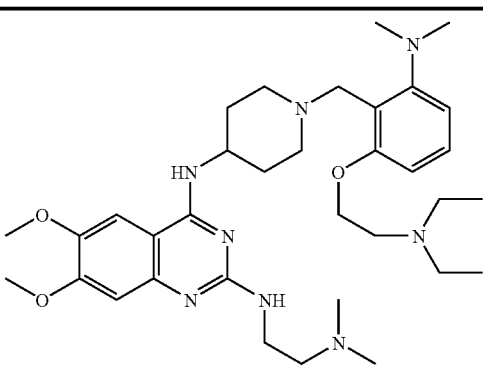 | 45 nM (94) |
| 193 | 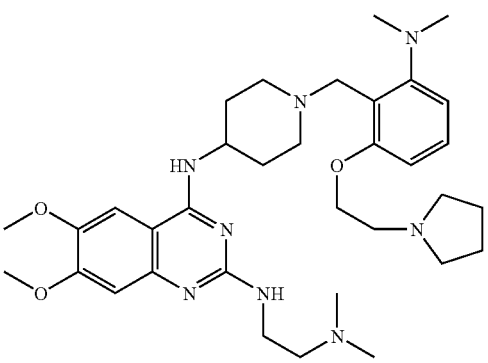 | 65 nM (95) |
| 194 | 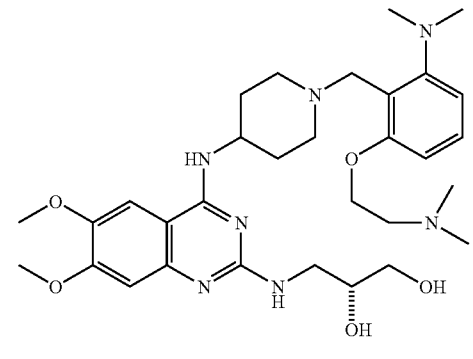 | 74 nM (96) |
| 195 | 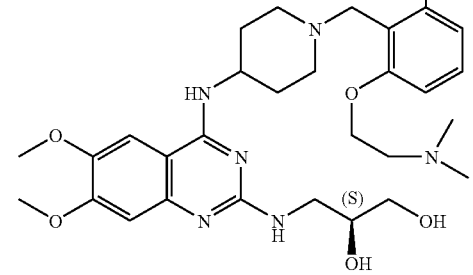 | 31 nM (98) |

-continued

| Compound Number | Structure | CXCR4 IC$_{50}$ (% Inh) |
|---|---|---|
| 196 | 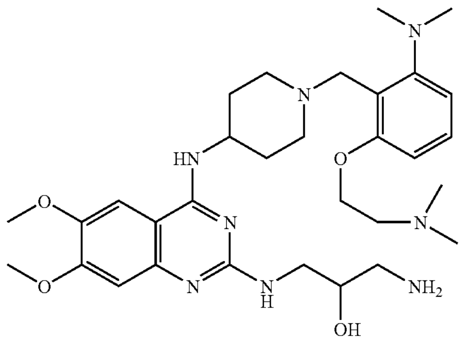 | 38 nM (95) |
| 197 | 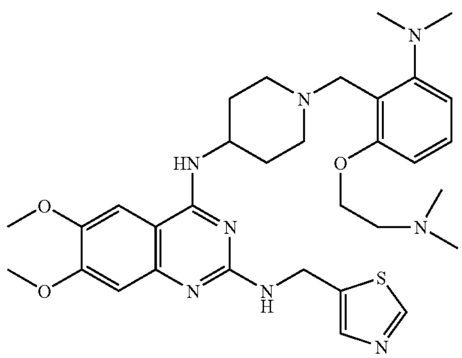 | 34 nM (85) |
| 198 | 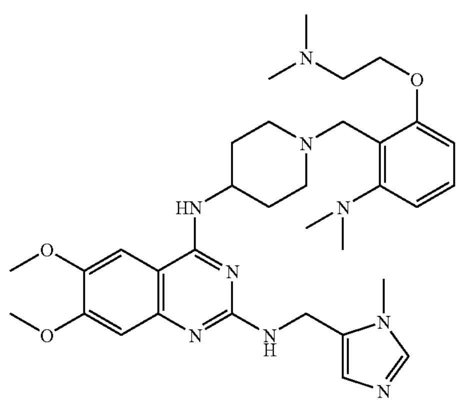 | 36 nM (98) |
| 203 | 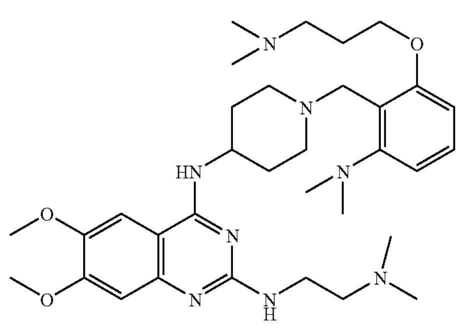 | 66 nM (94) |

-continued
| Compound Number | Structure | CXCR4 IC$_{50}$ (% Inh) |
|---|---|---|
| 204 | 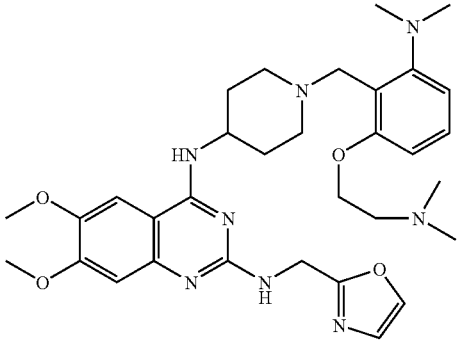 | 47 nM (92) |
| 205 | 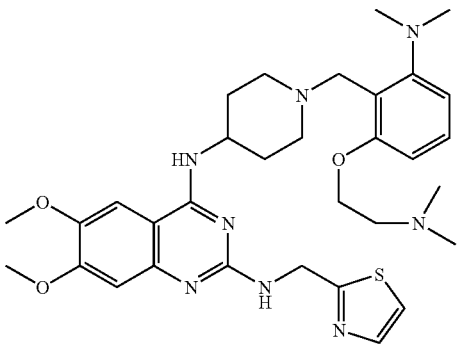 | 32 nM (100) |
| 206 | 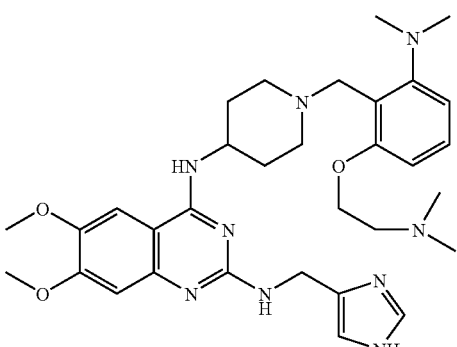 | 16 nM (96) |
| 207 | 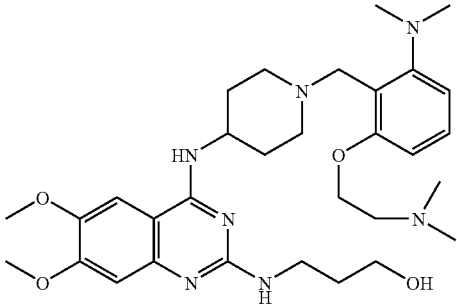 | 69 nM (99) |

-continued

| Compound Number | Structure | CXCR4 IC$_{50}$ (% Inh) |
|---|---|---|
| 208 | 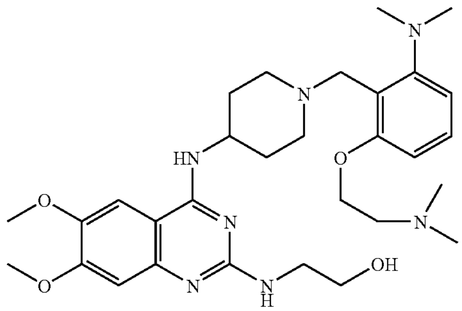 | 169 nM (98) |
| 209 | 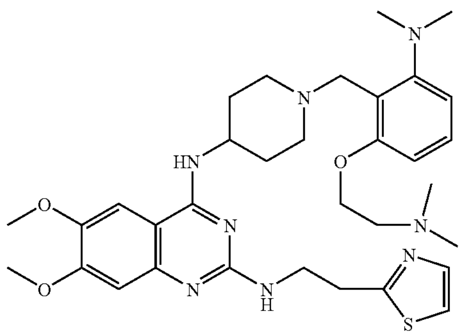 | 47 nM (92) |
| 210 | 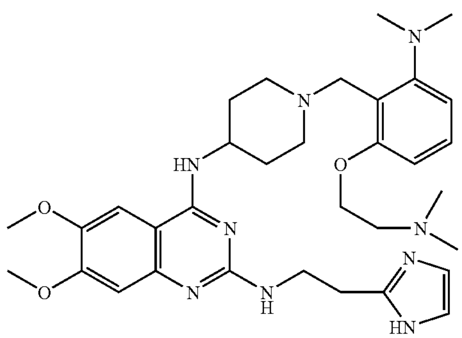 | 65 nM (97) |
| 211 | 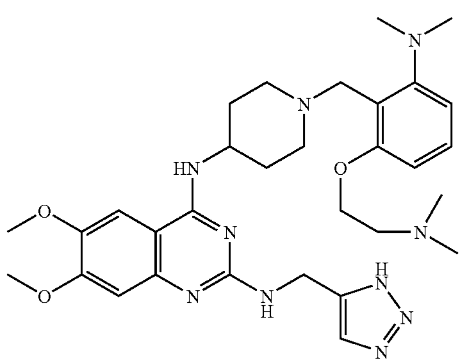 | 25 nM (98) |

-continued
| Compound Number | Structure | CXCR4 IC$_{50}$ (% Inh) |
|---|---|---|
| 212 | 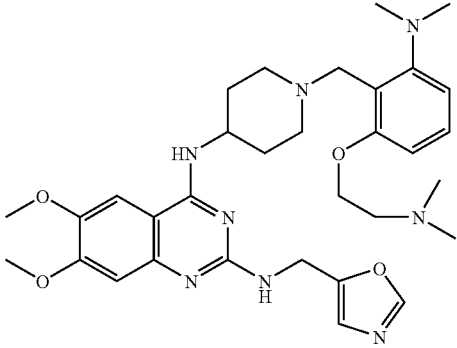 | 58 nM (98) |
| 213 | 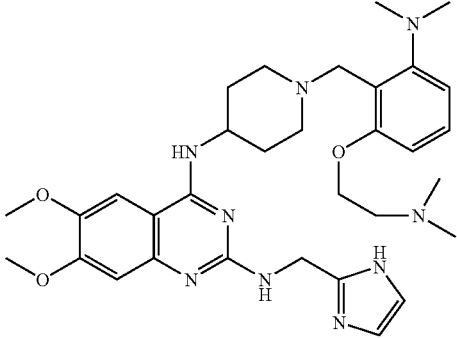 | 30 nM (100) |
| 215 | 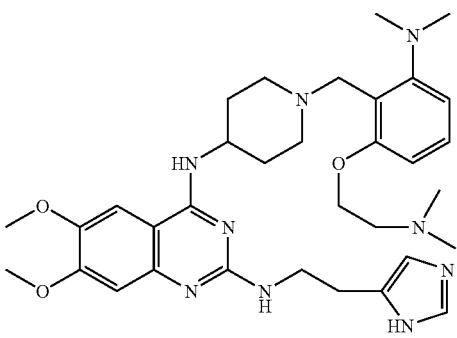 | 55 nM (100) |
| 215 | 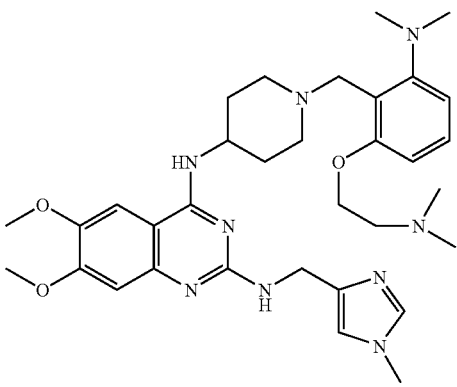 | 73 nM (99) |

-continued

| Compound Number | Structure | CXCR4 IC$_{50}$ (% Inh) |
|---|---|---|
| 216 | 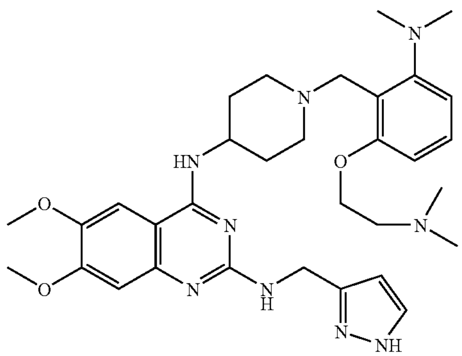 | 32 nM (100) |
| 217 | 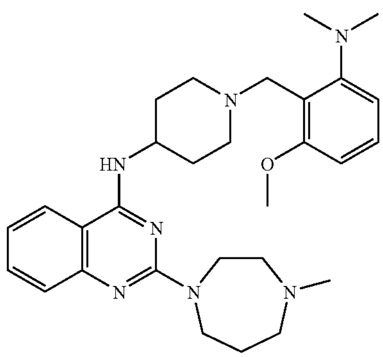 | 2.1 µM (100) |
| 218 | 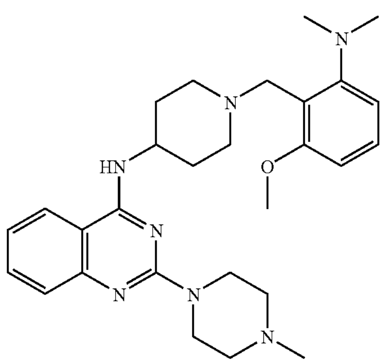 | 1.2 µM (84) |
| 224 | 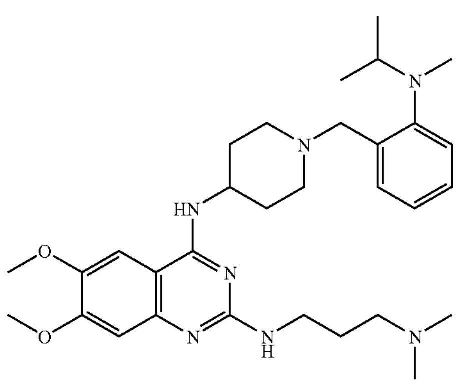 | 695 nM (92) |

-continued

| Compound Number | Structure | CXCR4 IC$_{50}$ (% Inh) |
|---|---|---|
| 225 | 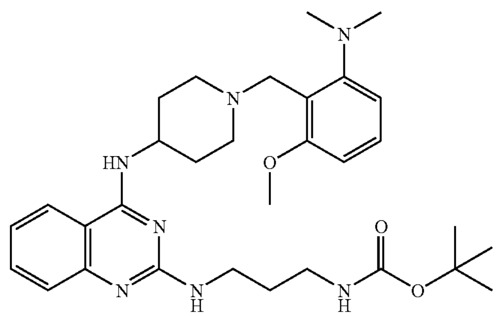 | 614 nM (88) |
| 227 | 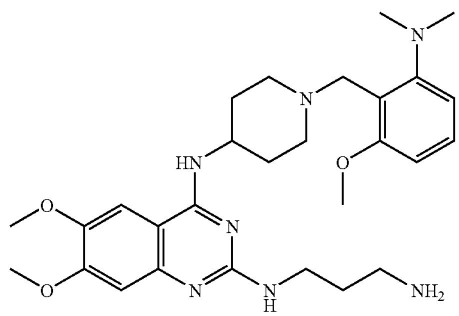 | 105 nM (94) |
| 228 | 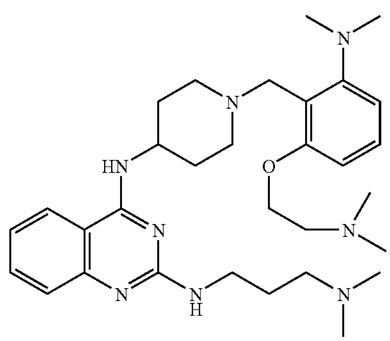 | 71 nM (98) |
| 229 | 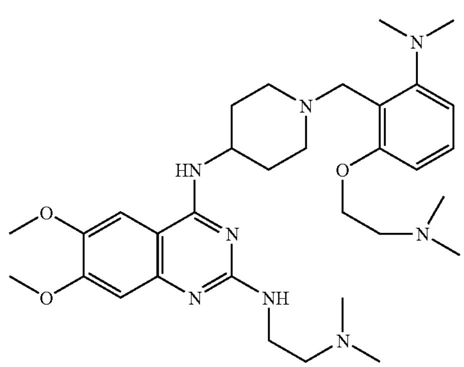 | 41 nM (96) |

| Compound Number | Structure | CXCR4 IC$_{50}$ (% Inh) |
|---|---|---|
| 230 | 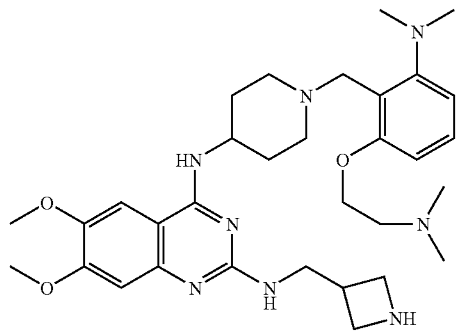 | 56 nM (96) |
| 231 | 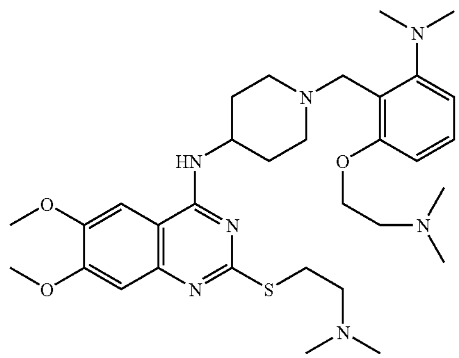 | 131 nM (96) |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

The invention claimed is:

1. A compound represented by the structural formula:

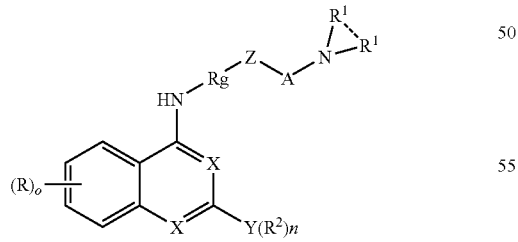

wherein a dashed line represents the presence or absence of a bond;
o is 0, 1, 2, 3 or 4;
X is N;
Y is N, NH, CH$_2$, CH, C, O, or S;
A is aryl or heteroaryl having 0, 1, 2, 3, or 4 substituents, wherein Z and the N atom are attached to adjacent carbon atoms, and wherein each substituent of A independently has a formula $C_{0-10}H_{0-27}N_{0-3}O_{0-3}S_{0-2}P_{0-1}F_{0-3}Cl_{0-1}Br_{0-1}I_{0-1}$;

Z is CH$_2$, CHOH, or C=O;
Rg is a 3- to 7-membered ring having a formula $C_{2-10}H_{2-21}N_{0-1}$, wherein if an N atom is present, it is directly attached to Z;
R is independently H, OH, SH, C$_{1-3}$ alkyl, O—(C$_{1-3}$ alkyl), S—(C$_{1-3}$ alkyl), or halo, wherein two R moieties may together form a ring;
R$^1$ is independently H, O, C$_{1-8}$ hydrocarbyl, C$_{1-8}$ hydroxyalkyl, C$_{1-8}$ alkylthiol, C$_{1-8}$ alkylalkoxy, C$_{1-8}$ alkylthioalkyl, or C$_{1-8}$ aminoalkyl; and
Y(R$^2$)$_n$ is a substituent having a formula $C_{1-20}H_{0-45}N_{0-50}O_{0-5}S_{0-5}F_{0-5}Cl_{0-5}Br_{0-5}I_{0-5}$, wherein Y(R$^2$)$_n$ may include one or more rings, each R$^2$ is independent, and n is 1, 2, or 3.

2. The compound of claim 1, further represented by the structural formula:

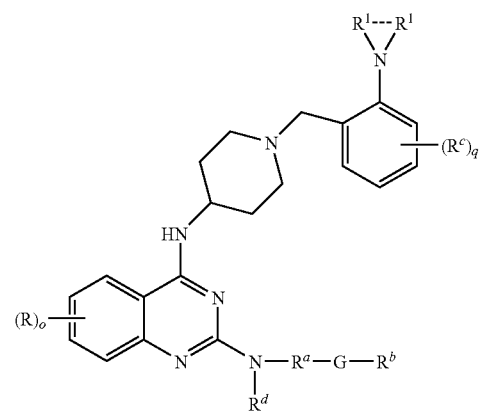

wherein each $R^c$ is independently F, Br, Cl, Br, —OH, —CN, $R^5$ or $Y^a$—$R^5$, wherein $Y^a$ is independently —O—, —S—, —N($R^5$)—, —C(O)$_2$—, —C(O)—, —OC(O)—, or —C(O)N($R^5$)—, wherein two $R^c$ moieties may together form a ring;

each $R^5$ is independently H, $C_{1-8}$ alkyl, $C_{1-8}$ hydroxyalkyl, $C_{1-8}$ alkylthiol, $C_{1-8}$ alkylalkoxy, $C_{1-8}$ alkylthioalkyl, or $C_{1-8}$ aminoalkyl;

o, q, r, and s are independently 0, 1, 2, 3, or 4;

$R^a$ is a bond, H, —(CH$_2$)$_t$— or $C_{1-8}$ alkyl;

t is from 1 to 8;

$R^b$ and $R^d$ are independently H, or $C_{1-8}$ alkyl; and

G is a bond or $Y^a$.

3. The compound of claim 2 wherein G is —N($R^5$)—.

4. The compound of claim 2 wherein $R^a$ is —(CH$_2$)$_t$—, wherein t is from 1 to 8.

5. The compound of claim 4 wherein t is from 2 to 4.

6. The compound of claim 2 wherein R is H or —OCH$_3$.

7. The compound of claim 5 wherein R is H or —OCH$_3$.

8. The compound of claim 2 wherein G is —C(O)N($R^5$)—.

9. The compound of claim 2 wherein $R^a$ and $R^d$ together form a ring with from 3 to 8 carbon atoms.

10. The compound of claim 2 selected from:

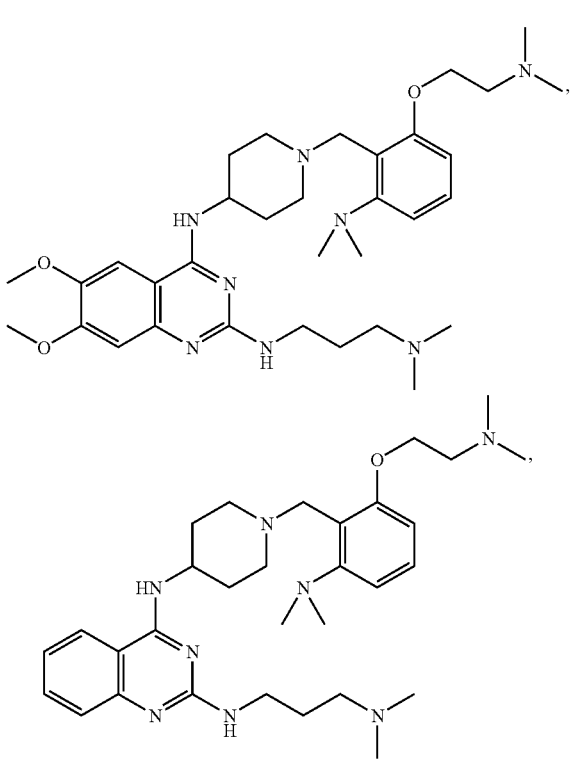

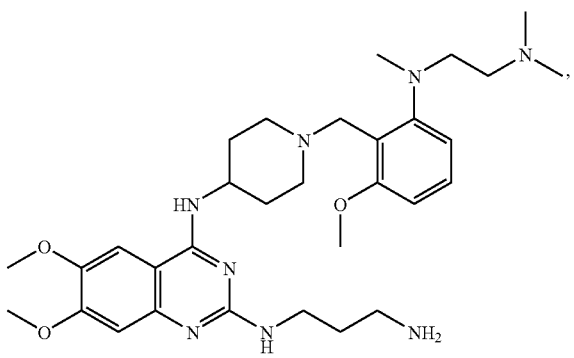

-continued

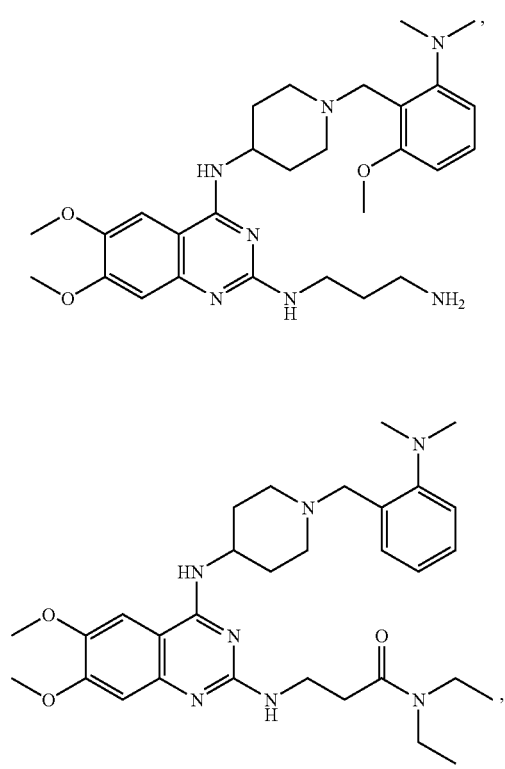

177
-continued
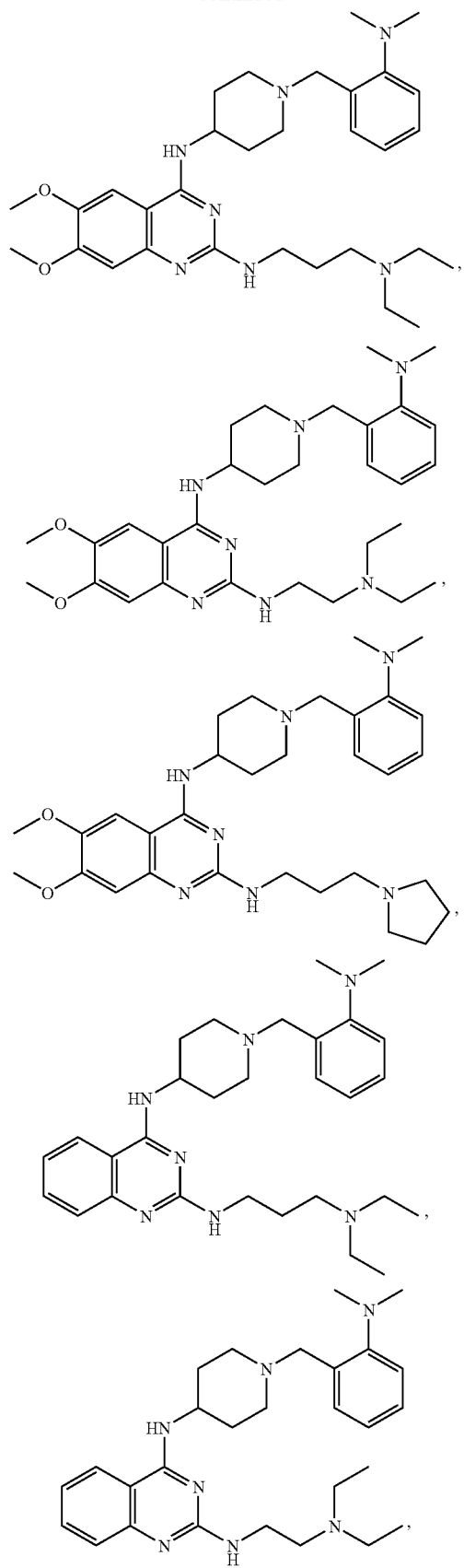
178
-continued
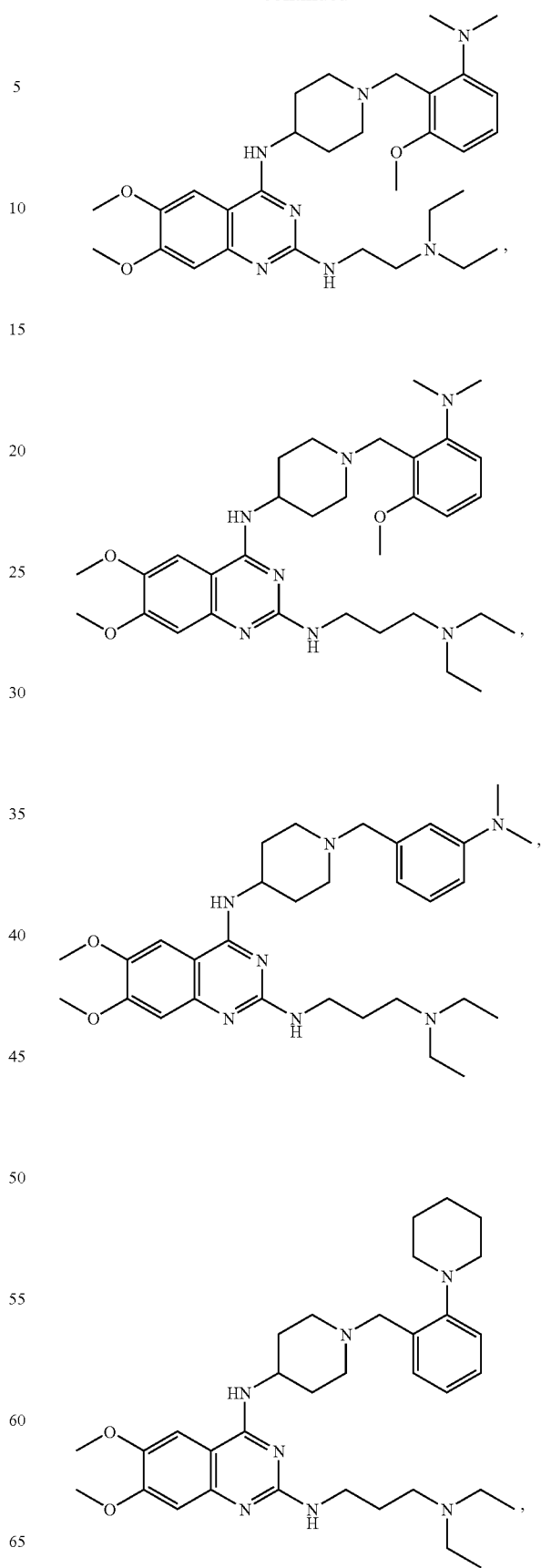

-continued
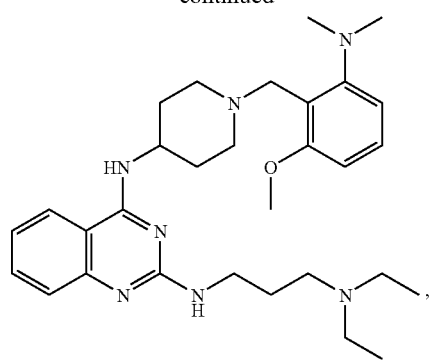
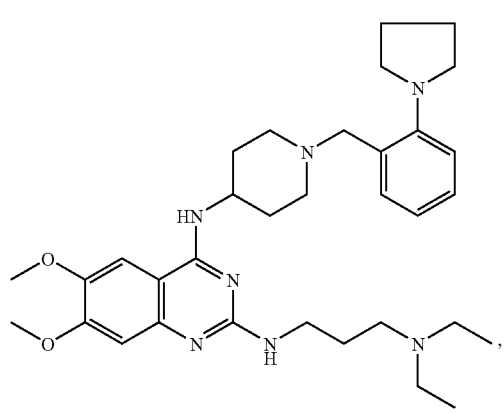
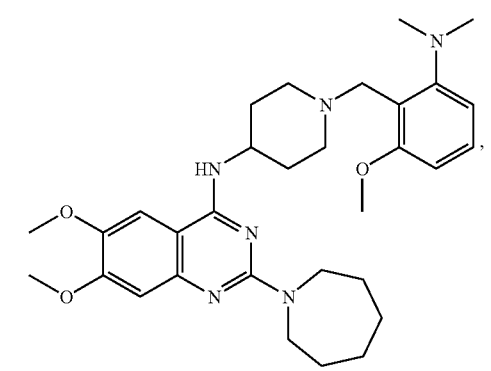
-continued
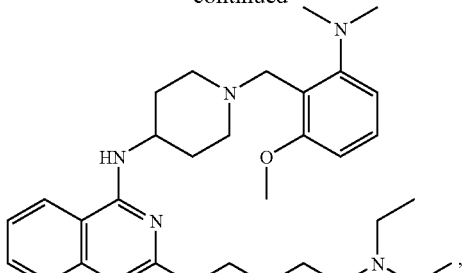
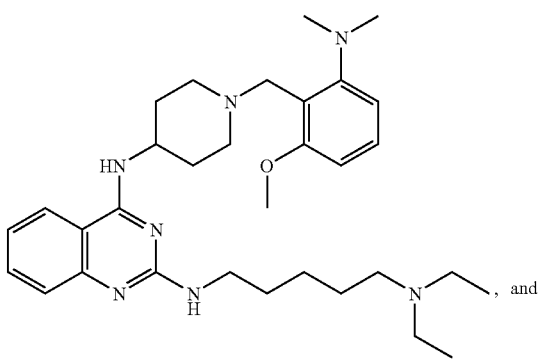
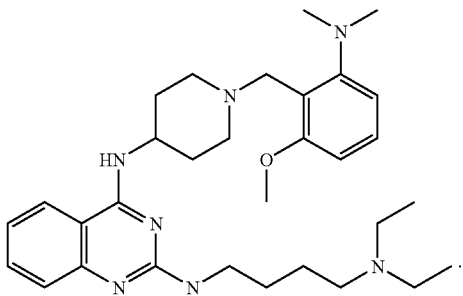
11. The compound of claim 1 wherein Rg is a 4-membered ring or a 6-membered ring.
12. The compound of claim 1 wherein A is phenyl having 0, 1, or 2 substituents.
13. The compound of claim 1 wherein A is pyridinyl having 0, 1, or 2 substituents.
14. The compound of claim 1 wherein A is thienyl having 0, 1, or 2 substituents.
15. The compound of claim 1 wherein A is furyl having 0, 1, or 2 substituents.
* * * * *